US011235049B2

(12) United States Patent
Carver, III et al.

(10) Patent No.: US 11,235,049 B2
(45) Date of Patent: Feb. 1, 2022

(54) POLYPEPTIDES OF FUSOBACTERIUM AND METHODS OF USE

(71) Applicant: EPITOPIX, LLC, Willmar, MN (US)

(72) Inventors: Charles Nelson Carver, III, Spicer, MN (US); Daryll A. Emery, New London, MN (US)

(73) Assignee: Epitopix, LLC, Willmar, MN (US)

( * ) Notice: Subject to any disclaimer, the term of this patent is extended or adjusted under 35 U.S.C. 154(b) by 0 days.

(21) Appl. No.: 15/774,168

(22) PCT Filed: Nov. 9, 2016

(86) PCT No.: PCT/US2016/061108
§ 371 (c)(1),
(2) Date: May 7, 2018

(87) PCT Pub. No.: WO2017/083367
PCT Pub. Date: May 18, 2017

(65) Prior Publication Data
US 2019/0224297 A1 Jul. 25, 2019

Related U.S. Application Data

(60) Provisional application No. 62/252,951, filed on Nov. 9, 2015.

(51) Int. Cl.

| | |
|---|---|
| ***C07K 1/00*** | (2006.01) |
| ***A61K 39/114*** | (2006.01) |
| ***C07K 14/195*** | (2006.01) |
| ***A61P 31/04*** | (2006.01) |
| ***A61K 39/39*** | (2006.01) |
| ***G01N 33/569*** | (2006.01) |

(52) U.S. Cl.
CPC ............ *A61K 39/114* (2013.01); *A61K 39/39* (2013.01); *A61P 31/04* (2018.01); *C07K 14/195* (2013.01); *G01N 33/56911* (2013.01); *C12N 2500/24* (2013.01)

(58) Field of Classification Search
None
See application file for complete search history.

(56) References Cited

U.S. PATENT DOCUMENTS

| | | | |
|---|---|---|---|
| 5,455,034 | A | 10/1995 | Nagaraja et al. |
| 5,538,733 | A | 7/1996 | Emery et al. |
| 6,027,736 | A | 2/2000 | Emery et al. |
| 6,241,992 | B1 | 6/2001 | Morck et al. |
| 6,632,439 | B2 | 10/2003 | Liem et al. |
| 6,669,940 | B2 | 12/2003 | Nagaraja et al. |
| 6,962,990 | B1 | 11/2005 | Attarian |
| 8,329,192 | B2 | 12/2012 | Straub |
| 9,308,247 | B2 | 4/2016 | Narayanan |
| 2002/0114817 | A1 | 8/2002 | Liem |
| 2003/0206922 | A1 | 11/2003 | Emery et al. |
| 2003/0211118 | A1 | 11/2003 | Emery et al. |
| 2004/0037851 | A1 | 2/2004 | Liem et al. |
| 2004/0047871 | A1 | 3/2004 | Nagaraja et al. |
| 2004/0197350 | A1 | 10/2004 | Emery et al. |
| 2004/0197869 | A1 | 10/2004 | Emery et al. |
| 2004/0265329 | A1 | 12/2004 | Emery et al. |
| 2005/0186217 | A1 | 5/2005 | Straub et al. |
| 2005/0095682 | A1 | 8/2005 | Emery et al. |
| 2006/0024323 | A1 | 2/2006 | Emery et al. |
| 2006/0083753 | A1 | 4/2006 | Straub et al. |

FOREIGN PATENT DOCUMENTS

| | | | |
|---|---|---|---|
| WO | WO 1996/001620 | A1 | 1/1996 |
| WO | WO 2001/37810 | A2 | 5/2001 |
| WO | WO 2001/37810 | A3 | 5/2001 |
| WO | WO 2006/026373 | A1 | 3/2006 |
| WO | WO 2006/079076 | A2 | 7/2006 |
| WO | WO 2014/084964 | A1 | 6/2014 |

OTHER PUBLICATIONS

Kittichotirat et al (Comparative genomics of Fusobacterium necrophorum wild isolates; Submitted (Jan. 2014) to the EMBL/GenBank/DDBJ databases; Accession Nos. A0A064A2K7, A0A0E2V0S3, A0A064AI82 and A0A064AI94).*
Ward et al (The Genome Sequence of *Fusobacterium* sp. 3_1_5R.; Submitted (Feb. 2009) to the EMBL/GenBank/DDBJ databases; Accession No. E5BGP3).*
Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
International Patent Application No. PCT/US2016/061108, filed Nov. 9, 2016; International Search Report / Written Opinion dated Feb. 14, 2017; 15 pages.
International Patent Application No. PCT/US2016/061108, filed Nov. 9, 2016; International Preliminary Report on Patentability dated May 24, 2018; 7 pages.
International Preliminary Report on Patentability for PCT application No. PCT/US2005/030290, dated Feb. 28, 2007; 10 pages.
International Search Report and Written Opinion for PCT application No. PCT/US2005/030290, dated Dec. 20, 2005; 6 pages.
Abe, "Fusobacterium necrophorum infection in mice as a model for the study of liver abscess formation and induction of immunity" May 1976 *Infect. Immun.*, 13(5):1473-1478.
Afra, "Incidence, risk factors, and outcomes of *Fusobacterium* species *bacteremia*" 2013 *Infectious Diseases*, 13: 264.
Ainsworth, "Outer membrane proteins of Fusobacterium necrophorum biovars A, AB and B: their taxonomic relationship to *F. necrophorum* subspecies *necrophorum* and *F. necrophorum* subspecies *funduliforme*" Apr. 1993 *J Vet Diagn Invest.*, 5:282-283.

(Continued)

*Primary Examiner* — Jennifer E Graser
(74) *Attorney, Agent, or Firm* — Mueting Raasch Group

(57) ABSTRACT

The present invention provides isolated polypeptides isolatable from a *Fusobacterium* spp. Also provided by the present invention are compositions that include one or more of the polypeptides, and methods for making and methods for using the polypeptides.

15 Claims, 49 Drawing Sheets

Specification includes a Sequence Listing.

(56) References Cited

OTHER PUBLICATIONS

Bachrach, "Identification of a *Fusobacterium nucleatum* 65 kDa Serine Protease," 2004 *Oral Microbiology Immunology*, 19:155-159.
Bakken, "Outer membrane proteins as major antigens" 1989 *FEMS Microbiology Immunology*, 47: 473-484.
Bakken, "Outer membrane proteins of Fusobacterium nucleatum Fevl" 1986 *Journal of General Microbiology*, 132: 1069-1078.
Bolstad, "Molecular characterization of a 40-kDa outer membrane protein, FomA, of *Fusobacterium periodonticum* and comparison with *Fusobacterium nucleatum*," Oct. 1995 *Oral Microbiol Immunol.*, 10(5): 257-264.
Bolstad, "Taxonomy, Biology, and Periodontal Aspects of *Fusobacterium nucleatum*," Jan. 1996 *Clinical Microbiology Reviews*, 9(1):55-71.
Conlon, "Evaluation of experimentally induced Fusobacterium necrophorum infections in mice" 1977 *Infect. Immun*, 15, 510-517.
Coyle, "Correlations between leukocidin production and virulence of two isolates of Fusobacterium necrophorum" 1979 *Am. J. Vet. Res.*, 40, 274-276.
Emery, "Generation of immunity against Fusobacterium necrophorum in mice inoculated with extracts containing leukotoxin" Sep. 1986 *Vet. Microbiol*, 12, 255-268.
E-TOXATE® (Technical Bulletin No. 210). SIGMA Chemical Company, St. Louis, MO, 1998. pp. 1-4.
Faraldo-Gomez, "Acquisition of Siderophores in Gram-Negative Bacteria," Feb. 2003 *Nature Reviews Molecular Cell Biology*, 4:105-116.
Garcia, "Intraperitoneal immunization against necrobacillosis in experimental animals" 1978 *Can. J. Comp. Med*, 42, 121-127.
Haake, "Cloning and expression of FOMA, the Major Outer-Membrane Protein Gene from *Fusobacterium nucleatum* T18" Jan. 1997 *Arch Oral Biol.*, 42(1): 19-24.
Harlow, *Antibodies, A Laboratory Manual*, Cold Spring Harbor Laboratory, Cold Spring Harbor, New York, NY: 1988. Cover page, publisher's page, and Chapter 5. 94 pages.
Hauptmeier, "Footrot In Beef Cattle," Iowa Beef Center, Mar. 1997, 2 pgs. Online at http:www.ioawbeef.org/Publications.footrot.pdf.
Heinrichs, "Identification and Characterization of SirA, an Iron-Regulated Protein from *Staphylococcus aureus*" 1999 *J. Bacteriol.*, 181, 1436-1443.
"HMPREF1127 0553—Outer membrane efflux protein—*Fusobacterium necrophorum* subsp. *funduliforme* Fnf 1007—HMPREF1127 0553 gene & protein," UniprotKB, Oct. 31, 2012 (Oct. 31, 2012), pp. 1-4, XP055341300, Retrieved from the Internet:http://www.uniprot.org/uniprot/J8W5G4 [retrieved on Feb. 1, 2017].
Hussain, "A Lithium Chloride-Extracted, Broad-Spectrum-Adhesive 42-Kilodalton Protein of *Staphylococcus epidermidis* Is Ornithine Carbamoyltransferase" 1999 *Infect. Immun.*, 67:6688-6690.
Kapatral, "Genome Analysis of *F. nucleatum* sub spp *vincentii* and Its Comparison With the Genome of F. nucleatum ATCC 25586" 2003 *Genome Res.*, 13:1180-1189.
Kapatral, "Genome sequence and analysis of the oral bacterium Fusobacterium nucleatum strain ATCC 25586" 2002 J. Bacteriol., 184:2005-2018.
Keler, "Metachromatic assay for the quantitative determination of bacterial endotoxins" 1986 *Analyt. Biochem.*, 156:189.
Kleivdal, "Identification of positively charged residues of FomA porin of *Fusobacterium nucleatum* which are important for pore function," Mar. 1999 *Eur. J. Biochem.*, 260(3):818-824.
Kleivdal, "The *Fusobacterium nucleatum* major outer-membrane protein (FomA) forms trimeric, water-filled channels in lipid bilayer membranes," Oct. 1995 *Eur. J. Biochem.*, 233(1):310-316.
Kleivdal, "Topological investigations of the FomA porin from *Fusobacterium nucleatum* and identification of the constriction loop L6," Apr. 2001 *Microbiology*, 147(4):1059-1067.
Kumar, "New bacterial species associated with chronic periodontitis" May 2003, *J Dent Res.*, 82(5):338-44.
Langworth, "Fusobacterium necrophorum: its characteristics and role as an animal pathogen" 1977 *Bacteriol. Rev.*, 41:373-390.
Lechtenberg, "Hepatic ultrasonography and blood changes in cattle with experimentally induced hepatic abscesses" 1991 *Am J Vet Res.*, 52(6)803-9.
Machado, "Subcutaneous immunization with inactivated bacterial components and purified protein of *Escherichia coli*, Fusobacterium necrophorum and *Trueperella pyogenes* prevents puerperal metritis in Holstein dairy cows" Mar. 2014 *PLoS One*, 9(3):e91734.
Mandell (Eds.), *Principles and Practice of Infectious Diseases, Second Edition*, John Wiley and Sons, New York, 1979, Title page, Publication page, and pp. 1377-1378.
Munson, "Molecular and cultural analysis of the microflora associated with endodontic infections" 2002 *J. Dent Res.*, 81:761.
Nagaoka, "Establishment of a new murine model of liver abscess induced by Fusobacterium necrophorum injected into the caudal vein" 2013 *J. Med. Micriobiol.*, 62(11):1755-1759.
Narayanan, "Cloning, Sequencing, and Expression of the Leukotoxin Gene from Fusobacterium necrophorum" 2001 *Infect. Imun.*, 69:5447-5455.
Narayanan, "Fusobacterium necrophorum Leukotoxin Induces Activation and Apoptosis of Bovine Leukocytes" 2002 *Infect. Immun.*, 70, 4609-4620.
Narayanan, "Immunogenicity and protective effects of truncated recombinant leukotoxin proteins of Fusobacterium necrophorum in mice" 2003 *Vet. Micro.*, 93:335-347.
Nikaido, "Outer membrane" in: Neidhardt (Ed.), *Escherichia coli and Salmonella: cellular and molecular biology*. 1987. Cover page, publisher's page and Chapter 5; 35 pages.
Paster, "The breadth of bacterial diversity in the human periodontal pocket and other oral sites" 2006 *Periodontology 2000*, 42:80.
Porcheron, "Iron, copper, zinc, and manganese transport and regulation in pathogenic Enterobacteria: correlations between strains, site of infection and the relative importance of the different metal transport systems for virulence" Dec. 2013 *Frontiers in Cellular and Infection Microbiology* 3:172-194.
Product data sheet: "Dairy Quality University—Volar Use in a Dairy Herd With Footrot" datasheet [online]. Bayer Corporation, Shawnee Mission, KS, 1996 [retrieved on Jul. 8, 2004]. Retrieved from the Internet: http://dqacenter.org/university/moreinfo/rh48.htm; 2 pgs.
Product data sheet: "Merck Vet. Edition—Liver Abscesses In Cattle: Introduction" datasheet [online]. Merck & Co., Inc., Whitehouse Station, New Jersey, 2003 [retrieved on Jun. 24, 2004]. Retrieved from the Internet: http://www.merckvetmanual.com/mvm/index.jsp?cfile=htm/bc/23500.htm; 2 pgs.
Product data sheet: "VOLAR®" datasheet [online]. Internet Inc., Millsboro, Delaware, 2004 [retrieved on Jun. 24, 2004]. Retrieved from the Internet:http://www.compasnac.com/cvp/11/1106/1106221.htm; 4 pgs.
Puntervoll, "Structural characterization of the fusobacterial non-specific porin FomA suggests a 14-stranded topology, unlike the classical porins," Nov. 2002 *Microbiology*, 148(11):3395-3403.
Quinde-Axtell, "Phenolic Compounds of Barley Grain and Their Implication in Food Product Discoloration" 2006 *J. Agric. Food Chem.*, 54(26):9978-9984.
Rae, "Injection Site Reactions," undated. Retrieved from internet Jun. 25, 2018. Online: animal.ifas.ufl.edu/beef_extension/bcsc/1994/docs/rae.pdf.
Rogers, "An aminopeptidase nutritionally important to Fusobacterium nucleatum," 1998 *Microbiology*, 144:1807-1813.
Saginala, "Effect of Fusobacterium necrophorum leukotoxoid vaccine on susceptibility to experimentally induced liver abscesses in cattle" Apr. 1997 *J. Anim. Sci.*,75, 1160-1166.
Smith, "Pathogenicity of Fusobacterium necrophorum strains from man and animals" Jun. 1993 *Epidemiol Infect.*, 110(3):499-506.
Tan, "Factors affecting the leukotoxin activity of *Fusobacterium necrophorum*," *Vet. Microbiol.*, Jul. 1992; 32(1):15-28.
Tan, "Biological and biochemical characterization of Fusobacterium necrophorum leukotoxin" Apr. 1994 *Am. J. Vet. Res.*, 55:515.

(56) References Cited

OTHER PUBLICATIONS

Tan, "Fusobacterium necrophorum infections: virulence factors, pathogenic mechanism, and control measures" 1996 *Vet Res. Commun.* 20:113-140.
Tan, "Purification and quantification of Fusobacterium necrophorum leukotoxin by using monoclonal antibodies" Nov. 1994 *Vet. Microbiol.*, 42:121-133.
Tatusova, "Blast 2 Sequences, a new tool for comparing protein and nucleotide sequences" 1999 *FEMS Microbiol Lett*, 174:247-250.
Tatusova, "RefSeq microbial genomes database: new representation and annotation strategy" Dec. 2013 *Nucleic Acids Res.*, 42:D553-D559.
Trivier, "Influence of iron depletion on growth kinetics, siderophore production, and protein expression of *Staphylococcus aureus*" Apr. 1995 *FEMS Microbiol. Lett.*, 127:195-199.
Vasstrand, "Composition of Peptidoglycans inBacteroidaceae: Determination and Distribution ofLanthionine," *Infection and Immunity*, Apr. 1982; 36(1):114-122.
Vasstrand, "Demonstration ofLanthionine as a Natural Constituent of the Peptidoglycan of *Fusobacterium nucleatum*," Sep. 1979 *Infection and Immunity*, 25(3):775-780.
Waldron, "How do bacterial cells ensure that metalloproteins get the correct metal?" 2009 *Nature Reviews Microbiology*, 7:25-35.
Watson, *Endotoxins and Their Detection with the Limulus and Amebocyte Lysate Test*. John Wiley & Sons Inc., Alan R. Liss, Inc., New York NY: 1982. Cover page, title page and table of contents.

* cited by examiner

FIG. 14

| *Fusobacterium necrophorum* 1694 FQ (rCopper) Gene Sequence (SEQ ID NO:1) |
|---|
| atgaaaaagctatggatattatttttcctgctggggagtgttgcttttggaagagaagttactttggaagaagcgattcaagc<br>gtcaatggagaatagcaaggcggtcaaaatttcagataagcagttagaaatttcaaaactaaaaatgaatcaggcaattaaaa<br>aagcactgccaagcgtagtgtacagtgccaactatcaacgtggagaatatgagagaaatatttataagaataaatcttctatg<br>gaatcggaaaaaggcggttacaaacaatcgattacaatcagccaacctatttttcaaggaggagccattcttgccggaattca<br>aggggcaaaagcctataaaaccatagcagatttgtcctatgttcaagagacactaaatactcgtttgaagacgattcgaactt<br>tttcgaatattgtcaacagcaaaagaaatttacaagctttggaatattccgagaaacaattgcaaaatcgatataaaaagcag<br>gaagctcaattggagttgcgactgattacgaagacggatttattgaaaacggaatactctttattggaagtacaatctttaat<br>ttccaaagcgaaaagtaatattgaagtacagacggaagatttaaaatttcaaatgggagtggacaaaaaagaagcattggaag<br>tcaaggaatttatcgttcccaatcatttgacagaacgtattacatttgaaaaagataaagagagggcattggaatccagtatt<br>caggctttgattgcaaaatctcaagtgaagatagcaaaggcacaggaaacggcagcactgggaaatatgcttcctaaggtaaa<br>tgcctttgtgagttatggagtggcttcggagagaacacattggaaacaaacgaaagaagatgcggaatggatgggaggtttgt<br>ctgtttcttggaatgtcttttcttttgggagtgactatgatgcttatcaaattgcaaaattggaaaaagagtccaaagagtta<br>tcagaaacgacagctcaggacaatatagctttgagccttaagacagcttatttggaattgcaaagattggaaattttaagaga<br>gtccagaaagagaggattggaagcggcagaattgaattttacaatggatcaagaaaaatttgatgcaggcttgctttccacag<br>tggattatttatcatcggaaacacaattgcgggaagcaagagtgaattattaccaagcagaattagattattactatgctttt<br>gaatattatagatcgttgttagtataa |
| *Fusobacterium necrophorum* 1694 FQ (rCopper) amino acid sequence (SEQ ID NO:2)<br><br>MKKLWILFFLLGSVAFGREVTLEEAIQASMENSKAVKISDKQLEISKLKMNQAIKKALPSVVYSANYQRGEYERNIYKNKSSM<br>ESEKGGYKQSITISQPIFQGGAILAGIQGAKAYKTIADLSYVQETLNTRLKTIRTFSNIVNSKRNLQALEYSEKQLQNRYKKQ<br>EAQLELRLITKTDLLKTEYSLLEVQSLISKAKSNIEVQTEDLKFQMGVDKKEALEVKEFIVPNHLTERITFEKDKERALESSI<br>QALIAKSQVKIAKAQETAALGNMLPKVNAFVSYGVASERTHWKQTKEDAEWMGGLSVSWNVFSFGSDYDAYQIAKLEKESKEL<br>SETTAQDNIALSLKTAYLELQRLEILRESRKRGLEAAELNFTMDQEKFDAGLLSTVDYLSSETQLREARVNYYQAELDYYYAF<br>EYYRSLLV |

FIG. 15

| *Fusobacterium necrophorum* 1694 FT (rZinc) Gene Sequence (SEQ ID NO:3) |
|---|
| atgaaaaaagtggtatttgggatttacagtatcttaatgtcctctgctatgcttggagcagaaattgatcttggaacacagaa<br>tatctattcggaaaccggatttgaaacgagtcttcgaagctctgtttcttctccttatatcgttacttcaaaagaaatcaaag<br>aaaaacattatacccgtgtttctgaaattttgagagatattccgcatatctacatcggtcccggtggcagtgtagatatgcgt<br>ggtcagggaagtgctcatgccagaacaacagttcaactgttaattgatggagttcctgccaatttttggatacttcccacat<br>caatcttcctatcgatactttaaatccagaagatattaagagaattgaagtcatccctggaggaggagctgttttatatggaa<br>gtggaacttccggaggagtgatcaacatcattaccaaaaaatacacgggaaactatgcaaaggcaagctatcaaataggaagc<br>tatcacaatcataaatatgacgtagctgccggaacttctttgggaaattttgacattaacctaagttattcaaaaaataatag<br>ggatggatatcgtaaaaagccttttccgattccgatttcttctccggaaaattacgttatcacttcaatcccacagacagtc<br>ttgaattcaaatatagctattttgataataagttcagaggtgttaaatccctaaccagagaacaagtcgagaaagatcgaagg<br>caaagtggtctttctcctgaagacaatttgaaaaataccatccgaaaagaagaatggaatttaacttacgatgcaaaatggac<br>aagctggctggaacacaaatccaatcttttctatcagtccacagaaataaaatctagtgaatatgaagatgctcttcctttct<br>atcaatatcaaatttcttcttatcaaaaaatgcttactatgccagggattcctcctatgatgcaagcacaattgaaaaagcag<br>ataaaagccctacaaaatttgataacgagtaatccaaggatggaattacatcaaggaagtcgtttcaaagatcaaaaattcgg<br>ttttaaaatgaagaataaatttaagtatggagaaaatagtgattttattttaggtttgggatacattcacaacaaaatggatc<br>gagattcttgggcttatacgaaaaatacgcaaacgaatcaaacaatagcaactcttacaaatactaaaattcctttaaataag<br>aaaacattcgaaattttcggattaaatacctatcgtcataataattgggaatttgttcagggcttacgctttgaaaaagcgaa<br>atataatggaaaaagacaatataaaaatctggaatatcctttaaaagatcgtagcatgaataatgttgcggcaaatctggctg<br>tcaattatctctattccgatacaggaaatgtctatgtaaaatatgaaagaggatttacttctcctgctcctgcacagttaatg<br>gataaaatcagaaaaggaggagtgaacgattatgtcaataatgatttaaaatctgaaaaatcaaactcctttgaagttggatg<br>gaatgactatctcttccattctttagtcagtgctgatgtttttttcagtgaaacgaaagatgaaatttctaccatattctcgg<br>gagggcatgggacaacattcagcaatttgaaccttggtcaaacgaaacgatatggttttgatctaaaagccagtcaagttttt<br>gaaaagtggacattctcggaagcttacagttatatccatgcaaaaatcatgaaagataaaacaaaggcttatgaaggaaaata<br>tatcagttatgttccaaggcataaattttctttgaatgctgattatgcaatcactccaaaatggactcttggggggagaatatc<br>aatacagttcttccgtatatctggacaatgcaaataaaaatggaaaagatggagcgagatctgttttaatcttcaaacctct<br>tatgagttcaattcacatttttctatctatgcaggaattaaaaatgtgttaaatcataagtattatgaatctgtcagtgcagg<br>ttccagtcaaaagtattatagtccggctccggaaagaaattactatgccggattccgttatcaattttaa |
| *Fusobacterium necrophorum* 1694 FT (rZinc) amino acid sequence (SEQ ID NO:4)<br><br>MKKVVFGIYSILMSSAMLGAEIDLGTQNIYSETGFETSLRSSVSSPYIVTSKEIKEKHYTRVSEILRDIPHIYIGPGGSVDMR<br>GQGSAHARTTVQLLIDGVPANFLDTSHINLPIDTLNPEDIKRIEVIPGGGAVLYGSGTSGGVINIITKKYTGNYAKASYQIGS<br>YHNHKYDVAAGTSLGNFDINLSYSKNNRDGYRKKAFSDSDFFSGKLRYHFNPTDSLEFKYSYFDNKFRGVKSLTREQVEKDRR<br>QSGLSPEDNLKNTIRKEEWNLTYDAKWTSWLEHKSNLFYQSTEIKSSEYEDALPFYQYQISSYQKMLTMPGIPPMMQAQLKKQ<br>IKALQNLITSNPRMELHQGSRFKDQKFGFKMKNKFKYGENSDFILGLGYIHNKMDRDSWAYTKNTQTNQTIATLTNTKIPLNK<br>KTFEIFGLNTYRHNNWEFVQGLRFEKAKYNGKRQYKNLEYPLKDRSMNNVAANLAVNYLYSDTGNVYVKYERGFTSPAPAQLM<br>DKIRKGGVNDYVNNDLKSEKSNSFEVGWNDYLFHSLVSADVFFSETKDEISTIFSGGHGTTFSNLNLGQTKRYGFDLKASQVF<br>EKWTFSEAYSYIHAKIMKDKTKAYEGKYISYVPRHKFSLNADYAITPKWTLGGEYQYSSSVYLDNANKNGKDGARSVFNLQTS<br>YEFNSHFSIYAGIKNVLNHKYYESVSAGSSQKYYSPAPERNYYAGFRYQF |

FIG. 16

| |
|---|
| *Fusobacterium necrophorum* 1694 FN rHemin TonB-dependent receptor. Gene Sequence (SEQ ID NO:5) |
| atgaaaaaaattttgtttttagttggggctttgttttctatttctgcttttgcggagcagactatagaattaggaagtacttc<br>cataaaaggaaatagaaagacagattatactttaacaccaaaagagtataaaaatacatataccattacgcaagaaaaaattc<br>aagaacgaaactataaaaatgtagaagatgttttacgagatgctcctggtattgttgttcaaaatacagcatttggacctcga<br>attgatatgagagggagtggggagaaatctttgtcaagagtaaaggttcttgtggatggaattagtatcaatcctacagagga<br>aacgatggcgagtttaccaattaattcgattcccattgaaagtgttaaaaagattgaaattattccaggaggaggagctactt<br>tatatggaagtggctctgtaggaggagttgtcagtatttctacgaattccaatgtaacgaagaataatttctttatggatttg<br>aactatggttcttttgataatagaaactttggatttgcaggaggatataatgtaagtgacaaattatatgtgaactatggttt<br>taattatttgaacagtgaagattatagagaacatgaggagaaggaaaataaaatttatttgttgggttttgactataaaatca<br>acccaaagaatcgtttcagagtacaaacaagatatagtaaaatgaagcatgatggaagtaactggctaagtcaggaggaatta<br>aagatttcgcgaaagaaagctggattgaatttggacctagatacaacagataaaagttacactttcgattatgagtatagatc<br>tagtcaaaatttaacgctagccgctactgcctataaacaacaacaagatagagacattacaaccgatgatattcgagatattg<br>aaattatagcttctaaccgaaactacactgatttaaaagaatatatgacttttatgatgtaaaatctactttaaaggcaaag<br>tttaaagaaaaaaaatatggactaaaattaaaaggaaaatacgagtatggaagaggggaagttattttcgggtatgattatca<br>agattctaacaataaaagaaactctcttgtacaatcagagactttaaaaacttataatgacaaaatcagtgacttaaatttat<br>ctcctgaagatagaaagccaatcatcaatagagtcaacattgatttaacaaagaaatctcacggtttttatgtgtttaataag<br>ttagaattaacagataaatgggattttacgacaggatttagaaccgaaattacaaaatataatggatatcgaaaaaatgggcc<br>aaataccatgccaatcgtctctccgaaagtaaatgaaatcagaacagacgagaagatgacaaactatgcgggagaagcaggaa<br>tgttgtacaagtatagtgacacaggaagagcctttgttcgatatgaaagaggatttgtaacaccgtttgcaaaccagttgaca<br>gataaaattcatgatacaaaattaaaaagtccagctggattttcaccccaccaattgtgaacgtttcttctttgtatgtagc<br>aaataacttgaaatcagaaatcacagatactatagaagtgggattccgagattatatttttaattccttaatcagtgcttcct<br>tctttgcaacggacactaccgatgaaattacacttatcagttccggaattacgaatccggcagtcaatagatggaaatttcga<br>aatataggaaaaacaagaagattaggaattgaattggaagcggaacaaaaatggggaaaatttgatttcagtcaatcgctaac<br>ttttgtagatacaaaagtattaaaaacagatgcagaatccagaatttttagaggagataaggttccaatggttcctagaatca<br>aagcaacattaggattaaaatataatgtgacagataacttggctttgattggaacttatacgtatttgagtaaacgggaaacc<br>agagaattggatgaaaaagataaggtatataaacatactatcaaaggatatggaacagcggatttgggaatattgtataaggt<br>ggacaagtattcaaactttaaagtgggggcaaagaatatttttggaaagaaatataatttacgagagacaaaattagaagcat<br>tgccagcaccggaaagaaattactatttagaatttaatgtcaaatttaactaa |
| *Fusobacterium necrophorum* 1694 FN rHemin TonB-dependent receptor amino acid sequence (SEQ ID NO:6)<br><br>MKKILFLVGALFSISAFAEQTIELGSTSIKGNRKTDYTLTPKEYKNTYTITQEKIQERNYKNVEDVLRDAPGIVVQNTAFGPR<br>IDMRGSGEKSLSRVKVLVDGISINPTEETMASLPINSIPIESVKKIEIIPGGGATLYGSGSVGGVVSISTNSNVTKNNFFMDL<br>NYGSFDNRNFGFAGGYNVSDKLYVNYGFNYLNSEDYREHEEKENKIYLLGFDYKINPKNRFRVQTRYSKMKHDGSNWLSQEEL<br>KISRKKAGLNLDLDTTDKSYTFDYEYRSSQNLTLAATAYKQQQDRDITTDDIRDIEIIASNRNYTDLKEYMTFYDVKSTLKAK<br>FKEKKYGLKLKGKYEYGRGEVIFGYDYQDSNNKRNSLVQSETLKTYNDKISDLNLSPEDRKPIINRVNIDLTKKSHGFYVFNK<br>LELTDKWDFTTGFRTEITKYNGYRKNGPNTMPIVSPKVNEIRTDEKMTNYAGEAGMLYKYSDTGRAFVRYERGFVTPFANQLT<br>DKIHDTKLKSPAGFFTPPIVNVSSLYVANNLKSEITDTIEVGFRDYIFNSLISASFFATDTTDEITLISSGITNPAVNRWKFR<br>NIGKTRRLGIELEAEQKWGKFDFSQSLTFVDTKVLKTDAESRIFRGDKVPMVPRIKATLGLKYNVTDNLALIGTYTYLSKRET<br>RELDEKDKVYKHTIKGYGTADLGILYKVDKYSNFKVGAKNIFGKKYNLRETKLEALPAPERNYYLEFNVKFN |

FIG. 17

*Fusobacterium necrophorum* 1694 Hemin receptor Gene Sequence (SEQ ID NO:7)

atgaaaacaaacatttatttttaacatttttattttgtaatactgtttcttttgcagaaacaaccattcatctaccagaaag
caatattcaatccgattatgtggaaatcaataagatgaaaaatctcaaaaatataattgtgattgaaaaaaaagaaattcagg
agaaagggtatacaaatttatccgccgtattgcaagatatcccaaatattcatgtcggaacaaccggttggggagaaattgat
attcgaggtcagggagaaggaaatgcagcaaaaaatttgcaggtgttaatcgatggagctccgattaccactttggtaaacca
tcctttgcaaacgaattacgacgtagttccggtagaaaatattgaaagaattgaaattattcccggaggaggttccatcattt
atggttccgggacagctggaggagttatcaatattactaccaatctaagtcgtttacacagaccaataaacattgtagaagtt
tccgccggaaccggtggagaaaaatataatcttgcctttggtcatagagttactaagaaactaaacgtacaattatcatatct
tcgaaataatcagaatctatatttcaaagatacctatcgacatagcaactatttcacggcaggattacattatcaaatctccg
acagacaaaatttgtctctgcgatatagtactctcacagaagacggaaaatttgttcgaaatattttatataaaaaattgaat
caggatggaaaaaattatcgaccggaaaagaaaaaagtaaccgccggtttggacaaagacggacataaaattgaaaaatggat
ggacggatattccaatgccaagagaaatatggacagcttcaatctaagttatcgtttccgacttggggaaaactcaacttatc
ttatggatgccttttacaataagggacattttccaatatggctttgagtgatcagaccatgtatcatcatacctacggagtt
aaaaataaattggactttttctatgcaaagaatagtgcttttgacggaagtagcttgttgattggattggattcttaccaaca
ggatgcaaaattggaatacaatgattacaaattttagattacaaaaagaaaacttattacatcagaccgctttcctttaaat
ataaaaagaaaaccaatgctttttatctattgaatactctaaaatatggaaattgggagtcttcacaaggaattcgaagagat
tatacctattggcattttgacaaggttacttccaaaaatgaaggaaaagaaaccagccatcgtcacaataccaattacgaatt
cagtcttgcctataaatatcgtgataccggaaggatctatgctcgttacgaaagaggctttacttcccctgatggtctagaaa
ttacagatgacttttccaaacaagacattaagcctacaaaaggaaaagatgaaatctatgacttatatgaaatcggttggaga
gaatacttcggatttactaccataaacttaactgcattctattcttttacagacaatgaaatgagccgaaattatgttttcaa
tgaactaggattcggaaggaaaaccatcaacattctaaaaaccaaaagaaaaggaatagaattaagtctattccaaaaattag
gaaatttggaattaaaagaaagttacgcttatttaaaaggaaaaagaacttacaacggaaaagaatctcaattcttagatccg
gatgactatgtagattggtccaatacgggacttcccaaagtcccaaaacagtctctaaccttggaagcaaaatatcattttag
cccaaaaatttcagtcggtttacgatataaatacaatggaaaatatagtaatttcagtgatttaagacaaaaagaagaagaag
gatacatcaaatctcattctgtaacggacttatctttacattatcaaaatgaaaaaggatttcatctgtatggaggaatcaat
aatgtattcaatgaaaaatattttgaatataccggttctaaaatgtataccatcatccctgcggaagaaagaacattctttgt
gggagcgaaatatcaattttaa

*Fusobacterium necrophorum* 1694 Hemin receptor amino acid sequence (SEQ ID NO:8)

MKTNILFLTFLFCNTVSFAETTIHLPESNIQSDYVEINKMKNLKNIIVIEKKEIQEKGYTNLSAVLQDIPNIHVGTTGWGEID
IRGQGEGNAAKNLQVLIDGAPITTLVNHPLQTNYDVVPVENIERIEIIPGGGSIIYGSGTAGGVINITTNLSRLHRPINIVEV
SAGTGGEKYNLAFGHRVTKKLNVQLSYLRNNQNLYFKDTYRHSNYFTAGLHYQISDRQNLSLRYSTLTEDGKFVRNILYKKLN
QDGKNYRPEKKKVTAGLDKDGHKIEKWMDGYSNAKRNMDSFNLSYRFRLGENSTYLMDAFYNKGHFSNMALSDQTMYHHTYGV
KNKLDFFYAKNSAFDGSSLLIGLDSYQQDAKLEYNDYKFLDYKKKTYYIRPLSFKYKKKTNAFYLLNTLKYGNWESSQGIRRD
YTYWHFDKVTSKNEGKETSHRHNTNYEFSLAYKYRDTGRIYARYERGFTSPDGLEITDDFSKQDIKPTKGKDEIYDLYEIGWR
EYFGFTTINLTAFYSFTDNEMSRNYVFNELGFGRKTINILKTKRKGIELSLFQKLGNLELKESYAYLKGKRTYNGKESQFLDP
DDYVDWSNTGLPKVPKQSLTLEAKYHFSPKISVGLRYKYNGKYSNFSDLRQKEEEGYIKSHSVTDLSLHYQNEKGFHLYGGIN
NVFNEKYFEYTGSKMYTIIPAEERTFFVGAKYQF

FIG. 18

| *Fusobacterium necrophorum* 1694 TonB-dependent receptor Gene Sequence (SEQ ID NO:9) |
|---|
| atgaaaaagtactttgttgcagtgtcgatttccttagcactttcgtatcagatttttgcagaggaaaatcctgttatcaaatt<br>aaatgaaactgttataacttctgaaagttttggaacaaatattttgagaactccaaagaatattacagtaattactgcaagaa<br>atattaaaattcaaggagcaaagaatatagaagatgctttaagaggggttgcaggcttaactgcttataataatatgggcggc<br>tctgatcccaaaatttctcttcgaggaatggctccgggaaaagaagaacaaagtattctgtttttattagatggaatcccta<br>taacagtacagtagatactggagcggtaaatctgaatttgattcctattgacatcgtagagagaattgaaattattcctaatg<br>gggaaacgtagtttatggagaaggagctgtcggaggagttatcaatattatcactaaaaaggaaaaaataaaaaatattac<br>ggttctttttcaatagatggaggatcttatgatttaaaggagtataaggtaaatttggggagcaacctgacggagcagctttc<br>tctagatttgaaatataataatagaaggcaaaaaaattaccgggatcaccacacaagagacattgaatatatcaatttggaa<br>tggaatataaagaaaatgagcacagtatttatttcgattttcagaattcagaaacagaatatcgttttcctggttatctgaca<br>aagaaacaaatagaagagggtaagattaaaaaatcaacaggaaatataaagggaaaagaaaaattaagaatttaccgtgcaaa<br>atacgagggaaaatgggctaaaaatttattttttaatattgcaggagattttaaagataaattatataagtccattgatgaaa<br>aaacaaataccgtcagtaccataagagatacggaatctttttacatcagtccacaaatcaaatatcaatatatgccgaattct<br>tactttatactaggaggagatttcctgaaagggaaatcaaaatatagatataaaaaagacattaaaacagaaacaagcagaaa<br>atctgtcggagtgtttcttaccaataatataaaatgggaaaattttatatttacacagggatatcgacatcaaaaaatcaagt<br>atgatgtaaaggataagttgtatccttccccaaaccataaacaaaaaattctattggataaaactttccaacaggattcctat<br>gaactgacagcaaattatcttttgtcggatacaggtagtatatacgcttcttacacaaaagctttcagagcccctactgcaga<br>tgaagcaggtagatggcgaaaaggatacgatgtaaaaatacaagaagcggatacttttgaagttggaggaaagcttgcttgga<br>agaactggtatatatctggttctatctttcataccagaaccgaaaatgagattctatatattgcctatgaagatggaaagctg<br>ggtaaaaattataacttgcccggaaagaatataagacagggaattgagctttctctggaacaatacttagaaaaattaacgtt<br>acgggaaagtttccattatttaaaacataaaatcaaaaaaggaactttcgccggaaataagattccaggagtccctcagtaca<br>tttatagtttaggtatggattatagaatattagatcatgttatctggagtaattcttttcattattatggaagtgcctatgga<br>aattatgattatcataataaatttggaaaacagaaagggcatacggaattaaacaccagtcttcgctatgaaatgaaaaacgg<br>cttgagtttttatggagggattcacaatcttctggataaggaatattttactccaaaattaaatgcggccggaacagggatga<br>attattattatggcagcagaagaaattactatattggattccagtataccttctaa |
| *Fusobacterium necrophorum* 1694 TonB-dependent receptor amino acid sequence (SEQ ID NO:10)<br><br>MKKYFVAVSISLALSYQIFAEENPVIKLNETVITSESFGTNILRTPKNITVITARNIKIQGAKNIEDALRGVAGLTAYNNMGG<br>SDPKISLRGMAPGKEEQSILFLLDGIPYNSTVDTGAVNLNLIPIDIVERIEIIPNGGNVVYGEGAVGGVINIITKKGKNKKYY<br>GSFSIDGGSYDLKEYKVNLGSNLTEQLSLDLKYNNRRQKNYRDHHTRDIEYINLGMEYKENEHSIYFDFQNSETEYRFPGYLT<br>KKQIEEGKIKKSTGNIKGKEKLRIYRAKYEGKWAKNLFFNIAGDFKDKLYKSIDEKTNTVSTIRDTESFYISPQIKYQYMPNS<br>YFILGGDFLKGKSKYRYKKDIKTETSRKSVGVFLTNNIKWENFIFTQGYRHQKIKYDVKDKLYPSPNHKQKILLDKTFQQDSY<br>ELTANYLLSDTGSIYASYTKAFRAPTADEAGRWRKGYDVKIQEADTFEVGGKLAWKNWYISGSIFHTRTENEILYIAYEDGKL<br>GKNYNLPGKNIRQGIELSLEQYLEKLTLRESFHYLKHKIKKGTFAGNKIPGVPQYIYSLGMDYRILDHVIWSNSFHYYGSAYG<br>NYDYHNKFGKQKGHTELNTSLRYEMKNGLSFYGGIHNLLDKEYFTPKLNAAGTGMNYYYGSRRNYYIGFQ |

FIG. 19

| *Fusobacterium necrophorum* 1694 Hemin receptor Gene Sequence (SEQ ID NO:11) |
| --- |
| atgaaaaaaattttttatggtaacagcaattttagcaacagcttccggtcttggttttgcaaaggagatttctcctattgaact<br>ggagcaaacagtcgtaacttctgaatctttcggaacatcaactcataggacagccaaaaatatacaggtaattacagcaaagg<br>aaatggaagaaaaaggggcattaacagtagatgaagcattaaagggagtacccggagttatggtaagaaaaatggatggagga<br>actcctgttattgatttacgggggtcaggagcggcatccagtttcagttccagcatactcttgttggatggagttccgttaaa<br>cggtttggtgaaattggacatcaattccattcctctaagtgaaatcagtcgtatcgaaattattcaaggaggaggagctgtta<br>tgtatggggatggctccacaggaggggttgttaatattattacgaagagtccgaaatacaaaaaacattatggaagtgcaggc<br>ttggaatacggttcttggaaaacaagtcgggcaagcttacattacggaacggctttaacagataaattatccgtcagtgcttc<br>ctattccggatatgcttctatggaataccgagatcgaggacatggaaaaacttggagcggagaaagtttcgattacagaaata<br>aaaaagataagaaatattccctttggttacaaggaaaatatcaattggaagacggaagtatcggcttcaagtataatcataac<br>gaaagaaaggattattacaccggatatttggaaaagaaacagtatgaagaaaatcctaaacaaataggaagttattcaggtaa<br>aatacaggatgtgacggatatttataatctttcttatcaaacaaagttgacagataccttggaattttagtttacggaggat<br>attatcgaggaaagagcatcgaccaaaatcagcttaccagtgaatattttataaacctcaattcaaatatacttacggagaa<br>aacagctatgttattttaggtggggattaccgagatggaaagcgggaattcaaagaaaaagttctggtaaacggaaggatgca<br>aaaagctcccaacgatgaaagagaatccaaagcaatctatgttatgaataaaacttctttgggaaactgggaattttctcaag<br>gatatcgttatgaaaaggtggattataaatacagttccaaaatttatggaccaggctggtcattatccgaaattaaaccgatg<br>aattcaaaatattctcataatgacagctttgaattgggagtgaattatctatattccgatacgggaaatgtatatttcaatta<br>taccaaagcgatgagaactccgacaattggagaggcaggagcttggtacggagatgtaaagacacagaaaaatgatatttttg<br>aaataggattaagggattatttcaaaaatacacaaatctcttcttctattttctatattacttccaaaaatgaagtctactat<br>gataaaacgaatccgaataattcaaataacagaaactttgacggaagggtaagaagaacgggggcacaattgtctttgaccca<br>ttatttggataaattaagtgtaagagaaagaatttcttacatccatccaaaagtatccagtggaatttatagcggaaaaactt<br>ttgcaggagttccaaaatggactttaaatctaggggcaacttatcatgttacggataagtttttagtaaatacagatttatat<br>tatcaatccaaagcttatgcagaagatgattttgacaactattttaagaaggataattcttatgcaactttggatatcaatac<br>ttcttatgcgtttgaaaatggaatggaagtatacggaggagtcaaaaatgtatttgataaaaaatatgccaatacgataactt<br>ctagcagaagcacatggtctccgggacctagaactgtgttctatcctgcagatggaaagagtgtttatgtaggattcaaatat<br>catttttaa |
| *Fusobacterium necrophorum* 1694 Hemin receptor amino acid sequence (SEQ ID NO:12)<br><br>MKKIFMVTAILATASGLGFAKEISPIELEQTVVTSESFGTSTHRTAKNIQVITAKEMEEKGALTVDEALKGVPGVMVRKMDGG<br>TPVIDLRGSGAASSFSSSILLLDGVPLNGLVKLDINSIPLSEISRIEIIQGGGAVMYGDGSTGGVVNIITKSPKYKKHYGSAG<br>LEYGSWKTSRASLHYGTALTDKLSVSASYSGYASMEYRDRGHGKTWSGESFDYRNKKDKKYSLWLQGKYQLEDGSIGFKYNHN<br>ERKDYYTGYLEKKQYEENPKQIGSYSGKIQDVTDIYNLSYQTKLTDTLEFLVYGGYYRGKSIDQNQLTSEYFIKPQFKYTYGE<br>NSYVILGGDYRDGKREFKEKVLVNGRMQKAPNDERESKAIYVMNKTSLGNWEFSQGYRYEKVDYKYSSKIYGPGWSLSEIKPM<br>NSKYSHNDSFELGVNYLYSDTGNVYFNYTKAMRTPTIGEAGAWYGDVKTQKNDIFEIGLRDYFKNTQISSSIFYITSKNEVYY<br>DKTNPNNSNNRNFDGRVRRTGAQLSLTHYLDKLSVRERISYIHPKVSSGIYSGKTFAGVPKWTLNLGATYHVTDKFLVNTDLY<br>YQSKAYAEDDFDNYFKKDNSYATLDINTSYAFENGMEVYGGVKNVFDKKYANTITSSRSTWSPGPRTVFYPADGKSVYVGFKY<br>HF |

FIG. 20

| |
|---|
| *Fusobacterium necrophorum* 1694 Hemin uptake system outer membrane receptor gene sequence (SEQ ID NO:13) |
| atggaagaaaacaatggaacgattgtcatcacggaagaaatgatacaaaagaagcattatgacagcgttgccaaaatttttga<br>agattctccggtttccgtcgtaagacatacggcattcggaccgattgtcgatttgcgaggaagcggagagagaaccatcagtc<br>gagtgaaagtgatgattgatggcacaccgatcaaccctttagaagaaactcacggaaccatccctttgataccattccggtg<br>gaatccattgccaagatagaaattgttccgggaacaggaacgacaaaatatggaggaggaaccacaggagggtatatcaacat<br>tcatacgaaaaaacagaaacagaataattacattacgatcaatgcggacaatgcctcttataatgccaagagtattggaattg<br>ctgcgggaatgaatgtaaccaagaaattatttgtttatgcgggagaagcctatcaaagaaaagacggctatcgaaagaaagac<br>cattcggacagaaacaatttttttaggaggctttgattatcaaatcaatgcaaaacataggatcaaaggacaaggaaatctcta<br>ccgagaggatttaaaatccacaacggaagtaactcatgaagaattgaaagaagatagaagaaaagcgggagaagatacaaaga<br>tagaaatggatcgagattttgcttctttggactatgaatacacacctacttcccattttaaattaagaaccaatgtcaatcga<br>gctcattttacaagagatgtatctatgaatgcgaagcaggatcaacttgttcttgcttttatgccaagagatgaacaaggata<br>tttttttgcattttgatgcaggattattggcagatcctaagttatctgatgtaaggccggttcttctggattttgaatctacta<br>tggaaggaaaattcaaggaaaaaaatcaggagggaaagctggacggagaatggaaatacaatcaaggaaaagggcatttacaa<br>tttggatatagttataatgagaagaaattgaatcaagatttaaaatcaatttccaaaccttttactttaaaaaatcaattggg<br>atatttgattcaaggtgacccggctccgaaaggatatgaagattacaccggaaaaattattgccccggaagaaatgtttaaaa<br>taaaatttaaagatttcctcaaatactggaaactttttaggacttaggagagaaggcgtcgaaaaggaaaaaattgatttt<br>caaaattataataaaattgatgcttttaaggatactcatgccttgtatttgttaaatgattacaaattaactccaaaatttaa<br>ttttagagcaggtttaagatgggaacattcagaatatggttctgatagaaaaaatagaatgattttgggagttcataatgcac<br>aatcatcaggaatggcaaatagaatggcaattgcgggtcttcttaatgagtatcaaatggaggcttatgtacaaggaaaatta<br>tcctacttggatgttgatttatctttgaaagaaactcatgtcaaagataggagtgataatttcggaggagagcttggatttac<br>ttatcaatatcatcgaaaaggaagtgtatttttccgatatgaaagaggattttatctccattgccttcccaacttaccaata<br>aggatttcttaacaggaatttattatccaagtcatgtcaaatcggaaaaagtagacactattgaaatgggaatcaaacattct<br>ctatggaacaatactcatatcgaagccactactttcttttctttgacaaaagatgaaattacaaatatgcgatacaatgcgaa<br>caaccatatgaatatgcgttgggcatatgccaatatttctaaaacaagaagattgggattggaattgaatgcggaacatattt<br>tcgacaaattaaagattcgagagtccttcagttatgtggatgctaagatagcaaaagataccggattcaaagattactatcat<br>tccgattacaaagtgaaatcggaaaaagaatttaaagacgccccctatattataaaaaggacaacaagtacctcttgtttc<br>taaggtcaaagtgacggtaggagcagaatatcaatttacagataaattgagtttaggaggaaactataactatgtcagtggct<br>atgatacccgagaaccgggcgaaggcttccaagcaaagacctataaagtaaaaggccatggaactttggacctgtttggaaga<br>tattctttcacagactatgcctatgtacgatttggagtgaataatgtgctaggagaaaaatacaatttacgagaagactctca<br>ctatgcagtaccggctccaaaacaaaattattatgcaggatttagttataagttctaa |
| *Fusobacterium necrophorum* 1694 Hemin uptake system outer membrane receptor amino acid sequence (SEQ ID NO:14)<br><br>MEENNGTIVITEEMIQKKHYDSVAKIFEDSPVSVVRHTAFGPIVDLRGSGERTISRVKVMIDGTPINPLEETHGTIPFDTIPV<br>ESIAKIEIVPGTGTTKYGGGTTGGYINIHTKKQKQNNYITINADNASYNAKSIGIAAGMNVTKKLFVYAGEAYQRKDGYRKKD<br>HSDRNNFLGGFDYQINAKHRIKGQGNLYREDLKSTTEVTHEELKEDRRKAGEDTKIEMDRDFASLDYEYTPTSHFKLRTNVNR<br>AHFTRDVSMNAKQDQLVLAFMPRDEQGYFLHFDAGLLADPKLSDVRPVLLDFESTMEGKFKEKNQEGKLDGEWKYNQGKGHLQ<br>FGYSYNEKKLNQDLKSISKPFTLKNQLGYLIQGDPAPKGYEDYTGKIIAPEEMFKIKFKDFPQILETFLGLRREGVEKEKIDF<br>QNYNKIDAFKDTHALYLLNDYKLTPKFNFRAGLRWEHSEYGSDRKNRMILGVHNAQSSGMANRMAIAGLLNEYQMEAYVQGKL<br>SYLDVDLSLKETHVKDRSDNFGGELGFTYQYHRKGSVFFRYERGFLSPLPSQLTNKDFLTGIYYPSHVKSEKVDTIEMGIKHS<br>LWNNTHIEATTFFSLTKDEITNMRYNANNHMNMRWAYANISKTRRLGLELNAEHIFDKLKIRESFSYVDAKIAKDTGFKDYYH<br>SDYKVKSEKEFKDAPLYYKKGQQVPLVSKVKVTVGAEYQFTDKLSLGGNYNYVSGYDTREPGEGFQAKTYKVKGHGTLDLFGR<br>YSFTDYAYVRFGVNNVLGEKYNLREDSHYAVPAPKQNYYAGFSYKF |

FIG. 21

| *Fusobacterium necrophorum* 1694 TonB-dependent receptor Gene Sequence (SEQ ID NO:15) |
|---|
| atgaaaaaagaaaatacgggtatgtggcaaaggattttgaaaatcggtatgttaagtataatactcttatactggacagactc<br>tctatatgcaatagagactagcgagaatatgcagtcgacaacgatgtcggtttccggagaaacggtaaacttcaaaatggaag<br>gaattaccgtggaggcaaaaagaccggattgggaatcgaaattatcaccgggaacagtgacggtcattcgtccggatgattat<br>aaaggagagcaaaaagatttacctgatttttgaaaatggttcccggagttcatgtgcgggaaatcaatggaaaagggcagta<br>caccacagtcagtgttcgtggttccactgcggctcaggtcggagtgtttgtagacggagttctttttaatctcggaggagatg<br>cggcagctgatatttcaacaattcccgtgcataatgtggaaagaattgaagtgtatcgtggatatattcctgcacgtttcggt<br>ggaacttttatgggaggagttatcaatatcgttaccaaaaaaccgaatcgaggaaatgtgagcgcaagcgtcggacgaagttc<br>ttttggcggtaaaaaagcaaatttgcagtttgatcttcccttgggaagcggaactttaatggtcggaatcaatcatgatgaaa<br>gcaaaggaaatttcaatataaaaacttctcctatgatagagataaagagtatcaaaaggaagtggaaaatgcaaaaagttcg<br>gaacgaggagcaatagataattataataaggcatttaaagaattaaaaaaatacgattttacagatgatagcggaaatatatt<br>taaggttgatactctggaagaagcaactcagattgtcaaaaataatcaggatcgttgggaaaagtctttgcaggaagctaaaa<br>atgacattgataataatttttaaaaaagaaacatattatagcaagattcccgggaattcccaaagaagagattcttcctctt<br>cttagaagtactcatattgatgcagagcaagctctttatgaatctgcttttaaagaatactctgtaaatcaaggcaataattt<br>tattccaaaatggaaagattccagtggtaactgggttgtccctgatagagtggaagattatgttgaagcttataataagagtc<br>atgaaataggatatcaacattttcaacagattatagcaaagggtgtgcagggagatatagaaagatggatagcaaaatatgga<br>aaaagctatgctgttaattatgcacaacaggcggagtatagtgtcaaagaaatggaaaaacataaaaaacaggcggaagcggt<br>gaaagaccactatagacgaagaaaagccaatgattataaaaatatggatattattttaaaatggcaggatgaacattggatgg<br>cgaaggcaacttggaaaagaatcaaaagacatctgccgtttcctattgatgagaactatggtaatgcaccatatatagatacc<br>gaccttatggcaaataatccgctctctatcttttatcatcgaaatcagaaattgaccgttcaggaatttcttttcggaagacg<br>ggatactttcaggaatcttgaatggggctggagtgttaattatctaaaacaagagaaagattactatgttgatgattgggaat<br>ggttggaaaaaaatacgggaagtctcttaaacagctatcgtccaaacactctgtggagtaaatatgacagtcatcgctggggt<br>gcaaaattggatggaagctacaaagcgggagaacgtcatatcatagaatttatggtaaacgcttccaaagaaaaaatggatat<br>tgacggctggcgtatgaaggatttcagttctcacagttcagatacacttgccagatggagaaattattatgagcaggatattt<br>tcaatgcacagcttcaggataccatcactttaaatcggaaaggagatctgtggttaaccccgagcattcgttataatcgttct<br>acaatactcggacgcagtgaacgctacgataaaaagaaagatccgcaaaagtggaaatttttcagccgggaagacaaacaaac<br>cgatgataaagtgacttggcaagtcgcaatcaaaaaacaattcaatgagcatttcaccttgcgtgctaccggaggaagctatt<br>atcgtctgttgaatatgtatgaaattgccggagacggagcaggaattatccctatgcccaatatcaaaggggatggaagtatc<br>gaagaaggagggaaaactcatgtttttcctatgccggaagaaggaaaacaatgggatgtcagtgctatctgggacggagctgc<br>attgggagcaaaggcggccaagcttcaactgacatatttcggacgagattccaaaagaattttggaactgggttcctggaatc<br>gtttttctttgtttataccaatgccatcagtgccaaggttcacggagcggaaatacaggcggatttatcttggaaaaaatgg<br>gatctcaacctacaggcaacttataccagacccagaaatgtagtgtatgacaatagtgctctgccggaagctatattctggaa<br>tggaggagtctttaagggctttctgacatatcagccgaaatgggaagggacggcaagaattacctatcgtccgaatccacgtt<br>ggagtatcttttctcaatttcgttatgtcggagaaatgattacgagcagaattcctttggcaacgggagattttatgcatcag<br>tcttcactgacagcttgggatttgggaatcaagtgtaaactaacggaacattttcaaatcgctcttggagtgaatgatctatt<br>caataaagcaaacgatatgtatcataaatataaaagcatcaattatcagaccaacattcaatatcctattcagggaagaagct<br>actatgcaagctttcaatacaaattttaa |
| *Fusobacterium necrophorum* 1694 TonB-dependent receptor amino acid sequence (SEQ ID NO:16)<br><br>MKKENTGMWQRILKIGMLSIILLYWTDSLYAIETSENMQSTTMSVSGETVNFKMEGITVEAKRPDWESKLSPGTVTVIRPDDY<br>KGEQKDLPDFLKMVPGVHVREINGKGQYTTVSVRGSTAAQVGVFVDGVLFNLGGDAAADISTIPVHNVERIEVYRGYIPARFG<br>GTFMGGVINIVTKKPNRGNVSASVGRSSFGGKKANLQFDLPLGSGTLMVGINHDESKGNFKYKNFSYDRDKEYQKEVENAKSS<br>ERGAIDNYNKAFKELKKYDFTDDSGNIFKVDTLEEATQIVKNNQDRWEKSLQEAKNDIDNNFLKKKHIIARFPGIPKEEILPL<br>LRSTHIDAEQALYESAFKEYSVNQGNNFIPKWKDSSGNWVVPDRVEDYVEAYNKSHEIGYQHFQQIIAKGVQGDIERWIAKYG<br>KSYAVNYAQQAEYSVKEMEKHKKQAEAVKDHYRRRKANDYKNMDIILKWQDEHWMAKATWKRIKRHLPFPIDENYGNAPYIDT<br>DLMANNPLSIFYHRNQKLTVQEFLFGRRDTFRNLEWGWSVNYLKQEKDYYVDDWEWLEKNTGSLLNSYRPNTLWSKYDSHRWG<br>AKLDGSYKAGERHIIEFMVNASKEKMDIDGWRMKDFSSHSSDTLARWRNYYEQDIFNAQLQDTITLNRKGDLWLTPSIRYNRS<br>TILGRSERYDKKKDPQKWKFFSREDKQTDDKVTWQVAIKKQFNEHFTLRATGGSYYRLLNMYEIAGDGAGIIPMPNIKGDGSI<br>EEGGKTHVFPMPEEGKQWDVSAIWDGAALGAKAAKLQLTYFGRDSKRILELGSWNRFFFVYTNAISAKVHGAEIQADLSWKKW<br>DLNLQATYTRPRNVVYDNSALPEAIFWNGGVFKGFLTYQPKWEGTARITYRPNPRWSIFSQFRYVGEMITSRIPLATGDFMHQ<br>SSLTAWDLGIKCKLTEHFQIALGVNDLFNKANDMYHKYKSINYQTNIQYPIQGRSYYASFQYKF |

FIG. 22

| *Fusobacterium necrophorum* 1694 Hemin receptor Gene Sequence (SEQ ID NO:17) |
|---|
| atgagaaaaaatttttttattggcaagtttttttggtatttggagtaaatatagcttttgcggaagaaaacccggtgttgacatt<br>ggaacaaacgattgtgagtacggaatcctttggaacatctgctcgaaagacaccaagaaatgtaagagtgatgacagagaaag<br>aaattaaagagaaaggagccttgaccatagaggaagctctcaaaggacttccgggagtgatagtcagaagaatagatggctct<br>gctcctattattgacttaagaggaacaggtatggcttccagtatcagttccagtcttcttcttttaaacggagttcctttaaa<br>tggacttattgtatttgatattaattccattcctatcaacgaagtggaaagaattgaaattattcaaggaggaggagctctga<br>tgtatggggatggtgccgttggtggaatgataaatatcatcacaaaatctcctaagaataagaaatattttggaagtgtcaat<br>ctggaacttggttcttggaagactaaacgagccaatatcaattatggaatgaaagtgggagaaaaattatcggtgaatgcttc<br>ctattctggatattcctctatggattatcgggacaggtatcatggaatggattggacaggacagtaccttgattaccgaaatc<br>gagcggataagaaatattctgtttggtttagcggaaagtatgacttacaagatggaaatatagaattacgctacaatcatact<br>gaaaatagagacatctttgccggttctttggataaaaaacaatttcaagacaatccaaaacaaaccggcggttttggaaggga<br>agtgaaaaatatatctgatgtttggaatctatcttatcagaaagcattgaaagaaaatttagaattttcacttattggaggac<br>atcaccaagacaagagtatcctttttgaatcaaatttcttccgagtattttatcaaaccacaattaaaatatcgctatggaaaa<br>aatagttatcttatttttggaggagattataaaaatggaaaacgtgtctttaagacaccccttattacaaatcataaaaaagc<br>cccagatgataagagaaaagctatggcattctattttatgaataaattttccaatggaaaatgggaattttcacaaggataca<br>gaagagaaagagtagaatatgattatacttccaaagcctatagaaatctttactatttatcagaagcaaatccagtttcttcg<br>cgttcttctaataacaatagttttgaattgggagtaaattatttatattctgatacaggaaatatgtatttcaattacacaag<br>ggctgttagaactccaacaatagaagatgctaaaatttggtatggagaggtaaagagtaaaaaaagtgatattttttgagatag<br>gaatgagagactatttcaaaaataccttaatctcctcctctatttttttatatgaatgcaaaaaatgaagtttattatgatacg<br>agagatatgttgcgtatcaaaagtagaaattttgatggaacagtaagacggattggggcacagttagcattaagccattatct<br>tgggaaattcgttttgaaagaaaatatttcttatgttaatcccaaaattgtgagtggaccctataaaggaaaaagctttgtta<br>cggtgccaaattggattttgaatctgggggcagcttatcgtttttcagaacaatttttaataaatgcagacttatattatcaa<br>tccaaaatgtatgcagaagatgatttcgagaatattcttggaaaagataattcctatgtaactttgaatatgaacgcatccta<br>taagtttgataatggaattgagatttatggaggaattaaaaatctgttgaatgaaagatatgcggatacgatagcgataaatc<br>cttatccaagccctaaaatagcatattatccgggagatgggagaaatttttatatgggatttcgatatcagttttag |
| *Fusobacterium necrophorum* 1694 Hemin receptor amino acid sequence (SEQ ID NO:18)<br><br>MRKNFLLASFLVFGVNIAFAEENPVLTLEQTIVSTESFGTSARKTPRNVRVMTEKEIKEKGALTIEEALKGLPGVIVRRIDGS<br>APIIDLRGTGMASSISSSLLLLNGVPLNGLIVFDINSIPINEVERIEIIQGGGALMYGDGAVGGMINIITKSPKNKKYFGSVN<br>LELGSWKTKRANINYGMKVGEKLSVNASYSGYSSMDYRDRYHGMDWTGQYLDYRNRADKKYSVWFSGKYDLQDGNIELRYNHT<br>ENRDIFAGSLDKKQFQDNPKQTGGFGREVKNISDVWNLSYQKALKENLEFSLIGGHHQDKSILLNQISSEYFIKPQLKYRYGK<br>NSYLIFGGDYKNGKRVFKTPLITNHKKAPDDKRKAMAFYFMNKFSNGKWEFSQGYRRERVEYDYTSKAYRNLYYLSEANPVSS<br>RSSNNNSFELGVNYLYSDTGNMYFNYTRAVRTPTIEDAKIWYGEVKSKKSDIFEIGMRDYFKNTLISSSIFYMNAKNEVYYDT<br>RDMLRIKSRNFDGTVRRIGAQLALSHYLGKFVLKENISYVNPKIVSGPYKGKSFVTVPNWILNLGAAYRFSEQFLINADLYYQ<br>SKMYAEDDFENILGKDNSYVTLNMNASYKFDNGIEIYGGIKNLLNERYADTIAINPYPSPKIAYYPGDGRNFYMGFRYQF |

FIG. 23

| *Fusobacterium necrophorum* Hemin uptake system outer membrane receptor Gene Sequence (SEQ ID NO:19) |
|---|
| atgagagtgaaagtattggtagacggaaactcgatgacttcgattgatgaaagtatgggagtgattcctttcaattccattcc<br>cgcaggaagcattaagagaattgaaatcattccgggggaggaatcactttatacggaagcggaagttccagtggagtcatca<br>atattgtgaccaaaatgggagaacttaaaaattatggaagcgtaagcgtttccacaggttcctttgacacctacaaggcggaa<br>atcacaaaagggatccgtatcaatcgatatttgtttagtaatctttctttagaggcgaaaaaaggaaaaggataccgggaccg<br>ggagcaagataaaagaatcaatgcacttctcggacttaacatcaattttcatcccaaacatcgaatgaaaattcaaggaagcc<br>attttcaagaggacgcggaagggaccaatgaattgtatttgacagaattacaaaaaaatcgtaggggagcgggagattctttt<br>tctaccatagattcaaaacgaactgccctttctattgattatgaatacagtccgacagaaaattggactctaactgccaatgt<br>caatcaatcgaaatttacacgggacattcgccaagattctcacccttatttgactttttttgccttccattgatttgagttttt<br>atggagtgcctcaaggatatacagcggaaatggtttctgtgaatactcccatggaattaaaaggaaacatggaagagaagatt<br>aagggagcaagaatcaaatcggaatatcgttatgcggaacaaaaaggaaaatttacatttggagcggaacatagtgagcatag<br>cctacaccgagatatgaatatggaagtgaaaccttttcatccttttaacagtatggctttttttgattcataaagaagacgata<br>aaatttttacggaagaaagattgaaaaatagtcatgaacttatggatattaattcagtttttttaccttttattattgagaaa<br>aataatacacctactttaaaggaagagaaaataaataaatggaaagaaaatttttttatatcaaaaagctagtgaagaagaaaa<br>aaaagcttatgatgcgggggggaggaatagcagctttggctaattcttggtatgaaaaccaaggaattatgaattatgaatttt<br>cacatttcaagataaaagattattttgatttggtggaaaaagatgggaaaaaaggaatttattatattttttagagagaaaaaa<br>aaggtagaaataactttgccaaatgggaaaaaaagaaaaaagacagttactgtggaaagacctgaatttatggaagtgaatga<br>tgaaagtcgattaaaagatattcttaattttatacaaaaggataaagtagatccctctttaacagtaaatactttgatacaat<br>caaaaatagatgtaaaaaagaaaacagattctttctatttacataacagctatccgctaaccgagaaattaactgtcaatgca<br>ggacttcgttatgaaaaggcaaagtatcatggaaatcgggaaacacagacaatacaacgaattacaggaaatgcggataagaa<br>agaaacacaggatgctgtaaatttatatatttccgtttcggatgtggaatatttgaaaaaagatccaagaatcaattggaatg<br>ctaatatcaatgcagaaacacaggcaaagttaaaagaattgaaagaaacaggaagcacacagattgtcatgtcacaattattc<br>cgaaaagaaaagagagaagaggaaaatttgggtggagaaattggctttgattataaaatcaatgatagtgatttggcatatgt<br>gaaatatgaaagagctttcaattctcctttaccaaatcaactaaccaataaaacctatgacccgattcataaagtgaagacat<br>attgggaaagtgatttgaaaacggagaaaatggataattttgaaattggaattcgtggggcttggaatgagcatattacctac<br>ggattggcaggattttttgagtacaacctatgatgaaattgtttctgtggtaaaagatggaaattcccatatgtcaagagaatg<br>gagatttatcaatttggacaaaacgagaagaatgggaatagaattgcaatcggaacaagtctttgataaatggagattacgcc<br>aatctttgacttatgtggatccgaaagtgttgtccaatgattataaaaaacaagtggcaagaatcgcacaggagcagtccgat<br>gcgatgatagacagtcatgagaaaattatgagaaacaatgtatatccaattcgtttagacattgctgcatggaagggaaagat<br>atccgaagctgagtttcaaaaattgaaacctcaaattatggcattaacagatcatggtttagagggaaagatttcacaagtgg<br>aaatgaacgcacagttggaaaaattattggaaagtctttctaatatggcgaagaaggaaatcaaggaaacggtcaaggcaaga<br>tttacagaccgagatatttacaaagagcgagtggaaaagcaatttagagaacagtatcaaactgagggaggaagctttattaa<br>aaaaggagatagaattcctttggcaccgaaaatcaaagcgacttttggagcggattaccaatttacaaatcatttaaaaatgg<br>gaacaaatgtcacttatgtaggaaattatatgacagcggaaccaagtaagggctatgaaattgtacaagtgaaagttccttct<br>cacttgctaacggattttttatggaagttatgagtttgacagcggcttttctataaaattcggaattaacaatgtcttcaatca<br>taagtactatttaagacaagattccagaacggcaacacctgcaccgggaagaacttacagtgcaggatttagttatcgttttt<br>aa |
| *Fusobacterium necrophorum* Hemin uptake system outer membrane receptor amino acid sequence (SEQ ID NO:20)<br>MRVKVLVDGNSMTSIDESMGVIPFNSIPAGSIKRIEIIPGGGITLYGSGSSSGVINIVTKMGELKNYGSVSVSTGSFDTYKAE<br>ITKGIRINRYLFSNLSLEAKKGKGYRDREQDKRINALLGLNINFHPKHRMKIQGSHFQEDAEGTNELYLTELQKNRRGAGDSF<br>STIDSKRTALSIDYEYSPTENWTLTANVNQSKFTRDIRQDSHPYLTFLPSIDLSFYGVPQGYTAEMVSVNTPMELKGNMEEKI<br>KGARIKSEYRYAEQKGKFTFGAEHSEHSLHRDMNMEVKPFHPFNSMAFLIHKEDDKIFTEERLKNSHELMDINSVFLPFIIEK<br>NNTPTLKEEKINKWKENFLYQKASEEEKKAYDAGGGIAALANSWYENQGIMNYEFSHFKIKDYFDLVEKDGKKGIYYIFREKK<br>KVEITLPNGKKRKKTVTVERPEFMEVNDESRLKDILNFIQKDKVDPSLTVNTLIQSKIDVKKKTDSFYLHNSYPLTEKLTVNA<br>GLRYEKAKYHGNRETQTIQRITGNADKKETQDAVNLYISVSDVEYLKKDPRINWNANINAETQAKLKELKETGSTQIVMSQLF<br>RKEKREEENLGGEIGFDYKINDSDLAYVKYERAFNSPLPNQLTNKTYDPIHKVKTYWESDLKTEKMDNFEIGIRGAWNEHITY<br>GLAGFLSTTYDEIVSVVKDGNSHMSREWRFINLDKTRRMGIELQSEQVFDKWRLRQSLTYVDPKVLSNDYKKQVARIAQEQSD<br>AMIDSHEKIMRNNVYPIRLDIAAWKGKISEAEFQKLKPQIMALTDHGLEGKISQVEMNAQLEKLLESLSNMAKKEIKETVKAR<br>FTDRDIYKERVEKQFREQYQTEGGSFIKKGDRIPLAPKIKATFGADYQFTNHLKMGTNVTYVGNYMTAEPSKGYEIVQVKVPS<br>HLLTDFYGSYEFDSGFSIKFGINNVFNHKYYLRQDSRTATPAPGRTYSAGFSYRF |

FIG. 24A

| *Fusobacterium necrophorum* Hemin uptake system outer membrane receptor Gene Sequence (SEQ ID NO:21) |
|---|
| atgagaaaagaaatgcttttgacattgttgtgttttgtttctttgcatgctatggcagcaacacaggaagtggagttgaaccc<br>gacaaaaattcgaggagggggggcgacctataatggctcggttctctccaatgaaaagaaaaatgtaatcatcattacgaaag<br>cagatattgaaaagaaaaattatagagatttggaatctattttaaggattctccggttacttctgtcgtttatacggaggcg<br>ggtcctttggtcaccttaagaggaagtggacaaaagacggcaatgagagttaaagtactcttagatggcgtttccatcaatac<br>cgtggatgattctatgggagtgattcctttcaacgccattccggttgccagtattgaaaaaattgaaattattccgggaggag<br>ggattactcttcacggttccggaacttccagcggagtcatcaacatcgtgacgggaaaatcgagtaagaaagattatggagag<br>cttggttttactgtaagttctttcaatacttacaatacaaccttcaataagggaatttcctttggagataagctgtattggaa<br>tattggagtggaagcggaaaaaggaaaggcatatcgagagaaagaggatagtaaaaagataaatctgctgtccggaatcaact<br>ataaaatcaatgaaaaacatcaaattaaattacatggaagtaaatattggtcggattttaacggaacaaatgaattggatctt<br>atcagtttgcaaaaaaatcgaagaggggcaggaaaatcagatgccgaagtaaagtcaaatcgatattccctttctttcgatta<br>tgaatataaacctacagaagatttgaccgttacttccggatacaatcaacaaaaatttcgaaggaattttacacagaacaaca<br>aaccttatcttactttcttatcgtcggaatgggtggaagatatgtttggaattcccgacggaatgaatgcagatttagtcatt<br>aaaaatgtaaataaccatttaacgggacgtattgaagaaaaaataaaaaatggaaaagtcaaagtggactggaaacacagtaa<br>caatcgtggaaaattaacttttggatatgattattcttctcatgaattaaaacgaagaatgaatgtacaagttgatgcttta<br>atccgatcgataataattactttttttgagaaaaaaagaggagagaattatcaatgaagaaattttagaacaacatccggat<br>cagttaatgcatttttcgataacactttagcggcaattctaatatttgatcctgattctatggatagttatggctagattc<br>tgttaaactaaagaaaaaaatagacgaactctattatcatttgactacttcggaaaaagataagaaaaaatatgaaaatggag<br>aagaaaatccttgggattattgggaaaccatcaaaccgaatatgtggaaaatgatttatcatttgacagaagaaaagattcaa<br>gagtatgcaaaagacggaaaaaatattcttaagagagaagatgaaaatgattgggattctgaaccaagcgttcaggttccgat<br>tgaggggaaaaaatttaaagaatttttaagattgattattcctagtatgtatgaccccgattttagtatgacaccaatcacgc<br>aaagtatggtagatgtgaagaagacaacgaattccttttatctatttgacagctataaacttactgatcgtttagaaatcaat<br>ggaggtttgcgatatgaaaaagcaaaatactccggaaatcgttatacaaaaacggaacaatttatcaaaggaaatgcggagaa<br>taaatctaccaactctatgatagcgatgtatacggaattgtcagaagcggaatcggcaaagaaaaacataggagatactcatc<br>actggaatggaaatgatacttccaaagaaaaaataaaagaactgaaagaaaaaggatatactaccattttaatgacggattta<br>actcgaaaagagaaaagagaagaggaaaatctgggaggagaaattgggattaattaccgtttcaatgatacagacacagtata<br>tttaaaatatgaaagaggctttaatactcctcttcctacacaattgaccaataaaacctttgatccgaaaaccaagataaaag<br>catattgggaaagcaatataaagacagaaaaaatagacaatgtagaactgggaattcgaggaatgttacacccaaaagtgacc<br>tattctttgacaggatttatcagtgatactcaaaatgaaattctatccattgtgaagaatggaagttctcatatgctccgaga<br>atggagatttatcaatattgataaaacgagaagaatgggactggagttccaatctcaacaaaattttgataaattgactttaa<br>aagaatctcttacttatgtggatccaaagattctatccaatgattatgaaaaacaggttcataaaattggagtggacagagcg<br>gaggaaatgtaccaaaacaatcaaaaagtacgagattggacaattgaaaatatcagatttcatgaaaatggctttacaattcc<br>ggcaggaacttcggaagaagaaattgtaaaaatgaaggcggagtccaagcgattgggaaaagaagcggttaaaatcattcaaa<br>aactaagagagacaggagtaaaagtggactatagtgcacgagatgccaaactgaaagaaattgttccgggaatgtcttctgcc<br>gaacaatctaagattagaatggaagcttcaaaattagcacaagaagctgaaaatagagctgtggcagaacctagaaaagcctt<br>ggaagatcttcttgcaaactcagcttatcctgacattttaaagaaaaattgcgttcattcaataaccataccttaattcagg<br>aaggaacgatgaaagaaattatttatgaacattttgaaaaagagataaagtcttcttatacgaaaggaaccttagaaaaggga<br>agcagaatcccgctttctccaaaatggaaaggaactttcagtgcggactatcaattcacggataggttaaaattaggaatgaa<br>tactacttatataggaagctatgattccgcggaaccgggaaaaggatatgaaattgtaatgacaaaagtaccgcatcatatgg<br>tagccgatttctatggaagttatgatattcaggaagatttttccattaaattcggaattaacaatgtatttaatcatcaatat<br>tatttacgacaagattccagaacggcaactccggcacccggaagaacctacagtgcgggattcagttatcgattttaa |

FIG. 24B

*Fusobacterium necrophorum* Hemin uptake system outer membrane receptor amino acid sequence (SEQ ID NO:22)

MRKEMLLTLLCFVSLHAMAATQEVELNPTKIRGGGATYNGSVLSNEKKNVIIITKADIEKKNYRDLESIFKDSPVTSVVYTEA
GPLVTLRGSGQKTAMRVKVLLDGVSINTVDDSMGVIPFNAIPVASIEKIEIIPGGGITLHGSGTSSGVINIVTGKSSKKDYGE
LGFTVSSFNTYNTTFNKGISFGDKLYWNIGVEAEKGKAYREKEDSKKINLLSGINYKINEKHQIKLHGSKYWSDFNGTNELDL
ISLQKNRRGAGKSDAEVKSNRYSLSFDYEYKPTEDLTVTSGYNQQKFRRNFTQNNKPYLTFLSSEWVEDMFGIPDGMNADLVI
KNVNNHLTGRIEEKIKNGKVKVDWKHSNNRGKLTFGYDYSSHELKRRMNVQVDAFNPIDNNYFFLRKKEERIINEEILEQHPD
QLMHFFDNTLAAILIFDPDSMDSYGLDSVKLKKKIDELYYHLTTSEKDKKKYENGEENPWDYWETIKPNMWKMIYHLTEEKIQ
EYAKDGKNILKREDENDWDSEPSVQVPIEGKKFKEFLRLIIPSMYDPDFSMTPITQSMVDVKKTTNSFYLFDSYKLTDRLEIN
GGLRYEKAKYSGNRYTKTEQFIKGNAENKSTNSMIAMYTELSEAESAKKNIGDTHHWNGNDTSKEKIKELKEKGYTTILMTDL
TRKEKREEENLGGEIGINYRFNDTDTVYLKYERGFNTPLPTQLTNKTFDPKTKIKAYWESNIKTEKIDNVELGIRGMLHPKVT
YSLTGFISDTQNEILSIVKNGSSHMLREWRFINIDKTRRMGLEFQSQQNFDKLTLKESLTYVDPKILSNDYEKQVHKIGVDRA
EEMYQNNQKVRDWTIENIRFHENGFTIPAGTSEEEIVKMKAESKRLGKEAVKIIQKLRETGVKVDYSARDAKLKEIVPGMSSA
EQSKIRMEASKLAQEAENRAVAEPRKALEDLLANSAYPDIFKEKLRSFNNHTLIQEGTMKEIIYEHFEKEIKSSYTKGTLEKG
SRIPLSPKWKGTFSADYQFTDRLKLGMNTTYIGSYDSAEPGKGYEIVMTKVPHHMVADFYGSYDIQEDFSIKFGINNVFNHQY
YLRQDSRTATPAPGRTYSAGFSYRF

FIG. 25

| |
|---|
| *Fusobacterium necrophorum* Hemin Receptor Gene Sequence (SEQ ID NO:23) |
| atgaaaaaaaagttaatgattttggcaattttaagtatttcagtttcagcatttgctatgaaggaggaaattcctgtgcaaag<br>attaaatgaaacagtaataacaactcctgaaagattcggtacaaaggttagaaatatatcaaaaaatatacaaataattacaa<br>aaaaagatatgaaggaaaaggggcaaaaaaccttttgaggcattgagaggactcccaggagtagttatacgtagagatgga<br>ggaggacatatagatcttcgtggttctggagaaaatgataaaaaaaatatgatatttttaatagatggaatacccctatagtgg<br>attaagtatatttgacattaattctatctcaatggaagaaattgaaagaattgaaattatccaaagtggtggtgttttatatg<br>gagatggagctataggaggagttataaatttagttactaagcctattactactggaaaatacagcaatagcattggtttggaa<br>tacggctcttgggaaacggctaaattaaatgtaaatgtcggaactaaattaacagataattttgttgtaagtgtttcttactc<br>tggtgaacaaactgaagaatataaaaatagaagcatagatttcaaagataaaaaagatagccgggaatctatttggttaaaaa<br>ctaaatataatttaaatgatggggaaattgagttaaaatataatcatttgaaaaacaatgactacatcacaggacttctatca<br>gcaaaagactttaaagaaaatcctaaaaaagcaggtacaacaaatgcttcttttaaagctgaatcagatttatggaacctatc<br>ttttaataaaaaattaaatagtaagtttgaagttttcttacaaggtggatattatactgatgaaacaaaatactatgaaatag<br>gtccaggatatgcagattttcaaaaaatggaaataaaagtcattttataagacctcaaataaaatataattatatggaagat<br>agttgcatcatattaggaggagatagaaaaaaagaaactgttactaataaattatctccaaattctcctaaaactataaggaa<br>aaaagaatctatttacttattaaatagtaataagataggaaactttgaaattacagaaggatatagaatagaaaaaattgatt<br>taaaaagaaagaatagagctaaagactttaaagaagatggaatggaattaggaataaactatctttattcagatactggaaat<br>ctttattttaattacacaaaaggatttagagtacctacattgggtgaaatgaatagttgggttggtgatatgaaatcacataa<br>aaatcatacttttgaattaggtttaagagatgtatatgaaaatacttctataaatacttctattttcacattgtattccaaag<br>atgaaatcttttatgatagtttagttgcaaacccttcaccaaaaaatcctaatagaaaaggagcaaatagaaactttgaaggt<br>aaggttagaagaataggtgcacagttagctttagaacacaatattggtaaattatcattaagagaaaaaatttcttacatgga<br>tcctaaaataattgatggatattataaagagaaagttttcccgggagttcctaaattaacagcagcactaggtttaacttata<br>attttgaaaattcccttaaattaaatattgatgggtattatcaagaaaaaatttatgccggaactgatttttttaaataaatat<br>ggtaaacacaatagttatacagtagtagatgctaatatttcatatacttttgaaaatggtttggaactttatggtggagttaa<br>aaacttatttgataaaacatatgctactgcctttttcccaagagcaacaggagaattaagatatgatccagataatggaagaa<br>gtttttacactgggtttaagtatactttttaa |
| *Fusobacterium necrophorum* Hemin Receptor amino acid sequence (SEQ ID NO:24)<br><br>MKKKLMILAILSISVSAFAMKEEIPVQRLNETVITTPERFGTKVRNISKNIQIITKKDMKEKGAKNLFEALRGLPGVVIRRDG<br>GGHIDLRGSGENDKKNMIFLIDGIPYSGLSIFDINSISMEEIERIEIIQSGGVLYGDGAIGGVINLVTKPITTGKYSNSIGLE<br>YGSWETAKLNVNVGTKLTDNFVVSVSYSGEQTEEYKNRSIDFKDKKDSRESIWLKTKYNLNDGEIELKYNHLKNNDYITGLLS<br>AKDFKENPKKAGTTNASFKAESDLWNLSFNKKLNSKFEVFLQGGYYTDETKYYEIGPGYADFSKNGNKSHFIRPQIKYNYMED<br>SCIILGGDRKKETVTNKLSPNSPKTIRKKESIYLLNSNKIGNFEITEGYRIEKIDLKRKNRAKDFKEDGMELGINYLYSDTGN<br>LYFNYTKGFRVPTLGEMNSWVGDMKSHKNHTFELGLRDVYENTSINTSIFTLYSKDEIFYDSLVANPSPKNPNRKGANRNFEG<br>KVRRIGAQLALEHNIGKLSLREKISYMDPKIIDGYYKEKVFPGVPKLTAALGLTYNFENSLKLNIDGYYQEKIYAGTDFLNKY<br>GKHNSYTVVDANISYTFENGLELYGGVKNLFDKTYATAFFPRATGELRYDPDNGRSFYTGFKYTF |

FIG. 26

| *Fusobacterium necrophorum* Heamin uptake system outer membrane receptor Gene Sequence (SEQ ID NO:25) |
|---|
| atgaaaaaaaatttttacttactgtctattttcatgttggcaactgttcaaacagtttttggaaaagaggatcccactgtgac<br>attggagcaaacaattgtcagtatggattcttttggaagttctccccacaggactgcaaaaaatgttcgtgtggttaccaaag<br>aagaaataaaagaaaaaggagctttgaatgtagaagatgctttgaagggaattccggggcttctcatacggaacttggatgga<br>gctcctccggtcattgatttaaggggagccggaatggcttccagtttgacttccactctgttgcttctcaatggagttccctt<br>aagtggagttcgagtttttgatgtcaattccattcctgtttctgaaattgagagaattgaaatcattcagggaggaggagctt<br>tgatgtatggagacggtgctgcgggaggagttgtcaacattatcacacagacgatgaagaataaaaaatattatggaaatgtc<br>gatttggaatatggttcttggaaaacgggaagaattcatttgggaataggaggtcaaatggagaaaaacttttctctccaagc<br>ttcctattcaggatattcttctatggattggagagatagagcacatgggattgacatgagcggaaagactttcgactacagac<br>ataaaaaagataggaaagacagtttttggttgagtgggaaaaaggaagggaaagaccaaagtattgaattacgttacagtcat<br>atgaaaagcaaagactattttaccacttttctgaacaaaaaacagtatgaagaaaatccgaaacaagcgggaatgacaggtaa<br>ctacatagaggatgtcacggatatctggaatctatcctatcgtaaaaaatggaatgataagcttgatttttttactttatggag<br>gctatcatcacggaaaaaatgaaaatcaacattttctaatggaagaatattttgtgactccgcagataaagtatctctacgga<br>aacaatagctatgtcatcgtcggtggggacattagaaacggaaaaagggaatggaaggataccttcctatcgaatggaaaaaa<br>ggctccgaacgataccagaaaatcgaaggctctctatctcatgaataaaattaccgttaagaattgggaatttacacaaggct<br>atcgaagagaaagggtaaattatgattacacttccaaagtttacggtcctgtttggaatttgttggaagcaaatcctgtatcc<br>tccacttcttccaataacaacagttttgaactgggagtcaattatctttattccgacagcggaaacttgtatttcaattacac<br>aaattcgatgagaactccaagtatcggggatatggaggcatggaccggagatgtgaaaacgaaaaaagacagtatttatgaac<br>tgggatggcgagattatcttgcgaacactcttttctcgacttctattttctggatggatactcgaaatgaagtatattacgat<br>aaaacgggattgtatcaagtcaaaacaagaaattttgatgggaaaacaagaagaaggggagctcaaatctccttgattcatta<br>tttggataagctgtccctacgagaaaatatctcctatatccatcccaagatagaaagtggaatctatcaagggaaaacgttcc<br>cggaagttccgaaatggattgtgaatttgggagccagctatcatgttacagaacaatttcatatcaatacggatgtatattat<br>caatcgaaggcttatgctgacgacgattttaaaaatgaattttcaaaagaaaattcttacacaacatgggaccttcatctttc<br>ctaccgttttcaaaatggaatggaaatttatggggggagctaaaaacctattcgataaaaaatatgctcacagtgtagcgatta<br>tgcgaagtccttttgcttctcagaaggtatatcatccggcaaatggaagaaatgtctatgtaggatttaaatatcgtttttaa |
| *Fusobacterium necrophorum* Heamin uptake system outer membrane receptor amino acid sequence (SEQ ID NO:26)<br><br>MKKNFYLLSIFMLATVQTVFGKEDPTVTLEQTIVSMDSFGSSPHRTAKNVRVVTKEEIKEKGALNVEDALKGIPGLLIRNLDG<br>APPVIDLRGAGMASSLTSTLLLLNGVPLSGVRVFDVNSIPVSEIERIEIIQGGGALMYGDGAAGGVVNIITQTMKNKKYYGNV<br>DLEYGSWKTGRIHLGIGGQMEKNFSLQASYSGYSSMDWRDRAHGIDMSGKTFDYRHKKDRKDSFWLSGKKEGKDQSIELRYSH<br>MKSKDYFTTFLNKKQYEENPKQAGMTGNYIEDVTDIWNLSYRKKWNDKLDFLLYGGYHHGKNENQHFLMEEYFVTPQIKYLYG<br>NNSYVIVGGDIRNGKREWKDTFLSNGKKAPNDTRKSKALYLMNKITVKNWEFTQGYRRERVNYDYTSKVYGPVWNLLEANPVS<br>STSSNNNSFELGVNYLYSDSGNLYFNYTNSMRTPSIGDMEAWTGDVKTKKDSIYELGWRDYLANTLFSTSIFWMDTRNEVYYD<br>KTGLYQVKTRNFDGKTRRRGAQISLIHYLDKLSLRENISYIHPKIESGIYQGKTFPEVPKWIVNLGASYHVTEQFHINTDVYY<br>QSKAYADDDFKNEFSKENSYTTWDLHLSYRFQNGMEIYGGAKNLFDKKYAHSVAIMRSPFASQKVYHPANGRNVYVGFKYRF |

FIG. 27

*Fusobacterium necrophorum* Hemin uptake system outer membrane receptor Gene sequence (SEQ ID NO:27)

atgaaaaaattattcttactattttctttgattgcctgttccaattcggtttactccgaaatcatccatttgggggcaagtga
catttactctgatactggttatgcgaccaatataagaagtacgacttcatctccttttataataactgcaaaagaaattcagg
aaaaaaggtttgcaagtctctctgaaattttggcaagtcttccgggaatcactatacgagagggatacgaacctgaaattgat
ttgagaggacagggatactcgaaagcaagggcaaccattcaggtcatgatagacggtgtgcctgtcaatatgctggattcttc
tcatagaaaagttcccttaaatactgtaaatccgaatcaaatcgaacgaatcgaagtcattccgggtggaggagctgttttat
atgggaatggaacggcaggcggtgtcatcaatattcttactaaaaaacatcgaggaaattttggaaatataggctatcgttat
ggaagttttggagatcgtaaatacgatattgccgcaggaaccagtttaggaaactttgactttgctcttgattattccaatga
agataaaaacggctacagaagaaattctccttccgattcggattatttttctgccagaattgcttataacttcaataaaaatg
atacaattgctctaaaatacagaggatatagaacagagtataaacagtacaacggtttaagcaaaaagcaagtacaggaagac
agaagacagaacggaatggcccccggacaaaaaggttccactgatagaaagttggatgaatacagtttcaattttcataaaag
agtaggaaaaaacaacgatcttagtttccatgcctataaactagaaagcgatataaaaacaagatcacaaactccaaaattaa
cgagaattgtaaaagcggaagataatagatcaggagtaaaaatcaaagataaattgaattatggaaatggtaacaacattatt
atcggtgcaggttataccaatcataccatgtttttaagcaacataaaagtagagaaaaagactctggaaagcttcgccttgaa
cacattgaaattcggaaaacttgaattttcacaaggattgagatttgaaaaatccaaatatcaaggagatgccgccaaagctt
tcggattaaaaagtggagaaacttctaaaacactggagaactatggtgcttccctagctcttaattatttgtattctcatgca
ggaaatgtatatgtgaaatatgagagagcttttaatactcctgcccctttacaaaccataaaaaatattaactggcaaaccta
taacagtgatgcaaaatcagaaaaaagtaatacctatgaaatcggcttccgagactatattctaaattccatagtcagtgctt
ccgcttattatagtgaaaccgcaaatgaattaaaaacagtttggttaggtagccatttccatgatctttccaattttaatacc
atcaactatggaaagacaaagagatacggattcgatttgaaggcggaacagaaatttgaaaaattcagaatttcagaatccta
ttcctttgtaaatgctaaaatcataaaaagtggggaaactgccagtcaaaaagcaacggaaggaaaatatattcctgatgttc
cgaaacacaagtttgtactttcgactgattatgattttaatgaaaaattctctattggagcaagctatcaataccaagctgct
gcatatattgactctcgaaacagcttgggaaaagaagggaaaaaatcaattgtgaatttgagagcaaactataaattcaatga
tcatttccacatttatgccggaattaaaaatctatttaatgcaaaatactatgattctgtgggttatactactgccaaaccaa
ataggatatataaggtttacaaccctgcaccaagcagaaattactatatgggatttgattataaattctaa

*Fusobacterium necrophorum* Hemin uptake system outer membrane receptor amino acid sequence (SEQ ID NO:28)

MKKLFLLFSLIACSNSVYSEIIHLGASDIYSDTGYATNIRSTTSSPFIITAKEIQEKRFASLSEILASLPGITIREGYEPEID
LRGQGYSKARATIQVMIDGVPVNMLDSSHRKVPLNTVNPNQIERIEVIPGGGAVLYGNGTAGGVINILTKKHRGNFGNIGYRY
GSFGDRKYDIAAGTSLGNFDFALDYSNEDKNGYRRNSPSDSDYFSARIAYNFNKNDTIALKYRGYRTEYKQYNGLSKKQVQED
RRQNGMAPGQKGSTDRKLDEYSFNFHKRVGKNNDLSFHAYKLESDIKTRSQTPKLTRIVKAEDNRSGVKIKDKLNYGNGNNII
IGAGYTNHTMFLSNIKVEKKTLESFALNTLKFGKLEFSQGLRFEKSKYQGDAAKAFGLKSGETSKTLENYGASLALNYLYSHA
GNVYVKYERAFNTPAPLQTIKNINWQTYNSDAKSEKSNTYEIGFRDYILNSIVSASAYYSETANELKTVWLGSHFHDLSNFNT
INYGKTKRYGFDLKAEQKFEKFRISESYSFVNAKIIKSGETASQKATEGKYIPDVPKHKFVLSTDYDFNEKFSIGASYQYQAA
AYIDSRNSLGKEGKKSIVNLRANYKFNDHFHIYAGIKNLFNAKYYDSVGYTTAKPNRIYKVYNPAPSRNYYMGFDYKF

FIG. 28

*Fusobacterium necrophorum* Hemin uptake system outer membrane receptor Gene sequence (SEQ ID NO:29)

atgaaaaaagtggtatttgggatttacagtatcttaatgtcctctgctatgcttggagcagaaattgatcttggaacacagaa
tatctattcggaaaccggatttgaaacgagtcttcgaagctctgtttcttctccttatatcgttacttcaaaagaaatcaaag
aaaaacattatacccgtgtttctgaaattttgagagatattccgcatatctacatcggtcccggtggcagtgtagatatgcgt
ggtcagggaagtgctcatgccagaacaacagttcaactgttaattgatggagttcctgccaatttttggatacttcccacat
caatcttcctatcgatactttaaatccagaagatattaagagaattgaagtcatccctggaggaggagctgttttatatggaa
gtggaacttccggaggagtgatcaacatcattaccaaaaaatacacgggaaactatgcaaaggcaagctatcaaataggaagc
tatcacaatcataaatatgacgtagctgccggaacttctttgggaaattttgacattaacctaagttattcaaaaaataatag
ggatggatatcgtaaaaaagccttttccgattccgatttcttctccggaaaattacgttatcacttcaatcccacagacagtc
ttgaattcaaatatagctattttgataataagttcagaggtgttaaatccctaaccagagaacaagtcgagaaagatcgaagg
caaagtggtctttctcctgaagacaatttgaaaaataccatccgaaaagaagaatggaatttaacttacgatgcaaaatggac
aagctggctggaacacaaatccaatcttttctatcagtccacagaaataaaatctagtgaatatgaagatgctcttcctttct
atcaatatcaaatttcttcttatcaaaaaatgcttactatgccagggattcctcctatgatgcaagcacaattgaaaaagcag
ataaaagccctacaaaatttgataacgagtaatccaaggatggaattacatcaaggaagtcgtttcaaagatcaaaaattcgg
ttttaaaatgaagaataaatttaagtatggagaaaatagtgattttattttaggtttgggatacattcacaacaaaatggatc
gagattcttgggcttatacgaaaaatacgcaaacgaatcaaacaatagcaactcttacaaatactaaaattcctttaaataag
aaaacattcgaaattttcggattaaatacctatcgtcataataattgggaatttgttcaggcttacgctttgaaaaagcgaa
atataatggaaaaagacaatataaaaatctggaatatcctttaaaagatcgtagcatgaataatgttgcggcaaatctggctg
tcaattatctctattccgatacaggaaatgtctatgtaaaatatgaaagaggatttacttctcctgctcctgcacagttaatg
gataaaatcagaaaaggaggagtgaacgattatgtcaataatgatttaaaatctgaaaaatcaaactcctttgaagttggatg
gaatgactatctcttccattctttagtcagtgctgatgtttttttcagtgaaacgaaagatgaaatttctaccatattctcgg
gagggcatgggacaacattcagcaatttgaaccttggtcaaacgaaacgatatggttttgatctaaaagccagtcaagttttt
gaaaagtggacattctcggaagcttacagttatatccatgcaaaaatcatgaaagataaaacaaaggcttatgaaggaaaata
tatcagttatgttccaaggcataaattttctttgaatgctgattatgcaatcactccaaaatggactcttggggggagaatatc
aatacagttcttccgtatatctggacaatgcaaataaaaatggaaaagatggagcgagatctgtttttaatcttcaaacctct
tatgagttcaattcacattttctatctatgcaggaattaaaaatgtgttaaatcataagtattatgaatctgtcagtgcagg
ttccagtcaaaagtattatagtccggctccggaaagaaattactatgccggattccgttatcaattttaa

*Fusobacterium necrophorum* Hemin uptake system outer membrane receptor amino acid sequence (SEQ ID NO:30)

MKKVVFGIYSILMSSAMLGAEIDLGTQNIYSETGFETSLRSSVSSPYIVTSKEIKEKHYTRVSEILRDIPHIYIGPGGSVDMR
GQGSAHARTTVQLLIDGVPANFLDTSHINLPIDTLNPEDIKRIEVIPGGGAVLYGSGTSGGVINIITKKYTGNYAKASYQIGS
YHNHKYDVAAGTSLGNFDINLSYSKNNRDGYRKKAFSDSDFFSGKLRYHFNPTDSLEFKYSYFDNKFRGVKSLTREQVEKDRR
QSGLSPEDNLKNTIRKEEWNLTYDAKWTSWLEHKSNLFYQSTEIKSSEYEDALPFYQYQISSYQKMLTMPGIPPMMQAQLKKQ
IKALQNLITSNPRMELHQGSRFKDQKFGFKMKNKFKYGENSDFILGLGYIHNKMDRDSWAYTKNTQTNQTIATLTNTKIPLNK
KTFEIFGLNTYRHNNWEFVQGLRFEKAKYNGKRQYKNLEYPLKDRSMNNVAANLAVNYLYSDTGNVYVKYERGFTSPAPAQLM
DKIRKGGVNDYVNNDLKSEKSNSFEVGWNDYLFHSLVSADVFFSETKDEISTIFSGGHGTTFSNLNLGQTKRYGFDLKASQVF
EKWTFSEAYSYIHAKIMKDKTKAYEGKYISYVPRHKFSLNADYAITPKWTLGGEYQYSSSVYLDNANKNGKDGARSVFNLQTS
YEFNSHFSIYAGIKNVLNHKYYESVSAGSSQKYYSPAPERNYYAGFRYQF

FIG. 29

| *Fusobacterium necrophorum* TonB-dependent receptor Gene sequence (SEQ ID NO:31) |
|---|
| atgaatttaaaattaaaatgtatattacttagtagtctactaagcatgacagcatatggagcatccatagaccatattcaaac<br>gtatgcaccagaatatttaggaaatcaagctcaaaatggagcaattaacggagtttctccttattacaatcctgccggaacta<br>ctcagctagaagaaggattctatatcaatggtggattacaaatagcagctggacatgagcaatcagaatacaaagagaaagaa<br>tataaagctatttttatacaacctgttccaagtattgcattgacgaaagtaaacaaagatagttcgacttattttacttttag<br>tgctattgcgggaggaggaacattaaactataaacatggagtagtaggaactgcaattattcctgatttagtggcaaatttaa<br>aagtcggatatttaaattcagctgcttttggtatgccaacaattccatctacattagctggaaaaaaagtggcagttcaagtt<br>ttagatggaacaagagcaaaaggaagtaatctatacagtcaaatgacattaggaaaagcatttcaagtgaatgataaattatc<br>tctttctgcaggaattcgatttgtacatggaagaagagatttagagggaaacattaaattaaaagcatattccccagattctc<br>caaatttggatcctgttttagcaaaattgcctttagaagcagaaattgattctaaaagaagagcaaaaggatttggatttgta<br>ttgggagcgaactacaaggtaaatgataagtggaatgttggaatgagatacgattctagagtaaaattaaatttcaaagcttc<br>tacaagcgaaaaagaaattagcattcctacagtaggggggaataaagcatatcggatttacttctgatttatattatcctcaat<br>ataaagatggaaagaaagtaagaagggatttaccagctattttagcattaggaacaacttatcaggtatcagatacatggaaa<br>actggtctatctgtaaattattatttcaataaaaatgctaaaatggatggacaaaaatacaaaaatggctttgaagtggcttt<br>cggaaatgaatataaattaaatgaaaaatggactttgctagcttctattaactatgcaaaaacaggagcattaaaggaaagtt<br>atagtgatgtggaatatgctttggattctatcatgttaggaacaggagtgaaatatcaatatagccctactttagaattaaca<br>gcaactgtaggacactatttttatagatcggaagagggagatatcaaaggaagagttgctaaaaagacggattccatgataaa<br>acaattgcaaaatgtaaatgaacaacaaaaatacagaaaaagtattactgcttttgggcttggctttaccaaaaaattctag |
| *Fusobacterium necrophorum* TonB-dependent receptor Gene sequence (SEQ ID NO:32) |
| MNLKLKCILLSSLLSMTAYGASIDHIQTYAPEYLGNQAQNGAINGVSPYYNPAGTTQLEEGFYINGGLQIAAGHEQSEYKEKE<br>YKAIFIQPVPSIALTKVNKDSSTYFTFSAIAGGGTLNYKHGVVGTAIIPDLVANLKVGYLNSAAFGMPTIPSTLAGKKVAVQV<br>LDGTRAKGSNLYSQMTLGKAFQVNDKLSLSAGIRFVHGRRDLEGNIKLKAYSPDSPNLDPVLAKLPLEAEIDSKRRAKGFGFV<br>LGANYKVNDKWNVGMRYDSRVKLNFKASTSEKEISIPTVGGIKHIGFTSDLYYPQYKDGKKVRRDLPAILALGTTYQVSDTWK<br>TGLSVNYYFNKNAKMDGQKYKNGFEVAFGNEYKLNEKWTLLASINYAKTGALKESYSDVEYALDSIMLGTGVKYQYSPTLELT<br>ATVGHYFYRSEEGDIKGRVAKKTDSMIKQLQNVNEQQKYRKSITAFGLGFTKKF |

FIG. 30

| |
|---|
| *Fusobacterium necrophorum* Cell surface Protein Gene sequence (YadA-like protein) (SEQ ID NO:33) |
| atggggaattttaatttaaaatttttaccatatctttattaattttattggtacaaaattcttttgcagaagatccggtaat<br>aaaaagaggaaataaccaagatagtatagtagccggtctccataacaaagctgtaaacggatattccttagcttatggagatg<br>ctaatgaggccactggagatgcagccagtgtagcttttggcttaaaaaatgtggcaagtgggaaaagtgcaacagcctttggt<br>aatgccaataaggcgggtggagatacagcagcagcttttgggaacaataacacagcaggcggtcgttttagcttagcttttgg<br>taataaaaatgaggtcagtggaacaagcagtgcagcttttggtttccaaaataaggctaaatctaaagaaagtgttgctgtag<br>gtcatgagaatgaggtagaagcggactacggcattgctttgggtaatggaaatgaagtaaaatcacaaaaaggtgtagcagta<br>ggatatcaaaatgaagcaaaaggtttttcaaattctgttttcggtattgaaagtagagtcagtgggacaagcagtacagttgt<br>aggaaattcttatgaagtttcaggaactaaatcgggtgcctttggagtgggagaagccggactaaagtcttcaggaataagct<br>acaaatataaaaatgaaggtaatgaatcttacactataggaaatagaaacagtatagcaacaaggacgaataataactttata<br>ttgggaaatgatgttactataggtgacggaataaacggtgctgtagttttaggtaaaagttctaaggtaacggaaagcaatac<br>agtttctgtcggttctgaaaacgaaagaagaagaatagtatttgtggcggatggaactcaggatacagatgcggctactgtag<br>ggcaagtcaagaaactaatttcttcaagtacagtactgggagctggaatgggaaatgtttatacaaaggctgagagtgatgct<br>aaatttgctactaaagatgcaggtaatttgtcggcaagtgatgttgatgcttggagaagtaagttaggagttattgctaacac<br>agcagcagatccaaaaagtacaagtataggaaataataataaagtgaccggaacttattcaacagcggttggttacaaaaatg<br>aagttagcggaaataaatctggagcttttggagatccaaatatagttacagggaatcgttcctatgcctttggcaatgataat<br>actattgcaggggatgataattttgttttaggttctaatgtaaatataggagtgggaatatcaaattctgttgcgcttggaaa<br>taactcaaaagtaaaagcttctaatgaagtttctgtaggttcggtaggaaatgaaagaaagataacgaatatggcagatggag<br>aagtttcatctacatcgacagatgcaattacaggtagacaactatatcatgtaatgcaaaattcaggaacaacaggaatagaa<br>aatttaagaaatgaagtaaatgaaaagttctcagatgttaaaaatgaagtgaaccatgtaggttccttgagcgcggcactttc<br>tgcattaaatcctatgcagtatgatccgaaagctcctaatcaaatcatggcaggcttgggacattatagaaataaacaggctg<br>ttgcagtaggactaagccatcatttcaataatagtgcgatgatgacagcagggcttgccttagggaatgagtcaaagataaaa<br>gctatggcaaatcttggatttacaataagattgggaagaggcggagaaacttcggctgaaattcctcaaagtgtaattcaaaa<br>tgaaatggcaagattagctagagagaatcaagaactaaaaaaagagttatttatcataagagagcagttagaagaattaataa<br>acaaataa |
| *Fusobacterium necrophorum* Cell surface Protein amino acid sequence (YadA-like protein) (SEQ ID NO:34)<br><br>MGNFNLKFFTISLLILLVQNSFAEDPVIKRGNNQDSIVAGLHNKAVNGYSLAYGDANEATGDAASVAFGLKNVASGKSATAFG<br>NANKAGGDTAAAFGNNNTAGGRFSLAFGNKNEVSGTSSAAFGFQNKAKSKESVAVGHENEVEADYGIALGNGNEVKSQKGVAV<br>GYQNEAKGFSNSVFGIESRVSGTSSTVVGNSYEVSGTKSGAFGVGEAGLKSSGISYKYKNEGNESYTIGNRNSIATRTNNNFI<br>LGNDVTIGDGINGAVVLGKSSKVTESNTVSVGSENERRRIVFVADGTQDTDAATVGQVKKLISSSTVLGAGMGNVYTKAESDA<br>KFATKDAGNLSASDVDAWRSKLGVIANTAADPKSTSIGNNNKVTGTYSTAVGYKNEVSGNKSGAFGDPNIVTGNRSYAFGNDN<br>TIAGDDNFVLGSNVNIGVGISNSVALGNNSKVKASNEVSVGSVGNERKITNMADGEVSSTSTDAITGRQLYHVMQNSGTTGIE<br>NLRNEVNEKFSDVKNEVNHVGSLSAALSALNPMQYDPKAPNQIMAGLGHYRNKQAVAVGLSHHFNNSAMMTAGLALGNESKIK<br>AMANLGFTIRLGRGGETSAEIPQSVIQNEMARLARENQELKKELFIIREQLEELINK |

FIG. 31

O-antigen polymerase, 60.6 kDa. (SEQ ID NO:35)

LGIFSFLGIIQFLIRNSSDQKMLILGIFFLYLSSLLFVYSFQSILKEKDMGLFFFLGILFPYYFQKHPYVFKDLMRESHNIRN
INYVYIFIFSIFFLKYFFYNTKKNWKEYLEVENIRNYLLYLMPFFILRAKDIKMIGFFYGIVVFVFCYKKDWNILLEKRKKIC
LLFLVLLFLFFSYMSNYVWGIPNQFGEQLLGNYVYNYFLLLILLLIPISEEMMKKIKMSIAISLFYPILLIVLEWMQNHYTLE
IAMGTEEWTSIWAVRAGLVSLISLFFYLSEKRKVYLFGVIFSLLSLFLGQGRGPILSFIASFCILFFFFYEKKTDRKKVFTSL
GIVLLLLFVIYNTENYIIKKFQLVFLGADSSTNTRIELYHGAIEQWKSQKWIGYGLGSYKETVELLKQEYLEKYDLIRIPHAH
NNILELLRSLGILGTFIYIFLNGYLCFWLLGKYWKTREKLYILPFVLIVNFELSGITDFSLMMYKSQLLLFFICSLSLSYTVS
MSTDVEYKI

FIG. 32

Membrane Spanning Protein, 26.8 kDa. (SEQ ID NO:36)

VEMFVLFGTSHMIMILIGVISVLLLIILGFLIRPQLLAKWISVSVLVIKLAEMYYRHRVLGEEIYRMLPFHLCNLTIILSLFM
MFFHSKFLFQLVYFWFVGAIFAILTPDIIFAYPNFWTISFFITHFYLVFSALFALIHFHFRPTKRGMLMAFLFINLWAVLMYF
VNQELGTNYLFVNRIPETTTLLSYFGAWPYYLLPVEGIYIIESILLYLPFRKSNIKFHF

FIG. 33

Outer membrane protein, 18.9 kDa. (SEQ ID NO:37)

MRANSIRINALEINIIEALKEELPEEMTIVLDDRALNFDFDKSVVKPKYNEMLTNLKEFITKNNYEVTIEGHTDYIASNEYNM
GLSKRRAEAVKAKLIELGLEPSRIVAILPKGEEEPIADNKTTEGRAKNRRVEFKLVKRDSVGEVNSEESRIIDVKKGVVEAEN

FIG. 34

Outer membrane porin F, 20.2 kDa. (SEQ ID NO:38)

MKKYLGMTVLLASFVLAACGKTSNTSVRDLSTEGNQNFAIEDIDTAKKPLEDIIVFNQDGVTIRREGNNLILSMPELILFDFD
KYEVKDGIKPSLRTLANALGANSDIKIKIDGYTDFIGSEGYNLELSVNRAKAIKSYLVNHGAIENNISIEGYGKQNPVASNAT
ESGRARNRRVEFIISRS

FIG. 35

Outer membrane protein, 19.7 kDa. (SEQ ID NO:39)

VGRKSTKIGILFFLFLFSLPSFAVQKLTTTQMRENSIRINALELKEMDIHLKKVTVVLDERALNFDFDKWNIKEQYYEVLENL
KEYILANDYEVVIEGHTDSIGTNAYNIGLSFKRANSTKEKLIEFGLPADRIVGISGKGEESPIATNETPEGRSQNRRVEFHLE
KIGDKE

FIG. 36

Hemin uptake system outer membrane receptor, 90.2 kD. (SEQ ID NO:40)

MEENNGTIVITEEMIQKKHYDSVAKIFEDSPVSVVRHTAFGPIVDLRGSGERTISRVKVMIDGTPINPLEETHGTIPFDTIPV
ESIAKIEIVPGTGTTKYGGGTTGGYINIHTKKDKQKNYITINADHASYHANSIGIAAGMNASKKLFVYAGEAYQRKDGYRKKD
HSDRNNFLGGFDYQINAKHRIKGQGNLYREDLKSTTEVTHEELKQDRRKAGEDTKIEMDRDFASLDYEYTPTSHFTLRANVNR
AHFTRDVSMDAKQEQLTLVNAFRFTHNMSMVDDEVKTLKPVLKDFQSTMEGKFKEENQEGKVDGEWKYNQGKGHLQFGYAYNK
KSLDQNLKIQSKPFNLGKSLYYLFPGDPAPHPFEDYAGKVLDQETMWRVIFNDLGYSQEYIDTHAPSMAGDNSGEILDLQNYN
QVDSFRNTHSLYLLNDYKITPKLNFRSGLRWEYSKYGSKRKNYMAIGIHKAQHSDLAASAGLAGLLDSYEKEALLLGKLDYVD
IELSIKDTDMKDSSHNFGGEVGFSYQYHKKGNLYFRYERGFLSPLPSQLTNKDFLTGNYYPSGVKSEKVDTIEIGIKHSLWNN
THIEANTFFSLTKDEITNMRYNANNHMNMRWAYANISKTRRLGFELNAEHIFDKLKIRESFSYVDAKIAKDTGFKDYYHSDYK
EGTKNEFKDAPLYYKKGQTVPLVSKVKVTVGAEYQCTDKLSLGGNYNYVSGYDTREPGEGFQAKTYKVKGHGTLDLFGRYYFT
DYAYVRFGVNNVLGEKYNLREDSHYAVPAPKQNYYAGFSYKF

FIG. 37

Outer membrane protein H precursor, 17.5 kDa. (SEQ ID NO:41)

MKKMLLVLGLVSAFSMSAFADKIAVVDSQEVIGRYSGTKGVEATLQKEVKRIENDVNQRQVALQKEEVALQAKGDKLTDAEKK
AFQAKVEGFYKYVNTSRESLAKMEQTKMSAIFTKANKAVQAVAAEGKYDYVLDRGAVLVGGEDITDKVIKKMETIK

FIG. 38

Major outer membrane protein, 42.9 kDa. (SEQ ID NO:42)

MKKLALVLGSLLVIGSAASAKEVMPAPMPEPEVKIVEKPVEVIVYRDRVVQAPAKWKPNGSVGVELRTQGKVENKGKKATEEN
ARKGWAGKEPNVRLETKASVNFTENQNLEVRTRQTHVLTKTDSDKEESNHKDTQVRIRHTYNFGKLGSSKVGFKVASQYLHDD
HVDSLRTRAVFDFADYIYSNSLFKTTALEIGPSYKYVWGGNDDRYYNALGLYANAEFELPYGFGFQAEFEDAFTYTSTGKGDG
KRDKAKLGHADFVLSHSLDLYKEGKHSLAFLNELEYETFWAWDKKDASMEEWPHVDGHGRVNSEGKNKKWGAYELTYTPKLQY
NYQATEFVKLYAAIGGEYVNRENNKSTARYWRWNPTAWAGMKVTF

FIG. 39

Outer membrane protein, 27.8 kDa. (SEQ ID NO:43)

MKKNFIIAIFCSFAAFSYAEEKMSGVNLGITASHAKEIYKVSAKEKYSVLPLISVNYKDFYINQSELGYQFQVHDNFLISGYF
DFLDGYPVKGKEMQKEYKSIQTRRSQIVGGGRITYFKDNFQTSIFAQGGKRGSSTGADLSLSFPLTEKLFFTTGLNYTIYSKN
FTNYYFGVHKEDFGGKLTKVYSPKASYSYGAEASLEYQITEPFSIFTSVSATNYSKEITNSPLVKDKTNISTTIGLQYSF

FIG. 40

Outer membrane protein tolC, 54.6 kDa. (SEQ ID NO:44)

MKQKWSFFLCLLFLSSCSSVNKEISETSLLQELKRKETETQRILTEQRLSLEEAIQIAKERNLELKTKQLEREISKIDSKIAF
GNFLPRISAFYTRSFWEEALSGQVDLPASLSQFPLIGPMLPKEIQGRLLDKSYSVYGLQASMPIFAPATWFLYSARRKGEEIQ
SLVLTLTEKMISIQVIQQYYWILALEAEEIQLKASLKSAEQLLHNMKIALDTQSILEWQYQKAQAYYKQKKLALAQNQRDLKL
AKMGLLSTLNLSPLSSVRLQKTQNITKRKEDNYEEVIYQALVHNDALGIQEKVLEVEKEKLKISFSRFLPVIGLQGFYGEHSL
SLLSSSHYLLGILGGVFSIFNGFQDISAYQKAKIEQRKAMLKKESLILQSIAETTNVYQKLQSSIEEEEIAEINEKAERGKFH
QKSLERKVGMIDELSYLQAVQSYEEAKSLALKAEYQSAVLQEILDTLVGRGRFVEEGENND

FIG. 41

Major outer membrane protein, 53.8 kDa. (SEQ ID NO:45)

MKKNVFMLGGFILLTSSVLAKEALVVPEQKPEILVVEKPVEVIVYRDRVLETPAKWRPNGSIDIQYRVYGKTENKVASPRTVP
PIPIEPPRIPLVPLEPPHIPLVPLEPPHIPLVPLLPPPTLEEDDGETHWQAASLLEGEGEVYDDEDVDDLSETVEIPPMQAAE
ALEEKEDEKTSKWARKKRYNTGRLQVEAKLNFTEKQSLEIRERVYHALRTTKVDENERYGKAAADEDELRLRHFYRFGNLGNS
KVNASSRLEYNTLHNSEKMSGSAYLAFDISSYLFQNNFIKTDYFRVGPTYTYAMKNKTNYSNQIGLLLESYFSLPYNFGLELN
VHPKYMAYNKEFEIGEGKTKKHEFYAEVEAKLFHSLNLYKNNKWRLDLNTEGGYDPYQFHQYKVVKNREKKVEKRAYSLYALP
TFQVSYQATEYVNVYATAGAEYRNWVDTAESTASHWRWQPTAWAGMKVTF

FIG. 42

Outer membrane protein TolC, 49.7 kDa. (SEQ ID NO:46)

MKKIAAIFFLTGTVLFAGEITLEEAIARALKHSREVQIAEKKFLSSKIKAKQAIKKALPSLVYSGSYQQSEYERMQAKNRTEK
QGEKIGYRQSVTLTQPLFQGGSIVAEIQGAKYYESLFEIEYLQKKIETRLKTIQIYSHIIRAKKELEALRYSKKQLEQRYEKQ
KVQLELQLITRTDLLKTEYHLLSVESQMEKAKNEIEVQMENLKIQMGLFKDEKIEIQEFFVPKQCSAKIDFDKDRKQAMETSM
SVLSAKYRLEIAKAEQRGRAGEMLPEINLFASYENVGERRTFNQSRKDMEWIGGVEVRWKLFSFGREYDSYKVATLEKETQEL
SQEKIQDSLRLKLREAYLDLCRLEILRDSKTKALETAELNFQMEQEKYDAGLISVVDYLDSEKQLREAKVSYYQTELEYYYAF
EYYQSLLV

FIG. 43

Outer membrane protein, 19.7 kDa. (SEQ ID NO:47)

VGRKSTKIGILFFLFLFSLPSFAVQKLTTTQMRENSIRINALELKEMDIHLKKVTVVLDERALNFDFDKWNIKEQYYEVLENL
KEYILANDYEVVIEGHTDSIGTNAYNIGLSFKRANSTKEKLIEFGLPADRIVGISGKGEESPIATNETPEGRSQNRRVEFHLE
KIGDKE

FIG. 44

Major outer membrane protein, 44.5 kDa. (SEQ ID NO:48)

MKKLALVLGSLLVIGSAASAKEVMPAPMPEPEVKIVEKPVEVIVYRDRVVQAPAKWKPNGSVDVQYRWYGETENKVDGQLKQE
GLAEGEHDWANDENNYGRLQTEAKINFTENQRLEIRTRNFHTWAQGKNTKDYSKAKAEDDKIRLRHFYNFGKIANTKVNATSR
LEWDQKSGDGAKKLEASVGFNFADYLFNNDFVKTTNFTVRPLYAHKWTAHRGGGRKGAEVLGLNLESNFEFPYGFELEFKLEP
TYTFYGTKQTISDKDGENQREKKRAFDMDVTLILSNSVNLYTQDKFALDFNFEGGYDPYSFHQYRIYDKEEKEVGVKRSYSLY
ALPTLEANYQATEFVKLYAGAGAEYRNWKIEDEDYATRWRWQPTAYAGMKVNF

FIG. 45

Putative hemolysin, 37.9 kDa. (SEQ ID NO:49)

VKTKNFVLESKQDTSERKDSSYGGSFSIDLGNPSNLSVTMNGRKGNGEKEWVEKQTSFIARNGGKIDTDSLTNIGAVIGSESE
TEKLKVSANQVIVKDLEDKNQYENMGGGISIGTSIPNISIKHDKIEKEQINRATAANTEFGISGKKTSAEDLGFNTDINKTQE
VTKNEEKHLDAELHADLIGEDKRNEIKYAFKKLGSLHEILDQKKFKESMEGVLVDKFKDEHQKEFHLIKDENLSLEDKQKLAQ
NLVEKYLRENGYQGIIPEVLLTEEAHSFTVDSKDKTTGAKRGEKIYFSIHDIANPDLAFSQLFGHEKAHMNTYDEGKYGEETS
FHCKLQ

FIG. 46

Exoprotein involved in heme utilization or adhesion of ShlA/HecA/FhaA family, 62.0 kDa. (SEQ ID NO:50)

VKGSVNNSKTIEATNIDITGENLVNSSSIKADNILATVKTTKNDGDILALKDITLNTKKLDNTKKIAALQNITANNTALTNSG
EIVSNHKIELNHSNISNTNKILSNTIDMKNTSNFNNTGTISGTDVTLTSVNDIHLIANLHGENSLIIEGKNIVNENSISANDL
HMNAKNLTNHDLIAAENNANINVKNKVTNTENSSIYAGNKLNIQASELFNDSAEILGTDVKLEANQITNHIGTLQALNTMHIK
AGKFENIGKVEDLDRYESYYETWDGQRIEANQIEDWKVHFSKSSSKRSNGSAGKTIRKRQREAYHEISEKMKNDKYASLLFPK
YDKLMRGYLGDRGEYTEKTGSARIQTVPLQEKLRSLGKTTHAKVLAGNNILIEKKSDSNNEVMNKDGILSAGNTIKIDANQVQ
NLVSVGDEKIKVKTGEESMYIKLERTGKKPRKKVKMEVSYDRDFANDYITKKIPKLDEKGRQVYQKKFGGRKKPVYEYVTEYV
GRYAYVTGQPSVIEGKNVVIDNASLVRQGIEEANGYIKSGKDVNIQNFTSKNFHTGLSNGN

FIG. 47

Outer membrane protein, 19.7 kDa. (SEQ ID NO:51)

VGRKSTKIGILFFLFLFSLPSFAVQKLTTTQMRENSIRINALELKEMDIHLKKVTVVLDERALNFDFDKWNIKEQYYEVLENL
KEYILANDYEVVIEGHTDSIGTNAYNIGLSFKRANSTKEKLIEFGLPADRIVGISGKGEESPIATNETPEGRSQNRRVEFHLE
KIGDKE

FIG. 48

Exoprotein involved in heme utilization or adhesion of ShlA/HecA/FhaA family, 27.8 kDa. (SEQ ID NO:52)

LEKKKKGLSLSISKNSFKVAYGKNQFNYDEKDKTNIKSNLVLGDGTVLNKGAEITATNFNHGDITINNGDVIYGARKDERDVK
TSTKKSSFGISANVSSPALERIKQGANALEQIGNGDALGGLVNVGNVVTGTVDGLASNIKTKDGKQATAKDVKDNKFTSNNSF
YVQAGGSAGYSKSKQKTKSHTEKAVVTNITGLDENAKITYNDNKNVKYQGTQTQNTTFVYNNXXXXDSYIDGKLTTDSKAIYN
KYILESIGIFFF

FIG. 49A

| *Fusobacterium necrophorum* filamentous hemagglutinin gene sequence (SEQ ID NO:78) |
|---|
| atgaaaaaattaaaaaattttgaaaatgttttaaaatcgcatttaaaacaaagagtaagaattacgacagcattca<br>ttgttgctttttttaattcatgggatgctaagctttgatgttgaagcaagagatttaagagttaggaatcaaataac<br>tccgtcaaattcaaataatggcttaagaataacttcaagccaaaatgggaccgatgttattaatattgttgatcct<br>aataatggaatatctcacaataagtatgtagattttaatgttggggacaaaaataatgttatttttaacaacagtc<br>aaaaaaatggaacttctgttacaggaggagaagtcagtgcaaacccaaatttaacaaactctgcttctgttatctt<br>gaatgaaattcaaggaaattctgcttcagaattaaacggaggacttgaagtttttgggaaaagagcagatcttgtt<br>attgccaatgaaaatggaataaatgtaaatggagcaagatttataaacacttcagctctaacattatcaacaggaa<br>aagtctcagtcgataataaaaaaatttcttttaacacagctacaaataatgcaaagatagcagtaaaagaaaaagg<br>aatagaaacagattctgattacttgaatatcctttcaagaagggctgaactagatggagcaatcaactctgaacat<br>aataaaaatttaaatatcaatgttatagctggtgcaaatactgttacagctgtaaatgatactttcgaattaaatg<br>ctgaaaacgccaaagatggaattaccaatgtagaagctatttccgcttcaaaatttggagctatgtatggaaataa<br>catttttatcttgagtactaataaaggcgaaggaatcaaatatgaaggaagcctaaaagcaaaggatgaagtggag<br>ataatctctgaaggaaaagttgtaagttctgacataaatggaaaagatatcaaaatatcgtctaaagaagaaatta<br>acaatattggaaaaatgaaagcggataaaaatgtcagtcttaatgctcctatcgtaaaaaatatgtccagattaga<br>aggaagtgttagattaaaatcaaatgaacataataaaaagtatcaaaatagagaaagaggaattatctattatgac<br>tattatttaaatgtgaaaaatatgtcagaagtggaaaatgaattaaaattagttaaatcgtctattgaagccggaa<br>ataatattgaaataaataataatcttgaaaatggaagttttgaaaatttatctggggatttaaaagcaggaaatga<br>tatcaaagtaaaaggaaattttaaaacaaaacatttgtcagaaggaataaagctagaagatcttttaaaaagaata<br>aaagtagatcttcgttgggagcacagaagtctagttgataacgcatattttaatggaaactcttctttaacagatg<br>gaagcttgttggatgctttaaaaataatgactcaaaagaaaaataaagaatattacacagccttaaaacaaattga<br>tgaccctcaattaaataaagttttaagtggtttattaggggctgattggagaacaagggaacgaataaaagatgaa<br>aaagattggaataaagaagcagccataagttttacaaatggaacttattcaatagaagcaggaaatgacttgaaag<br>cttctggaaaagtgattgaacttggtggttctaatgttatgactaaaaaagaaatatttgaagtagcatctacgaa<br>aacggaaagtttacaatcaacgatttcagatgttaaaaatgctaatataaaagcgaaaaatgtttatatggaagcc<br>gataatataacaaatgtaaatgcagatattgcagcggaagacagtgcgattctttattctaaaaacaatattgatg<br>tgaagggagctaaagtttctgctgataaaattcttcttgaagctggtaaagatataaatttatcttcagaacttgg<br>tttcaaatcttctggggaacatgcgattattaaagaaacagatgttactgcaaataaggctgttggaatcaaatcc<br>aagaacttaaatatttatggtgcagatgtagaggcaaaagatggacttataaaaatagactctgataagttaaatg<br>taaaagatatcagtacaatcaatgcaaattataaggccgaattaatagaaggaaaaaaatatatttaagagatca<br>tcaatatacaaaagctttacaagctaaagtggaatctacaccttctaaaataattgctaataaaatttttatcact<br>gcaaaagatggtgctgctattgagggttcactgatttcaggaaaaaatgctgacagcataatccaaatcatttctg<br>agggaaatgtcaatatcaaaaatagcaataatattgattatagtaatttttattcagatagcagaggaaaaaataa<br>aaaaggagtctacaaattattaaaaatagataaggcttcaaaagaaaatcttgacatagtaggaagcaacttaaaa<br>tcggaaggaaatataaatataaaatcaaaaaatttaactgttgtatcaagtaaaataaaagcaggaaaaaaagtta<br>acttagaagccgaagaagatataaaattactagcttctttgaattctaagaaagaggaattaaataagatggaatg<br>gggtagcggtgctatcaatagttataaaaagtctttggagaaaaaagatgtagtgtctactatgattgaagctgga<br>gaaaaagcaaatgtacatgcaaaaagagatttgtataaacaatctgtttttgtgaaagctggaagcgtaactatga<br>atggtgaggcaaataattacagtgatgctttagcttcaacagaaataaaaaaagaaacagatgtgaaagctggctt<br>tggtgtagaaggaaagattgcttttgctggaatgggagcagctggggaagcaaacactttagataatacagcaaca<br>ggaaaaacttccgggataaaggtcttttagaaaaagagaatgaatttaaaaaagcggaagccagagcgaaagttt<br>acgcaaaaatggaagttaataagagcataaaagaaagtaaaaattatgtaaataacaacattacctcggaaagtgg<br>tgatgtgactataggttctaatggggtcactgatataggaaataccgatatcaattctcaaaatgatgttaactta<br>agaggtaaaaaagtagaaaccactacaaaggaaaatgtaacgaaagaggttaatcataagcttgatctttctgtaa<br>aaggtgacatcgctttttctaatgaaaatgtcaataaattgaatgatttggcaaatgatgttctaaaaagtaaaga<br>gatgttagaaaagaaagatatactcgggttagctcaaaaagcagaagaaacaatcaaagatttaaaagaaacgatt<br>ccaaatctaactaaaaaagacattttaggaataaaatcaagtcagggagtaggggtagaatacactaataaaactt |

FIG. 49B

| |
|---|
| tactttaaaaaacacttatttaaaagctcaagagtttaacacagaaactcctggaaaagttaatcttttagcaggg<br>aagaaaacgattcataaagaagaaaattctttaaaggttggtgtatcagttaacgaaaatgtaggagtcaatatag<br>cagatggagccaatgctaaaattggtgtaggtgttcaagctagttacaatggcggaactgatttgaataaaaaaag<br>tttaaatacaactgtagaggtaggaaaagtgaatcataaagctgcagctgtaaatgaagataataaaacagacttt<br>tattacaaagataaaagaggtgcaggagttgatgttgatttaaaaataggagtttcttcgaatcatatagtagcgg<br>cagatggaaatgtaggaggaaatgtgaattattcttttgcggctggaaaatcaacaacagatgttgtaacaaataa<br>gacagaaagtactgatgtaaaagcaggggttggactgaaagcttctgttggaatagatggaaaaagtccagatttt<br>tcaatttcaacagaccaaattgaatataaaaaagatggaaaagtattagttaatattgacgcaaaagataaaatga<br>tcaccaaagagagaattgaacagatgagagataaggtaaaaaattggagaactccaacaaatagtgcggaaaaatt<br>aatctaa |
| *Fusobacterium necrophorum* filamentous hemagglutinin amino acid sequence, 154 kDa.<br>(SEQ ID NO:53)<br>MKKLKNFENVLKSHLKQRVRITTAFIVAFLIHGMLSFDVEARDLRVRNQITPSNSNNGLRITSSQNGTDV<br>INIVDPNNGISHNKYVDFNVGDKNNVIFNNSQKNGTSVTGGEVSANPNLTNSASVILNEIQGNSASELNG<br>GLEVFGKRADLVIANENGINVNGARFINTSALTLSTGKVSVDNKKISFNTATNNAKIAVKEKGIETDSDY<br>LNILSRRAELDGAINSEHNKNLNINVIAGANTVTAVNDTFELNAENAKDGITNVEAISASKFGAMYGNNI<br>FILSTNKGEGIKYEGSLKAKDEVEIISEGKVVSSDINGKDIKISSKEEINNIGKMKADKNVSLNAPIVKN<br>MSRLEGSVRLKSNEHNKKYQNRERGIIYYDYYLNVKNMSEVENELKLVKSSIEAGNNIEINNNLENGSFE<br>NLSGDLKAGNDIKVKGNFKTKHLSEGIKLEDLLKRIKVDLRWEHRSLVDNAYFNGNSSLTDGSLLDALKI<br>MTQKKNKEYYTALKQIDDPQLNKVLSGLLGADWRTRERIKDEKDWNKEAAISFTNGTYSIEAGNDLKASG<br>KVIELGGSNVMTKKEIFEVASTKTESLQSTISDVKNANIKAKNVYMEADNITNVNADIAAEDSAILYSKN<br>NIDVKGAKVSADKILLEAGKDINLSSELGFKSSGEHAIIKETDVTANKAVGIKSKNLNIYGADVEAKDGL<br>IKIDSDKLNVKDISTINANYKAELIEGKKYILRDHQYTKALQAKVESTPSKIIANKIFITAKDGAAIEGS<br>LISGKNADSIIQIISEGNVNIKNSNNIDYSNFYSDSRGKNKKGVYKLLKIDKASKENLDIVGSNLKSEGN<br>INIKSKNLTVVSSKIKAGKKVNLEAEEDIKLLASLNSKKEELNKMEWGSGAINSYKKSLEKKDVVSTMIE<br>AGEKANVHAKRDLYKQSVFVKAGSVTMNGEANNYSDALASTEIKKETDVKAGFGVEGKIAFAGMGAAGEA<br>NTLDNTATGKTSGIKGLLEKENEFKKAEARAKVYAKMEVNKSIKESKNYVNNNITSESGDVTIGSNGVTD<br>IGNTDINSQNDVNLRGKKVETTTKENVTKEVNHKLDLSVKGDIAFSNENVNKLNDLANDVLKSKEMLEKK<br>DILGLAQKAEETIKDLKETIPNLTKKDILGIKSSQGVGVEYTNKTSTTTETTASSLKAKGKLNIKADEGD<br>ITLKNTYLKAQEFNTETPGKVNLLAGKKTIHKEENSLKVGVSVNENVGVNIADGANAKIGVGVQASYNGG<br>TDLNKKSLNTTVEVGKVNHKAAAVNEDNKTDFYYKDKRGAGVDVDLKIGVSSNHIVAADGNVGGNVNYSF<br>AAGKSTTDVVTNKTESTDVKAGVGLKASVGIDGKSPDFSISTDQIEYKKDGKVLVNIDAKDKMITKERIE<br>QMRDKVKNWRTPTNSAEKLI |

FIG. 50

Membrane protein, 79.4 kDa. (SEQ ID NO:54)

MKRTLVAMLLFLVSMVSFAAGGSLIVKKVEVLNNQEVPASIILNQMDLKEGKPFSTEIMLHDFQTLKKSKYLEDVLIQPQAYE
GGVNVVVNVIEKKDVQSLLREDGVISMSEQANVDKSLILSDIIISGNQFVSTADLKKVLSVKQGGYFSKTAIEDGQKALLATG
YFREVTPNTQKNGNGVKIIYTVVENPVIQGINIHGNTLFSTPDILKVLKTKIGEVLNINSLREDRDTIMNLYQDQGYTLSEIS
DMGLNDRGELEVVISEGIIRNVSFQKMVTKQKGNRRKPTDDILKTQDYVIQREIELQEGKIYNAKDYDNTVQNLMRLGVFKNI
KSEIRRVPGDPNGRDIVLLIDEDRTAILQGAISYGSETGLMGTLSLKDNNWKGRAQEFGVNFEKSNKDYTGFTIDFFDPWIRD
TDRISWGWSLYKTSYGDSDSALFNDIDTIGAKINVGKGFARNWRFSLGFKGEYVKEKANKGNFRQLPDGTWYYTGKNKNDASN
TPLPKDAVNDKYMVFSIFPYLTYDTRNNPWNATTGEYAKLQLETGYAGGYKSGSFSNVTLELRKYHRGFWKKNTFAYKVVGGV
MTQSTKEGQRFWVGGGNTLRGYDGGTFRGTQKLAATIENRTQINDILGIVFFADAGRAWKQNGRDPEYGNDEKFSKGIATTAG
VGLRLNTPMGPLRFDFGWPVGKSQDKYSNDRGMKFYFNMGQSF

```
 FQ

MKKLWILFFLLGSVAFGREVTLEEAIQASMENSKAVKISDKQLEISKLKMNQAIKKALPS
MKKLWILFFLLGSVAFGREVTLEEAIQASMENSKAVKISDKQLEISKLKMNQAIKKALPS
MKKLWILFFLLGSVAFGREVTLEEAIQASMENSKAVKISDKQLEISKLKMNQAIKKALPS
MKKLWILFFLLGNVAFGREVTLEEAIQASMENSKAVKISDKQLEISKLKMNQAIKKALPS
MKKIWTMFFLVGSLAFAREITLEEAIQESMNHSKTLKISEKKLQISKLNRSQAIKKALPS
MKKILGLLLILSSSVFAREITLDQAIQMSLENSKEIKISEKDVEVSKLRVGMAFKDALPS
MKKILGLLLILSSSLFAREITLDQAIQMALENSKEIKVSEKDVEVSKLKVGIAFKDALPS
MKKILTIFMLMASVALARDLTLEQAIDLSLNNSKEMRISEKNLEISKLNVSKAFKNALPS
MKKTLGLLLLLSSSVFARELTLDQAIQMALDNSKEMQISQRDVETAKLNVGIAFKNALPS
MKKLLSIFFLLTGSLFARELTLDEAINLSLTNSKDIQISEKNLEISEINLQKAFKLALPT

***                *   **   **        **     *                *  *  ***

FQ

VVYSANYQRGEYERNI-YKNKS---SMES-------EKGGYKQSITISQPIFQGGAILAG
VVYSANYQRGEYERNI-YKNKS---SMES-------EKGGYKQSITISQPIFQGGAILAG
VVYSANYQRGEYERNI-YKNKS---SMES-------EKGGYKQSITISQPIFQGGAILAG
VVYSTNYQRGEYERNI-YKNKS---SMES-------EKGGYKQSITISQPIFQGGAILAG
VLYNTSYQRTEYERNI-SKNKS---SMQL-------EKGGYKQSITISQPIFQGGAIIAG
VVYSGTYTRGESDRKM-Y-----RHGWED----QVERKGGYTQTISISQPLFQGGAVLGG
VVYNGKYTRGEYERKM-Y-----KHGWEE----QVDRKGGYTQTISISQPLFQGGAILGG
VTYSGTYAVGEHERQILTQSER---NYAS-------KKRGYTQNLRLTQPLFTGGTITAG
VVYTGSYTRSEYDRKI-TAEERPNHRLEKNGSREVEAKGGYTQKITISQPIFQGGAILGG
VTYNGKYSRTNYDRKI-AIDD---HSSEK-------GRGSYSQSITIAQPLFAGGTIFAG

*  *     *       *                                 *  *      **  *  **     *

FQ

IQGAKAYKTIADLSYVQETLNTRLKTIRTFSNIVNSKRNLQALEYSEKQLQNRYKKQEAQ
IQGAKAYKTIADLSYVQETLNTRLKTIRTFSNIVNSKRNLQALEYSEKQLQNRYKKQEAQ
IQGAKAYKTIADLSYVQETLNTRLKTIRTFSNIVNSKRNLQALEYSEKQLQNRYKKQEAQ
IQGAKAYKTIADLSYVQETLNTRLKAIRTFSNIVNSKRNLQALEYSEKQLQNRYKKQEAQ
IQGAKAYETIADLSYVQEGLNTRLKTIRTFSNIVNSKRNLQALENSEKQLQKRYQKQEAQ
IKGAKAYKTIANLLYLGERRDTRLKTIQNYSNIVKYEKDLEALESSKRELQARYNKQKAQ
IKGAKAYKSIANLLYLGERRDTRLRTIQNYSNIVKYQKDLEALEASKKELQARYNKQKAQ
IKGAKAYENIASYSYLQSKIQNRLDTIKIFSDIINAERNLEALEYSENILQKRYQKQEEQ
IQYAKAYKSVANLMYLSSQRDVRLETIQIYSDIVKSEKDLEALMSSKEELKATYDKQKAQ
IKGAQAYENIANYNFLNSKIKMRIETIAAYFSLLNAEKDLNALKNSKSILQKRYDKQKVQ

*   * **    *           *    *                *  **   *    *    *  **   *
```

```
LELRLITKTDLLKTEYSLLEVQSLISKAKSNIEVQTEDLKFQMGVDKKEALEVKEFIVPN
LELRLITKTDLLKTEYSLLEVQSLISKAKSNIEVQTEDLKFQMGVDKKEALEVKEFIVPN
LELRLITKTDLLKTEYSLLEVQSLISKAKSNIEVQTEDLKFQMGVNKKEALEVKEFIVPN
LELRLITKTDLLKTEYSLLEVQSLISKAKSNIEVQTEDLKFQMGVDKKEVLEVKEFIVPN
LELRLITKTDLLKTKYNLLEIQSLIAKAKSNIEVQTEDLKFQMGIDKEEQLEVKEFNVPN
LDLRLITKTDLLKTEYSLLEVESQIIGTKNGITIEKENLKIKTGIPKQEDVTVVDFNVPM
LDLRLITKTDLLKTEYSLLDVESQIIGTKNGITIEKENLKIKTGIPKHEDVSVVEFEVPM
LNLRLITRTDILQTEYSIEDIRAQMINAKNTIDTNMEKLYIRTGINKSESLNLIPFDIPN
LDLRLITKADLLKTEYSMLEVDSQIIGTQNQITVQKENLKLKLGLPKTEDLTVVEFDVPM
LELRLIRKSDISQTEYSLLNVESNIIAIKSQIDTYREQLRIKTGLAKNEFITVVDFNVPM
* ****   *   * *               *    * *    *  * *      *  *
```

FQ

```
HLTERITFEKDKERALESSIQALIAKSQVKIAKAQETAALGNMLPKVNAFVSYGVASERT
HLTERITFEKDKERALESSIQALIAKSQVKIAKAQETAALGNMLPKVNAFVSYGVASERT
HLTERITFEKDKERALESSIQALIAKSQVKIAKAQETAALGNMLPKVNAFVSYGVASERT
HLTERITFEKDKEKALESSIQALIAKSQVKIAKAQETAALGNMLPKVNAFVSYGVASERT
HLTDTIDFQKDKEKALESSIQSLIAKSQVEIAKAQETAALGNMLPKINAFASYGVATERT
YLSRNINFKADLDQAMNESINALVAKNYVEAADASKMVSRADMLPKVNAFASYGT-SERT
YLSRNINFKADLDQAMNESINALVAKNYVEAADASRIVSRADMLPKVNAFASYGT-SERT
NFSEKINLNNDLKQAINESLSAKVAEEQVKVASATRMAAVGDLLPQVNAYASYGTG-ERT
YLSRNIDFQADLNQALTESIDAMVANKYVDMADAQRKVARADMLPQVSAFASYGVDSDRR
NLSKNINIDKDLEQAINESLNAKIAEEMYKISEAQTIAAAGSILPKVSAFATYGT-TERT

     *    *   *   *     *        *         **   *   **    *
```

FQ

```
HWKQTKEDAEWMGGLSVSWNVFSFGSDYDAYQIAKLEKESKELSETTAQDNIALSLKTAY
HWKQTREDAEWMGGLSVSWNVFSFGSDYDAYQIAKLEKESKELSETTAQDNIALSLKTAY
HWKQTREDAEWMGGLSVSWNVFSFGSDYDAYQIAKLEKESKELSETTAQDNIALSLKTAY
HWKQTREDAEWMGGLSVSWNVFSFGSDYDAYQIAKLEKESKELSEMTAQDSIALSLKTAY
KWKQTREDAEWMGGLSVSWNVFSFGSDYDNYQIAKLEKENKELSEMTAQDTIELTLKTAY
KYNPTIDEAEWRGGVQVTWNVFEFGKNYDSYKVAAIGKEQEILREKISKDSIDISVTDAY
KYNPTIDEAEWRGGIEVTWNVFEFGKNYDNYRVAAIGKEQEMLREKISKDSIDINVTDAY
SFERSYKDGEWTGGIEVSWKVFSFGSDLDSYRVAKLQEEQEELRETSTKEDIEVNVRSAY
KYNATMDDAEWRGGVQVTWNVFEFGKNYDTYKTAAIAKEQEELREKISKDTIDINVTDAY
KFENSYRDAKWVGGIQVTWNVFSFGSDIDEYRIAKLEEEQQKLKEISTKENIEIAVKSAY

          * **  * * ** **   * *  *    *   * *      *      **
```

```
FQ

LELQRLEILRESRKRGLEAAELNFTMDQEKFDAGLLSTVDYLSSETQLREARVNYYQAEL
LELQRLEILRESRKRGLEAAELNFTMDQEKFDAGLLSTVDYLSSETQLREARVNYYQAEL
LELQRLEILRESRKRGLEAAELNFTMDQEKFDAGLLSTVDYLSSETQLREARVNYYQAEL
LELQRLEILRESRKRGLEAAELNFTMDQEKFDAGLLSTVDYLSSETQLREARVNYYQAEL
SELQRLEILRESRKRGLEAAELNFSMDQEKFDSGLISTIDYLLSETQLREARVNYYQAEL
LELIRMEKERDSKERAMEAAIENFRMDQERYDAGLISTVDYLLSESQEREAKVSYNQIVI
LELIKMEKERDSKERAMEAAIENFRMDQERYDAGLISTVDYLLSESQVREATVAYNQIVI
LNVLSLEKQIDSQAKALEAAKVNFELNQEKYDAGLISTVDYLDFENTYRQARIAYNKVLL
LELVRMEKDRDSKGRALEAAMENYKIDKEKYTAGLISTIDFLASETQLREAKVAYNQVVI
FDLLRLEKLRESKSKALEVAKLNFEMDQERYDAGLISTIDYLDTENTYRNANIDYNKTLM
      *    *     * *  *     *    ** ** * *  *   * *   *

FQ

DYYYAFEYYRSLLV (SEQ ID NO:4)
DYYYAFEYYRSLLV F. necrophorum (SEQ ID NO:63)
DYYYAFEYYRSLLV F. necrophorum (SEQ ID NO:64)
DYYYAFEYYRSLLV F. necrophorum (SEQ ID NO:65)
DYYYAFEYYRSLLV F. gonidiaformans (SEQ ID NO:66)
DYLYAFEKYRSLLI F. ulcerans (SEQ ID NO:67)
DYLYAFEKYRSLLI F. varium (SEQ ID NO:68)
DYYYAFETYRSLLI F. nucleatum (SEQ ID NO:69)
DYLYAFEKYRSMLI F. mortiferum (SEQ ID NO:70)
DYYLAFEKYRSLII F. russii (SEQ ID NO:71)
**  *** ***
```

```
MKKVVFGIYSILMSSAMLGAEIDLGTQNIYSETGFETSLRSSVSSPYIVTSKEIKEKHYT
MKKVVFGICSILISSAMLGAEIDLGTQNIYSETGFETSLRSSVSSPYIVTSKEIKEKHYT
MKKVVFGICSILISSAMLGAEIDLGTQNIYSETGFETSLRSSVSSPYIVTSKEIKEKHYT
MKKVVFGICSILMSSAMLGAEIDLGTQNIYSETGFETSLRSSVSSPYIVTSKKIKEKHYT
MKKVIFGIYSILLSSAMLGAEIDLGTQNIYSETGFETSLRSSVSSPYIVTSKKIKEKHYT
MKKVVFGIYSILMSSAMLGAEIDLGTQNIYSETGFETSLRSSVSSPYIVTSKKIKEKHYT
MKKVVFGICSILMSSAMLGAEIDLGTQNIYSETGFETSLRSSVSSPYIVTSKKIKEKHYT
**** *** *** *************************************** *******
```

FT

```
RVSEILRDIPHIYIGPGGSVDMRGQGSAHARTTVQLLIDGVPANFLDTSHINLPIDTLNP
RVSEILRDIPHIYIGPGGSVDMRGQGSAHARTTVQLLIDGVPANFLDTSHINLPIDTLNP
RVSEILRDIPHIYIGPGGSVDMRGQGSAHARTTVQLLIDGVPANFLDTSHINLPIDTLNP
RVSEILRDIPNIYIGSGGSVDMRGQGSIHSRTTVQLLIDGVPANFLDTSHINLPIDTLNP
RVSEILRDIPNIYIGSGGSVDMRGQGSIHSRTTVQLLIDGVPANFLDTSHINLPIDTLNP
RVSEILRDIPNIYIGSGGSVDMRGQGSIHSRTTVQLLIDGVPANFLDTSHINLPIDTLNP
RVSEILRDIPNIYIGSGGSVDMRGQGSIHSRTTVQLLIDGVPANFLDTSHINLPIDTLNP
********** **** *********** * ******************************
```

FT

```
EDIKRIEVIPGGGAVLYGSGTSGGVINIITKKYTGNYAKASYQIGSYHNHKYDVAAGTSL
EDIKRIEVIPGGGAVLYGSGTSGGVINIITKKYTGNYAKASYQIGSYHNHKYDVAAGTSL
EDIKRIEVIPGGGAVLYGSGTSGGVINIITKKYTGNYAKASYQIGSYHNHKYDVAAGTSL
EDIERIEVIPGGGAVLYGSGTSGGVINIITKKYTGNYAKAGYQIGSYHNHKYDVAAGTSL
EDIERIEVIPGGGAVLYGSGTSGGVINIITKKYTGNYAKAGYQIGSYHNHKYDVAAGTSL
EDIERIEVIPGGGAVLYGSGTSGGVINIITKKYTGNYAKAGYQIGSYHNHKYDVAAGTSL
EDIERIEVIPGGGAVLYGSGTSGGVINIITKKYTGNYAKAGYQIGSYHNHKYDVAAGTSL
*** ************************************ *******************
```

FT

```
GNFDINLSYSKNNRDGYRKKAFSDSDFFSGKLRYHFNPTDSLEFKYSYFDNKFRGVKSLT
GNFDINLSYSKNNRDGYRKKAFSDSDFFSGKLRYHFNPTDSLEFKYSYFDNKFRGVKSLT
GNFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRDVKSLT
* ***************************************************** *****
```

```
REQVEKDRRQSGLSPEDNLKNTIRKEEWNLTYDAKWTSWLEHKSNLFYQSTEIKSSEYED
REQVEKDRRQSGLSPEDNLKNTIRKEEWNLTYDAKWTSWLEHKSNLFYQSTEIKSSEYED
REQVEKDRRQSGLSPEDNLKNTIRKEEWNLTYDAKWTSWLEHKSNLFYQSTEIKSSEYED
REQVEKDRRQSDLSPEDNLKNTIRKEEWNLTYDAKWTSWLEHKSNLFYQSTEIKSSEYED
REQVEEDRRQSGLSPEDNLKNTIRKEEWNLTYDAKWTNWLEHKSNLFYQSSEIKSSDYED
GEQVEEDRRQSGLSPKDNLKNTIRKEEWNLTYDAKWTNWLEHKSNLFYQSSEIKSSDYED
REQVEEDRRQSGLSPKDNLKNTIRKEEWNLTYDAKWTNWLEHKSNLFYQSSEIKSSEYED
 **** ***** *** ********************* ************ ***** ***
```

FT

```
ALPFYQYQISSYQKMLTMPGIPPMMQAQLKKQIKALQNLITSNPRMELHQGSRFKDQKFG
ALPFYQYQISSYQKMLTMPGIPPMMQAQLKKQIKALQNLITSNPRMELHQGSRFKDQKFG
ALPFYQYQISSYQKMLTMPGIPPMMQAQLKKQIKALQNLITSNPRMELHQGSRFKDQKFG
ALPFYQYQISSYQKMLTMPGIPPMMQAQLKKQIKALQNLIMSNPRMELHQGSRFKDQKFG
AIPFYQARIAMYQQMLATPGIPPMMLEKLKKQIQIWENIITNNPKMELRQGSLFKDRKFG
AIPFYQARIAMYQQMLATPGIPPMMLEKLKKQIQIWENIITNNPKMELRQGSLFKDRKFG
AIPFYQARIAMYQQMLATPGIPSMMLEKLKKQIQFWENIITNNPKMELRQGSLFKDRKFG
* ****  *  ** **  **** **   *****    * *  ** *** *** *** ***
```

FT

```
FKMKNKFKYGENSDFILGLGYIHNKMDRDSWAYTKNTQTNQTIATLTNTKIPLNKKTFEI
FKMKNKFKYGENSDFILGLGYIHNKMDRDSWAYTKNTQTNQTIATLTNTKIPLNKKTFEI
FKMKNKFKYGENSDFILGLGYIHNKMDRDSWAYTKNTQTNQTIATLTNTKIPLNKKTFEI
FKMKNKFKYGENSDFILGLGYIHNKMDRDSWAYTKNTQTNQTIATLTNTKIPLNKKTFEI
FKMKNKFKYGENSDFILGLGYIHNKMNRNSWAYTKNTQTNQTIETITDTKIPLNKKTFEI
FKMKNKFKYGENSDFILGLGYIHNKMNRNSWAYTKNTQTNQTIETITDTKIPLNKKTFEI
FKMKNKFKYGENSDFILGLGYIHNKMNRNSWAYTKNTQTNQTIETITDTKIPLNKKTFEI
************************** * ************** * * ************
```

FT

```
FGLNTYRHNNWEFVQGLRFEKAKYNGKRQYKNLEYPLKDRSMNNVAANLAVNYLYSDTGN
FGLNTYRHNNWEFVQGLRFEKAKYNGKRQYKNLEYPLKDRSMNNVAANLAVNYLYSDTGN
FGLNTYRHNNWEFVQGLRFEKAKYNGKRQYKNLEYPLKDRSMNNVAANLAVNYLYSDTGN
FGLNTYRHNNWEFVQGLRFEKAKYNGKRQYKNLEYPLKDRSMNNVAANLAVNYLYSDTGN
FGLNTYRHNNWEFVQGLRFEKAKYSGKRQYKNLEYPLKDRSMNNVAANLAVNYLYSDTGN
FGLNTYRHNNWEFVQGLRFEKAKYSGKRQYKNLEYPLKDRSMNNVAANLAVNYLYSDTGN
FGLNTYRHNNWEFVQGLRFEKAKYSGKRQYKNLEYPLKDRSMNNVAANLAVNYLYSDTGN
************************ ***********************************
```

FT

```
VYVKYERGFTSPAPAQLMDKIRKGGVNDYVNNDLKSEKSNSFEVGWNDYLFHSLVSADVF
VYVKYERGFTSPAPAQLMDKIRKGGVNDYVNNDLKSEKSNSFEVGWNDYLFHSLVSADVF
VYVKYERGFTSPAPAQLMDKIRKGGVNDYVNNDLKSEKSNSFEVGWNDYLFHSLVSADVF
VYVKYERGFTSPAPAQLMDKIRKGGVNDYVNNDLKSEKSNSFEVGWNDYLFHSLVSADVF
VYVKYERGFTSPAPAQLMDKIKKGGVNDYVNNDLKSEKSNSFEVGWNDYLFHSLVSADVF
VYVKYERGFTSPAPAQLMDKVKKGGVNDYVNNDLKSEKSNSFEVGWNDYLFHSLVSADVF
VYVKYERGFTSPAPAQLMDKIKKGGVNDYVNNDLKSEKSNSFEVGWNDYLFHSLVSADVF
********************  **************************************
```

```
FSETKDEISTIFSGGHGTTFSNLNLGQTKRYGFDLKASQVFEKWTFSEAYSYIHAKIMKD
FSETKDEISTIFSGGHGTTFSNLNLGQTKRYGFDLKASQVFEKWTFSEAYSYIHAKIMKD
FSETKDEISTIFSGGHGTAFSNLNLGQTKRYGFDLKASQVFQKWTFSEAYSYIHAKIVKD
FSETKDEISTIFSGGHGTTFSNLNLGQTKRYGFDLKASQVFEKWTFSEAYSYIHAKIMKD
FSETKDEISTIFSGGHGTAFSNLNLGQTKRYGFDLKASQVFRKWTFSEAYSYIHAKIVKD
FSETKDEISTIFSGGHGTAFSNLNLGQTKRYGFDLKASQVFQKWTFSEAYSYIHAKIVKD
FSETKDEISTIFSGGHGTAFSNLNLGQTKRYGFDLKASQVFQKWTFSEAYSYIHAKIVKD
****************** ********************** *************** **
```

FT

```
KTKAYEGKYISYVPRHKFSLNADYAITPKWTLGGEYQYSSSVYLDNANKNGKDGARSVFN
KTKAYEGKYISYVPRHKFSLNADYAITPKWTLGGEYQYSSSVYLDNANKNGKDGARSVFN
KNKAYEGKYISYVPRHKFSLNADYAITPKWTLGGEYQYSSSVYLDNANKNGKDGARAVFN
KTKAYEGKYISYVPRHKFSLNADYAITPKWTLGGEYQYSSSVYLDNANKNGKDGARSVFN
KNKAYEGKYISYVPRHKFSLNADYAITPKWTLGGEYQYSSSVYLDNANKNGKDGARAVFN
KNKAYEGKYISYVPRHKFSLNADYAITPKWTLGGEYQYSSSVYLDNANKNGKDGARAVFN
KNKAYEGKYISYVPRHKFSLNADYAITPKWTLGGEYQYSSSVYLDNANKNGKDGARAVFN
* ***************************************************** ***
```

FT

```
LQTSYEFNSHFSIYAGIKNVLNHKYYESVSAGSSQKYYSPAPERNYY
LQTSYEFNSHFSIYAGIKNVLNHKYYESVSAGSSQKYYSPAPERNYY
LQTSYEFNSHFSIYAGIKNVLNHKYYESVTAGSGQKYYSPAPERNYY
LQTSYEFNSHFSIYAGIKNVLNHKYYESVSAGSSQKYYSPAPERNYY
LQTSYEFNSHFSIYAGIKNVLNHKYYESVTAGSGQKYYSPAPERNYY
LQTSYEFNSHFSIYAGIKNVLNHKYYESVTAGSGQKYYSPAPERNYY
LQTSYEFNSHFSIYAGIKNVLNHKYYESVTAGSGQKYYSPAPERNYY
***************************** *** *************
```

FT

```
AGFRYQF (SEQ ID NO:2)
AGFRYQF F. necrophorum (SEQ ID NO:72)
AGFRYQF F. necrophorum (SEQ ID NO:73)
AGFRYQF F. necrophorum (SEQ ID NO:74)
AGFHYQF F. necrophorum (SEQ ID NO:75)
AGFRYQF F. necrophorum (SEQ ID NO:76)
AGFRYQF F. gonidiaformans (SEQ ID NO:77)
*** ***
```

```
-------------MKKILFLVGALFSISAFAEQTIELGSTSIKGN-RKTDYTLTPKEYKN
-------------MKKILFLVGALFSISAFAEQTIELGSTSIKGN-RKTDYTLTPKEYKN
-------------MKKILFLVGALFSISAFAEQTIELGSTSIKGN-RKTDYTLTPKEYKN
LKVNFIMKRESEKMKKILFLVGALFSISAFAEQTIELGSTSIKGN-RKTDYTLTPKEYKN
-------------MRKMLFLIGALLSISAFAEQTVELGSTSIKGN-RKADYTLTPKEYKN
-------------MRKTLLLFSILATL-AYAEQTVELGSSSIRSSAKKTDYTLIPKEYKN
-------------MKKLLVLLTILSSIIAHAEDTIELKETTVKSSPRSSDYTLIPKEQKN
-------------MKKLLVLLTILSSIIAYAEDTIELNQTTVKSSPRSSDYTLIPKEQKN
-------------MKKLLVLLTILTSIASFSEDVIELGQTTVKGS-KTSDYTAPPKEQKN
-------------* * * *   *       *   **            ***  *** **
```

FN

```
TYTITQEKIQERNYKNVEDVLRDAPGIVVQNTAFGPRIDMRGSGEKSLSRVKVLVDGISI
TYTITQEKIQERNYKNVEDVLRDAPGIVVQNTAFGPRIDMRGSGEKSLSRVKVLVDGISI
TYTITQEKIRERNYKNVEDVLRDAPGVVVQNTAFGPRIDMRGSGEKSLSRVKVLVDGISI
TYTITQEKIRERNYKNVEDVLRDAPGVVVQNTAFGPRIDMRGSGEKSLSRVKVLVDGISI
TYTITQEKIQERNYKNVEDVLRDAPGVVIQNTAFGPRIDMRGSGEKSLSRVKVLVDGVSI
TYTITQETIRERNYKNVEDVLRDAPGVIIQNTAFGPRVDMRGSGEKSLARVKVLVDGISI
TYVITQEKIRERNYKNVEDVLRDAPGVTIQNTAFGPRVDMRGSGEKSLSRVKVLIDGVSI
TYVITQEKIRERNYKNVEDVLRDAPGVTIQNTAFGPRVDMRGSGEKSLSRVKVLIDGVSI
TFVITQERIREKNYKNVEDILRDAPGVVVQNTAFGPRIDMRGSGEKSLSRVKVLVDGVSI
*  **** * * ******* ******   ******** ********** ***** ** **
```

FN

```
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVVSISTNSNVTKNNFFMDL
NPTEETMASLPINSIPIETVKKIEIIPGGGATLYGSGSVGGVVSITTNSNATKNNFFMDL
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVISITTNSNVTKNNFFADL
NPTEETMASLPINSIPIESVKKIEIIPGGGATLYGSGSVGGVISITTNSNVTKNNFFADL
NPTEETMASLPINAIPVESIKKIEIIPGGGATLYGSGSVGGVVNISTNSNVTKDNFFMDL
************* ** *  **********************  * **** ** *** **
```

FN

```
NYGSFDNRNFGFAGGYNVSDKLYVNYGFNYLNSEDYREHEEKENKIYLLGFDYKINPKNR
NYGSFDNRNFGFAGGYNVSDKLYVNYGFNYLNSEDYREHEEKENKIYLLGFDYKINPKNR
NYGSFDNRNFGFAGGYNVSDKLYVNYGFNYLNSEDYREHEEKENKIYLLGFDYKINPKNR
NYGSFDNRNFGFAGGYNVSDKLYVNYGFNYLNSEDYREHEEKENKIYLLGFDYKINPKNR
NYGSFDNRNFGFAGGYNVTDKLYVNYGFNYLNSEDYREHEEKENKIYLLGFDYKINAKNR
NYGSFDNRNFGFAGGYNVNKKLYVNYGFNYLNSESYRKHEEKENKIYLVGFDYKFNGKNR
NYGSFDNRNFGFAGGYNVTKNLYVNYGFNYLNSEGYRREEEKENKIYLLGFDYKINSKNR
NYGSFDNRNFGFAGGYNVTKNLYVNYGFNYLNSEGYRREEEKENKIYLLGFDYKINAKNR
NYGSFDNRNFGFAGGYNFNKHLYVNYGFSYLNSEDYREHEEKENKIYLLGFDYKINAKHR
*****************    ******* ***** **  ********* ***** * * *
```

```
FN

FRVQTRYSKMKHDGSNWLSQEELKISRKKAGLNLDLDTTDKSYTFDYEYRSSQNLTLAAT
FRVQTRYSKMKHDGSNWLSQEELKISRKKAGLNLDLDTTDKSYTFDYEYRPSQNLTLAAT
FRVQTRYSKMKHDGSNWLSQEELKISRKKAGLNLDLDTTDKSYTFDYEYRPSQNLTLAAT
FRVQTRYSKMKHDGSNWLSQEELKISRKKAGLNLDLDTTDKSYTFDYEYRPSQNLTLAAT
FRVQTRYSKMKHDGSNWLSQDELKTSRKKAGLNLDLDTTDKSYTFDYEYRPTENLTLAAT
VRFQTRQSDIMDHGSNQLRKTELEGDRRAPGLALNLDTKDQSYTMDYEYRPTEKLTLGAT
FRFQTRYSKFKDDGSNQVTREVLEYDRRAIGLNLDMITKDKSYTFDYEYRPKNNLTLAAT
FRFQTRYSKFKDDGSNQVAREVLEYDRRAVGLNLDMITKDKSYTFDYEYRPKNNLTLAAT
FRFQTRFSDIKQDSSNQIPVEELKNDRRKAGLNMDINTKDRSYTFDYEYRPTQNATLSTT
 * *** *      **      *   *   **     * * *** ******    **  *

FN
AYKQQQDRDITTDDIRDIEIIASNRNYTDLKEYMTFYDVKSTLKAKFKEKKYGLKLKG
AYKQQQDRDITTDDIRDIEIIASNRNYT--DLKEYMTFYDVKSTLKAKFKEKKYGLKLKG
AYKQQQDRDITTDDIRDIEIIASNRNYT--DLKEYMTFYDVKSTLKAKFKEKKYGLKLKG
AYKQQQDRDITTDDIRDIEIIASNRNYT--DLKEYMTFYDVKSTLKAKFKEKKYGLKLKG
AYKQQQDRDITTDDIRDIEIVASNRNYT--DLKEYMTFYDVKSTLKAKFKEEKHGIKLKG
AYQQQQDRDIYTEDIRDIEIVASDRNYT--DIKEYMIFHDVKSTMKAKFKEKKHGIKLKG
IYKQEQDRDIQTESIDDIRIVSSPAGYTYGSYKEEMNFYGVTSKMNAKFEEDKKGLKLKS
IYKQEQDRDIQTESIDDIRIVSSPAGYTYGSYKEEMNFYGVTSKMNAKFEEDKKGLKLKS
FYKQKQERDIDTESIDDIKIIASDRTHTW--HKEEMNFYDIKSKMHADFKEDKDGAKLKA
 * * *** *  * ** *  *    *    ** * *    *   * * * * * ***

FN
KYEYG-----RGEVIFGYDYQDSNNKRNSLVQSETLKTYNDKISDLNLSPEDRKPIINRV
KYEYG-----RGEVIFGYDYQDSNNKRNSLVQSETLKTYNDKISDLNLSPEDRKPIINRV
KYEYG-----RGEVIFGYDYQDSNNKRNSLVQSETLKTYNDKISDLNLSPEDRKPIINRV
KYEYG-----RGEVIFGYDYQDSNNKRNSLVQSETLKTYNDKISDLNLSPEDRKPIINRV
KYEYG-----NGEVIFGYDYQDSNNKRNSLVQSETLKTYNDRISDLNLDPTDRKPIVNRV
KYDYG-----KGEIIFGYDYYDSNNRRDSHVRSETLKTYNTKYTDSVLSPEERLPIINNV
KYDYS-----NGQIIFGYDYQKAVNKRDSFVQSETLKSYNNGYSNKTLEGEDIQPVINRV
KYDYS-----NGQIIFGYDYQKAVNKRDSFVQSETLKSYNNGYSNKTLEGEDIQPVINRV
KFDYNLVENLPSETIIGYDYQSATNKRNSLVQSETLKTYNNGYMDINLSQSERLPVINRV
*  *          * ****    * * * * ***** **       *      *  * *

FN
NIDLTKKSHGFYVFNKLELTDKWDFTTGFRTEITKYNGYRKNGPNTMPIVSPKVNEIRTD
NIDLTKKSHGFYVFNKLELTDKWDFTTGFRTEITKYNGYRKNGPNTMPIVSPKVNEIRTD
NIDLTKKSHGFYVFNKLELTDKWDFTTGFRTEITKYNGYRKNGPNTMPIVSPKVNEIRTD
NIDLTKKSHGFYVFNKLELTDKWDFTTGFRTEITKYNGYRKNGPNTMPIVSPKVNEIRTD
DIDLTKKSHGFYAFNKLELGKKFDFTTGFRTEITEYNGYRKNGPNTMPIISPKTNEIKTN
KIDLTKKSHGFYAFNKWNVNKNFDFTTGFRIEKTKYNGYRKNGKNTMPIAVAKTDVIRTD
KVNMEKESHGFYVFNKFDVTDKLDITTGFRTEITKYNGKRVNGPNTMPFVAAKTAEINTD
KVNMEKESHGFYVFNKFDATDKLDITTGFRTEITKYNGKRVNGPNTMPFVAAKTAEINTD
DMEMKRKSQGIYVFNKWGLANWLDVTLGGRMEKTKYNGYRENGPNVMPYVEPEVKRIETN
 * * ***        * * * * * * *** * ** * **        * *
```

FIG. 51I

```
FN
EKMTNYAGEAGMLYKYSDTGRAFVRYERGFVTPFANQLTDKIHDTKLKSPAGFFTPPIV
EKMTNYAGEAGMLYKYSDTGRAFVRYERGFVTPFANQLTDKIHDTKLKSP-AGFFTPPIV
EKMTNYAGEAGMLYKYSDTGRAFVRYERGFVTPFANQLTDKIHDTKLKSP-AGFFTPPIV
EKMTNYAGEAGMLYKYSDTGRAFVRYERGFVTPFANQLTDKIHDTKLKSP-AGFFTPPIV
EKMTNYAGEAGMLYKYSDTGRAFVRYERGFVTPFANQLTDKIHDTELKNP-GGFFTPPIV
ERHTNFAGEVGGLWKYSDTGRFFTRYERGFVTPFSTQLTDKIHDTELKNP-NGFFIPPIV
RKLENYAGEFGALYEYRDTGRVFLRYEKGFVTPFANQLTDKVRDTTLPKK-VGFFDPPQV
RKLENYAGEFGALYKYRDTGRVFLRYEKGFVTPFANQLTDKVRDTTLPKK-VGFFDPPQV
RKLDNYAEELGFLFKYNDTGRFYTRYERGFVTPFGNQLTDKIHDTTLKNPNSGFIIPPTV
* * * * *  * ****   *** ******  *****  ** *     **  ** *

FN

NVSSLYVANNLKSEITDTIEVGFRDYIFNSLISASFFATDTTDEITLISSGITNPAVNRW
NVSSLYVANNLKSEVTDTIEVGFRDYIFNSLISASFFATDTTDEITLISSGITNPAVNRW
NVSSLYVANNLKSEITDTIEVGFRDYIFNSLISASFFATDTTDEITLISSGITNPAVNRW
NVSSLYVANNLKSEITDTIEVGFRDYIFNSLISASFFATDTTDEITLISSGITNPAVNRW
NVASLYVANNLKSEITDTIEVGFRDYIFDSLVSASFFATDTTDEITLISSGITNPAVNRW
NSASKYVANHLQPEITDTVEIGFRDYFYNSLFSASFFVTDTKDEITLISSGITNPAVNRW
NVASKYVDNNLKSEKTDTVELGVRDYFFGSLFSASVFLTDTKDEITLISSGVTNPAVNRW
NVASKYVDNNLKSEKTDTVELGVRDYFFGSLFSASVFLTDTKDEITLISSGVTNPAVNRW
NVASKYVDNNLNAEKTDTFEIGFRDYILGSTLSTSFFLTNTKDEITLISSGVTNPAVNRW
*  * ** * *  * *** * * ***   *  * * * * * ********* ********

FN

KFRNIGKTRRLGIELEAEQKWGKFDFSQSLTFVDTKVLKTDAESRIFRGDKVPMVPRIKA
KFRNIGKTRRLGIELEAEQKWGKFDFSQSLTFVDTKVLKTDAESRIFRGDKVPMVPRIKA
KFRNIGKTRRLGIELEAEQKWGKFDFSQSLTFVDTKVLKTDAESRIFRGDKVPMVPRIKA
KFRNIGKTRRLGIELEAEQKWGKFDFSQSLTFVDTKVLKTDAESRIFRGDKVPMVPRIKA
KFRNIGKTRRLGIELEAEQKWGDFEFSQSLTFVDTKVLKTDKESNIYRGDKVPMVPNIKA
RYRNIGKTRRFGIELEAEQKFGKFGLTESLTFVDSKVLKTDANSNIFRGDRVPMVPRLKA
KYRNIGKTRRMGLELEAEQNFGNWSLSQSLTLLNTKVLKANEEARLEKGDKVPLVPRVKA
KYRNIGKTRRMGLELEAEQNFGNWSLSQSLTLLNTKVLKANEEARLEKGDQVPLVPRVKA
KYRNIGKTRRFGLEFEAEQNFGKFRFNQSLTLVRTKVLVANEEAKLERGDQVPMVPRLKA
******** * * ****  *      ***    ***          ** ** **  **
```

```
FN

TLGLKYNVTDNLALIGTYTYLSKRETRE------LDEKDKVYKHTIKGYGTADLGILYKV
TLGLKYNVTDNLALIGTYTYLSKRETRE------LDEKDKVYKHTIKGYGTADLGILYKV
TLGLKYNVTDNLALIGTYTYLSKRETRE------LDEKDKVYKHTIKGYGTADLGILYKV
TLGLKYNVTDNLALIGTYTYLSKRETRE------LDEKDKVYKHTIKGYGTADLGILYKV
TLGLKYNVTDNLSLIGTYTYLSKRETRE------LDEKDKVYKHTIKGYGTADLGVLYKV
TLGIKYRMTDDLTLLANYTYLSKREARE------LDEKDKIYRHTIKGHGVLDVGALYRI
TLGVKYNFTDKIALIGTYTYFSKRETREIRESEDLNKDDNIIKHTIGGYGITDLGVLYKA
TLGVKYNFTDKIALVGTYTYFSKRDTREIRESEDLNKDDDIIKHTIGGYGVTDLGVLYKA
TLGLRYNFTDRLAGFVNYTYLAKQESRELRENEDLNKDDIVVKHTIGGHGVVDAGFSYKP
***  *  **       ***  *   **       *   *    *** * *  * *  *


FN

DKYSNFKVGAKNIFGKKYNLRETKLEALPAPERNYYLEFNVKFN (SEQ ID NO:6)
DKYSNFKVGAKNIFGKKYNLRETKLEALPAPERNYYLEFNVKFN F. necrophorum (SEQ ID NO:79)
DKYSNFKVGAKNIFGKKYNLRETKLEALPAPERNYYLEFNVKFN F. necrophorum (SEQ ID NO:80)
DKYSNFKVGAKNIFGKKYNLRETKLEALPAPERNYYLEFNVKFN F. necrophorum (SEQ ID NO:81)
DKYSNFKVGAKNLFGKKYNLRETKLEALPAPERNYYLEFNVKF- F. gonidiaformans (SEQ ID NO:82)
DKYSNVKVGAKNLFSKKYNLRETKVEALPAPERNYYLEFNVKFD F. necrophorum (SEQ ID NO:83)
DAYSNIKVGAKNIFNKKYNLRETSLEALPAPEKTYYLEMNVRF- F. nucleatum (SEQ ID NO:84)
DAYSNIKVGAKNIFNKKYNLRETSLEALPAPEKTYYLEMNVRF- F. nucleatum (SEQ ID NO:85)
DAYSDIKIGAKNLFSKKYNLRETSLEALPAPERNYYLELNVRF- F. periodonticum (SEQ ID NO:86)
* **  * **** * ********  *******  **** ** *
```

POLYPEPTIDES OF FUSOBACTERIUM AND METHODS OF USE

This application is the § 371 U.S. National Stage of International Application No. PCT/US2016/061108, filed 9 Nov. 2016, which claims the benefit of U.S. Provisional Application Ser. No. 62/252,951, filed Nov. 9, 2015, the disclosures of which are incorporated by reference herein in their entireties.

SEQUENCE LISTING

This application contains a Sequence Listing electronically submitted via EFS-Web to the United States Patent and Trademark Office as an ASCII text file entitled "29300540201_SequenceListing_ST25.txt" having a size of 339 kilobytes and created on Nov. 9, 2016. The information contained in the Sequence Listing is incorporated by reference herein.

BACKGROUND

*Fusobacterium* spp. are gram-negative, obligately anaerobic and pleomorphically rod shaped bacterium responsible for a variety of necrotic infections in animals and in humans (Langworth, Bacteriol. Rev., 41, 373-390 (1977)). Pathogenic species in the Genus *Fusobacterium* include *F. necrophorum, F. nucleatum, F. canifelinum, F. gonidiaformans, F. mortiferum, F. naviforme, F. necrogenes, F. russii, F. ulcerans*, and *F. varium. Fusobacterium necrophorum* is the most pathogenic and is classified into two subspecies: *F. necrophorum* subsp. *necrophorum* and *F. necrophorum* subsp. *funduliforme* and are responsible for a number of clinical manifestations in various species of animals, such as cattle, horses, goats, sheep, fowl, and swine, including hepatic abscesses, foot rot, laminitis, purulent and interdigital dermatitis, contagious ecthyma, necrotic rhinitis, and necrotic laryngitis. Taxa formally in the genus *Fusobacterium* include *Fillfactor alocis*, commonly found in the periodontal pockets of patients having periodontitis (Kumar et al., 2003, J Dent Res., 82(5):338-44); *Faecalibacterium prausnitzii*, and *Eubacterium sulci*, also associated with odontogenic infections (Munson et al., 2002, J. Dent Res., 81:761, Paster et al., 2006, Periodontology 2000, 42:80). Although the primary etiologic agent of liver abscesses has been shown to be *Fusobacterium necrophorum* abscessation has been associated with other bacteriological agents such as *Arcanobacterium pyogenes. Bacteroides* spp., *Salmonella* spp., *Clostridium* spp., *Pasteurella* spp., *E. coli* spp., and *Peptostreptococcus* spp.

In humans, *F. necrophorum* and *F. nucleatum* are considered to be the most pathogenic and is the causative agent of skin ulcers, peritonsillar abscesses, septic arthritis, Lemierre's syndrome, periodontal diseases, endocarditis and metastatic abscesses in the lungs, liver, joints, and pleural spaces. On a population-based perspective *Fusobacterium* bacteremia is relatively uncommon in humans with an overall annual incidence of 0.55 per 100,000 population. The incidence of *F. nucleatum* was found to be 0.34/100,000 and *F. necrophorum* was 0.14/100,000 with a median age of 53.5 years while *F. necrophorum* cases had a median age of 21 years. Overall mortality due to bacteremia was 11 percent. *F. necrophorum* affects mostly young health adults. In contrast, *F. nucleatum* affects older individuals with seemingly compromised healthy conditions (Afra, Infectious Diseases, 13: 264 (2013)). A number of other species of fusobacteria have been implicated as the etiological agent in a variety of diseases, for example, *F. ulcercans* (skin ulcers), *F. russi* (animal bite infections), and *F. varium* (eye infections) (Smith et al., Epidemiol Infect., 110, 499-506 (1993)).

In beef-breed and Holstein steers, the incidence of liver abscesses average from 12 to 32% in most feedlots, and has been shown to be influenced by a number of dietary and management factors. Liver abscesses are categorized as mild, moderate or severe. Severe liver lesions are most often associated with high economic losses to producers, packers, and ultimately consumers. Besides liver condemnation, economic impacts include reduced feed intake, reduced weight gain, decreased feed efficiency, and decreased carcass yield.

*F. necrophorum* possesses a number of virulence factors that participate in the penetration and colonization of the ruminal epithelium and subsequent entry and establishment of infection in the liver, including a potent secreted leukotoxin which has been shown to be specifically toxic to ruminant polymorphonuclear leukocytes (Tan et al., Vet. Res. Commun. 20, 113-140 (1996)). The role of leukotoxin as a virulence factor has been documented. For instance, experiments have indicated a correlation between toxin production and the ability of *F. necrophorum* to induce abscesses in laboratory animals (Coyle et al., Am. J. Vet. Res., 40, 274-276. (1979), and Tan et al., Am. J. Vet. Res., 55, 515. (1994)). Experiments have also shown that non-leukotoxin producing strains are unable to induce foot abscesses in cattle following challenge. It has also been shown that neutralizing antibody produced by an inactivated toxoid derived from leukotoxin reduced infection and liver abscesses in vaccinated cattle.

Control of liver abscesses in feedlot cattle generally has depended on the use of antimicrobial compounds. Five antibiotics (i.e., bacitracin methylene disalicylate, chlortetracycline, oxytetracycline, tylosin, and virginiamycin) are approved for prevention of liver abscesses in feedlot cattle. Tylosin is the most effective and the most commonly used feed additive.

A number of commercial killed whole cell bacterins have been used to control necrotic infection in farm animals incorporating multiple strains including the most prevalent serotypes such as biotype A (*F. necrophorum* subsp. *necrophorum*). Another approach to vaccine development has been the incorporation of leukotoxin as a toxoid to prevent the pathological effect of the secreted toxin (Saginala et al., J. Anim. Sci., 75, 11601166 (1997)).

Divalent metal ions such as iron, cobalt, copper, magnesium, manganese, molybdenum, nickel, selenium, and zinc and are trace elements often required for the survival of bacteria infecting both animal and human hosts. These trace metal elements are used by bacteria as cofactors for enzymes that catalyze biochemical reactions for various metabolic pathways required by the organism. The impact of iron on the pathogenesis of bacteria has been studied extensively. Iron is essential for nearly all life and is required for enzymatic and metabolic pathways of cells at all phylogenic levels. It has been well-documented that during bacterial sepsis there is an alteration in the concentration of a number of metal ions in serum such as, iron, copper, and zinc. For instance, serum levels of zinc decrease from 10 percent to 60 percent with the onset of infection. Following the onset of infection, zinc is then redistributed from plasma to liver where it is bound to metallothionein. Decreases in serum iron of up to 50 percent have been described during infectious illness, whereas serum copper has been shown to increase in response to inflammatory stimuli. The alteration of these trace metal ions in serum may directly affect the severity or progression of any bacterial infection.

The ability of *Fusobacterium* to evade the natural defense mechanisms of the vertebrate host depends in part on its ability to obtain host iron, which in turn, directly influences the host-pathogen interaction. Because of iron's essential nature, vertebrate hosts have developed elaborate mechanisms to bind iron in body fluids (e.g., transferrin in blood and lymph fluids and lactoferrin in external secretions). These high affinity iron binding proteins create an iron restricted environment within the host, reducing the level of iron to approximately $10^{-18}$ molar, a concentration too low to support the growth of nearly all bacteria. These iron sequestering mechanisms of the host act as a natural defense mechanism to combat bacterial invasion. To circumvent these iron-restrictive conditions many bacterial species have evolved mechanisms for obtaining iron. The most common mechanisms include the diffusion of soluble iron through porins and specialized transport systems that mediate the uptake of iron by siderophores. This latter system is one of the most common and well-studied mechanisms for iron acquisition and involves the specific chelation of ferric iron by siderophores and the synthesis of their cognate transport systems, which permits the bacteria to continue to replicate and overcome the non-specific defense mechanisms of the host. Continued replication, and thus each step in the infectious process, is ultimately dependent on the ability of the organism to obtain iron from its host.

With so many basic functions relying on the availability of iron, bacteria have evolved a complex regulatory network for acquiring iron under varying physiological conditions. Under anaerobic conditions, iron is present in the soluble ferrous form (Fe II) and can freely diffuse through outer membrane porins into the periplasm. For instance, in *E. coli* the FeoAB transport system present in the cytoplasmic membrane will transport the ferrous iron molecules into the cell cytoplasm. Under aerobic conditions and neutral pH, iron is primarily present in the insoluble ferric form (Fe III) and cannot pass through the outer membrane porins by passive diffusion. Instead, molecules called siderophores are secreted by bacteria, which have a high affinity for ferric iron. The ferric-siderophore complexes are recognized by receptors in the outer membrane collectively referred to as the TonB-dependent receptors. These receptors, once bound to loaded siderophores, are believed to interact with TonB and its associated proteins localized in the periplasm and cytoplasmic membrane. These protein-protein interactions, though poorly understood, serve to provide the energy necessary to transport the ferri-siderophore complexes across the outer membrane and through the periplasmic space. ABC transport systems present in the cytoplasmic membrane serve to transport the iron-siderophore complexes across the cytoplasmic membrane. Reductase enzymes reduce the ferric iron to its ferrous form, which dissociates it from the siderophore and releases iron into the cell.

Several species of pathogenic bacteria use additional mechanisms to obtain iron from mammalian hosts, including the direct binding of transferrin, heme, and other heme-containing compounds. The receptor proteins that bind these iron-containing molecules most likely rely on the TonB complex for the energy required to transport heme across the outer membrane, similar to the iron-siderophore complexes. Specialized ABC transporters are then used to transport the heme across the cytoplasmic membrane. In addition, some bacteria secrete hemophores, small molecules that can bind heme and present it to receptors on the bacterial cell surface. Several pathogenic species also produce hemolysins, which are toxins that lyse red blood cells, releasing heme and hemoglobin for uptake by the bacteria.

The outer membrane proteins of gram-negative bacteria control the selective permeability of many essential nutrients critical to the survival of bacteria, including all pathogenic bacteria that cause disease in animals and man. This selective permeability of nutrients is controlled by a class of membrane proteins called porins. It now appears that the majority of the outer membrane proteins on the surface of gram-negative bacteria are porins, identified as the general porins (e.g., OmpF), monomeric porins (e.g., OmpA), the specific porins (e.g., the maltose-specific porin LamB) and the TonB-dependent, gated porins (e.g., the siderophore receptor FepA). The porin class of proteins generally share structural features, including the presence of beta-barrels that span the outer membrane.

Little is known regarding the iron-acquisition by *Fusobacterium* spp, and genomic comparisons are difficult since the genome of only five strains of *Fusobacterium nucleatum* have been completely sequenced and made publicly available: *F. nucleatum* subspecies *nucleatum*, strain ATCC 25586 (Kapatral et al., J. Bacteriol., 184, 2005-2018 (2002)); *Fusobacterium nucleatum* subsp. *vincentii* 3_1_36A2; *Fusobacterium nucleatum* subsp. *vincentii* 3_1_36A2; *Fusobacterium nucleatum* subsp. *animalis* 7_1; and *Fusobacterium nucleatum* subsp. *animalis* 4_8 (Tatusova T, et al. Nucleic Acids Res 42, D553-D559 (2014). No complete sequence of *Fusobacterium necrophorum* strains have been published, although there are a number of partial sequences in the NCBI database The genomic sequence of ATCC 25586 was used in a comparison with a partially sequenced genome of *F. nucleatum* subspp. *vincentii* (Kapatral et al., Genome Res., 13, 1180-1189 (2003)) to investigate differences among these two subspecies. The results suggested that there were differences between the two genomes with respect to the iron uptake systems. Although iron transport systems were discovered in both genomes, the genome of strain ATCC 25586 contains three additional iron-specific ABC transport systems. In addition, hemin receptor proteins appear to be encoded by both genomes, but while the subspp. *vincentii* isolate encodes three receptors, the genome of strain ATCC 25586 apparently encodes five such proteins. Furthermore, the feoAB genes, encoding a putative ferrous iron transport system, are only found in the genome of the subspp. *vincentii* isolate. Since both organisms are obligate anaerobes and ferrous iron is the predominant form of the metal under anaerobic conditions, strain ATCC 25586 may have a second mechanism for uptake of ferrous iron. Given the differences among these two subspecies of *F. nucleatum*, it is likely that there will be many differences among the iron uptake systems between other *Fusobacterium* species. Therefore, the *F. nucleatum* genomic data may not be useful for predicting the presence or absence of iron acquisition systems in other species of *Fusobacterium*.

*Fusobacterium necrophorum* is ubiquitous in the environment of cattle and is considered a normal inhabitant of the intestine and rumen, and is present in feces. The organism is the causative agent of both liver abscesses and footrot. The disease is rarely fatal but can result in substantial economic losses to both the producer and packer due to cost in treatment and performance losses. It is thought that liver abscessation follows a condition of ruminal acidosis which impairs the integrity of the rumen wall allowing *Fusobacterium* to transverse to the blood stream to the liver and cause abscessation.

Beyond the role of iron as an essential nutrient for microbial survival, there are now many other well-defined transitional metals that play critical roles in bacterial survival, homeostasis and pathogenesis such as iron, manganese, copper, zinc, magnesium, cobalt, and nickel (Waldron and Robinson, 2009, Nature Reviews Microbiology, 7:25-35; Porcheron, 2013, Frontiers in Cellular and Infection Microbiology 3:172-194). Iron, zinc and copper are the three most abundant divalent metal ions in mammals in descending order of concentration. The ability of a bacterium to use these transitional metals by finely regulated uptake or acquisition systems significantly contributes to the virulence of pathogenic bacteria. It is well known that bacteria within the same genus/species do not have the same uptake systems for the acquisition of transitional metals owing to the difference in pathogenicity from one strain of bacteria to another. These differences in the ability of bacteria to use different transitional metals based on expressed uptake systems may specifically direct what organ or tissue an organism can invade.

Copper is the third most prevalent transitional metal behind iron and zinc and plays a major role in many enzymatic pathways. Copper is present in every tissue of the body but is stored in its highest concentration in the liver. What role copper plays in the virulence of *Fusobacterium* is unknown. With the concentration of copper being the highest in the liver it would make sense that *Fusobacterium* has adapted some mechanism to utilize this divalent metal ion once in the liver.

In the following examples we show the expression of unique proteins that are expressed in *Fusobacterium* when grown under iron, zinc and copper chelation.

SUMMARY OF THE INVENTION

Provided herein are compositions. In one embodiment, a composition includes at least one isolated polypeptide having a molecular weight of 92 kDa to 79 kDa, 73 kDa to 63 kDa, 62 kDa to 58 kDa, or 57 kDa to 47 kDa, wherein the at least one polypeptide is isolatable from a *Fusobacterium necrophorum* when incubated in media including an iron chelator and not isolatable when grown in the media without the iron chelator; at least one isolated polypeptide having a molecular weight of 108 kDa to 98 kDa or 79 kDa to 69 kDa, wherein the at least one polypeptide is isolatable from a *Fusobacterium necrophorum* when incubated in media including an iron chelator, is expressed by the *Fusobacterium necrophorum* when incubated in media without the iron chelator and expressed at an enhanced level during growth in media including an iron chelator; and at least one protein selected from the group consisting of a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, and a polypeptide having at least 85% similarity to SEQ ID NO:53 or a fragment thereof.

In one embodiment, a composition includes isolated polypeptides having molecular weights of 92 kDa to 79 kDa, 73 kDa to 63 kDa, 62 kDa to 58 kDa, and 57 kDa to 47 kDa, wherein the polypeptides are isolatable from a *Fusobacterium necrophorum* when incubated in media including an iron chelator and not isolatable when grown in the media without the iron chelator; isolated polypeptides having molecular weights of 155 kDa to 145 kDa or 89 kDa to 79 kDa, wherein the at least one polypeptide is isolatable from a *Fusobacterium necrophorum* when incubated in media including an iron chelator and an iron-containing porphyrin and not isolatable when grown in the media without the iron chelator and iron-containing porphyrin, and not isolatable when grown in the media with the iron chelator and in the absence of the iron-containing porphyrin; and isolated polypeptides having molecular weights of 108 kDa to 98 kDa and 79 kDa to 69 kDa, wherein the polypeptides are isolatable from a *Fusobacterium necrophorum* when incubated in media including an iron chelator, are expressed by the *Fusobacterium necrophorum* when incubated in media without the iron chelator and expressed at an enhanced level during growth in media including an iron chelator.

In one embodiment, a composition includes at least one isolated polypeptide having a molecular weight of 131 kDa to 121 kDa, 79 kDa to 69 kDa, or 33 kDa to 23 kDa, wherein the at least one polypeptide is isolatable from a *Fusobacterium necrophorum* when incubated in media including a copper chelator and not isolatable when grown in the media without the copper chelator; and at least one isolated polypeptide having a molecular weight of 93 kDa to 83 kDa, 65 kDa to 55 kDa, or 52 kDa to 42 kDa, wherein the at least one polypeptide is isolatable from the *Fusobacterium necrophorum* when incubated in media including a copper chelator, is expressed by the *Fusobacterium necrophorum* when incubated in media without the copper chelator and expressed at an enhanced level during growth in media including an copper chelator.

In one embodiment, a composition includes at least one isolated polypeptide having a molecular weight of 131 kDa to 121 kDa, 108 kDa to 98 kDa, 92 kDa to 64 kDa, 53 kDa to 43 kDa, or 33 kDa to 19 kDa, wherein the polypeptide is isolatable from a *Fusobacterium necrophorum* when incubated in media including a zinc chelator and not isolatable when grown in the media without the zinc chelator; and at least one isolated polypeptide having a molecular weight of 79 kDa to 69 kDa or 65 kDa to 55 kDa, wherein the at least one polypeptide is isolatable from the *Fusobacterium necrophorum* when incubated in media including a zinc chelator, is expressed by the *Fusobacterium necrophorum* when incubated in media without the zinc chelator and expressed at an enhanced level during growth in media including the zinc chelator.

In one embodiment, a composition includes isolated polypeptides having molecular weights of 131 kDa to 121 kDa, 79 kDa to 69 kDa, and 33 kDa to 23 kDa, wherein the polypeptides are isolatable from a *Fusobacterium necrophorum* when incubated in media including a copper chelator and not isolatable when grown in the media without the copper chelator; and isolated polypeptides having molecular weights of 93 kDa to 83 kDa, 65 kDa to 55 kDa, and 52 kDa to 42 kDa, wherein the polypeptides are isolatable from the *Fusobacterium necrophorum* when incubated in media including a copper chelator, are expressed by the *Fusobacterium necrophorum* when incubated in media without the copper chelator and expressed at an enhanced level during growth in media including an copper chelator.

In one embodiment, a composition includes isolated polypeptides having molecular weights of 131 kDa to 121 kDa, 108 kDa to 98 kDa, 92 kDa to 64 kDa, 53 kDa to 43 kDa, and 33 kDa to 19 kDa, wherein the polypeptides are isolatable from a *Fusobacterium necrophorum* when incubated in media including a zinc chelator and not isolatable when grown in the media without the zinc chelator; and isolated polypeptides having molecular weights of 79 kDa to 69 kDa and 65 kDa to 55 kDa, wherein the polypeptides are isolatable from the *Fusobacterium necrophorum* when incubated in media including a zinc chelator, are expressed by the *Fusobacterium necrophorum* when incubated in media without the zinc chelator and expressed at an enhanced level during growth in media including the zinc chelator.

In one embodiment, a composition can further include a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, a polypeptide having at least 85% similarity to SEQ ID NO:53 or a fragment thereof, or a combination thereof.

In one embodiment, a composition includes an isolated polypeptide having at least 85% similarity to SEQ ID NO:2, 4, 6, 8, 10, 12, 14, 16, 18, 20, 22, 24, 26, 28, 30, 32, 34, 35, 36, 37, 38, 39, 40, 41, 43, 44, 45, 46, 47, 48, 49, 50, 51, 52, 53, or 54, or a fragment thereof.

In one embodiment, a composition can further include isolated polypeptides having molecular weights of 340 kDa to 330 kDa, 247 kDa to 237 kDa, 247 kDa to 237 kDa, 235 kDa to 215 kDa, 120 kDa to 110 kDa, 51 kDa to 25 kDa, and 21 kDa to 11 kDa.

A composition can further include a pharmaceutically acceptable carrier, such as an adjuvant. In one embodiment, a composition protects an animal against challenge with *Fusobacterium necrophorum.*

Also provided herein are methods. In one embodiment, a method includes administering to a subject an amount of a composition described herein effective to induce the subject to produce antibody that specifically binds to at least one polypeptide of the composition.

In one embodiment, a method is for treating an infection in a subject, and the method includes administering an effective amount of a composition described herein to a subject having or at risk of having an infection caused by a *Fusobacterium* spp.

In one embodiment, a method is for treating a symptom in a subject, and the method includes administering an effective amount of a composition described herein to a subject having or at risk of having an infection caused by a *Fusobacterium* spp.

In one embodiment, a method is for decreasing colonization in a subject, and the method includes administering an effective amount of a composition described herein to a subject colonized by a *Fusobacterium* spp.

In one embodiment, a method is for treating an infection in a subject, and the method includes administering an effective amount of a composition to a subject having or at risk of having an infection caused by a *Fusobacterium* spp., wherein the composition includes antibody that specifically binds to a polypeptide described herein. In one embodiment, a method is for treating a symptom in a subject, and the method includes administering an effective amount of a composition to a subject having or at risk of having an infection caused by a *Fusobacterium* spp., wherein the composition includes antibody that specifically binds to a polypeptide described herein. In one embodiment, an infection causes a condition selected from metritis, hepatic abscesses, and foot rot.

In one embodiment, a method is for decreasing colonization in a subject, and the method includes administering an effective amount of a composition to a subject colonized by a *Fusobacterium* spp., wherein the composition includes antibody that specifically binds to a polypeptide described herein.

Also provided are kits. In one embodiment, a kit is for detecting antibody that specifically binds a polypeptide, including in separate containers an isolated polypeptide described herein, and a reagent that detects an antibody that specifically binds the polypeptide. In one embodiment, a kit is for detecting a polypeptide, including in separate containers an antibody that specifically binds an isolated polypeptide described herein, and a second reagent that specifically binds the polypeptide.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2A shows SDS-PAGE gel with the banding profile of *Fusobacterium necrophorum* grown in mTSB containing Naringenin and Catechin. Lane 1, Molecular Weight Marker; Lane 2, 100 μM Naringenin in mTSB. Lane 3, 200 μM Catechin in mTSB. Brackets surround unique 60 kDa protein in lane 3 resulting from growth in the presence of the metal chelator Catechin. FIG. 2B shows the corresponding Western Blot probed with the convalescent bovine sera of Example 7. Lane 1, 100 μM Naringenin; Lane 2, 200 μM Catechin. Note the intense sero-reactive 60 kDa protein of lane 2 of FIG. 2B in contrast to lane 1 of FIG. B.

FIG. 4A shows an SDS-PAGE gel with the banding profile of *Fusobacterium necrophorum* grown in mTSB containing Quercetin and TPEN. Lane 1, Molecular Weight Marker; Lane 2, 100 μM Quercetin in mTSB, Lane 3, 50 μM TPEN in mTSB, Lane 4, 15 μg/ml 2,2-dipyridyl in mTSB. Brackets surround unique 81 kDa protein up-regulated during grown in the presence of the zinc chelator TPEN (Lane 3) compared to Lanes 2 and 4 grown with Quercetin and 2,2-dipyridyl, respectively. FIG. 4B shows the corresponding Western Blot probed with the convalescent bovine sera of Example 7. Lane 1,100 μM Quercetin in mTSB; Lane 2, 50 μM TPEN in mTSB, Lane 3, 15 μg/ml 2,2-dipyridyl in mTSB. Note the intense sero-reactive 81 kDa protein of lane 2 grown in the presence TPEN in contrast to Lanes 1 and 3 grown in Quercetin and 2,2-dipyridyl.

FIG. 7A shows a Western Blot of the serological response to the rZinc protein. Lane 1, Molecular Weight Marker; Lane 2, Fuso-SRP Extract probed with sera derived from the 250 μg rZinc vaccine of Group C; Lane 3, rZinc protein probed with sera derived from the 100 μg rZinc vaccine of Group B; Lane 4, rZinc protein probed with sera derived from the 250 μg rZinc vaccine of Group C; Lane 5, rHemin protein probed sera derived from the 250 μg rZinc vaccine of Group C. FIG. 7B shows a Fuso-SRP Extract probed with sera derived from the combination vaccine of Group D at 10 μg Fuso-SRP Extract plus 50 μg rZinc protein. Lane 1, Fuso SRP extract probed with the sera derived from the combination vaccine of group D. Lane 2, rZinc protein probed with sera derived from the combination vaccine of Group D.

FIG. 14-50. Amino acid sequences and examples of nucleotide sequences encoding the amino acid sequences.

FIG. 51. CLUSTL Alignment of polypeptides using Clustl Omega. * (asterisk), indicates positions which have a single, fully conserved residue.

DETAILED DESCRIPTION OF EXEMPLARY EMBODIMENTS

Polypeptides

Figure 1:
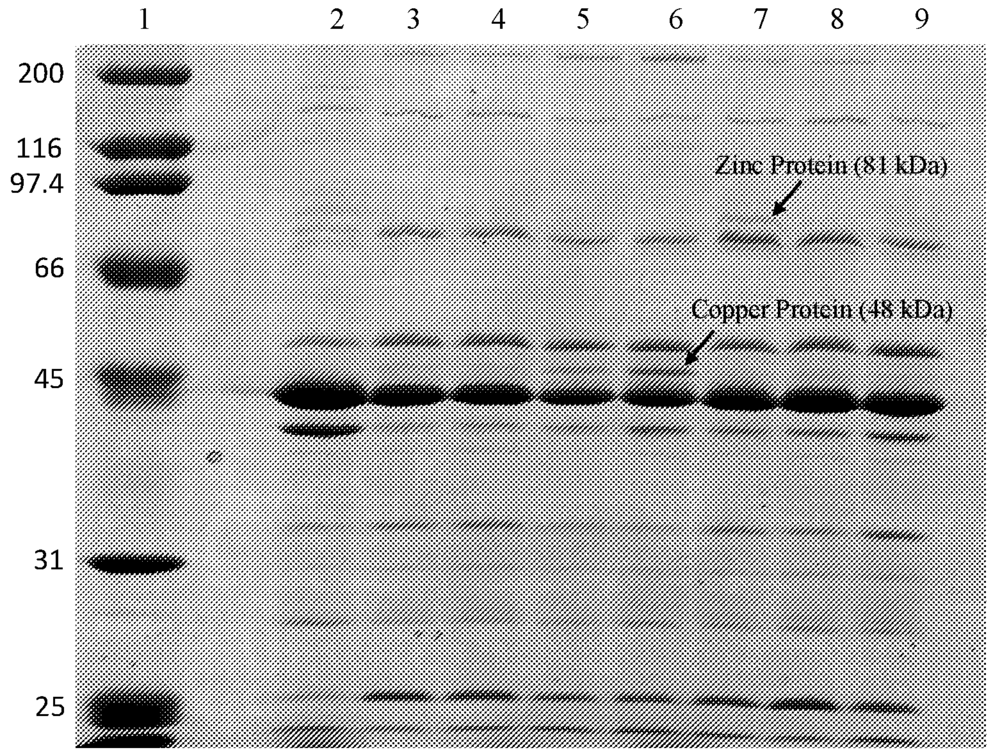
FIG. 1. SDS-PAGE of Gel image of extracted proteins derived from *Fusobacterium necrophorum* grown under metal-depleted growth conditions using different chelators. Lane 1-Molecular Weight Marker; Lane 2-15 μg/ml 2,2-dipyridyl in mTSB; Lane 3-100 μM Naringenin in mTSB; Lane 4-200 μM Catechin in mTSB; Lane 5-50 μM Quercetin in mTSB; Lane 6-100 μM Quercetin in mTSB; Lane 7-50 μM TPEN in mTSB; Lane 8-50 μM ammonium tetrathiomolybdate in mTSB and Lane 9-15 μg/ml 2,2-dipyridyl in pBHI. Lane 6 shows the expression of a novel copper protein expressed when *Fusobacterium necrophorum* when grown under copper chelation and lane 7 shows a novel zinc protein when *Fusobacterium necrophorum* was grown under zinc chelation.

In one aspect, this disclosure provides polypeptides and compositions including polypeptides. As used herein, "polypeptide" refers to a polymer of amino acids linked by peptide bonds. Thus, for example, the terms peptide, oligopeptide, protein, and enzyme are included within the definition of polypeptide. This term also includes polypeptides that may include one or more post-expression modifications of the polypeptide such as, for example, a glycosylation, an acetylation, a phosphorylation, and the like. The term polypeptide does not connote a specific length of a polymer of amino acids. A polypeptide may be isolatable directly from a natural source or can be prepared with the aid of recombinant, enzymatic, or chemical techniques. In the case of a polypeptide that is naturally occurring, such a polypeptide is typically isolated.

An "isolated" polypeptide is one that has been removed from its natural environment. For instance, an isolated polypeptide is a polypeptide that has been removed from the cytoplasm or from the membrane of a cell, and many of the polypeptides, nucleic acids, and other cellular material of its natural environment are no longer present.

A polypeptide characterized as "isolatable" from a particular source is a polypeptide that, under appropriate conditions, is produced by the identified source, although the polypeptide may be obtained from alternate sources using, for example, conventional recombinant, chemical, or enzymatic techniques. Thus, characterizing a polypeptide as "isolatable" from a particular source does not imply any specific source from which the polypeptide must be obtained or any particular conditions or processes under which the polypeptide must be obtained.

A "purified" polypeptide is one that is at least 60% free, preferably at least 75% free, and most preferably at least 90% free from other components with which they are naturally associated. Polypeptides that are produced outside the organism in which they naturally occur, e.g., through chemical or recombinant means, are considered to be isolated and purified by definition, since they were never present in a natural environment.

Generally, a polypeptide may be characterized by molecular weight, amino acid sequence, nucleic acid that encodes the polypeptide, immunological activity, or any combination of two or more such characteristics. The molecular weight of a polypeptide, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence. Unless indicated otherwise, reference to molecular weight refers to molecular weight as determined by resolving a polypeptide using an SDS polyacrylamide gel having a stacking gel of about 4% and a resolving gel of about 10% under reducing and denaturing conditions. A molecular weight of a protein determined by SDS-PAGE is also referred to herein as an apparent molecular weight. In one embodiment, the molecular weight of a protein identified by SDS-PAGE includes molecular weights of 1, 2, 3, 4, or 5 kDa above and below the stated value.

The polypeptides described herein may be metal-regulated. As used herein, a "metal-regulated polypeptide" is a polypeptide that is expressed by a microbe at a greater level when the microbe is grown in low metal conditions compared to when the same microbe is grown in high metal conditions. Low metal and high metal conditions are described herein. For instance, certain metal-regulated polypeptides produced by *Fusobacterium* spp. are not expressed at detectable levels during growth of the microbe in high metal conditions but are expressed at detectable levels during growth in low metal conditions. In one embodiment, certain metal-regulated polypeptides produced by *Fusobacterium* spp. are not expressed at detectable levels during growth of the microbe in high metal conditions but are expressed at detectable levels during growth in low metal conditions that also include hemin as a supplement. Table 1 summarizes the expression of proteins in the absence of different metals.

TABLE 1

| Protein Analysis of Isolate 1694 | The Comparison of MW in kDA of the vaccine compositions of *Fusobacterium necrophorum* 1694 as examined by SDS-PAGE and MALDI-TOF-MS under various conditions of metal ion restriction Molecular Weights in Kilodaltons (kDa) | | | | | | | | | | | | | | | | | | | | | | |
|---|---|---|---|---|---|---|---|---|---|---|---|---|---|---|---|---|---|---|---|---|---|---|---|
| SDS-PAGE | | | | | | | | | | | | | | | | | | | | | | | |
| Iron-deplete | | | | | | | | 103* | 88 | | | 74* | 68 | 60 | 52 | | | | | | | | | |
| Iron-deplete, hemin supplemented | | | | | 150 | | | 103* | 88 | 84 | | 74* | 68 | 60 | 52 | | | | | | | | |
| copper-deplete | | | | | | 126 | | | 88* | | | 74 | | 60* | | 48* | | | | | | 28 | | |
| zinc-deplete | | | | | | 126 | | 103 | 88 | | 81 | 74* | 68 | 60* | | 48 | | | | | | 28 | 24 | |
| MALDI-TOF-MS | | | | | | | | | | | | | | | | | | | | | | | | |
| Iron-deplete | | | | | | | | | | | | | | | | | | | | | | | | |
| iron deplete, hemin supplemented | | | | | | | | | | 84,309 | | | | | | | | | | | | | | |
| copper-deplete | | | | | | | | | | | | | | | | 48,413 | | | | | | | | |
| zinc-deplete | | | | | | | | | | | 81,723 | | | | | | | | | | | | | |
| Proteins Present in All Conditions | 335 | 243 | 230 | 220 | | | 115 | | | | | | | | | | 45 | 42 | 38 | 35 | 30 | | | 16 |

Protein Analysis: The molecular weights of the metal regulated proteins and porins of *Fusobacterium necrophorum* were analyzed by single dimension SDS-PAGE and MALDI-TOF-MS.

Note:

The organism was grow under conditions of metal ion restriction i.e., iron-restriction; iron restriction with hemin supplementation, zinc restriction and copper restriction.

*protein is additionally enhanced under these conditions.

Examples of metal-regulated polypeptides isolatable from a *Fusobacterium* spp., such as *F. necrophorum*, after growth in low iron conditions include metal-regulated polypeptides having molecular weights of 92 kDa to 79 kDa, 73 kDa to 63 kDa, 62 kDa to 58 kDa, and 57 kDa to 47 kDa. Specific examples of metal-regulated polypeptides isolatable from a *Fusobacterium* spp., such as *F. necrophorum*, after growth in low iron conditions include polypeptides of 88 kDa, 68 kDa, 60 kDa, and 52 kDa. In one embodiment, the low iron condition is growth in the presence of 2,2'-dipyridyl.

Examples of metal-regulated polypeptides isolatable from a *Fusobacterium* spp., such as *F. necrophorum*, after growth in low iron conditions supplemented with an iron-containing porphyrin, such as hemin, include metal-regulated polypeptides having molecular weights of 155 kDa to 145 kDa and 89 kDa to 79 kDa. Specific examples of this type of metal-regulated polypeptide isolatable from a *Fusobacterium* spp. after growth in low iron conditions in the presence of an iron-containing porphyrin include polypeptides of 150 kDa and 84 kDa. In one embodiment, the low iron condition is growth in the presence of 2,2'-dipyridyl and hemin.

Examples of metal-regulated polypeptides isolatable from a *Fusobacterium* spp., such as *F. necrophorum*, after growth in low copper conditions include metal-regulated polypeptides having molecular weights of 131 kDa to 121 kDa, 79 kDa to 69 kDa, and 33 kDa to 23 kDa. Specific examples of metal-regulated polypeptides isolatable from a *Fusobacterium* spp., such as *F. necrophorum*, after growth in low copper conditions include polypeptides of 126 kDa, 74 kDa, and 28 kDa. In one embodiment, the low copper condition is growth in the presence of catechin. In one embodiment, the low copper condition is growth in the presence of quercetin.

Examples of metal-regulated polypeptides isolatable from a *Fusobacterium* spp., such as *F. necrophorum*, after growth in low zinc conditions include metal-regulated polypeptides having molecular weights of 131 kDa to 121 kDa, 108 kDa to 98 kDa, 92 kDa to 64 kDa, 53 kDa to 43 kDa, and 33 kDa to 19 kDa. Specific examples of metal-regulated polypeptides isolatable from a *Fusobacterium* spp., such as *F. necrophorum*, after growth in low zinc conditions include polypeptides of 126 kDa, 103 kDa, 88 kDa, 81 kDa, 68 kDa, 48 kDa, 28 kDa, and 24 kDa. In one embodiment, the low zinc condition is growth in the presence of TPEN.

In one embodiment, polypeptides described herein are expressed at detectable levels during growth of the microbe in high metal conditions but more of the polypeptide is expressed during growth in low metal conditions. The expression of such polypeptides is referred to herein as "enhanced" during growth in low metal conditions. Typically, the increase in expression of a polypeptide during growth in low metal conditions is between 20% and 500% compared to the expression of the polypeptide during growth in high metal conditions.

Examples of metal-regulated polypeptides having enhanced expression and isolatable from *F. necrophorum* after growth in low iron conditions include metal-regulated polypeptides having molecular weights of 108 kDa to 98 kDa and 79 kDa to 69 kDa. Specific examples of metal-regulated polypeptides isolatable from a *Fusobacterium* spp., such as *F. necrophorum*, after growth in low iron conditions include polypeptides of 103 kDa and 74 kDa.

Examples of metal-regulated polypeptides having enhanced expression and isolatable from *F. necrophorum* after growth in low copper conditions include metal-regulated polypeptides having molecular weights of 93 kDa to 83 kDa, 65 kDa to 55 kDa, and 52 kDa to 42 kDa. Specific examples of metal-regulated polypeptides isolatable from a *Fusobacterium* spp., such as *F. necrophorum*, after growth in low copper conditions include polypeptides of 88 kDa, 60 kDa, and 48 kDa.

Examples of metal-regulated polypeptides having enhanced expression and isolatable from *F. necrophorum* after growth in low zinc conditions include metal-regulated polypeptides having molecular weights of 79 kDa to 69 kDa, and 65 kDa to 55 kDa. Specific examples of metal-regulated polypeptides isolatable from a *Fusobacterium* spp., such as *F. necrophorum*, after growth in low zinc conditions include polypeptides of 73 kDa and 60 kDa.

This disclosure also describes certain polypeptides that are not metal-regulated. Such polypeptides are expressed in the presence of a metal ion such as, for example, in the presence of ferric chloride, and also expressed when grown in low iron conditions. Examples of this type of polypeptide isolatable from *Fusobacterium* spp., such as *F. necrophorum*, have molecular weights 340 kDa to 330 kDa, 247 kDa to 237 kDa, 235 kDa to 215 kDa, 120 kDa to 110 kDa, 51 kDa to 25 kDa, and 21 kDa to 11 kDa. Examples of molecular weights of this type of polypeptide include 335 kDa, 243 kDa, 230 kDa, 220 kDa, 115 kDa, 45 kDa, 42 kDa, 38 kDa, 35 kDa, 30 kDa, and 16 kDa.

Other proteins provided herein include a protein at SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54 (FIGS. 14-50).

In one embodiment, a polypeptide disclosed herein, for instance at SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54 lacks one or more amino acids from the amino terminus, e.g., the polypeptide lacks a signal sequence. Thus, a fragment can lack at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, or at least 63 amino acids from the amino terminus of the polypeptide.

For instance, in one embodiment a polypeptide includes the following amino acids of SEQ ID NO:2; amino acids 2 through 423, amino acids 3 through 423, amino acids 4 through 423, amino acids 5 through 423, amino acids 6 through 423, amino acids 7 through 423, amino acids 8 through 423, amino acids 9 through 423, amino acids 10 through 423, amino acids 11 through 423, amino acids 12 through 423, amino acids 13 through 423, amino acids 14 through 423, amino acids 15 through 423, amino acids 16 through 423, amino acids 17 through 423, amino acids 18 through 423, amino acids 19 through 423, amino acids 20 through 423, amino acids 21 through 423, amino acids 22 through 423, amino acids 23 through 423, amino acids 24 through 423, amino acids 25 through 423, amino acids 26 through 423, amino acids 27 through 423, amino acids 28 through 423, amino acids 29 through 423, amino acids 30 through 423, amino acids 31 through 423, amino acids 32 through 423, amino acids 33 through 423, amino acids 34 through 423, amino acids 35 through 423, amino acids 36 through 423, amino acids 37 through 423, amino acids 38 through 423, amino acids 39 through 423, amino acids 40 through 423, amino acids 41 through 423, amino acids 42 through 423, amino acids 43 through 423, amino acids 44 through 423, amino acids 45 through 423, amino acids 46 through 423, amino acids 47 through 423, amino acids 48 through 423, amino acids 49 through 423, amino acids 50 through 423, amino acids 51 through 423, amino acids 52 through 423, amino acids 53 through 423, amino acids 54 through 423, amino acids 55 through 423, amino acids 56 through 423, amino acids 57 through 423, amino acids 58 through 423, amino acids 59 through 423, amino acids 60 through 423, amino acids 61 through 423, amino acids 62 through 423, or amino acids 63 through 423.

In one embodiment, a polypeptide includes the following amino acids of SEQ ID NO:4; amino acids 2 through 714, amino acids 3 through 714, amino acids 4 through 714, amino acids 5 through 714, amino acids 6 through 714, amino acids 7 through 714, amino acids 8 through 714, amino acids 9 through 714, amino acids 10 through 714, amino acids 11 through 714, amino acids 12 through 714, amino acids 13 through 714, amino acids 14 through 714, amino acids 15 through 714, amino acids 16 through 714, amino acids 17 through 714, amino acids 18 through 714, amino acids 19 through 714, amino acids 20 through 714, amino acids 21 through 714, amino acids 22 through 714, amino acids 23 through 714, amino acids 24 through 714, amino acids 25 through 714, amino acids 26 through 714, amino acids 27 through 714, amino acids 28 through 714, amino acids 29 through 714, amino acids 30 through 714, amino acids 31 through 714, amino acids 32 through 714, amino acids 33 through 714, amino acids 34 through 714, amino acids 35 through 714, amino acids 36 through 714, amino acids 37 through 714, amino acids 38 through 714, amino acids 39 through 714, amino acids 40 through 714, amino acids 41 through 714, amino acids 42 through 714, amino acids 43 through 714, amino acids 44 through 714, amino acids 45 through 714, amino acids 46 through 714, amino acids 47 through 714, amino acids 48 through 714, amino acids 49 through 714, amino acids 50 through 714, amino acids 51 through 714, amino acids 52 through 714, amino acids 53 through 714, amino acids 54 through 714, amino acids 55 through 714, amino acids 56 through 714, amino acids 57 through 714, amino acids 58 through 714, amino acids 59 through 714, amino acids 60 through 714, amino acids 61 through 714, amino acids 62 through 714, or amino acids 63 through 714.

In one embodiment, a polypeptide includes the following amino acids of SEQ ID NO:6; amino acids 2 through 736, amino acids 3 through 736, amino acids 4 through 736, amino acids 5 through 736, amino acids 6 through 736, amino acids 7 through 736, amino acids 8 through 736, amino acids 9 through 736, amino acids 10 through 736, amino acids 11 through 736, amino acids 12 through 736, amino acids 13 through 736, amino acids 14 through 736, amino acids 15 through 736, amino acids 16 through 736, amino acids 17 through 736, amino acids 18 through 736, amino acids 19 through 736, amino acids 20 through 736, amino acids 21 through 736, amino acids 22 through 736, amino acids 23 through 736, amino acids 24 through 736, amino acids 25 through 736, amino acids 26 through 736, amino acids 27 through 736, amino acids 28 through 736, amino acids 29 through 736, amino acids 30 through 736, amino acids 31 through 736, amino acids 32 through 736, amino acids 33 through 736, amino acids 34 through 736, amino acids 35 through 736, amino acids 36 through 736, amino acids 37 through 736, amino acids 38 through 736, amino acids 39 through 736, amino acids 40 through 736, amino acids 41 through 736, amino acids 42 through 736, amino acids 43 through 736, amino acids 44 through 736, amino acids 45 through 736, amino acids 46 through 736, amino acids 47 through 736, amino acids 48 through 736, amino acids 49 through 736, amino acids 50 through 736, amino acids 51 through 736, amino acids 52 through 736, amino acids 53 through 736, amino acids 54 through 736, amino acids 55 through 736, amino acids 56 through 736, amino acids 57 through 736, amino acids 58 through 736, amino acids 59 through 736, amino acids 60 through 736, amino acids 61 through 736, amino acids 62 through 736, or amino acids 63 through 736.

In one embodiment, a polypeptide includes the following amino acids of SEQ ID NO:34; amino acids 2 through 638, amino acids 3 through 638, amino acids 4 through 638, amino acids 5 through 638, amino acids 6 through 638, amino acids 7 through 638, amino acids 8 through 638, amino acids 9 through 638, amino acids 10 through 638, amino acids 11 through 638, amino acids 12 through 638, amino acids 13 through 638, amino acids 14 through 638, amino acids 15 through 638, amino acids 16 through 638, amino acids 17 through 638, amino acids 18 through 638, amino acids 19 through 638, amino acids 20 through 638, amino acids 21 through 638, amino acids 22 through 638, amino acids 23 through 638, amino acids 24 through 638, amino acids 25 through 638, amino acids 26 through 638, amino acids 27 through 638, amino acids 28 through 638, amino acids 29 through 638, amino acids 30 through 638, amino acids 31 through 638, amino acids 32 through 638, amino acids 33 through 638, amino acids 34 through 638, amino acids 35 through 638, amino acids 36 through 638, amino acids 37 through 638, amino acids 38 through 638, amino acids 39 through 638, amino acids 40 through 638, amino acids 41 through 638, amino acids 42 through 638, amino acids 43 through 638, amino acids 44 through 638, amino acids 45 through 638, amino acids 46 through 638, amino acids 47 through 638, amino acids 48 through 638, amino acids 49 through 638, amino acids 50 through 638, amino acids 51 through 638, amino acids 52 through 638, amino acids 53 through 638, amino acids 54 through 638, amino acids 55 through 638, amino acids 56 through 638, amino acids 57 through 638, amino acids 58 through 638, amino acids 59 through 638, amino acids 60 through 638, amino acids 61 through 638, amino acids 62 through 638, or amino acids 63 through 638.

In one embodiment, a polypeptide includes the following amino acids of SEQ ID NO:53; amino acids 2 through 1420, amino acids 3 through 1420, amino acids 4 through 1420, amino acids 5 through 1420, amino acids 6 through 1420, amino acids 7 through 1420, amino acids 8 through 1420, amino acids 9 through 1420, amino acids 10 through 1420, amino acids 11 through 1420, amino acids 12 through 1420, amino acids 13 through 1420, amino acids 14 through 1420, amino acids 15 through 1420, amino acids 16 through 1420, amino acids 17 through 1420, amino acids 18 through 1420, amino acids 19 through 1420, amino acids 20 through 1420, amino acids 21 through 1420, amino acids 22 through 1420, amino acids 23 through 1420, amino acids 24 through 1420, amino acids 25 through 1420, amino acids 26 through 1420, amino acids 27 through 1420, amino acids 28 through 1420, amino acids 29 through 1420, amino acids 30 through 1420, amino acids 31 through 1420, amino acids 32 through 1420, amino acids 33 through 1420, amino acids 34 through 1420, amino acids 35 through 1420, amino acids 36 through 1420, amino acids 37 through 1420, amino acids 38 through 1420, amino acids 39 through 1420, amino acids 40 through 1420, amino acids 41 through 1420, amino acids 42 through 1420, amino acids 43 through 1420, amino acids 44 through 1420, amino acids 45 through 1420, amino acids 46 through 1420, amino acids 47 through 1420, amino acids 48 through 1420, amino acids 49 through 1420, amino acids 50 through 1420, amino acids 51 through 1420, amino acids 52 through 1420, amino acids 53 through 1420, amino acids 54 through 1420, amino acids 55 through 1420, amino acids 56 through 1420, amino acids 57 through 1420, amino acids 58 through 1420, amino acids 59 through 1420, amino acids 60 through 1420, amino acids 61 through 1420, amino acids 62 through 1420, or amino acids 63 through 1420.

Additional examples of polypeptides include recombinantly-produced versions of polypeptides described herein. A recombinantly-produced polypeptide may include the entire amino acid sequence translatable from an mRNA transcript. Alternatively, a recombinantly-produced metal-regulated polypeptide can include a fragment of the entire translatable amino acid sequence. For example, a recombinantly-produced metal-regulated polypeptide may lack a cleavable sequence at either terminal of the polypeptide—e.g., a cleavable signal sequence at the amino terminus of the polypeptide.

Whether a polypeptide is a metal-regulated polypeptide or a non-metal-regulated polypeptide can be determined by methods useful for comparing the presence of polypeptides, including, for example, gel filtration, gel electrophoresis including sodium dodecyl sulfate-polyacrylamide gel electrophoresis (SDS-PAGE), capillary electrophoresis, mass spectrometry, isobaric tags for relative and absolute quantification (iTRAQ), and liquid chromatography including HPLC. Separate cultures of a microbe can be grown under high metal conditions and under low metal conditions, polypeptides may be isolated as described herein, and the polypeptides present in each culture can be resolved and compared. Typically, an equal amount of polypeptides from each culture is used. Preferably, the polypeptides can be resolved using an SDS polyacrylamide gel having a stacking gel of about 4% and a resolving gel of about 10% under reducing and denaturing conditions. For instance, 30 micrograms (μg) of total polypeptide from each culture may be used and loaded into wells of a gel. After running the gel and staining the polypeptides with Coomassie Brilliant Blue, the two lanes can be compared. When determining whether a polypeptide is or is not expressed at a detectable level, 30 μg of total polypeptide from a culture is resolved on an SDS-PAGE gel and stained with Coomassie Brilliant Blue using methods known in the art. A polypeptide that can be visualized by eye is considered to be expressed at a detectable level, while a polypeptide that cannot be visualized by eye is considered to not be expressed at a detectable level.

Alternatively, whether a polypeptide is a metal-regulated polypeptide or a non-metal-regulated polypeptide can be determined using microarray-based gene expression analysis. Separate cultures of a microbe can be grown under high metal conditions and under low metal conditions, RNA can be extracted from cells of each culture, and differences in RNA expression in cells grown in high metal conditions versus RNA expression in cells grown in low metal conditions can be detected and compared. For example, labeled cDNA can be prepared from 8-10 μg of bacterial RNA using established protocols. The labeled cDNA can be applied to a microarray of the *Fusobacterium* spp. genome. Such microarrays are commercially available and evaluating gene expression using such arrays is routine.

The polypeptides described herein may have immunological activity. "Immunological activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced. The immunological activity may be protective. "Protective immunological activity" refers to the ability of a polypeptide to elicit an immunological response in an animal that inhibits or limits infection by *Fusobacterium* spp. Whether a polypeptide has protective immunological activity can be determined by methods known in the art such as, for example, methods described in Examples 2 and 7-11. A polypeptide may have seroactive activity. As used herein, "seroactive activity" refers to the ability of a candidate polypeptide to react with antibody present in convalescent serum from an animal infected with a *Fusobacterium* spp.

A polypeptide as described herein may have the characteristics of a polypeptide expressed by a reference microbe—i.e., a reference polypeptide. The characteristics can include, for example, molecular weight, mass fingerprint, amino acid sequence, or any combination thereof. The reference microbe can be a gram negative, preferably a member of the family Bacteroidaceae, such as the genus *Fusobacterium*. A member of the genus *Fusobacterium* is also referred to herein as *Fusobacterium* spp. Examples of *Fusobacterium* spp. include *F. necrophorum* (including *F. necrophorum* subsp. *necrophorum* and *F. necrophorum* subsp. *funduliforme*), *F. nucleatum, F. ulcercans, F. russi, F. varium, F. mortiferum, F. gonidiaformans, F. canifelinum; F. necrogenes*; and *F. naviforme*. An example of a representative strain is *F. necrophorum* 1694.

In one embodiment, a candidate polypeptide can be considered to be a polypeptide as described herein if it has an amino acid sequence that is structurally similar, as described in detail below, to a reference amino acid sequence disclosed herein, for instance, SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54, or a fragment thereof, such as a fragment that lacks one or more amino acids from the amino terminus. In one embodiment, such a polypeptide is metal-regulated when expressed by a *Fusobacterium* spp., such as *F. necrophorum* 1694.

As used herein, a polypeptide may be "structurally similar" to a reference polypeptide if the amino acid sequence of the polypeptide possesses a specified amount of sequence similarity and/or sequence identity compared to the reference polypeptide. A polypeptide also may be "structurally similar" to a reference polypeptide if the polypeptide exhibits a mass fingerprint possessing a specified amount of identity compared to a comparable mass fingerprint of the reference polypeptide. Thus, a polypeptide may be "structurally similar" to a reference polypeptide if, compared to the reference polypeptide, it possesses a sufficient level of amino acid sequence identity, amino acid sequence similarity, or a combination thereof.

Polypeptide Sequence Similarity and Polypeptide Sequence Identity

Structural similarity of two polypeptides can be determined by aligning the residues of the two polypeptides (for example, a candidate polypeptide and any appropriate reference polypeptide described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference polypeptide may be a polypeptide described herein or any known metal-regulated polypeptide, as appropriate. A candidate polypeptide is the polypeptide being compared to the reference polypeptide. A candidate polypeptide can be isolated, for example, from a microbe, or can be produced using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al. (*FEMS Microbiol Lett,* 174:247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a polypeptide containing deletions or additions of one or more contiguous or noncontiguous amino acids that do not eliminate a functional activity—such as, for example, immunological activity—of the polypeptide are also contemplated.

Thus, as used herein, reference to a polypeptide as described herein and/or reference to the amino acid sequence of one or more SEQ ID NOs can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to a polypeptide as described herein and/or reference to the amino acid sequence of one or more SEQ ID NOs can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

FIG. 51 shows cross-species sequence alignment for polypeptides having the amino acid sequences shown in SEQ ID NO:2, 4 and 6 (also referred to herein as proteins FT, FQ, and FN, respectively). The alignment indicates amino acids that are conserved in the variants of each polypeptide across different *Fusobacterium* species. The alignment also shows regions of variability in the variants of each polypeptide across the different *Fusobacterium* species. A person of ordinary skill in the art can deduce from such data regions of the polypeptide in which substitutions, particularly conservative substitutions, may be permitted without unduly affecting biological activity of the modified polypeptide. Further, the skilled person can use readily available algorithms, such as Clustl Omega, to produce alignments with related proteins and identify regions of conservation and variability.

Consequently, a polypeptide as described herein can include certain variants including, for example, homologous polypeptides that originate—biologically and/or recombinantly—from microbial species or strains other than the microbial species or strain from which the polypeptide was originally isolated and/or identified.

A polypeptide as described herein also can be designed to provide one or more additional sequences such as, for example, the addition of coding sequences for added C-terminal and/or N-terminal amino acids that may facilitate purification by trapping on columns or use of antibodies. Such tags include, for example, histidine-rich tags that allow purification of polypeptides on nickel columns. Such gene modification techniques and suitable additional sequences are well known in the molecular biology arts. A polypeptide as described herein also may be designed so that certain amino acids at the C-terminal and/or N-terminal are deleted.

A "modification" of a polypeptide as described herein includes a polypeptide (or an analog thereof such as, e.g., a fragment thereof) that is chemically or enzymatically derivatized at one or more constituent amino acids. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified polypeptides as described herein may retain the biological activity—such as, for example, immunological activity—of the unmodified polypeptide or may exhibit a reduced or increased biological activity compared to the unmodified polypeptide.

A polypeptide as described herein (including a biologically active analog thereof and/or a modification thereof) can include a native (naturally occurring), a recombinant, a chemically synthesized, or an enzymatically synthesized polypeptide. For example, a polypeptide as described herein may be prepared by isolating the polypeptide from a natural source or may be prepared recombinantly by conventional methods including, for example, preparation as fusion proteins in bacteria or other host cells.

A polypeptide expressed by a reference microbe can be obtained by growing the reference microbe under low metal conditions as described herein and the subsequent isolation of a polypeptide by the processes disclosed herein. Alternatively, a polypeptide expressed by a reference microbe can be obtained by identifying coding regions expressed at higher levels when the microbe is grown in low metal conditions—i.e., metal-regulated. A metal-regulated coding region can be cloned and expressed, and the expressed metal-regulated polypeptide may be identified by the processes described herein. A candidate polypeptide can be isolatable from a microbe or identified from a microbe, preferably a gram negative microbe, more preferably, a member of the family Bacteroidaceae, such as the genus *Fusobacterium*, including *F. necrophorum* (e.g., *F. necrophorum* subsp. *necrophorum* and *F. necrophorum* subsp. *funduliforme*), *F. nucleatum, F. ulcercans, F. russi, F. varium, F. mortiferum, F. gonidiaformans, F. canifelinum; F. necrogenes*; and *F. naviforme.*

Polynucleotide sequence similarity and polynucleotide sequence identity Polypeptides as described herein also may be identified in terms of the polynucleotide that encodes the polypeptide. Thus, this disclosure provides polynucleotides that encode a polypeptide as described herein or hybridize, under standard hybridization conditions, to a polynucleotide that encodes a polypeptide as described herein, and the complements of such polynucleotide sequences.

As used herein, reference to a polynucleotide as described herein and/or reference to the nucleic acid sequence of one or more SEQ ID NOs can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides (for example, aligning the nucleotide sequence of the candidate sequence and a nucleotide sequence that includes, for example, a nucleotide sequence disclosed herein, such as SEQ ID NO: 1, 3, 5, 7, 9, 11, 13, 15, 17, 19, 21, 23, 25, 27, 29, 31, 33, 78, or a fragment thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes a nucleotide sequence described herein, for example, SEQ ID NO: 1, 3, 5, 7, 9, 11, 13, 15, 17, 19, 21, 23, 25, 27, 29, 31, 33, 78, or a fragment thereof. For example, two polynucleotide sequences can be compared using the Blastn program of the BLAST 2 search algorithm, as described by Tatusova et al., (*FEMS Microbiol Lett.,* 174:247-250 (1999)), and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

Finally, a polynucleotide as described herein can include any polynucleotide that encodes a polypeptide as described herein. Thus, the nucleotide sequence of the polynucleotide may be deduced from the amino acid sequence that is to be encoded by the polynucleotide.

This disclosure also provides whole cell preparations of a microbe, where the microbe expresses one or more of the polypeptides described herein. The cells present in a whole cell preparation may be inactivated such that the cells cannot replicate but the immunological activity of the polypeptides as described herein expressed by the microbe is maintained. Typically, the cells may be killed by exposure to agents such as glutaraldehyde, formalin, or formaldehyde. In one embodiment, the whole cell is a member of the family Bacteroidaceae, such as the genus *Fusobacterium*, including *F. necrophorum* (e.g., *F. necrophorum* subsp. *necrophorum* and *F. necrophorum* subsp. *funduliforme*), *F. nucleatum, F. ulcercans, F. russi, F. varium, F. mortiferum, F. gonidiaformans, F. canifelinum; F. necrogenes*; and *F. naviforme.*

In one embodiment, a fusobacteria is engineered to express a recombinantly produced protein that has structural similarity (sequence similarity or sequence identity) with SEQ ID NO:2 or a fragment thereof, structural similarity (sequence similarity or sequence identity) with SEQ ID NO:4 or a fragment thereof, structural similarity (sequence similarity or sequence identity) with SEQ ID NO:6 or a fragment thereof, structural similarity (sequence similarity or sequence identity) with SEQ ID NO:34 or a fragment thereof, structural similarity (sequence similarity or sequence identity) with SEQ ID NO:53 or a fragment thereof, or a combination thereof.

In one embodiment, a microbe, such as fusobacteria or *E. coli*, is engineered to express one or more recombinantly produced proteins that have structural similarity (sequence similarity or sequence identity) with SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54, or a fragment thereof.

Compositions

A composition as described herein may include at least one isolated polypeptide described herein, or a number of polypeptides that is an integer greater than one (e.g., at least two, at least three, at least four, at least five, at least six, at least seven, at least eight, at least nine, at least 10, at least 11, at least 12, at least 13, at least 14, at least 15, and so on), in any combination. Unless a specific level of sequence similarity and/or identity is expressly indicated herein (e.g., at least 80% sequence similarity, at least 85% sequence similarity, at least 90% sequence identity, etc.), reference to the amino acid sequence of an identified SEQ ID NO includes variants having the levels of sequence similarity and/or the levels of sequence identity described herein in the section headed "Polypeptide sequence similarity and polypeptide sequence identity."

A recombinantly-produced polypeptide may be expressed from a vector that permits expression of the polypeptide when the vector is introduced into an appropriate host cell. A host cell may be constructed to produce one or more recombinantly-produced polypeptides as described herein and, therefore, can include one or more vectors that include at least one polynucleotide encoding a polypeptide described herein. Thus, each vector can include one or more polynucleotides as described herein—i.e., a polynucleotide that encodes a polypeptide as described herein. Examples of host cells include, but are not limited to, *E. coli* and Fusobacteria. Methods for the genetic manipulation of Fusobacteria are known and routine in to art (see, for instance, Attarian et al., U.S. Pat. No. 6,962,990).

Certain compositions such as, for example, those including recombinantly-produced polypeptides, can include a maximum number of different types of polypeptides. In some embodiments, the maximum number of different types of polypeptides can refer to the maximum total number of polypeptides. Certain compositions can include, for example, no more than 50 polypeptides such as, for example, no more than 40 polypeptides, no more than 30 polypeptides, no more than 25 polypeptides, no more than 20 polypeptides, no more than 17 polypeptides, no more than 16 polypeptides, no more than 15 polypeptides, no more than 14 polypeptides, no more than 13 polypeptides, no more than 10 polypeptides, no more than eight polypeptides, no more than seven polypeptides, no more than six polypeptides, no more than five polypeptides, no more than four polypeptides, no more than three polypeptides, no more than two polypeptides, or no more than one polypeptide. A non-limiting example of a composition having no more than two polypeptides is one having the polypeptide SEQ ID NO:2 and the polypeptide SEQ ID NO:4. In other embodiments, a maximum number of recombinantly-produced polypeptides may be specified in a similar manner. In still other embodiments, a maximum number of nonrecombinantly-produced polypeptides may be specified in a similar manner.

A composition can include polypeptides isolatable from one microbe, or can be isolatable from a combination of two or more microbes. For instance, a composition can include polypeptides isolatable from two or more *Fusobacterium* spp., or from a *Fusobacterium* spp. and a different microbe that is not a member of the genus *Fusobacterium*. In certain embodiments, a composition can include a whole cell preparation in which the whole cell expresses one or more of the polypeptides as described herein. In some of these embodiments, the whole cell can be a *Fusobacterium* spp. In some embodiments, a composition can include whole cell preparations from two, three, four, five, or six strains.

In one embodiment, a composition includes at least one, at least two, at least three, at least four, or at least five recombinantly produced proteins, for instance SEQ ID NO:2, SEQ ID NO:4, SEQ ID NO:6, SEQ ID NO:34, and SEQ ID NO:53, or a fragment thereof. In one embodiment, a composition includes polypeptides expressed by a *Fusobacterium* spp. during growth in low iron and SEQ ID NO:2 (which is not expressed at a detectable level in low iron), SEQ ID NO:4 (which is not expressed at a detectable level in low iron), SEQ ID NO:6 (which is not expressed at a detectable level in low iron when a chelator such as 2,2-dipyridyl is used to reduce the amount of available iron and is expressed at a detectable level when 2,2-dipyridyl and hemin are present), SEQ ID NO:34, SEQ ID NO:53 (which is not expressed at a detectable level in low iron when a chelator such as 2,2-dipyridyl is used to reduce the amount of available iron and is expressed at a detectable level when 2,2-dipyridyl and hemin are present), or a combination thereof. Such compositions are not naturally occurring. A specific example of such a composition is one including proteins that are not detectable during growth of a *Fusobacterium* spp., such as *F. necrophorum*, after growth in low iron conditions (proteins having molecular weights of 88 kDa, 68 kDa, 60 kDa, and 52 kDa), proteins having enhanced expression by a *Fusobacterium* spp., such as *F. necrophorum*, after growth in low iron conditions (proteins having molecular weights of 103 kDa and 74 kDa), non-metal-regulated proteins expressed by a *Fusobacterium* spp., such as *F. necrophorum*, (335 kDa, 243 kDa, 230 kDa, 220 kDa, 115 kDa, 45 kDa, 42 kDa, 38 kDa, 35 kDa, 30 kDa, and 16 kDa), and one or more recombinantly produced proteins selected from SEQ ID NO:2, SEQ ID NO:4, SEQ ID NO:6, SEQ ID NO:34, SEQ ID NO:53, or a fragment thereof. Optionally, such a composition also includes metal-regulated proteins that are expressed after growth in low metal conditions supplemented with hemin (150 kDa and 84 kDa).

In one embodiment, a composition includes one or more polypeptides, for instance SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54, or a fragment thereof.

Optionally, a polypeptide of the present invention can be covalently bound to a carrier polypeptide to improve the immunological properties of the polypeptide. Useful carrier polypeptides are known in the art, and include, for instance, leukotoxin derived from *Fusobacterium* spp. The chemical coupling of a polypeptide of the present invention can be carried out using known and routine methods. For instance, various homobifunctional and/or heterobifunctional cross-linker reagents such as bis(sulfosuccinimidyl) suberate, bis (diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl) cycloheane-1-carboxylate, sulfosuccinimidyl 4-(p-maleimido-phenyl) butyrate and (1-ethyl-3-(dimethyl-aminopropyl) carbodiimide can be used (Harlow and Lane, Antibodies, A Laboratory Manual, generally and Chapter 5, Cold Spring Harbor Laboratory, Cold Spring Harbor, N.Y., N.Y. (1988)). In one embodiment, a protein described herein covalently bound to a carrier protein (such as a leukotoxin) has structural similarity (sequence similarity or sequence identity) with SEQ ID NO:2 or a fragment thereof, has structural similarity (sequence similarity or sequence identity) with SEQ ID NO:4 or a fragment thereof, has structural similarity (sequence similarity or sequence identity) with SEQ ID NO:6 or a fragment thereof, has structural similarity (sequence similarity or sequence identity) with SEQ ID NO:34 or a fragment thereof, or has structural similarity (sequence similarity or sequence identity) with SEQ ID NO:53 or a fragment thereof.

Preferably, such compositions of the present invention include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (O-specific chain, the outer and inner core) and the lipid A region. The lipid A component of LPS is the most biologically active component of the LPS structure and together induces a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scarring or blemishes of the tissue at the injection site (see, for instance, Rae, Injection Site Reactions, available at www.animal.ufl.edu/extension/beef/documents/SHORT94/RAE.HTM, which is available through the website maintained by the Department of Animal Sciences of the University of Florida, Gainesville, Fla.).

The concentration of LPS can be determined using routine methods known in the art. Such methods typically include measurement of dye binding by LPS (see, for instance, Keler and Nowotny, *Analyt. Biochem.,* 156, 189 (1986)) or the use of a *Limulus* amebocyte lysate (LAL) test (see, for instance, Endotoxins and Their Detection With the *Limulus* Amebocyte Lystate Test, Alan R. Liss, Inc., 150 Fifth Avenue, New York, N.Y. (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOXATE (Sigma Chemical Co., St. Louis, Mo.; see Sigma Technical Bulletin No. 210), and PYROTELL (Associates of Cape Cod, Inc., East Falmouth, Mass.). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for 1 hour undisturbed at 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, Md., Catalog No. 235503), and Associates of Cape Cod, Inc., (Catalog No. E0005). In general, when a composition of the present invention is prepared by isolating polypeptides from a *Fusobacterium* spp. by a method as described herein (e.g., a method that includes disrupting and solubilizing the cells, and collecting the insoluble polypeptides), the amount of LPS in a composition of the present invention is less than the amount of LPS present in a mixture of same amount of the *Fusobacterium* spp. that has been disrupted under the same conditions but not solubilized. Typically, the level of LPS in a composition of the present invention is decreased by, in increasing order of preference, at least 50%, at least 60%, at least 70%, at least 80%, or at least 90% relative to the level of LPS in a composition prepared by disrupting, but not solubilizing, the same *Fusobacterium* spp.

In some aspects, a composition of the present invention does not include a leukotoxin isolatable from a *Fusobacterium* spp. Leukotoxins that are optionally not present in a composition of the present invention include polypeptides having a molecular weight of 335 kDa based on analysis with an 10% SDS-PAGE gel under reducing and denaturing conditions, and having an activity that is toxic to bovine leukocytes (Narayanan et al., Infect. Imun., 69, 5447-5455 (2001), and Narayanan et al., Infect. Immun., 70, 4609-4620 (2002)). Whether a polypeptide has leukotoxin activity can be determined using the monoclonal antibody F7B10 which is reactive against a *F. necrophorum* leukotoxin (Tan et al., Vet. Microbiol., 42, 121-133 (1994), or by determining whether the polypeptide is toxic to ruminant leukocytes. Methods for measuring the toxicity of a polypeptide for ruminant leukocytes are known in the art (Narayanan et al., Infect. Imun., 69, 5447-5455 (2001), and Narayanan et al., Infect. Immun., 70, 4609-4620 (2002).

The compositions as described herein optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. Exemplary pharmaceutically acceptable carriers include buffer solutions and generally exclude blood products such as, for example, whole blood and/or plasma. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous, intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition as described herein can also be administered via a sustained or delayed release implant. Implants suitable for use according to the invention are known and include, for example, those disclosed in International Publication No. WO 2001/037810 and/or International Publication No. WO 1996/001620. Implants can be produced at sizes small enough to be administered by aerosol or spray. Implants also can include nanospheres and microspheres.

A composition of the present invention is administered in an amount sufficient to provide an immunological response to polypeptides or whole cells described herein. The amount of polypeptide present in a composition can vary. For instance, the dosage of polypeptide can be between 0.01 micrograms (μg) and 3000 milligrams (mg), typically between 10 μg and 2000 ug. When the composition is a whole cell preparation, the cells can be present at a concentration of $10^6$ bacteria/ml, $10^7$ bacteria/ml, $10^8$ bacteria/ml, or $10^9$ bacteria/ml. For an injectable composition (e.g. subcutaneous, intramuscular, etc.) the polypeptide is preferably present in the composition in an amount such that the total volume of the composition administered is 0.5 ml to 5.0 ml, typically 1.0-3.0 ml. When the composition is a whole cell preparation, the cells are preferably present in the composition in an amount that the total volume of the composition administered is 0.5 ml to 5.0 ml, typically 1.0-2.0 ml. The amount administered will vary depending on various factors including, but not limited to, the specific polypeptides or cells chosen, the weight, physical condition and age of the animal, and the route of administration. Thus, the absolute weight of the polypeptide or number of cells included in a given unit dosage form can vary, and depends upon factors such as the species, age, weight and physical condition of the animal, as well as the method of administration. Such factors can be determined by one skilled in the art. Other examples of dosages suitable for the invention are disclosed in Emery et al. (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., a polypeptide or whole cell of the present invention) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldiocradecylammonium bromide (DDA), avridine, aluminum hydroxide, oils, saponins, alpha-tocopherol, polysaccharides, emulsified paraffins (available from under the tradename EMULSIGEN from MVP Laboratories, Ralston, Nebr.), ISA-70, RIBI and other substances known in the art.

In another embodiment, a composition of the invention including a pharmaceutically acceptable carrier can include a biological response modifier, such as, for example, IL-2, IL-4 and/or IL-6, TNF, IFN-alpha, IFN-gamma, and other cytokines that effect immune cells. A composition can also include an antibiotic, preservative, anti-oxidant, chelating agent, etc. Such components are known in the art.

Methods of Making

This disclosure also provides methods for obtaining the polypeptides and whole cells described herein. Polypeptides and whole cell preparations described herein may be obtained by incubating a member of the genus *Fusobacterium* under conditions that promote expression of one or more of the polypeptides described herein. The polypeptides and whole cells as described herein may be isolatable from a member of the family Bacteroidaceae, such as the genus *Fusobacterium*, including *F. necrophorum* (such as *F. necrophorum* subsp. *necrophorum* and *F. necrophorum* subsp. *funduliforme*), *F. nucleatum, F. ulcercans, F. russi, F. varium, F. mortiferum, F. gonidiaformans, F. canifelinum; F. necrogenes*; and *F. naviforme*. An example of a representative strain is *F. necrophorum* 1694. Microbes useful for obtaining polypeptides described herein and making whole cell preparations are commercially available from a depository such as American Type Culture Collection (ATCC). In addition, such microbes are readily obtainable by techniques routine and known in the art. The microbes may be derived from an infected animal as a field isolate, and used to obtain the polypeptides and/or the whole cell preparations as described herein, or stored for future use, for example, in a frozen repository at from −20° C. to −95° C., or from −40° C. to −50° C., in bacteriological media containing 20% glycerol, and other like media.

The present invention also includes compositions prepared by the processes disclosed herein. Typically, such conditions are low metal conditions. As used herein, the phrase "low metal conditions" refers to an environment, typically bacteriological media that contains amounts of a free metal that cause a microbe to express a metal regulated polypeptide at a detectable level. As used herein, the phrase "high metal conditions" refers to an environment that contains an amount of a free metal that causes a microbe to express a metal-regulated polypeptide at a decreased level compared to expression of the metal-regulated polypeptide under low metal conditions. In some cases, "high metal conditions" can refer to an environment that causes a cell to fail to express one or more of the metal-regulated polypeptides described herein at a detectable level.

In some cases, "high metal conditions" can include a metal-rich natural environment and/or culture in a metal-rich medium without a metal chelator. In contrast, in some cases, "low metal conditions" can include culture in a medium that includes a metal chelator, as described in more detail below. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron, copper, or zinc.

Low metal conditions are generally the result of the addition of a metal chelating compound to a bacteriological medium, the use of a bacteriological medium that contains low amounts of a metal, or a combination thereof. High metal conditions are generally present when a chelator is not present in the medium, when a metal is added to the medium, or a combination thereof. Examples of metal chelators include natural and synthetic compounds. Examples of natural compounds include plant phenolic compounds, such as flavonoids. Examples of flavonoids include the copper chelators catechin, naringenin, and quercetin, and the iron chelator myricetin. Examples of synthetic copper chelators include, for instance, ammonium tetrathiomolybdate, and examples of synthetic zinc chelators include, for instance, N,N,N',N'-Tetrakis (2-pyridylmethyl)-ethylene diamine (also referred to as TPEN). Examples of synthetic iron chelators include 2,2'-dipyridyl (also referred to in the art as α,α'-bipyridyl), 8-hydroxyquinoline, ethylenediamine-di-O-hydroxyphenylacetic acid (EDDHA), desferrioxamine methanesulfonate (desferol), transferrin, lactoferrin, ovotransferrin, biological siderophores, such as the catecholates and hydroxamates, and citrate.

In one embodiment, 2,2'-dipyridyl is used for the chelation of iron. Typically, 2,2'-dipyridyl is added to the media at a concentration of at least 0.0025 micrograms/milliliter (g/ml), at least 0.025 μg/ml, or at least 0.25 μg/ml. High levels of 2,2'-dipyridyl can be 10 μg/ml, 20 μg/ml, or 30 μg/ml.

In one embodiment, a medium is supplemented with an iron-containing porphyrin, such as hemin. Typically, hemin is added to the medium at a concentration of 20 ug/ml, and other concentrations can be used.

In one embodiment, quercetin is used for the chelation of copper. Typically, quercetin is added to the media at a concentration of 50 uM, and concentrations between 25 μM and 100 μM can be used.

In one embodiment, TPEN is used for the chelation of zinc. Typically, TPEN is added to the media at a concentration of 50 μM is used, and it is expected that higher concentrations can be used.

It is expected that a *Fusobacterium* spp. with a mutation in a fir gene will result in the constitutive expression of many, if not all, of the metal regulated polypeptides of the present invention. A potential fur gene has been identified in a *F. nucleatum* (Kapatral et al., J. Bacteriol. 184 (7), 2005-2018 (2002)). The production of a fur mutation in a *Fusobacterium* spp. can be produced using routine methods including, for instance, electroporation and genetic constructs useful for gene knock-out in gram negative bacteria.

In one embodiment, the fusobacteria used to make a composition described herein, e.g., a composition including isolated polypeptides or a composition including whole cells, may be produced using a fusobacteria that has been engineered to recombinantly express a protein that has structural similarity (sequence similarity or sequence identity) with SEQ ID NO:2 or a fragment thereof, structural similarity (sequence similarity or sequence identity) with SEQ ID NO:4 or a fragment thereof, structural similarity (sequence similarity or sequence identity) with SEQ ID NO:6 or a fragment thereof, a portion thereof, structural similarity (sequence similarity or sequence identity) with SEQ ID NO:34 or a fragment thereof, structural similarity (sequence similarity or sequence identity) with SEQ ID NO:53 or a fragment thereof, or a combination thereof. In one embodiment, such a fusobacteria is incubated in the presence of low iron conditions, and the one of more recombinant polypeptides are expressed during the incubation in the low iron conditions. The result is a fusobacteria that expresses iron-regulated proteins and the one of more recombinant polypeptides.

Many *Fusobacterium* spp. are able to grow in low metal conditions in vitro in artificial media only after adaptation. For instance, a *Fusobacterium* spp., such as the isolate given the identification number MS 040525 and *F. necrophorum* 1694 can be adapted to low iron conditions in vitro by growth in the presence of low concentrations of an iron chelator after growth in a medium containing the chelator, gradually increasing the concentration of the chelator. For instance, a *Fusobacterium* spp. can be adapted to growth in low iron conditions by adding 0.0025 μg/ml of 2,2'-dipyridyl to a medium, and exposing the culture to gradually increasing concentrations of the chelator to a greater concentration, for instance 20 μg/ml as previously reported Straub et al. (U.S. Pat. No. 8,329,192). Adaptation of *Fusobacterium* spp. to reduced zinc and copper is also possible. Repeat passage of at least five consecutive passes in 50 μM TPEN adapted *Fusobacterium* spp. to reduced zinc. Repeat passage of at least five consecutive passes in 50 or in 100 uM quercetin, repeat passage of at least five consecutive passes in 100 uM catechin, or repeat passage of at least five consecutive passes in 100 μM Naringenin adapted *Fusobacterium* spp. to reduced copper. Culture of adapted *Fusobacterium* spp. in the presence of any of these chelators resulted in increased expression of unique proteins. Adaptation of other *Fusobacterium* spp. strains to low metal conditions can be accomplished in this way.

The medium used to incubate the microbe is not critical, and conditions useful for the culture of fusobacteria are known to the skilled person. In one embodiment, supplements may be added to a culture medium, such as, but not limited to, hemin. The volume of medium used to incubate the microbe can vary. When a *Fusobacterium* spp. microbe is being evaluated for the ability to produce the polypeptides described herein, the microbe can be grown in a suitable volume, for instance, 10 milliliters to 1 liter of medium. When a microbe is being grown to obtain polypeptides for use in, for instance, administration to animals, the microbe may be grown in a fermenter to allow the isolation of larger amounts of polypeptides. Methods for growing microbes in a fermenter are routine and known in the art. The conditions used for growing a microbe preferably include a metal chelator, more preferably an iron chelator, for instance 2,2'-dipyridyl, TPEN, or quercetin, a pH of between 6.5 and 7.5, preferably between 6.9 and 7.1, and a temperature of 37° C. When a fermenter is used, the culture may be purged with an appropriate gas, for instance, nitrogen, to maintain anaerobic conditions. Members of the genus *Fusobacterium* are obligate anaerobes, thus growth conditions do not include levels of oxygen that will prevent growth.

In some aspects of the invention, a *Fusobacterium* spp. may be harvested after growth. Harvesting includes concentrating the microbe into a smaller volume and suspending in a media different than the growth media. Methods for concentrating a microbe are routine and known in the art, and include, for example, filtration and/or centrifugation. Typically, the concentrated microbe is suspended in decreasing amounts of buffer. Preferably, the final buffer includes a metal chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted. In one embodiment, bacterial cells may be concentrated into a pellet by, for instance, centrifugation, and the concentrated cells suspended in osmotic shock buffer (OMS; 7.26 grams/liter Tris-base and 0.93 grams/liter EDTA adjusted to a pH of 8.5). The ratio of cells to OMS may be 50 grams cell pellet, 60 grams cell pellet, or 70 grams cell pellet to 1 liter of OMS. The suspension of cells in OMS can be incubated at 2-8° C. for at least 24 hours, at least 48 hours, or at least 60 hours to remove excess endotoxin from the cells. In one embodiment, the incubation is for no greater than 72 hours. After the incubation the suspension is centrifuged again and the supernatant discarded to remove free endotoxin and any extracellular material, e.g., secreted proteins.

When the *Fusobacterium* spp. is to be used as a whole cell preparation, the harvested cells may be processed using routine and known methods to inactivate the cells. Alternatively, when a *Fusobacterium* spp. is to be used to prepare polypeptides of the present invention, the *Fusobacterium* spp. may be disrupted using chemical, physical, or mechanical methods routine and known in the art, including, for example, french press, sonication, or homogenization. Preferably, homogenization is used. As used herein, "disruption" refers to the breaking up of the cell. Disruption of a microbe can be measured by methods that are routine and known in the art, including, for instance, changes in optical density. Typically, a microbe is subjected to disruption until the percent transmittance is increased by 20% when a 1:100 dilution is measured. The temperature during disruption is typically kept at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., polypeptides, nucleic acids, carbohydrates) into the aqueous phase of the buffer in which the microbe was disrupted, and the formation of aggregates of insoluble cellular materials. The conditions for solubilization preferably result in the aggregation of polypeptides of the present invention into insoluble aggregates that are large enough to allow easy isolation by, for instance, centrifugation.

Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known in the art, including, for instance, changes in optical density. Typically, the solubilization is allowed to occur for at least 24 hours, more preferably, at least 48 hours, most preferably, at least 60 hours. The temperature during disruption is typically kept low, preferably at 4° C.

The insoluble aggregates that include the polypeptides described herein may be isolated by methods that are routine and known in the art, such as centrifugation, filtration, or a combination thereof. In one embodiment, the insoluble aggregates are isolated by filtration, such as tangential or crossflow filtration. Examples of a molecular weight cutoff to use with tangential filtration are 40 kDa, 50 kDa, or 60 kDa. In one embodiment, a tangential filtration system has a molecular weight cutoff of 50 kDa. Tangential filtration may aid in removal of residual sarcosine from the protein suspension. Tangential filtration results in concentration of the protein suspension. Thus, the insoluble aggregates can be isolated at a significantly lower cost.

In one embodiment, the sarcosine is removed from the isolated polypeptides. Methods for removing sarcosine from the isolated polypeptides are known in the art, and include, for instance, diafiltration, precipitation, hydrophobic chromatography, ion-exchange chromatography, and/or affinity chromatography, and ultrafiltration and washing the polypeptides in alcohol, such as isopropyl alcohol, by diafiltration. After isolation, the polypeptides suspended in buffer and stored at low temperature, for instance, −20° C. or below.

Polypeptides of the present invention may also be isolated from *Fusobacterium* spp. using methods that are known in the art. The isolation of the polypeptides may be accomplished as described in, for instance, Hussain, et al. *Infect. Immun.,* 67, 6688-6690 (1999); Trivier, et al., *FEMS Microbiol. Lett.,* 127, 195-199 (1995); Heinrichs, et al., *J. Bacteriol.,* 181, 1436-1443 (1999).

In those aspects of the present invention where a whole cell preparation is to be made, after growth of a *Fusobacterium* spp. the microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

In other aspects, an isolated polypeptide of the invention may be prepared recombinantly. When prepared recombinantly, a polynucleotide encoding the polypeptide may be identified and cloned into an appropriate expression host. The recombinant expression host may be grown in an appropriate medium, disrupted, and the polypeptides isolated as described above.

Methods of Use

Also provided are methods of using the polypeptides described herein. The methods include administering to an animal an effective amount of a composition that includes at least one polypeptide described herein. The composition may further include a pharmaceutically acceptable carrier. As used herein, an "effective amount" of a composition of the present invention is the amount able to elicit the desired response in the recipient. The composition can be administered at a time that maternal antibody may be present, for instance, as early as one day of age, or at a later time during the life of the animal. The animal can be, for instance, an ungulate, a companion animal, or a human. Examples of ungulates include animals that are bovine (including, for instance, cattle), caprine (including, for instance, goats), ovine (including, for instance, sheep), porcine (including, for instance, swine), equine (including, for instance, horses), avian (including, for instance, turkeys and chickens), members of the family Cervidae (including, for instance, deer, elk, moose, caribou and reindeer), and Bison (including, for instance, buffalo). Examples of companion animals include dogs and cats. In one embodiment, an animal is a mouse. In one embodiment, an animal is a hooved animal. In some aspects, the methods may further include additional administrations (e.g., one or more booster administrations) of the composition to the animal to enhance or stimulate a secondary immune response. A booster can be administered at a time after the first administration, for instance, 1 to 8 weeks, preferably 2 to 4 weeks, after the first administration of the composition. Subsequent boosters can be administered one, two, three, four, or more times annually. Without intending to be limited by theory, it is expected that annual boosters will not be necessary, as an animal will be challenged in the field by exposure to members of the genus *Fusobacterium* expressing polypeptides having epitopes that are identical to or structurally related to epitopes present on the polypeptides present in the composition administered to the animal.

In one aspect, the invention is directed to methods for making antibody to a polypeptide described herein, for instance, by inducing the production of antibody in an animal, or by recombinant techniques. The antibody produced includes antibody that specifically binds at least one polypeptide present in the composition. In this aspect of the invention, an "effective amount" is an amount effective to result in the production of antibody in the animal. Methods for determining whether an animal has produced antibodies that specifically bind polypeptides present in a composition of the present invention can be determined as described herein.

As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets.

In one aspect the invention is also directed to treating an infection in an animal caused by a member of the genus *Fusobacterium*. The infection may be caused exclusively by *Fusobacterium* spp., or may be a mixed infection of *Fusobacterium* spp. and, for instance, *Bacteroides nodosus*. The method includes administering an effective amount of the composition to an animal having an infection caused by a member of the genus *Fusobacterium*, and determining whether the *Fusobacterium* spp. causing the infection has decreased. Methods for determining whether an infection is caused by a member of the genus *Fusobacterium* are routine and known in the art. It is expected that compositions made with polypeptides isolatable from one species of *Fusobacterium* will be useful in the methods described herein against other species of *Fusobacterium.*

In another aspect, the present invention is directed to methods for treating one or more symptoms of certain conditions in animals that may be caused by infection by a member of the genus *Fusobacterium*. Examples of conditions caused by *Fusobacterium* spp. infections include hepatic abscesses, foot rot, laminitis, purulent dermatitis, interdigital dermatitis, contagious ecthyma, necrotic rhinitis, skin ulcers, peritonsillar abscesses, septic arthritis, Lemierre's syndrome, endocarditis, metritis, and shipping fever. Treatment of these conditions can be prophylactic or, alternatively, can be initiated after the development of a condition described herein. Treatment that is prophylactic, for instance, initiated before a subject manifests symptoms of a condition caused by *Fusobacterium* spp., is referred to herein as treatment of a subject that is "at risk" of developing the condition. Typically, an animal "at risk" of developing a condition is an animal likely to be exposed to a *Fusobacterium* spp. causing the condition. For instance, the animal is present in an area where the condition has been diagnosed in at least one other animal, or is being transported to an area where a *Fusobacterium* spp. is endemic, and/or where conditions caused by *Fusobacterium* spp. are prevalent. Accordingly, administration of a composition can be performed before, during, or after the occurrence of the conditions described herein. Treatment initiated after the development of a condition may result in decreasing the severity of the symptoms of one of the conditions, including completely removing the symptoms. In this aspect of the invention, an “effective amount” is an amount effective to prevent the manifestation of symptoms of a condition, decrease the severity of the symptoms of a condition, and/or completely remove the symptoms.

The potency of a composition described herein can be tested according to standard methods. For instance, the use of mice as an experimental model for *Fusobacterium* spp. infection in humans and large animals such as cattle is well established (Conion et al, Infect. Immun, 15, 510-517 (1977), Garcia and McKay, Can. J. Comp. Med, 42, 121-127 (1978), Abe et al, Infect. Immun, 13, 1473-1478 (1976), Emery and Vaughan, Vet. Microbiol, 12, 255-268 (1986), Smith et al, Epidemiol. Infect, 110, 499-506 (1993), and Narayanan et al., Vet. Micro. 93, 335-347 (2003)). A mouse model of *Fusobacterium* infection is available, and is recognized as correlating to with abscess formation and useful for evaluating the in vivo efficacy of antimicrobial agents (Nagaoka et al., 2013, J. Med. Micriobiol., 62(11):1755-1759). This model has proven to be a valuable model to evaluate the immunogenicity and identification of various target antigens provided by various fusobacteria species. Alternatively, when the condition is present in an animal such as, for instance, a sheep or cow, a controlled experimental trial can be run by vaccinating animals with varying levels of the composition and challenging vaccinated and unvaccinated animals with a *Fusobacterium* spp. Methods for determining whether an animal has the conditions disclosed herein and symptoms associated with the conditions are routine and known in the art. Symptoms often associated with hepatic abscesses can be a range of pathologies, from small foci of lymphocyte inflammation surrounded by low numbers of degenerating hepatocytes, to pronounced foci with necrosis and hemorrhage, loss of hepatocytes, fibrin and mixed inflammatory cells at the margin of the necrotic area.

A composition of the invention can be used to provide for passive immunization against infection by *Fusobacterium* spp. For instance, the composition can be administered to an animal to induce the production of immune products, such as antibodies, which can be collected from the producing animal and administered to another animal to provide passive immunity. Immune components, such as antibodies, can be collected to prepare antibody compositions from serum, plasma, blood, colostrum, etc. for passive immunization therapies. Antibody compositions including monoclonal antibodies, anti-idiotypes, and/or recombinant antibodies can also be prepared using known methods. Passive antibody compositions and fragments thereof, e.g., scFv, Fab, $F(ab')_2$ or Fv or other modified forms thereof, may be administered to a recipient in the form of serum, plasma, blood, colostrum, and the like. However, the antibodies may also be isolated from serum, plasma, blood, colostrum, and the like, using known methods and spray dried or lyophilized for later use in a concentrated or reconstituted form. Passive immunizing preparations may be particularly advantageous for treatment of acute systemic illness, or passive immunization of young animals that failed to receive adequate levels of passive immunity through maternal colostrum.

Another aspect of the present invention provides methods for detecting antibody that specifically binds polypeptides of the present invention. These methods are useful in, for instance, detecting whether an animal has antibody that specifically binds polypeptides of the present invention, and diagnosing whether an animal may have an infection caused by *Fusobacterium* spp. Preferably, such diagnostic systems are in kit form. The methods include contacting an antibody with a preparation that includes at least one polypeptide of the present invention to result in a mixture. Preferably, the antibody is present in a biological sample, more preferably blood, milk, or colostrum. The method further includes incubating the mixture under conditions to allow the antibody to specifically bind a polypeptide to form a polypeptide:antibody complex. As used herein, the term “polypeptide:antibody complex” refers to the complex that results when an antibody specifically binds to a polypeptide. The preparation that includes the polypeptides present in a composition of the present invention may also include reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase.

The methods for detecting the presence of antibodies that specifically bind to polypeptides of the present invention can be used in various formats that have been used to detect antibody, including radioimmunoassay and enzyme-linked immunosorbent assay.

The present invention also provides a kit for detecting antibody that specifically binds polypeptides of the present invention. The kit includes at least one polypeptide of the present invention in a suitable packaging material in an amount sufficient for at least one assay. Optionally, other reagents such as buffers and solutions needed to practice the invention are also included. Instructions for use of the packaged polypeptides are also typically included.

As used herein, the phrase “packaging material” refers to one or more physical structures used to house the contents of the kit. The packaging material is constructed by known methods, preferably to provide a sterile, contaminant-free environment. The packaging material has a label which indicates that the polypeptides can be used for detecting antibodies induced by infection with *Fusobacterium* spp. In addition, the packaging material contains instructions indicating how the materials within the kit are employed to detect such antibodies. As used herein, the term “package” refers to a solid matrix or material such as glass, plastic, paper, foil, and the like, capable of holding within fixed limits the polypeptides. Thus, for example, a package can be a microtiter plate well to which microgram quantities of polypeptides have been affixed. “Instructions for use” typically include a tangible expression describing the reagent concentration or at least one assay method parameter, such as the relative amounts of reagent and sample to be admixed, maintenance time periods for reagent/sample admixtures, temperature, buffer conditions, and the like.

ILLUSTRATIVE EMBODIMENTS

Embodiment 1

A composition comprising:

at least one isolated polypeptide having a molecular weight of 92 kDa to 79 kDa, 73 kDa to 63 kDa, 62 kDa to 58 kDa, or 57 kDa to 47 kDa, wherein the at least one polypeptide is isolatable from a *Fusobacterium necropho-*

*rum* when incubated in media comprising an iron chelator and not isolatable when grown in the media without the iron chelator, at least one isolated polypeptide having a molecular weight of 108 kDa to 98 kDa or 79 kDa to 69 kDa, wherein the at least one polypeptide is isolatable from a *Fusobacterium necrophorum* when incubated in media comprising an iron chelator, is expressed by the *Fusobacterium necrophorum* when incubated in media without the iron chelator and expressed at an enhanced level during growth in media comprising an iron chelator, and at least one protein selected from the group consisting of a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, and a polypeptide having at least 85% similarity to SEQ ID NO:53 or a fragment thereof, wherein the composition protects an animal against challenge with *Fusobacterium necrophorum.*

Embodiment 2

A composition comprising:

isolated polypeptides having molecular weights of 92 kDa to 79 kDa, 73 kDa to 63 kDa, 62 kDa to 58 kDa, and 57 kDa to 47 kDa, wherein the polypeptides are isolatable from a *Fusobacterium necrophorum* when incubated in media comprising an iron chelator and not isolatable when grown in the media without the iron chelator, isolated polypeptides having molecular weights of 108 kDa to 98 kDa and 79 kDa to 69 kDa, wherein the polypeptides are isolatable from a *Fusobacterium necrophorum* when incubated in media comprising an iron chelator, are expressed by the *Fusobacterium necrophorum* when incubated in media without the iron chelator and expressed at an enhanced level during growth in media comprising an iron chelator, and at least one protein selected from the group consisting of a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, a polypeptide having at least 85% similarity to SEQ ID NO:53 or a fragment thereof, wherein the composition protects an animal against challenge with *Fusobacterium necrophorum.*

Embodiment 3

A composition comprising:

isolated polypeptides having molecular weights of 92 kDa to 79 kDa, 73 kDa to 63 kDa, 62 kDa to 58 kDa, and 57 kDa to 47 kDa, wherein the polypeptides are isolatable from a *Fusobacterium necrophorum* when incubated in media comprising an iron chelator and not isolatable when grown in the media without the iron chelator, isolated polypeptide having molecular weights of 155 kDa to 145 kDa and 89 kDa to 79 kDa, wherein the at least one polypeptide is isolatable from a *Fusobacterium necrophorum* when incubated in media comprising an iron chelator and an iron-containing porphyrin and not isolatable when grown in the media without the iron chelator and iron-containing porphyrin, and not isolatable when grown in the media with the iron chelator and in the absence of the iron-containing porphyrin, and isolated polypeptides having molecular weights of 108 kDa to 98 kDa and 79 kDa to 69 kDa, wherein the polypeptides are isolatable from a *Fusobacterium necrophorum* when incubated in media comprising an iron chelator, are expressed by the *Fusobacterium necrophorum* when incubated in media without the iron chelator and expressed at an enhanced level during growth in media comprising an iron chelator, and wherein the composition protects an animal against challenge with *Fusobacterium necrophorum.*

Embodiment 4

A composition comprising:

at least one isolated polypeptide having a molecular weight of 131 kDa to 121 kDa, 79 kDa to 69 kDa, or 33 kDa to 23 kDa, wherein the at least one polypeptide is isolatable from a *Fusobacterium necrophorum* when incubated in media comprising a copper chelator and not isolatable when grown in the media without the copper chelator, and at least one isolated polypeptide having a molecular weight of 93 kDa to 83 kDa, 65 kDa to 55 kDa, or 52 kDa to 42 kDa, wherein the at least one polypeptide is isolatable from the *Fusobacterium necrophorum* when incubated in media comprising a copper chelator, is expressed by the *Fusobacterium necrophorum* when incubated in media without the copper chelator and expressed at an enhanced level during growth in media comprising an copper chelator, wherein the composition protects an animal against challenge with *Fusobacterium necrophorum.*

Embodiment 5

A composition comprising:

at least one isolated polypeptide having a molecular weight of 131 kDa to 121 kDa, 108 kDa to 98 kDa, 92 kDa to 64 kDa, 53 kDa to 43 kDa, or 33 kDa to 19 kDa, wherein the polypeptide is isolatable from a *Fusobacterium necrophorum* when incubated in media comprising a zinc chelator and not isolatable when grown in the media without the zinc chelator, at least one isolated polypeptide having a molecular weight of 79 kDa to 69 kDa or 65 kDa to 55 kDa, wherein the at least one polypeptide is isolatable from the *Fusobacterium necrophorum* when incubated in media comprising a zinc chelator, is expressed by the *Fusobacterium necrophorum* when incubated in media without the zinc chelator and expressed at an enhanced level during growth in media comprising the zinc chelator, wherein the composition protects an animal against challenge with *Fusobacterium necrophorum.*

Embodiment 6

A composition comprising:

isolated polypeptides having molecular weights of 131 kDa to 121 kDa, 79 kDa to 69 kDa, and 33 kDa to 23 kDa, wherein the polypeptides are isolatable from a *Fusobacterium necrophorum* when incubated in media comprising a copper chelator and not isolatable when grown in the media without the copper chelator, and isolated polypeptides having molecular weights of 93 kDa to 83 kDa, 65 kDa to 55 kDa, and 52 kDa to 42 kDa, wherein the polypeptides are isolatable from the *Fusobacterium*

*necrophorum* when incubated in media comprising a copper chelator, are expressed by the *Fusobacterium necrophorum* when incubated in media without the copper chelator and expressed at an enhanced level during growth in media comprising an copper chelator, wherein the composition protects an animal against challenge with *Fusobacterium necrophorum.*

Embodiment 7

A composition comprising:

isolated polypeptides having molecular weights of 131 kDa to 121 kDa, 108 kDa to 98 kDa, 92 kDa to 64 kDa, 53 kDa to 43 kDa, and 33 kDa to 19 kDa, wherein the polypeptides are isolatable from a *Fusobacterium necrophorum* when incubated in media comprising a zinc chelator and not isolatable when grown in the media without the zinc chelator, and isolated polypeptides having molecular weights of 79 kDa to 69 kDa and 65 kDa to 55 kDa, wherein the polypeptides are isolatable from the *Fusobacterium necrophorum* when incubated in media comprising a zinc chelator, are expressed by the *Fusobacterium necrophorum* when incubated in media without the zinc chelator and expressed at an enhanced level during growth in media comprising the zinc chelator, wherein the composition protects an animal against challenge with *Fusobacterium necrophorum.*

Embodiment 8

The composition of any one of embodiments 1-7 further comprising:

a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, a polypeptide having at least 85% similarity to SEQ ID NO:53 or a fragment thereof, or a combination thereof, wherein the composition protects an animal against challenge with *Fusobacterium necrophorum.*

Embodiment 9

A composition comprising:

an isolated polypeptide having at least 85% similarity to SEQ ID NO:2, 4, 6, 8, 10, 12, 14, 16, 18, 20, 22, 24, 26, 28, 30, 32, 34, 35, 36, 37, 38, 39, 40, 41, 43, 44, 45, 46, 47, 48, 49, 50, 51, 52, 53, or 54, or a fragment thereof, wherein the composition protects an animal against challenge with *Fusobacterium necrophorum.*

Embodiment 10

The composition of any one of embodiments 1-9 further comprising:

isolated polypeptides having molecular weights of 340 kDa to 330 kDa, 247 kDa to 237 kDa, 247 kDa to 237 kDa, 235 kDa to 215 kDa, 120 kDa to 110 kDa, 51 kDa to 25 kDa, and 21 kDa to 11 kDa, wherein the polypeptides are isolatable from a *Fusobacterium necrophorum.*

Embodiment 11

The composition of any one of embodiments 1-10 further comprising a pharmaceutically acceptable carrier.

Embodiment 12

The composition of any one of embodiments 1-11 further comprising an adjuvant.

Embodiment 13

A method comprising:

administering to a subject an amount of the composition of any one of embodiments 1-12 effective to induce the subject to produce antibody that specifically binds to at least one polypeptide of the composition.

Embodiment 14

A method for treating an infection in a subject, the method comprising:

administering an effective amount of the composition of any one of embodiments 1-12 to a subject having or at risk of having an infection caused by a *Fusobacterium* spp.

Embodiment 15

A method for treating a symptom in a subject, the method comprising:

administering an effective amount of the composition of any one of embodiments 1-12 to a subject having or at risk of having an infection caused by a *Fusobacterium* spp.

Embodiment 16

A method for decreasing colonization in a subject, the method comprising:

administering an effective amount of the composition of any one of embodiments 1-12 to a subject colonized by or at risk of being colonized by a *Fusobacterium* spp.

Embodiment 17

A method for treating an infection in a subject, the method comprising:

administering an effective amount of a composition to a subject having or at risk of having an infection caused by a *Fusobacterium* spp., wherein the composition comprises antibody that specifically binds to a polypeptide of the composition of any one of embodiments 1-12.

Embodiment 18

A method for treating a symptom in a subject comprising:

administering an effective amount of a composition to a subject having or at risk of having an infection caused by a *Fusobacterium* spp., wherein the composition comprises antibody that specifically binds to a polypeptide of the composition of any one of embodiments 1-12.

Embodiment 19

A method for decreasing colonization in a subject, the method comprising:

administering an effective amount of a composition to a subject colonized by a *Fusobacterium* spp., wherein the composition comprises antibody that specifically binds to a polypeptide of the composition of embodiment any one of embodiments 1-12.

Embodiment 20

The method of any one of embodiments 13-19 wherein the subject is a mammal.

Embodiment 21

The method of any one of embodiments 13-20 wherein the mammal is a human, a bovine, or an ovine.

Embodiment 22

The method of any one of embodiments 13-21 wherein the *Fusobacterium* spp. is *F. necrophorum.*

Embodiment 23

The method of any one of embodiments 13-22 wherein at least 10 micrograms (μg) and no greater than 2000 μg of polypeptide is administered.

Embodiment 24

The method of any one of embodiments 13-23 wherein the infection causes a condition selected from metritis, hepatic abscesses, and foot rot.

Embodiment 25

A kit for detecting antibody that specifically binds a polypeptide, comprising in separate containers:

an isolated polypeptide of the composition of any one of embodiments 1-12; and a reagent that detects an antibody that specifically binds the polypeptide.

Embodiment 26

A kit for detecting a polypeptide, comprising in separate containers:

an antibody that specifically binds an isolated polypeptide of the composition of any one of embodiments 1-12; and a second reagent that specifically binds the polypeptide.

Embodiment 27

A composition comprising:

isolated antibody that specifically binds to a polypeptide of the composition of any one of embodiments 1-12.

Embodiment 28

A composition comprising:

an isolated whole cell that comprises a polypeptide of the composition of any one of embodiments 1-12.

Embodiment 29

The composition of embodiment 28 wherein the isolated whole cell comprises the polypeptides of the composition of any one of embodiments 1-12.

Embodiment 30

A composition comprising:

isolated antibody that specifically binds to a whole cell of any one of embodiments 28-29.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

The present invention is illustrated by the following examples. It is to be understood that the particular examples, materials, amounts, and procedures are to be interpreted broadly in accordance with the scope and spirit of the invention as set forth herein.

In the following studies we examined the expression of proteins of *Fusobacterium necrophorum* subsp. *necrophorum* under various conditions of metal ion restriction in order to mimic the expression of novel proteins that may be expressed during systemic invasion and colonization of the liver.

Example 1

Selection of *Fusobacterium necrophorum* Isolates

More than a dozen clinical isolates of *Fusobacterium necrophorum* were isolated from infected livers of beef cattle obtained from multiple processing plants. To preserve the original isolates a master seed stock of each isolate was prepared under anaerobic conditions. Briefly, single colonies were selected off blood agar plates grown under anaerobic conditions at 37° C. for approximately 48 hours. Colonies were transferred to 10 mL modified Trypticase Soy Broth (mTSB) (Becton Dickenson and Company, Franklin Lakes, N.J.) containing 0.05% cysteine HCL and 5 g/L yeast extract. A frozen master seed of each isolate was prepared by inoculating the isolate into 10 ml mTSB. The cultures were incubated anaerobically for 16 hours at 37° C. Five ml of each culture was transferred into 100 ml bottles of mTSB with either 15 μg/ml 2,2'-dipyridyl (DP) (Sigma Chemicals, St Louis, Mo.) or 20 μg/mL $FeCl_3$ (Sigma) and allowed to grow anaerobically for 6 hours at 37° C. Fifty ml of the resulting cultures was combined with 50 ml of fresh mTSB containing 15 ug/ml DP and 20% glycerol, and the bacterial suspensions were sterilely dispensed into 2 ml cryogenic vials (1.5 ml per vial) and stored at −80° C. until use. Master seed stocks of each isolate were expanded into a working seeds. Briefly, one vial of the previously prepared master seed was grown as previously described, sterilely dispensed into 1.5 ml per vials and stored at −80° C. until use.

One isolate was selected based on its ability to grow well in metal ion chelators and showed good outer membrane protein expression. The isolate selected as the Master for the production of the Fuso-SRP Extract was designated as Master Seed 1694.

Example 2

Test for Novel Protein Expression

To test for novel protein expression under conditions of iron, zinc and copper chelation, frozen working seeds of *Fusobacterium necrophorum* as described above were transferred into 100 ml deplete modified Tryptic Soy Broth (TSB) containing 0.05% cysteine HCL and 5 g/L yeast extract and one of four metal ion chelators, 2,2'-dipyridyl (Dp), 2-pyridylmethyl-ethylene diamine (TPEN), catechin, and naringenin (all obtained from Sigma, St. Louis, Mo.). The metal ion chelators were used at the following concentration; 50 uM N,N,N',N'-tetrakis(2-pyridylmethyl)ethylenediamine (TPEN); 50 and 100 uM quercetin; 100 uM catechin; or 100 uM Naringenin respectively. Cultures were grown with each chelator for 12 hours, at which point the culture was subcultured a second time for an additional 12 hours. Each culture was subcultured for five consecutive passes at 12-hour intervals. At the end of the fifth pass, each culture was harvested by centrifugation at 10,000×g for 20 minutes. Each culture was washed twice by centrifugation at 10,000×g and resuspended in 20 ml Tris-buffered saline, pH 7.2 at 4° C.

The bacterial cell suspensions were disrupted by sonication for 1.5 minutes at 4° C. using a Branson 450 equipped with a half inch disruption horn (Branson, Danbury Conn.). The disrupted bacterial suspensions were clarified by centrifugation at 32,000×g for 12 minutes. The supernatants were collected and solubilized by the addition of sodium lauroyl sarcosinate (4% vol/vol) at 4° C. for 24 hours. The detergent-insoluble protein-enriched fractions were collected by centrifugation at 32,000×g for 2.5 hours at 4° C. The protein pellets were resuspended in 200 μl Tris-buffer (pH 7.2) and stored at −90° C.

Cell extracts, derived from each metal chelation, were size-fractionated on SDS-PAGE gels using a 4% stacking gel and 10% resolving gel. Samples for electrophoresis were prepared by combining 30 μg of sample with 30 μl of SDS reducing sample buffer (62.5 mM Tris-HCL pH 6.8, 20% glycerol, 2% SDS, 5% beta-mercaptoethanol) boiled for 4 minutes. A sample of each extract was resolved on a 10% SDS-PAGE gel per standard methods and visualized by Coomassie Blue staining.

The SDS-PAGE patterns of *Fusobacterium necrophorum* 1694 grown under iron, zinc, and/or copper chelation showed unique banding patterns that were different when compared to the same isolate when grown under iron-restriction in the presence of 2,2'-dyipyridyl. For example, when the *Fusobacterium necrophorum* 1694 isolate was grown under iron-restriction or in the presence of the chelator 2,2'-dyipyridyl, unique iron-regulated proteins were expressed at the 88, 84, 68, 60, and 52 kDa regions (Table 1). These proteins were not detected when the isolate was grown in the presence of ferric chloride. Growth of *Fusobacterium necrophorum* 1694 in iron restriction also resulted in the increased expression of proteins having molecular weights of 103 and 74 kDa (Table 1). These proteins were detected when the isolate was grown in the presence of ferric chloride, but expressed at higher levels during growth under iron restriction.

When *Fusobacterium necrophorum* 1694 isolate was grown under copper-restriction, unique copper-regulated proteins were expressed at the 126, 74, and 28 kDa regions (Table 1). These proteins were not detected when the isolate was grown in the presence of free copper. Growth of *Fusobacterium necrophorum* 1694 in copper restriction also resulted in the increased expression of proteins having molecular weights of 88, 60, and 48 kDa (Table 1). These proteins were detected when the isolate was grown in the presence of free copper, but expressed at higher levels during growth under copper restriction.

When *Fusobacterium necrophorum* 1694 isolate was grown under zinc-restriction, unique zinc-regulated proteins were expressed at the 126, 103, 88, 81, 68, 48, 28, and 24 kDa regions (Table 1). These proteins were not detected when the isolate was grown in the presence of free zinc. Growth of *Fusobacterium necrophorum* 1694 in zinc restriction also resulted in the increased expression of proteins having molecular weights of 73 and 60 kDa (Table 1). These proteins were detected when the isolate was grown in the presence of free zinc, but expressed at higher levels during growth under zinc restriction.

We show for the first time a novel subset of proteins expressed by *Fusobacterium necrophorum* when the organism is grown under Iron, copper and zinc-restriction that are not expressed when the same isolate is grown under non-restricted conditions. Since transitional metals are used by organisms to build enzymes that catalyze various biochemical reactions, the metal ions may play a vital role in microbial survival during a systemic infection and/or the tissues they infect. It is perhaps for this reason that during sepsis there is a transient decrease in the availability of these transitional metals, making them unavailable for growth of the organism. These novel proteins could very well enhance the protective efficacy of the existing composition grown under iron-restriction because they may also be expressed by the bacteria under the metal ion restriction.

Example 3

Analysis of Proteins

The electrophoretic banding profiles of the proteins isolated from the *Fusobacterium necrophorum* isolate grown in the following five conditions as described above were compared: iron-deplete media (400 ml mTSB containing 15 μg 2,2-dipyridyl), and controlled fermentation conditions (the iron-deplete fermentation conditions of Example 4); mTSB containing 100 uM naringenin; mTSB containing 100 uM catechin; mTSB containing 50 or 100 uM Quercetin; and mTSB containing 100 μM of N,N,N,N Tetrakis. The results revealed different banding profiles between each sample grown under different metal-depleting conditions.

Figure 2:
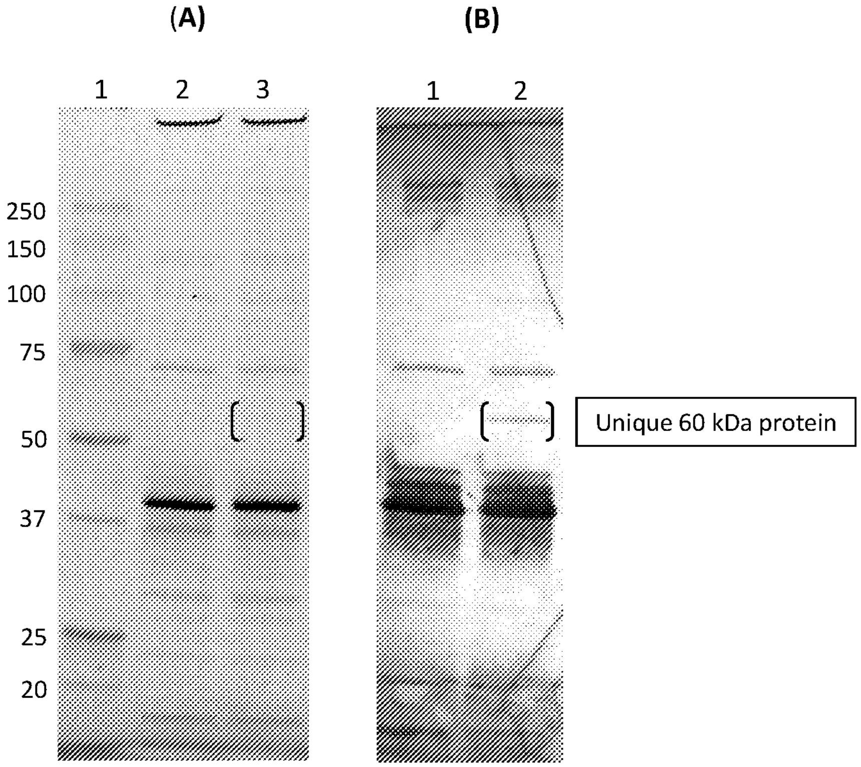
FIG. 2.

In the presence of catechin (Quinde-Axtell et al., 2006, J. Agric. Food Chem., 54(26):9978-9984), a unique protein of ~60 kDa by SDS-PAGE was visibly upregulated that was not enhanced in the presence of the other flavonoids and chelators (FIG. 2; Lane 3A). This protein was further shown to be immuno-reactive in a western blot against convalescent sera of a calf exposed to experimental challenge of Example 7 with *Fusobacterium necrophorum* (FIG. 2; Lane 2B).

Figure 3:
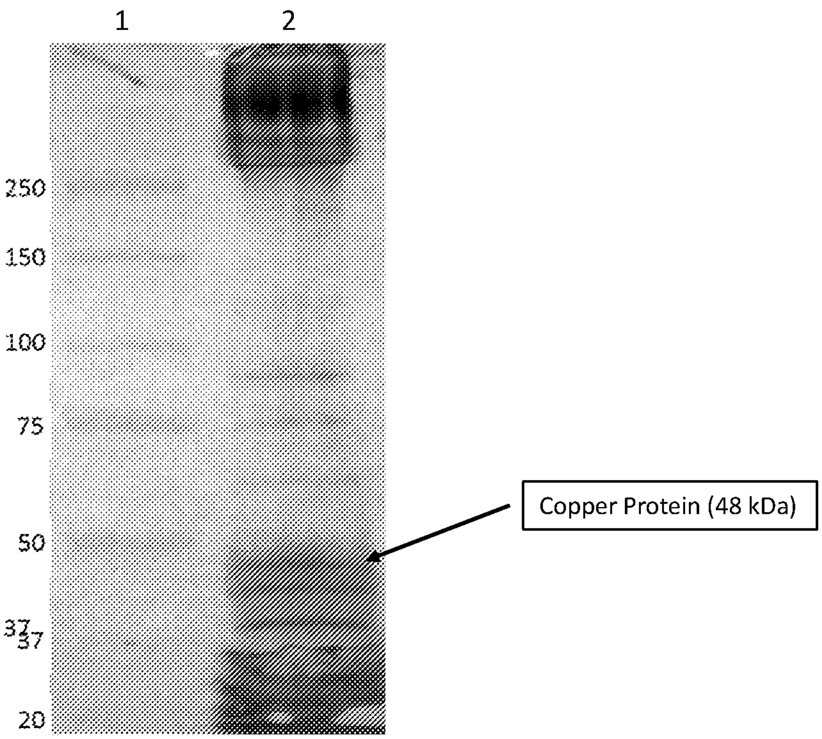
FIG. 3. Western Blot showing the sero-reactivity of the *Fusobacterium necrophorum* 48 kDa protein grown under copper deplete growth conditions. Lane 1, Molecular Weight Marker (MWM); Lane 2-Sero-reactivity of the 48 kDa copper protein. Arrow shows the up-regulation of a novel protein at 48 kDa that reacted with sera of Example 7.

In the presence of Quercetin (copper restriction) a protein of ~48 kDa by SDS-PAGE, was shown to be preferentially upregulated, as compared to the other flavonoids and chelators (FIG. 1; Lane 6). This protein was also shown to be immuno-reactive when exposed to the convalescent serum above (FIG. 3; Lane 2). The band from FIG. 1; Lane 6 was identified via matrix assisted laser desorption/ionization time-of-flight spectrometry (MALDI-TOF). The closest match found via Scaffold is the outer membrane protein of *Fusobacterium necrophorum* strain DAB KDE68083. The function of this protein is unknown. The identified protein sequence was used to search the nucleotide sequence of *F. necrophorum* 1694. The nucleotide sequence and amino acid sequence identified is shown in FIG. 14 (SEQ ID NOs: 1 and 2, respectively).

Figure 4:
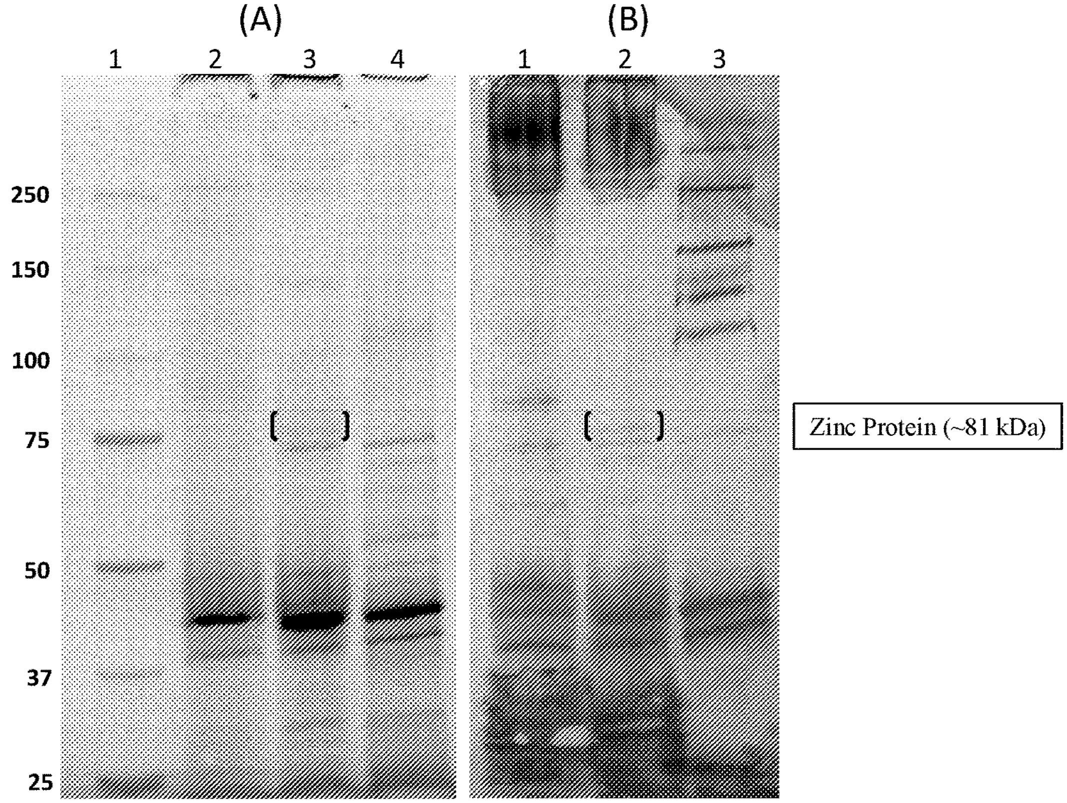
FIG. 4.

A protein of ~81 kDa by SDS-PAGE was shown to be upregulated in the presence of N,N,N,N tetrakis, a mostly zinc chelator (FIG. 1; Lane 7 and FIG. 4 Lane A3). This protein was shown to be immuno-reactive in a western blot against convalescent sera from an experimentally challenged calf of Example 7 as illustrated in FIG. 4; Lane B2. The closest match found via Scaffold was an outer membrane protein of *Fusobacterium necrophorum*. The function of this protein is listed as TonB-dependent receptor. The identified protein sequence was used to search the nucleotide sequence of *F. necrophorum* 1694. The nucleotide sequence and amino acid sequence identified is shown in FIG. 15 (SEQ ID NOs: 3 and 4, respectively).

Example 4

Production of Metal Regulated Proteins

Fermentation

A cryogenic vial of the working seed of *Fusobacterium necrophorum* 1694 (1 ml at $10^9$ CFU/ml) was used to inoculate 250 ml of 37° C. modified TSB (mTSB) containing 5 g/L yeast extract and 0.05% cysteine (Sigma) and incubated in an anaerobic chamber. The culture was incubated at 37° C. for 20 hours at which point was sterilely transferred into 1.25 liters of the above media plus 25 micrograms (μg) 2,2-dipyridyl. This second culture was allowed to grow for an additional 3 hours at 37° C. This culture was used to inoculate a 15-liter Bioflo IV bench-top fermentor, (New Brunswick Scientific Co, Edison N.J.) charged with 9.5 liters of the above-described media. The pH was held constant between 6.9 and 7.1 by automatic titration with 50% NaOH and 20% $H_3PO_4$. The stirring speed was adjusted to 250 revolutions per minute (rpm), and the culture purged with pure nitrogen to maintain an anaerobic condition. The culture was allowed to grow continuously at these conditions for 24 hours at which point the fermentation was terminated by raising the pH to 8.5.

Harvest

The bacterial cells were concentrated by centrifugation (Beckman Coultier, Brea, Calif.) at 7,000 rpm for 20 minutes. The bacterial pellet was then resuspended at a ratio of 60 g cell pellet to 1 liter sterile Osmotic Shock Buffer (OMS) containing 7.26 grams/liter Tris-base and 0.93 grams/liter EDTA adjusted to a pH of 8.5. The cell suspension was then incubated at 2-8° C. for 24 hours to remove excess endotoxin from the cells. The resulting suspension was then centrifuged again and the supernate discarded to remove free endotoxin and any extracellular material, e.g., secreted proteins. The cell pellet was resuspended in 3 liters of OMS. The cell suspension was mixed thoroughly and dispensed into a sterile four liter Nalgene containers and placed into a −20° C. freezer for storage. The pellet mass was calculated by centrifuging 30 ml samples of the fermented culture and final harvest. Briefly, pre-weighted 50 ml Nalgene conical tubes were centrifuged at 39,000×g for 90 minutes in a Beckman J2-21 centrifuge using a JA-21 rotor (Beckman Coulter, Brea, Calif.). At the end of the run, the supernate was poured off and the tubes were weighed again. The pellet mass was calculated for each stage.

Disruption (Homogenization)

One liter of the harvested three liter frozen bacterial cell slurry in OMS was thawed at 4° C. (60 gram pellet mass). The liquid culture suspension was disrupted by homogenization. Briefly, the tank containing the bacterial suspension was connected to a model Emulsiflex C500B Homogenizer, (Avisten Inc, Ottowa, Canada). A second process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of each pass, fluid was circulated at 40-65 psi through the homogenizer and back to the tank of origin, while the homogenizer pressure was adjusted to ≥20,000 psi. Prior to the first pass, two pre-homogenizing samples were withdrawn from the homogenizer to establish a baseline for determining the degree of disruption and monitoring of pH. The degree of disruption was monitored by transmittance (% T at 540 nanometers (nm) at 1:100 dilution) compared to the non-homogenized sample. The bacterial suspension was passed three times through the homogenizer to give a final percent transmittance >80% T at a 1:100 dilution.

After homogenization, Sodium Lauroyl Sarcosinate (Hamptosyl L-30, Chem/Serv, Minneapolis, Minn.) was aseptically added to the homogenized bacterial suspension for solubilization. The amount of Sarcosine (30%) added equaled 0.5% of the solubilizing volume, in liters. The process tank was removed from the homogenizer and kept at 4° C. while shaking at 120 rpm for 16-24 hours.

Protein Harvest and Diafiltration

The protein suspension (1 Liter) was adjusted to 5 liters using sterile Tris-buffer, pH 8.5. The suspension was washed and dialyzed using a Optisep 1000 SmartFlow Tangential Flow Filter device (NCSRT Inc, Apex, N.C.), equipped with a 0.8 $ft^2$ screen-channel series Alpha 50 kDa Centrasette filter (Pall Filtron) to remove residual sarcosine. The protein solution was concentrated by filtration to a target volume of 1 liter at which point 10 liters of Tris-buffer pH 7.2 containing 10% isopropyl alcohol was slowly added to the concentrate from a second process tank. Isopropyl alcohol is thought to cause a slight unfolding of the protein structure allowing for the removal of bound sarcosine without compromising the immunogenicity of the proteins. Diafiltration continued until the pH stabilized to 7.2 at which point 5 liters Tris-buffer pH 7.2 was slowly added by diafiltration to remove residual alcohol. The Fuso-SRP Extract suspension was then concentrated to approximately 325 ml. The protein concentrate was stored at −20° C. until use.

Alternative methods for bacterial harvest can be used. Bacterial harvest may be performed by the use of hollow fiber filter methods. Bacterial culture is harvested using filter cartridges ranging in size from 0.2 μM to 5 kDa; preferably with a 750 kDa cartridge. Culture is reduced in volume from 2-20× and subsequently washed 1-5× by diafiltration with buffer prior to storage at 4° C. or freezing at −20° C. In this manner, undesired media proteins, bacterial proteins and LPS are removed from the culture. In another alternative, bacterial harvest may be performed by the use of industrial scale centrifugation, for example, by use of a disc-stack centrifuge.

Example 5

*Fusobacterium* Recombinant Zinc Protein (rZinc) Construction

The full nucleotide sequence of the rZinc protein, including signal peptide, was submitted to GenScript USA Inc. (Piscataway, N.J.) for gene synthesis. The amino acid sequence was optimized for expression in *Escherichia coli*. Synthesized DNA was cloned in to plasmid pET-20b+ (Novagen) by GenScript using the NdeI-XhoI cloning sites allowing for a C-terminal 6× Histidine tag. The resulting plasmid is named rZinc_pET-20b+.

Plasmid pTHV (Epitopix, LLC) was amplified using primers 3 and 4 (Table 2) to exclude the existing gene insert and only amplify the plasmid backbone. Fragment rZinc, excluding the signal peptide, was amplified from plasmid FT_pET-20b+ using oligonucleotide primers 1 and 2 (Table 2). The primers include nucleotides that overlap with the destination plasmid, pTHV. The vector and fragment PCR products were assembled using the NEBuilder® HiFi DNA assembly protocol (New England Biolabs) and transformed into NEB 10-beta competent *E. coli* for expression.

TABLE 2

Fusobacterium rZinc Oligonucleotide Primers

| Primer No. | Name | Sequence (5'-3') |
|---|---|---|
| 1 | FT.Fragment. FOR | TCAATTTGCTAGGGGATCTGCCGAAAT CGATCTGGGCAC |
| 2 | FT.Fragment. REV | CCATGGCTAGCTAGCTAGTGGTGGTGG TGGTGGTGC |
| 3 | pTHV.Vector. FOR | TAGCTAGCTAGCCATGGCATCAC |
| 4 | pTHV.Vector. REV | AGATCCCCTAGCAAATTGAAGAGAAAG ATCT |

Example 6

*Fusobacterium* Recombinant Hemin Protein (rHemin) Construction

The full nucleotide sequence of the rHemin protein, including signal peptide, was submitted to GenScript USA Inc. (Piscataway, N.J.) for gene synthesis. The amino acid sequence was optimized for expression in *Escherichia coli*. Synthesized DNA was cloned in to plasmid pET-20b+ (Novagen) by GenScript using the NdeI-XhoI cloning sites allowing for a C-terminal 6× Histidine tag. The resulting plasmid is named rHemin_pET-20b+.

Plasmid pTHV (Epitopix, LLC) was amplified using primers 7 and 8 (Table 3) to exclude the existing gene insert and only amplify the plasmid backbone. Fragment rHemin, excluding the signal peptide, was amplified from plasmid rHemin_pET-20b+ using oligonucleotide primers 5 and 6 (Table 3). The primers include nucleotides that overlap with the destination plasmid, pTHV. The vector and fragment PCR products were assembled using the NEBuilder® HiFi DNA assembly protocol (New England Biolabs) and transformed into NEB 10-beta competent *E. coli* for expression.

TABLE 3

Fusobacterium rHemin Oligonucleotide Primers

| Primer No. | Name | Sequence (5'-3') |
|---|---|---|
| 5 | FH.Fragment. FOR | TACTGTTATAGATCTTTCTGAACAAACG ATTGAACTGGG |
| 6 | FH.Fragment. REV | TCCCTGCCTCTGTCACTTCCTTTCGGGCT TTGTTAG |
| 7 | pTHV.201601. FOR | TGACAGAGGCAGGGAGTG |
| 8 | pTHV.201601. REV | AGAAAGATCTATAACAGTAGCCATATTT AAAC |

Example 7

Preparation of Convalescent Sera in Holstein Calves

Convalescent serum was collected as part of a vaccination and challenge study in which steers with an average weight of approximately 350 pounds were used for generation of sera. Calf number 72 was an unvaccinated control animal challenged via the portal vein according to the method of K. Lechtenberg et al (Am J Vet Res. 1991 June; 52(6)803-9) with approximately $6\times10^8$ cfu of a virulent *Fusobacterium necrophorum* strain.

Example 8

Blood Sample Collection

Blood samples were collected from all steers on day 66 (10 days post-challenge). All blood was collected in sterile 13×75 millimeter vacutainer collection tubes (SST No. 369783, Becton Dickinson, Franklin Lakes, N.J.). After clotting the blood tubes were centrifuged at 800×g for thirty minutes and frozen at −20° C.

Example 9

Identification of Sero-Reactive Membrane Proteins of *Fusobacterium necrophorum* Using Western Blot Analysis The proteins in the vaccine composition as described in Example 2 were subjected to electrophoresis followed by western blot analysis with convalescent serum as described in Example 7. Briefly, the membrane proteins derived from *Fusobacterium necrophorum* grown under iron-limiting conditions were size-fractionated on an SDS-PAGE gel using a 4% stacking gel and 7.5% resolving gel. A 10 μl sample was combined with 10 μl of SDS reducing sample buffer (62.5 mM Tris-HCL ph 6.8, 20% glycerol, 2% SDS, 5% β-mercaptoethanol) and boiled for 4 minutes. Samples were electrophoresed at 18 mA constant current for 5 hour at 4° C. using a Protein II xi cell and model 1000/500 power supply (BioRad Laboratories, Richmond, Calif.). Band migration was visualized using broad range kaleidoscope standards (BioRad) to aid in the electro-blot transfer while biotinylated broad range standards were used as molecular weight references on the blot, see FIG. 7. For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo.) in Tris buffered saline (TBS-20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the polyclonal convalescent sera collected from the challenged steer as described in example 7. The primary antibody was diluted 1/500 in TBS containing 1% fish gelatin, 0.05% Tween 20 and 0.2% sodium azide (Antibody Buffer). The membrane was incubated with the primary antibody solution overnight on a shaker at room temperature. The membrane was then washed two times in TBS containing 0.05% Tween 20 (TTBS) and transferred to antibody buffer containing a 1/10,000 dilution of Alkaline phosphatase-conjugated mouse anti-bovine IgG clone BG-18 (Sigma) and a 1/3000 dilution of avidin conjugated to alkaline phosphatase (Bio-Rad). The membrane was incubated at 37° C. for 2 hours on a shaker, then washed in TTBS four times to remove unbound conjugate. The blot was resolved in substrate solution containing alkaline phosphate color reagent A and B in 1× AP color development Buffer (BioRad) for 30 min. at 37° C. on a shaker. The resulting Western immunoblot was documented using a BioRad GS-800 Densitometer (see FIGS. 2-4, 7 and 8).

The purpose of this analysis was to determine which of the proteins present in the immunizing composition induced antibody responses following challenge of steers. The results revealed unique immunological reactivity with proteins at 48 kDa in the presence of the copper chelator Quercetin, catechin, or narangenin (FIGS. 2, 3 and 4); at ~60 kDa in the presence of the copper chelator catechin (FIG. 2); and an ~82 kDa protein in the presence of the zinc chelator Tetrakis (TPEN) (FIG. 4); and an ~90 kDa protein in the presence of quercetin. In addition, the results revealed unique immunological reactivity proteins at 131 kDa, 85 kDa, 60 kDa, and in the area of 40-43 kDa in the presence of the copper chelator Quercetin; at 107 kDa, 75 kDa, 60 kDa, and in the area of 40-43 kDa in the presence of the copper chelator catechin; at 73 kDa and in the area of 40-43 kDa in the presence of the copper chelator naringenin; and at 82 kDa, 75 kDa, 73 kDa, 60 kDa, 48 kDa, and in the area of 40-43 kDa in the presence of the zinc chelator Tetrakis (TPEN). The molecular weights of the immunologically reactive proteins are not identical with the molecular weights of the metal regulated proteins described herein identified by SDS-PAGE; however, the molecular weights of the immunologically reactive were determined using the results of western immunoblot assays, and the skilled person will recognize that the ability to accurately determine molecular weights from a western immunoblot is reduced.

These results demonstrated that the membrane proteins of the composition described in Example 2 reacted strongly with the convalescent sera described in Example 7, suggesting that these components of the vaccine may provide protection against disease. However, the sensitivity limits of the assay may have prevented the detection of weaker interactions, that, although less evident, may still contribute to the vaccine's effectiveness by augmenting the immune response to the composition. In addition, the proteins that were not sero-reactive in this assay may elicit responses other than antibody production, such as stimulation of cytokines, intereferon, interleukins, T-cells, or colony-stimulating factors. Such responses could enhance, direct, or restore the ability of the host's immune system to fight disease.

Example 10

Preparation of the Immunizing Compositions Derived from *Fusobacterium necrophorum*

The composition made from *Fusobacterium necrophorum* strain 1694 of Example 4 was used as the vaccine in this experimental study. The vaccine was prepared from the composition by diluting the antigen into phosphate buffered saline (PBS) containing 8.0 g/l NaCl, 0.2 g/l KCl, 1.44 g/l $Na_2HPO_4$ and 0.24 g/l $KH_2PO_4$ pH 7.4 The suspension (500 μg total protein/ml) was then emulsified into the commercial adjuvant, EMULSIGEN, (MVP Laboratories, Ralston, Nebr.) using the syringe method of emulsification. The process can be summarized as follows: (1) force an amount of adjuvant from syringe B by pushing it into syringe A filled with antigen solution to mingle with the latter; (2) push the same volume of the mix from syringe A back to syringe B slowly; (3) repeat the above mixing process until the mixed portion becomes milky white. A mouse dose was administered to give a final dose of 100 μg total protein in a 0.1 ml injectable volume with an adjuvant concentration of 22.5% vol/vol. A placebo was prepared by replacing the antigen with physiological saline in the above formulation and emulsifying the suspension into EMULSIGEN to give an adjuvant concentration of 22.5%.

Example 11

Mouse Vaccination

The efficacy of the Fuso-SRP Extract derived from *Fusobacterium necrophorum* 1694 was carried out against a live virulent challenge in mice. Eighty (N=80) female CF-1 mice obtained from Charles River Laboratories (Wilmington Del.) weighing 16-22 grams were equally distributed into two groups (40 mice/group). Mice were housed in polycarbonate cages in a self-contained HEPA filtered Mobile Housing System (Thoren Caging systems; Hazleton; PA). Treatment groups were designated as Group-A (Placebo) and Group-B (Fuso-SRP Extract Vaccinated). Food and water was supplied ad libitum to all mice. Mice were vaccinated subcutaneously twice at 21 day intervals. The volume administered was 0.1 ml/mouse see Table 4.

TABLE 4

Experimental Design

| Groups | Mice | Vaccine | Total Antigen | Adjuvant | Vaccine Volume (ml) | # Vaccines | Vaccine Route |
|---|---|---|---|---|---|---|---|
| A | 40 | Placebo | N/A | 22.5% Emulsigen | 0.1 | 2 | SQ |
| B | 40 | Fuso-SRP Extract | 100 μg | 22.5% Emulsigen | 0.1 | 2 | SQ |

Example 12

Preparation of Challenge Organism

Twenty eight days after the second vaccination, mice in groups A and B were intravenously challenged. The *Fusobacterium necrophorum* isolate 1694 as previously described in Example 1 was used as the challenge strain. Briefly, a cryogenic vial of the frozen working seed of *Fusobacterium necrophorum* 1694 of Example 1 was used for challenge. Briefly, the frozen stock was thawed at 4° C. then diluted 1:10 in cold mTSB and the resulting dilution was used for challenge. All mice in groups A and B were intravenously challenged via the caudal vein with 0.1 ml of *Fusobacterium necrophorum* (~$1\times10^8$ colony forming units per ml) as previously enumerated as described in Example 7 Just prior to challenge, 100 μl of the above bacterial suspension was serially diluted tenfold to enumerate the number of CFU/dose. Mortality was recorded daily for 10 days post challenge at which point the experimental trial was terminated. All surviving mice from Groups A- and B were euthanized by carbon dioxide. The liver from all dead and surviving mice was aseptically removed and gross examination was performed to determine differences in liver abscessation.

Example 13

Challenge Results

The results showed a strong protective index against a caudal vein challenge as seen in Table 5. Ten out of 40 (25%) of the placebo-vaccinated mice (Group A) died within 10 days after challenge. In contrast, no mortality (0 out of 40) was seen in the vaccinated mice of Group B (degree of significance of P=0.001).

TABLE 5

Comparison of Mortality; Liver Abscess and Percent Survivability between Vaccinated and Placebo Controls Following Intravenous Challenge with *Fusobacterium necrophorum*

| Groups | Mice | [a]Mortality (%) | [b]Liver Lesions (%) | [c]Percent Survivability |
|---|---|---|---|---|
| A) Placebo | 40 | 10 (25) | 9 (22.5) | 75 |
| B) Fuso-SRP Extract | 40 | 0 | 1 (2.5) | 100 |

[a]The mortality of mice that died within 10 days after IV challenge with 3.0 × $10^8$ CFU of *Fusobacterium necrophorum*.
[b]The percent of mice that had visible liver abscess upon death or at 10 days post challenge (two-sided P value) was P = 0.0143.
[c]Percent Survivability; 100 percent of the vaccinated mice survived challenge compared to the non-vaccinated controls where only 75 percent survived (two-sided P value) was P = 0.0010.

Gross examination of each liver revealed a dramatic difference in the number of abscesses between the Placebo and Vaccinated mice. It was clearly evident that mice given the vaccine rapidly reduced the number of bacteria able to proliferate successfully in the liver as indicated by the reduction in visible abscesses as compared to the placebo vaccinated mice (Table 5). The difference in the number of abscessed livers of Placebo vaccinated controls and the vaccinated group was statistically significant (degree of significance of P=0.0143), indicating a direct correlation in the reduction of lesions through vaccination by preventing the proliferation and colonization of *Fusobacterium necrophorum* in the liver The number of mice with abscesses was 9 out of 40 (22.5%) in the placebo vaccinated group as compared to only 1 out of 40 (2.5%) in the vaccinated group (Table 5).

The Fuso-SRP Extract vaccine of Group B showed a high degree of systemic protection as compared to non-vaccinated mice of Group A; (Placebo vaccinated). The vaccine prepared from *Fusobacterium necrophorum* was highly efficacious in preventing mortality associated with an intravenous challenge with *Fusobacterium necrophorum* in a standardized mouse model as well as reducing the formation of liver abscesses.

Example 14

Vaccine-Mediated Protection of Novel Recombinant Zinc and Hemin Proteins of *Fusobacterium necrophorum* in a Mouse Sepsis Model The purpose of the following experimental study was to evaluate the vaccine efficacy of two recombinant proteins, rZinc and rHemin of *Fusobacterium necrophorum*. In addition, a vaccine formulation consisting of the rZinc protein in combination with the Fuso-SRP extract and the Fuso-SRP extract as a stand-alone vaccine formulation was evaluated as illustrated in Table 6. The bovine strain of *Fusobacterium necrophorum* 1694 was used as the challenge strain as previously described in Example 1. The outcome parameters used to evaluate vaccine efficacy in this experiment were 1) serological response to vaccination 1) the reduction in the incidence of lesions between vaccinates and placebo control mice 2) the difference in the size of lesions based on a lesion score, where a lesion ≤0.5 cm=1 and a lesion ≥0.5=2) the difference in the Prevented Fraction which is defined as the percentage of animals in each treatment group that is protected against liver lesions calculated as:

$$1-p_2/p_1$$

$p_2$=affected fraction in vaccine group $p_1$=affected fraction in control group where, the prevented fraction is the complement of the risk ratio $1-p_2/p_1$; where $p_2$ is the affected fraction in the experimental product and $p_1$ is the affected fraction in the placebo group. The precision of the estimate is evaluated by determining the 95% confidence interval.

Briefly, three hundred twenty (N=320) female Harlan CF-1 mice obtained from Charles River Laboratory (Wilmington, Mass.) weighing 16-22 grams were equally divided into 8 treatment groups (40 mice/group) designated as groups A-H (Table 6). Mice were housed in polycarbonate cages in a self-contained HEPA filtered Mobile Housing System (Thoren Caging systems; Hazleton; PA) at 5 mice per cage with food and water supplied ad libitum. All mice were allowed to acclimate one week prior to the first vaccination.

Example 15

Vaccine Preparation and Vaccination

Vaccines of the recombinant Zinc and Hemin proteins as well as the *Fusobacterium necrophorum* SRP extract was prepared at their appropriate dosage levels in phosphate buffered saline (PBS) containing 8.0 g/l NaCl, 0.2 g/l KCl, 1.44 g/l $Na_2HPO_4$ and 0.24 g/l $KH_2PO_4$ pH 7.4 formulated with 10 percent Rehydragel HPA; (General Chemical; Berkeley Heights; New Jersey). The antigen/aluminum hydroxide suspensions was stirred for 24 hours at 4° C. to allow maximum adsorption of the protein to the adjuvant. The antigen/aluminum hydroxide suspension was then emulsified into the commercial adjuvant, EMULSIGEN, (MVP Laboratories, Ralston, Nebr.) to give and adjuvant concentration of 22.5% vol/vol. The rZinc vaccine of groups B and C was formulated at 100 μg and 250 μg respectively. The combination vaccine of Group D was formulated containing 10 μg of the Fuso-SRP extract as previously described in Example 4 and 50 μg of the rZinc protein to give a mouse dose of 60 μg total protein. The rHemin protein of Groups E and F was formulated at 25 μg and 100 μg dose levels respectively, while the Fuso-SRP extract of Groups G and H was formulated at 10 and 100 μg total protein respectively. All vaccines of Groups A-H were formulated to be delivered at 0.1 ml injectable volume. A placebo vaccine was prepared by substituting physiological saline for the aqueous protein suspension as described above. Mice were vaccinated subcutaneously two times at 21 day intervals and then challenged 14 days following the last vaccination. Blood was taken randomly from five mice from each group three times during the course of the study 1) first vaccination (pre-immune); 2) second vaccination and 3) 24 hours pre-challenge. Individual blood samples were equally pooled and stored at −80° C. until analyzed by western blot and ELISA to determine the serological response to vaccination.

TABLE 6

Experimental Design

| Group | Mice | Vaccine | Total Antigen | Adjuvant | Vaccine Volume (ul) | # Vaccines | Vaccine Route |
|---|---|---|---|---|---|---|---|
| A | 40 | Placebo | N/A | 10% ALOH + 22.5% Emulsigen | N/A | 2 | SQ |
| *B | 40 | rZinc | 100 μg | 10% ALOH + 22.5% Emulsigen | 100 | 1 | SQ |
| C | 40 | rZinc | 250 μg | 10% ALOH + 22.5% Emulsigen | 100 | 2 | SQ |
| D | 40 | rZinc + Fuso-SRP Extract | 10 μg SRP + 50 μg rZinc | 10% ALOH + 22.5% Emulsigen | 100 | 2 | SQ |
| E | 40 | rHemin | 25 μg | 10% ALOH + 22.5% Emulsigen | 100 | 2 | SQ |
| F | 40 | rHemin | 100 μg | 10% ALOH + 22.5% Emulsigen | 100 | 2 | SQ |
| G | 40 | Fuso-SRP Extract | 10 μg | 10% ALOH + 22.5% Emulsigen | 100 | 2 | SQ |
| H | 40 | Fuso-SRP Extract | 100 μg | 10% ALOH + 22.5% Emulsigen | 100 | 2 | SQ |

Please note;
the recombinant zinc protein (*B) in the above experimental design was inadvertently vaccinated only one time rather than the proposed two time vaccination regimen.

Example 16

Preparation of Challenge Organism

The *Fusobacterium necrophorum* isolate 1694 as previously described in Example 1 was used as the challenge strain. Briefly, a cryogenic vial of the frozen working seed of *Fusobacterium necrophorum* 1694 of Example 1 was used for challenge. The frozen stock was thawed at 4° C. then diluted 1:10 in cold mTSB and the resulting dilution was used for challenge. All mice in groups A through H were intravenously challenged via the caudal vein with 0.1 ml of *Fusobacterium necrophorum* (~1×10$^8$ colony forming units per ml) as previously enumerated as described in Example 7. Just prior to challenge, 100 μl of the above bacterial suspension was serially diluted tenfold to enumerate the number of CFU/dose. Mortality was recorded daily for 7 days post challenge at which point the experimental trial was terminated. All surviving mice from Groups A-H were euthanized by carbon dioxide. The liver from all dead and surviving mice was aseptically removed and gross examination was done to determine differences in liver abscessation.

Example 17

Challenge Results

Figure 5:
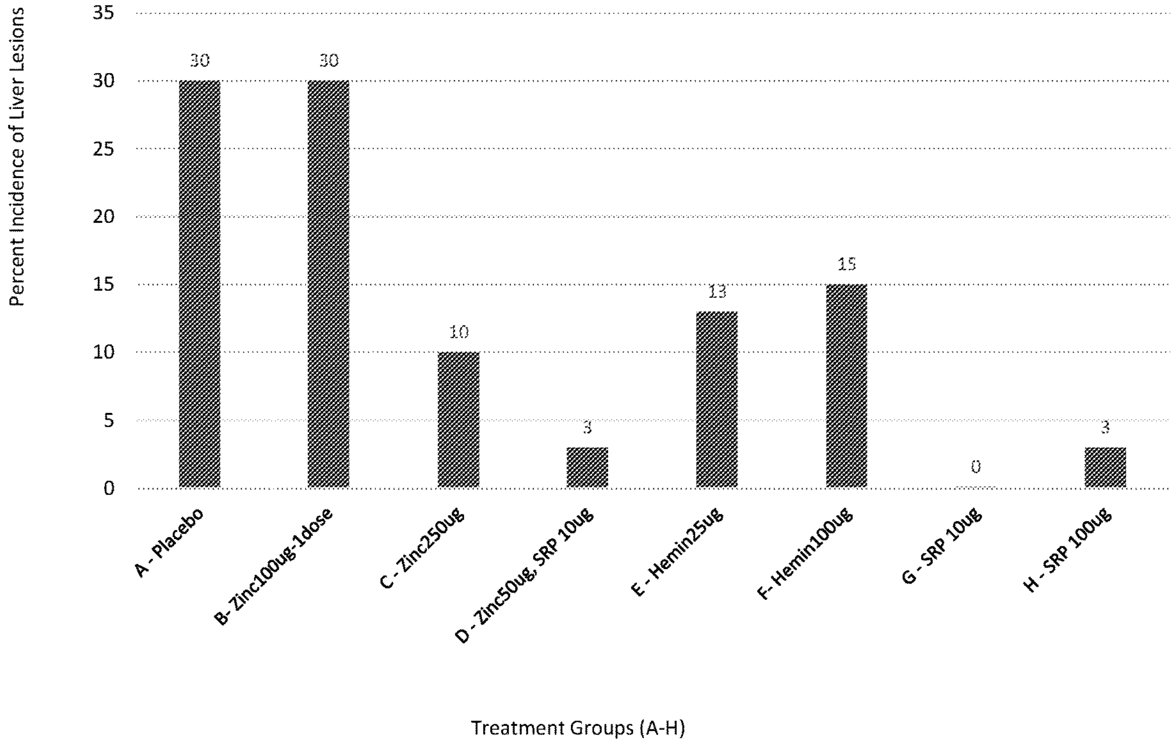
FIG. 5. The incidence of liver lesions between groups seven days post challenge with *Fusobacterium necrophorum*. All treatment groups were vaccinated two times except for Group B which received only one vaccination. There was a decrease in liver lesions between all treatment groups compared to controls. The only treatment group that did not show a significant difference compared to the non-vaccinated control was Group B.

Seven days post challenge the livers of all dead and surviving mice were aseptically removed and the difference in incidence and size of lesions was determined between vaccinates and placebo controls. Gross examination of each liver revealed a dramatic difference in both the size and incidence of lesions between the Placebo and Vaccinated mice. For example; thirty percent of the Placebo control mice had well defined foci in the livers in contrast to vaccinates; (Table 7; FIG. 5). Both the rZinc and rHemin proteins showed a reduction in the incidence of lesions to 10 and 15 percent respectively at the 250 μg (rZinc) and 25 μg (rHemin) dose level compared to controls which showed an incidence rate of 30 percent, see Table 7; FIG. 5). It is interesting note the difference in the vaccine dose between the two recombinant proteins that induced efficacy i.e., 250 μg for the rZinc protein and 25 μg for the rHemin protein of Groups C and E (Table 7; FIG. 5). Both vaccine formulations of the Fuso-SRP Extracts of Groups G and H at the 10 μg and 100 μg dose level were highly effective at reducing the incidence of lesions compared to the Placebo control of Group A. In fact; the vaccine at 10 μg dose level completely protected mice from abscessation and only 1 out of 40 mice in the 100 μg dose level of Group H showed lesions in the liver. In comparison; the combo vaccine of Group D containing 10 μg of the Fuso-SRP extract and 50 μg of the rZinc protein was also highly effective in reducing the incidence of lesions; only 3 percent or 1 out of 40 mice were found to have lesions.

TABLE 7

The percent difference of lesions in the liver and the calculated Prevented Fraction between vaccinates compared to the placebo control

| Treatment Groups (A-H) | Total Antigen | Mortality | [a]Liver Lesions (%) | [b]Prevented Fraction (%) |
|---|---|---|---|---|
| A) Placebo (N = 40) | N/A | 4 | 30 | 0 |
| B) rZinc | 100 μg | 2 | 30 | 0 |
| C) rZinc | 250 μg | 1 | 10 | 73 |
| D) rZinc + Fuso-SRP Extract | 10 μg SRP + 50 μg rZinc | 0 | 3 | 92 |
| E) rHemin | 25 ug | 3 | 13 | 58 |
| F) rHemin | 100 μg | 0 | 15 | 50 |
| G) Fuso-SRP Extract | 10 μg | 1 | 0 | 100 |
| H) Fuso-SRP Extract | 100 μg | 0 | 3 | 92 |

[a]Liver lesions - The difference in the number of mice having lesions calculated as a percent between treatment groups compared to controls.
[b]Prevented fraction is the percentage of mice in each treatment group that was protected against liver lesions.

Figure 6:
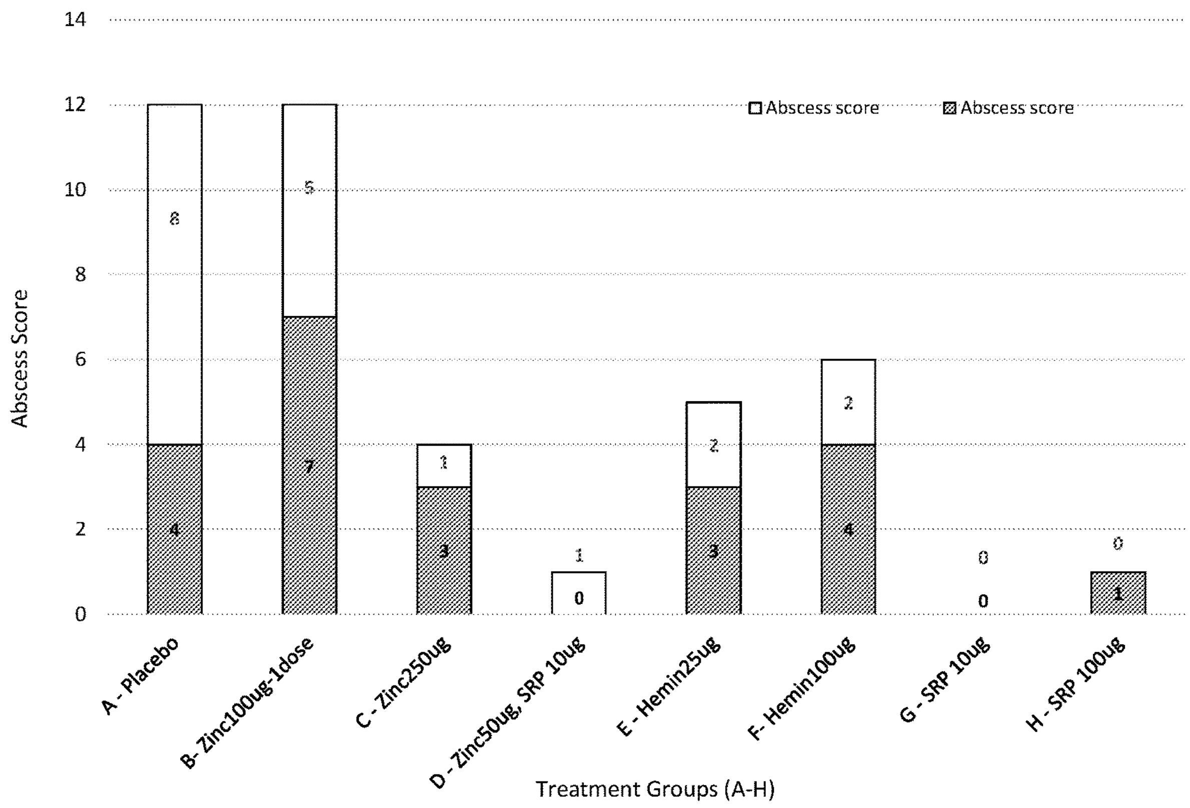
FIG. 6. The difference in the size of lesions between vaccinates and placebo controls. The lesion score was enumerated where a lesion ≤0.5 cm=1 (shaded boxes) and a lesion ≥0.5=2 (unshaded boxes). Each bar represents the number of challenged mice showing the total number of lesion per group that had a lesion size of ≤0.5 cm or ≥0.5.

FIG. 6 shows the difference in the size of lesions between vaccinates and controls. Please note; the significant reduction in the size of the lesions in all vaccinated groups (C-H) with the greatest reduction being in the Fuso-SRP Extract formulations at both the 10 and 100 μg dose levels. As illustrated; it is clearly evident that each vaccine formulation including the recombinant rZinc; rHemin and Extracted Fuso-SRP proteins reduced the number of bacteria able to proliferate successfully in the liver as indicated by the reduction in visible abscesses as well as the size of lesions compared to the placebo vaccinated mice; see FIGS. 5 and 6.

The only vaccinated group that was not significantly different than the placebo controls was the rZinc protein at the 100 μg dose level of Group B. This vaccine was inadvertently administered only one time rather than the proposed two time vaccine regimen (Table 6). These results clearly show that a single dose of the rZinc protein at a 100 μg is not sufficient to induce a proper protective response. The rZinc protein administered at the 250 μg dose level of Group C was highly effective in reducing both the incidence and the size of lesions, clearly demonstrating a dose response; as the dose increased the incidence and size of lesions decreased. It's interesting to speculate that if the dose of the rZinc protein was increased beyond the 250 μg dose level if one could have obtained a greater degree of protection that would have been equivalent to the Fuso-SRP Extract. These results clearly demonstrate that a single recombinant protein at an optimal dose can protect against a systemic challenge of *Fusobacterium*. The rZinc protein reduced the incidence and the size of lesions.

Not unlike the rZinc protein, the rHemin protein was also effective as a vaccine candidate in reducing both the incidence and the size of lesions compared to the non-vaccinated controls. Both the 25 μg and 100 μg dose levels of the rHemin protein reduced the incidence and overall size of lesions in the liver (FIGS. 5 and 6). Due to the lack of availability of final antigen of this protein the experiment did not allow for dose matching of the two recombinant proteins; i.e., it would have been more appropriate to compare the recombinant proteins at the same dose levels rather than at different protein amounts. Nevertheless, results clearly demonstrate that the rHemin protein is an excellent target antigen for controlling both the size and incident of liver lesions.

TABLE 8

The percentage of animals in each treatment group that is protected against liver lesions

| TREATMENT GROUPS | *PREVENTED FRACTION | P VALUE BY FISHER'S |
|---|---|---|
| ZINC 100 UG SINGLE DOSE | 0% | |
| ZINC 250 UG | 73% | 0.048 |
| ZINC 50 UG/SRP 10UG | 92% | 0.0015 |
| HEMIN 25 UG | 58% | 0.099 |
| HEMIN 100 UG | 50% | 0.18 |
| SRP 10 UG | 100% | 0.0002 |
| SRP 100 UG | 92% | 0.0015 |

*Prevented Fraction is defined as the percentage of animals in each treatment group that is protected against liver lesions calculated as $(1 - p_2/p_1)$ where $p_2$ is the affected fraction in the vaccine groups and $p_1$ is the affected fraction in placebo control group.

In addition, the results show the calculated Prevented Fraction as described in Example 14 for each treatment group compared to the non-vaccinated placebo controls. For example, the Fuso-SRP Extracts at both the 10 μg and 100 μg dose levels had calculated Prevented Fractions of 100 and 92 percent with p-values of 0.0002 and 0.0015 respectively (Table 8). In fact the only other group that equaled these values was the combo vaccine of Group D consisting of 50 μg of the rZinc protein plus 10 μg of the Fuso-SRP Extract having a Prevented Fraction of 92 percent. These results showed a high degree of statistical significance having a p-value of 0.0015. The rZinc at the 250 μg dose level had a Prevented Fraction of 73 percent with a degree of significance of p=0.048. The rHemin protein at the 25 μg and 100 μg dose levels had Prevented Fractions of 58 and 50 percent with degrees of significance of p=0.099 and p=0.180 respectively. The rHemin protein showed a reduction in the incidence and the size of lesions when compared to the non-vaccinated controls but was not statistically significant. Results may have been different if a more rigorous dose finding regiment would have been performed. Nevertheless, all vaccine formulations tested except for Group B showed a reduction in the incidence and the overall size of liver lesions.

Example 18

Western Blot

First the rZinc; rHemin and Fuso-SRP Extract were subjected to electrophoresis followed by western blot analysis with the sera taken 24 hours pre-challenge as described in Example 15. Briefly, rZinc; rHemin and Fuso-SRP Extract were size-fractionated on an SDS-PAGE gel using a 4% stacking gel and 7.5% resolving gel. A 10 μl sample was combined with 10 μl of SDS reducing sample buffer (62.5 mM Tris-HCL ph 6.8, 20% glycerol, 2% SDS, 5% β-mercaptoethanol) and boiled for 4 minutes. Samples were electrophoresed at 18 mA constant current for 5 hour at 4° C. using a Protein II xi cell and model 1000/500 power supply (BioRad Laboratories, Richmond, Calif.). Band migration was visualized using broad range kaleidoscope standards (BioRad) to aid in the electro-blot transfer while biotinylated broad range standards were used as molecular weight references on the blot, see FIGS. 7 and 8. For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo.) in Tris buffered saline (TBS-20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the mouse sera as described above. The primary antibody was diluted 1/50 in TBS containing 1% fish gelatin, 0.05% Tween 20 and 0.2% sodium azide (Antibody Buffer). The membrane was incubated with the primary antibody solution overnight on a shaker at room temperature. The membrane was then washed two times in TBS containing 0.05% Tween 20 (TTBS) and transferred to antibody buffer containing a 1/10,000 dilution of Alkaline phosphatase-conjugated mouse anti-bovine IgG clone BG-18 (Sigma) and a 1/3000 dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1× AP color development Buffer (BioRad) for 30 min. at 37° C. on a shaker. The resulting Western immunoblots was documented using a BioRad GS-800 Densitometer (see FIGS. 7 and 8).

Figure 7:
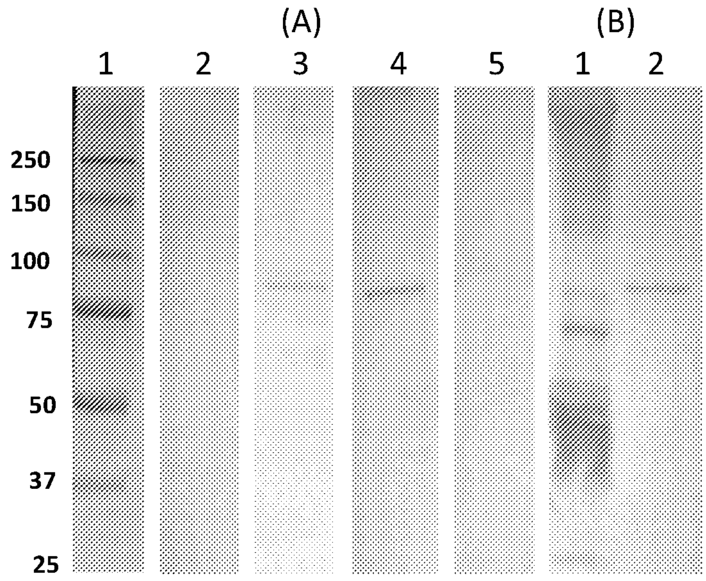
FIG. 7.

FIG. 7 shows the serological response to vaccination using the rZinc protein as examined by Western blot (A). Lane A1 shows the molecular weight marker from 250 kDa-25 kDa; Lane A2 shows the Fuso-SRP Extract of Example 4 probed with sera derived from mice vaccinated with the 250 μg rZinc vaccine of Group C. Note; the lack of reactivity in this lane (A2) clearly showing that this protein is not expressed under conditions of iron restriction in contrast to lanes A3 and A4. These lanes were run with the purified rZinc protein and probed with sera derived from mice vaccinated with the 100 μg rZinc vaccine dose and the 250 μg dose respectively. Both lanes show a single reactive band at the ~81 kDa region; clearly showing a serological response to vaccination using the rZinc protein. The results of this study clearly demonstrate a dose response to protection. For example; when the rZinc vaccine was administered a single time at the 100 μg dose level; no difference was seen in reducing the incidence and/or the size of lesions compared to the placebo controls even with a measurable serological response to the vaccine as demonstrated by Western blot. Nevertheless; when the rZinc vaccine was administered two times at the 250 μg dose level there was a clear difference in the efficacy of the vaccine in reducing both the incidence and the size of lesions; clearly demonstrating a dose response; as the dose increased the incidence and size of lesions decreased. These results clearly demonstrate that the zinc receptor protein of *Fusobacterium* is an excellent immunogenic target protein that can offer a high degree of protection against abscessation of the liver.

When the rHemin protein of Lane A5 was probed with sera derived from mice given the 250 μg rZinc vaccine of Group C no reactivity was seen; as expected.

The western blot (B) of the Fuso-SRP Extract grown under iron deplete conditions was probed with sera derived from the combo vaccine of Group D (10 μg Fuso-SRP Extract plus 50 μg rZinc protein). Note; multiple bands reacted in Lane B1 probed with sera derived from mice vaccinated with the combo vaccine. In contrast; the rZinc protein of Lane B2 was probed with sera derived from the combo vaccine of Group D consisting of 10 μg Fuso-SRP Extract plus 50 μg rZinc protein. Please note; the single rZinc band at the ~81 kDa region (Lane-B2) showing immunological reactivity and a band in Lane B1 but with a slightly lower molecular weight than the rZinc protein of Lane-B2 with an approximate molecular weight between the 76 kDa-79 kDa region. Results clearly have shown that the zinc protein is not expressed under iron-deplete conditions; please refer to Lane-A2; (Fuso-SRP Extract probed with sera derived from the 250 μg rZinc vaccine of Group C) showing no reactivity.

Figure 8:
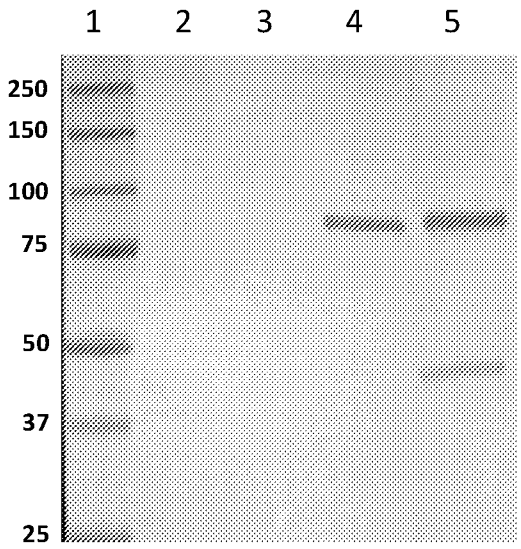
FIG. 8. Western Blot showing the serological response to the rHemin protein. Lane 1, Molecular Weight Marker; Lane 2, Fuso-SRP Extract probed with sera derived from the 100 μg rHemin vaccine of Group F; Lane 3, rZinc protein probed with sera derived from the 100 μg rHemin vaccine of Group E; Lane 4, rHemin protein probed with sera derived from the 25 μg rHemin vaccine of Group E, and Lane 5, rHemin protein probed with sera derived from the 100 μg rHemin vaccine of Group F.

The Western Blot showing the serological response to the rHemin protein is illustrated in FIG. 8. Lane 1 shows the molecular weight marker from 250 kDa-25 kDa range. Lane 2 shows the Fuso-SRP Extract of Example 4 probed with sera derived from mice vaccinated with the rHemin vaccine of Group E. Note; the lack of reactivity in this lane (2). If conditions were absolute the Hemin protein should have reacted with the same protein in the Fuso-SRP Extract since this protein is expressed under iron-restricted growth conditions; please refer to FIG. 1; lane 2 showing the Hemin protein expressed under iron-restricted conditions. This lack of reactivity to the sera derived from mice vaccinated with the 100 μg rHemin vaccine of Group F could simply be due to not enough protein of the Fuso-SRP Extract loaded in this lane.

Lane 3 shows the rZinc protein probed with sera derived from the 100 μg rHemin vaccine of Group F. Note the lack of reactivity in this lane (3) clearly showing that the rZinc protein has no homology to rHemin protein. In contrast; the rHemin protein run in lanes Lanes A4 and A5 probed with sera derived from the 25 g and 100 μg rHemin vaccinated mice reacted strongly with the purified recombinant protein in lanes A4 and A5 respectively.

Example 19

Enzyme-Linked Immunosorbent Assay (ELISA)

The immunological response to the Fuso-SRP Extract and individual recombinant proteins after vaccination was determined by measuring the IgG titers by ELISA. In brief, the two recombinant proteins were coated in 5M urea, 100 mM NaCl, 20 mM Sodium Phosphate Buffer and the Fuso-SRP Extract was coated in the Carbonate Coating Buffer (Sigma S8875 Capsules). 100 μl of each antigen was added at 250 ng/well of a 96-well Immulon 2HB plate and incubated overnight at 4° C. with gentle agitation. The plate was washed three times with PBS wash buffer (PBS containing 0.05% Tween 20) followed by the addition of 200 μl/well 1% PVA/PBS and incubated at 37 degrees Celsius, gentle agitation. After one hour, the plate was washed three times with PBS wash buffer. 100 μl of PVA/PBS was placed into columns 2-11, all rows. Serial 4 fold dilutions of the primary antisera were performed in the plate by the addition of 133 μl of a 1:100 dilution to rows 1 and 12, mixing 3-4 times, with transfer of 33 μl to the next row, towards the center of the plate for a total of 6 dilutions for each sample. The plate was incubated for 1 hour at 37 degrees Celsius followed by three washes and addition of 100 μl/well of an HRP conjugated goat anti-mouse IgG, (H+L) chain antibody (KPL #074-1806) at a 1:10,000 dilution. After 1 hour incubation, the plate was washed three times followed by the addition of 100 μl 2 component ABTS Peroxidase Substrate System (KPL 50-62-01). Color was allowed to develop for 15 minutes. The absorbance was measured at a wavelength of 405-490 nm.

Example 20

ELISA Results

Figure 9:
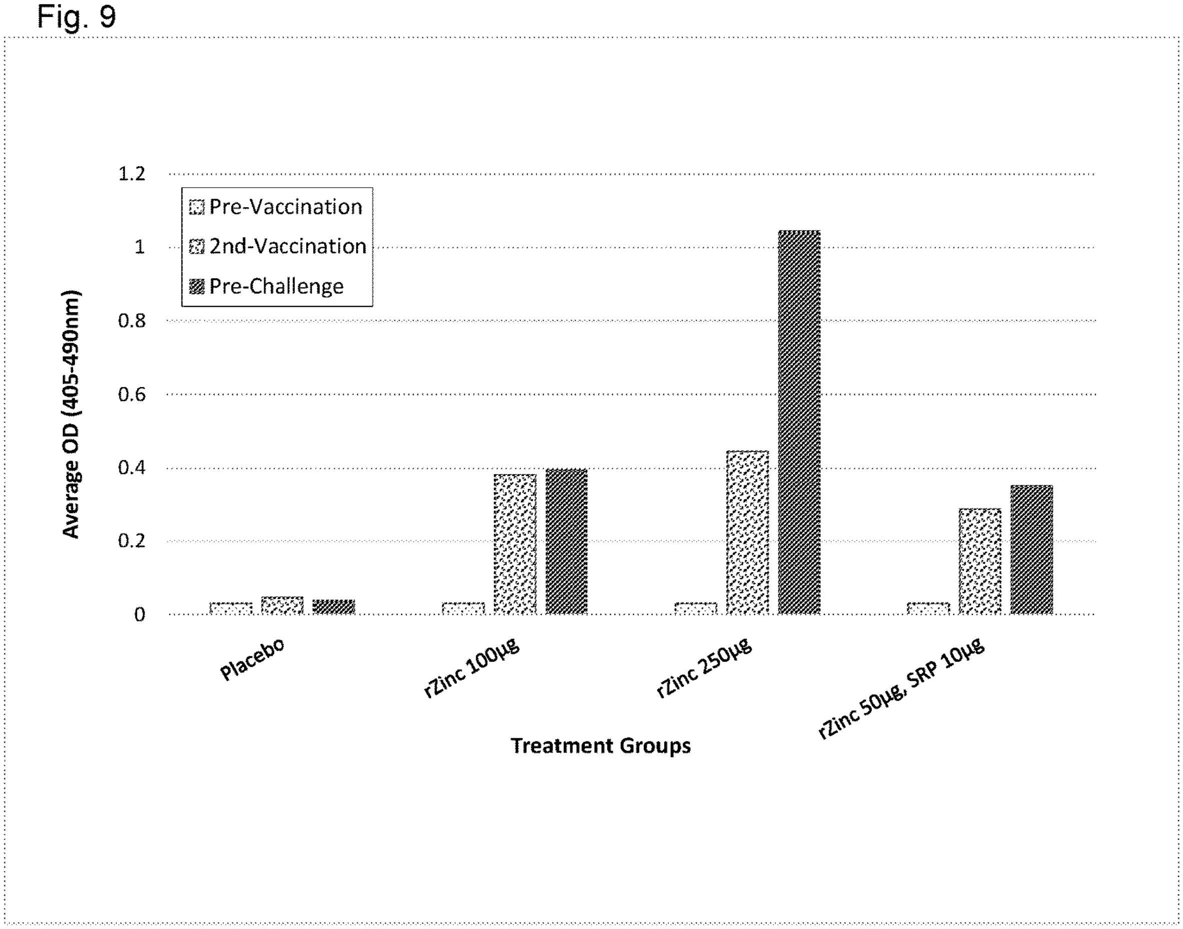
FIG. 9. The serological response to vaccination using the recombinant Zinc (rZinc) Protein of *Fusobacterium necrophorum* as analyzed by ELISA FIG. 10. The serological response to vaccination using the recombinant Hemin (rHemin) protein of *Fusobacterium necrophorum* as analyzed by ELISA FIG. 11. The serological response to vaccination using the Fuso-SRP Extract and the combo vaccine consisting of the rZinc protein plus the Fuso SRP-Extract of *Fusobacterium necrophorum* as analyzed by ELISA FIG. 12. SDS-PAGE gel showing the expression of the rHemin protein at approximately 84 kDa and a hemagglutinin protein at approximately 150 kDa. Lane 1, Molecular Weight Marker; Lane 2, Fuso iron-restricted and hemin supplemented SRP Extract; Lane 3, Fuso iron restricted SRP extract; Lane 4, Iron replete SRP Extract; Lane 5, Molecular weight marker. Note that the two proteins are expressed when iron is restricted and hemin is supplemented to the fermentation (in brackets), and not in the presence of ferric iron or iron-restriction alone.
Figure 11:
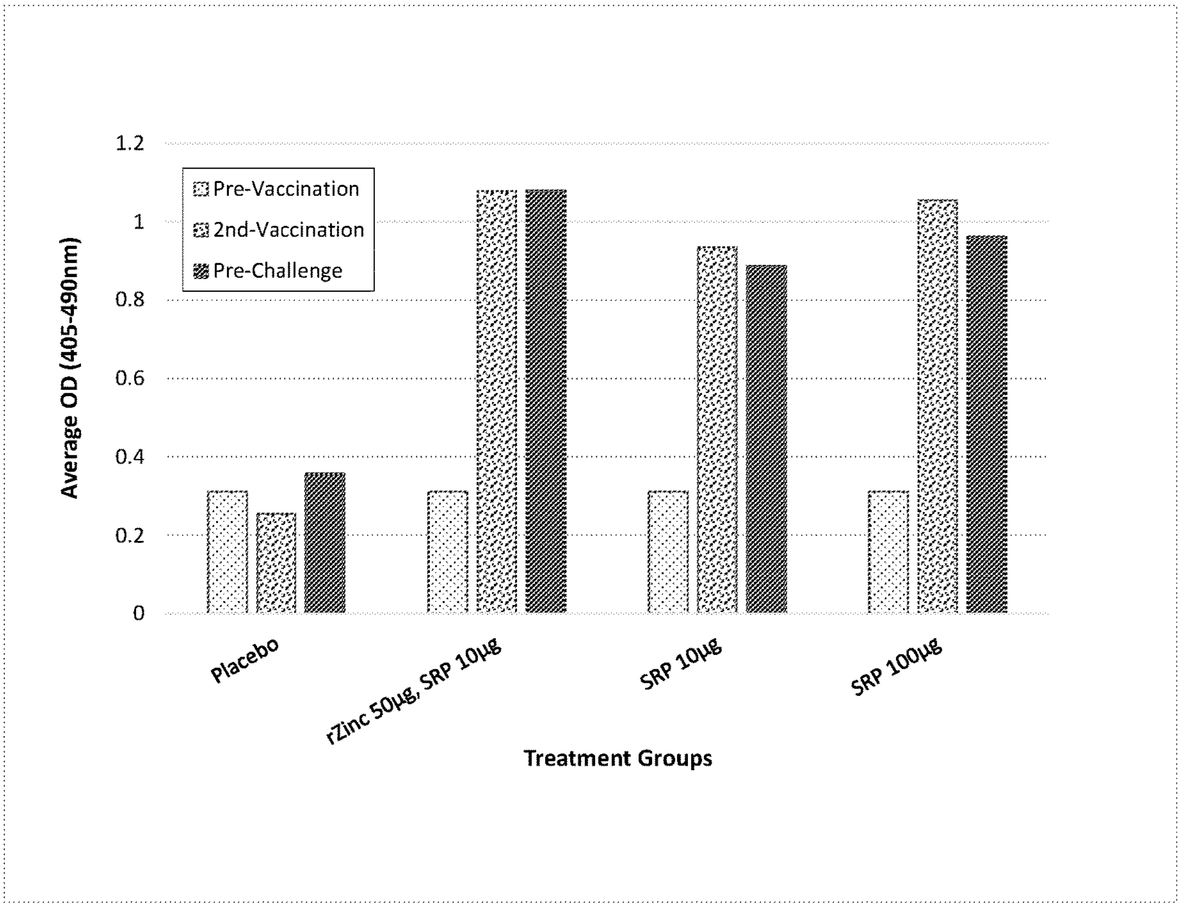

The serological response to vaccination was monitored by ELISA as described in Example 19. Blood samples were taken at the time first vaccination (pre-immune); second vaccination and 24 hours pre-challenge. Individual blood samples were equally pooled and analyzed by ELISA to determine the serological response to vaccination. FIG. 9 shows the serological response to the rZinc protein and FIG. 11 illustrates the response to the rZinc protein in combination with the addition of the Fuso-SRP Extract. First; note the amnestic response of the 250 μg rZinc vaccinated group. The results show an increasing titer from first vaccination to second vaccination in contrast to the placebo controls and the 100 μg rZinc vaccinated group. The lack of antibody response in the placebo controls shows that there was no pre-exposure to this protein. Now; in this study mice in the rZinc protein at the 100 μg dose level inadvertently received only one vaccination; resulting in a lack of any secondary immune response as seen in FIG. 9. This lack of secondary immunity clearly effected the overall efficacy of this group; since there was no difference in the reduction in the incidence and size of lesions compared to the non-vaccinated controls. In comparison; mice vaccinated with the combo vaccine consisting of 10 μg of the Fuso-SRP Extract plus 50 μg of the rZinc protein showed an immune response to vaccination with a very slight secondary response as shown in FIG. 9.; yet this group showed the highest degree of efficacy in reducing the incidence and size of lesions. These results suggest that efficacy is not completely antibody mediated and that protection from infection may be also influenced by a non-defined cell-mediated immune response. It is interesting to speculate that the addition of the rZinc protein to the Fuso-SRP Extract may induce some type of immune-modulative effect on the immune response.

Figure 10:
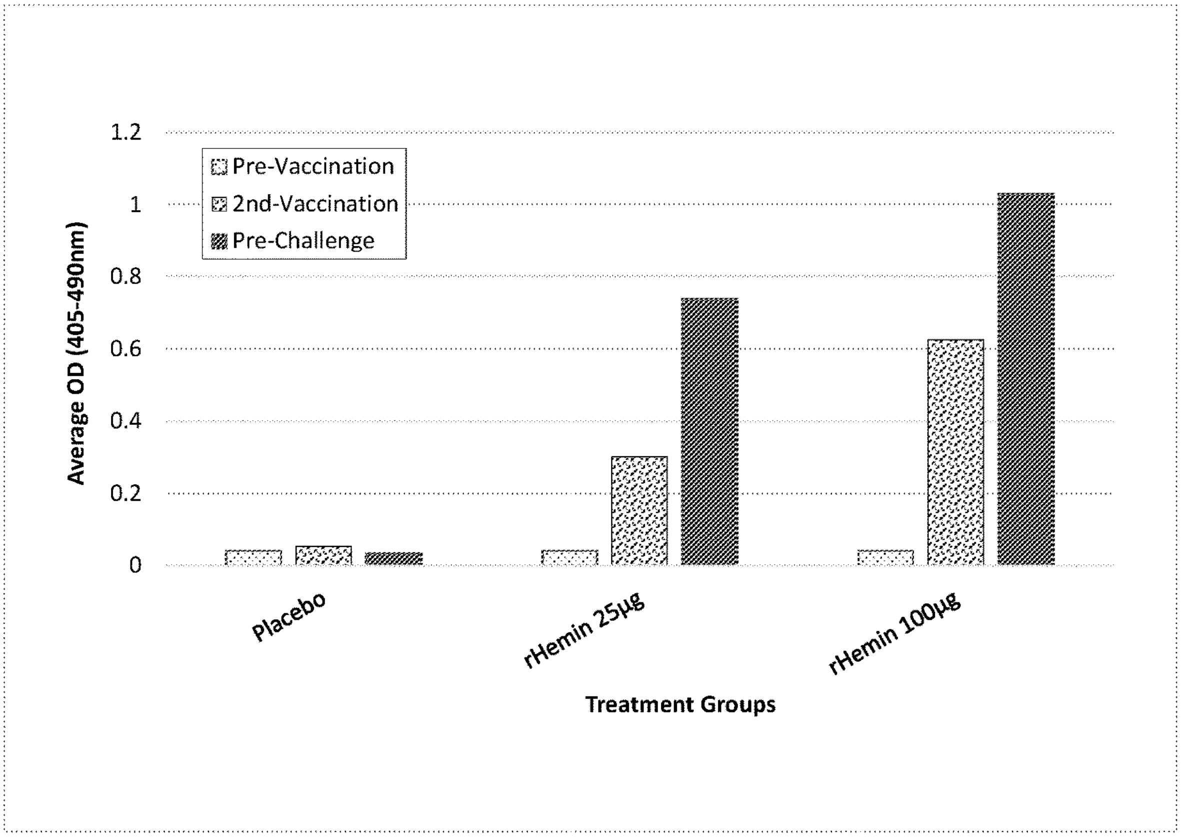

FIG. 10 shows the serological response in mice vaccinated with the rHemin at the 25 μg and 100 μg vaccine dose levels compared to non-vaccinated controls. Please note; the antibody response to vaccination with an increase in antibody titer from first vaccination followed by an amnestic response following second vaccination FIG. 10. The results showed a reduction in the incidence and size of lesions in mice vaccinated with the rHemin protein at both the 25 μg and 100 μg vaccine dose levels compared to controls. Numerically there was a significant reduction but was not statistically significant by Fisher Exact. Results may have been different if a more rigorous dose finding regiment would have been done; for example by increasing the dose to 250 μg as done in the rZinc protein of Group-C as defined in Table 6.

FIG. 11 shows the antibody response of the Fuso-SRP Extract at the 10 μg and 100 μg vaccine dose levels along with the combo vaccine consisting of 50 μg rZinc protein plus 10 μg of the Fuso-SRP Extract. All vaccine formulations showed both a primary and secondary antibody response following vaccination. This antibody response seemed to correlate well with high achievement of efficacy in all vaccinated groups; see summary Table 7. All of the Fuso-SRP Extract groups had the highest percentage in the Protected Fraction.

Example 22

Expression of Novel Hemin Proteins with the Addition of Hemin to Iron Restricted Fermentation Media The 1694 culture of example 1 was inoculated into 20 ml mTSB and incubated overnight at 37° C. in an anaerobic chamber. A 2.5 mg/ml solution of hemin was prepared by adding 0.05 g of hemin (Sigma, St Louis, Mo.) to 20 ml of 0.1 Normal Sodium Hydroxide solution and vortexed to mix. The solubilized hemin was then sterilized through a 0.2 micron filter into a sterile 50 ml conical tube. Three sets of mTSB were prepared according to Table 9.

TABLE 9

| Media Formulation | Base medium | Hemin concentration | 2,2' bipyridyl concentration | FeCl3 |
|---|---|---|---|---|
| A | mTSB | 20 ug/mL | 15 ug/mL | |
| B | mTSB | 0 | 20 ug/mL | |
| C | mTSB | 0 | 0 | 20 ug/mL |

2,2' bipyridyl was added to medium A at 15 ug/ml and autoclaved for 30 minutes at 121° C. The sterile hemin solution was added to media A at 800 uL per 100 mL for a final concentration of 20 ug/ml. Media B contained no hemin and 20 ug/ml 2,2' bipyridyl. Medium C contained no hemin or bipyridyl, but contained $FeCl_3$ at 20 ug/ml.

Five mL of the overnight culture was transferred to 100 mL of each medium A, B and C and incubated anaerobically for 7 hours at 37° C. After 7 hours, 25 ml of the cultures were transferred to fresh 500 ml volumes of their respective media and allowed to incubate overnight at 37° C. The following morning, strong growth was observed as measured by visual turbidity. All cultures were then centrifuged for 20 minutes at 7,500×G. The supernatant was decanted and discarded. The cell pellet was resuspended in 35 ml sterile Tris buffered water with 0.93 g/l EDTA salt. The cell suspension was then frozen at −80° C. for a minimum of 2 hours. The bacterial cell suspensions were disrupted by sonication for 90 seconds at 4° C. using a Branson 450 equipped with a half inch disruption horn (Branson, Danbury Conn.). The disrupted bacterial suspensions were clarified by centrifugation at 39,000×g for 20 minutes. The supernatants were collected and solubilized by the addition of sodium lauroyl sarcosinate (1% vol/vol) at 4° C. for 18 hours. The detergent-insoluble protein-enriched fractions were collected by centrifugation at 39,000×g for 2.5 hours at 4° C. The protein pellets were resuspended in 200 μl Tris-buffer (pH 7.2) and stored at −90° C.

The iron-restricted hemin-supplemented SRP extract, the iron-restricted SRP extract and the iron-supplemented SRP Extract were subjected to electrophoresis followed by western blot analysis with the mouse sera taken 24 hours pre-challenge as described in Example 16, and with the calf convalescent sera described in Example 7. Briefly, the SRP Extracts were size-fractionated on a Criterion TGX stain free pre-cast SDS-PAGE gel (BioRad Laboratories, Richmond Calif.) with a 4% stacking gel and 7.5% resolving gel. A 10 μl sample was combined with 10 μl of SDS reducing sample buffer (62.5 mM Tris-HCL ph 6.8, 20% glycerol, 2% SDS, 5% β-mercaptoethanol) and boiled for 4 minutes. Samples were electrophoresed at 200 volt constant current for 44 minutes at 4° C. using a Criterion cell and model 1000/500 power supply (BioRad). Band migration was visualized using broad range kaleidoscope standards (BioRad) to aid in the electro-blot transfer while biotinylated Precision Plus standards (BioRad) were used as molecular weight references on the blot, see FIGS. 12 and 13. The gel was documented by Gel Doc EZ (BioRad). For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo.) in Tris buffered saline (TBS-20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the mouse or calf sera as described above. The primary antibody was diluted 1/50 in TBS containing 1% fish gelatin, 0.05% Tween 20 and 0.2% sodium azide (Antibody Buffer). The membrane was incubated with the primary antibody solution overnight on a shaker at room temperature. The membrane was then washed two times in TBS containing 0.05% Tween 20 (TTBS) and transferred to antibody buffer containing a 1/10,000 dilution of Alkaline phosphatase-conjugated mouse anti-bovine IgG clone BG-18 (Sigma) and a 1/3000 dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1× AP color development Buffer (BioRad) for 30 min. at 37° C. on a shaker. The resulting Western immunoblots were documented using a BioRad GS-800 Densitometer (see FIGS. 12 and 13).

Figure 12:
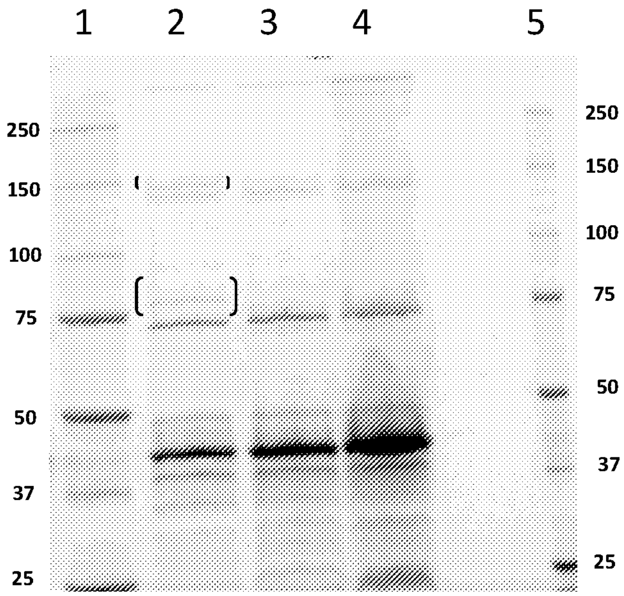

The SDS-PAGE showing the upregulation of the rHemin protein and the hemagglutinin protein is illustrated in FIG. 12. Lanes 1 and 5 show the molecular weight markers from 250 kDa-25 kDa range. Lane 2 shows the iron-restricted and hemin supplemented Fuso-SRP Extract from formulation (A) described in table 9. Note the upregulation of the rHemin protein at approximately 84 kDa, and a second protein, hemagglutinin, at approximately 150 kDa.

Lane 3 shows the iron restricted formulation B of table 9. Note the lack of expression of these two proteins in the presence of iron restriction alone without hemin supplementation. Lane 4 shows the iron replete formulation C of table 9. Note the lack of expression of the rHemin and hemagglutinin proteins in the presence of ferric iron. This demonstrates that iron restriction alone is not enough to upregulate these proteins; only by limiting iron and adding back hemin as an iron source are these proteins expressed.

Figure 13:
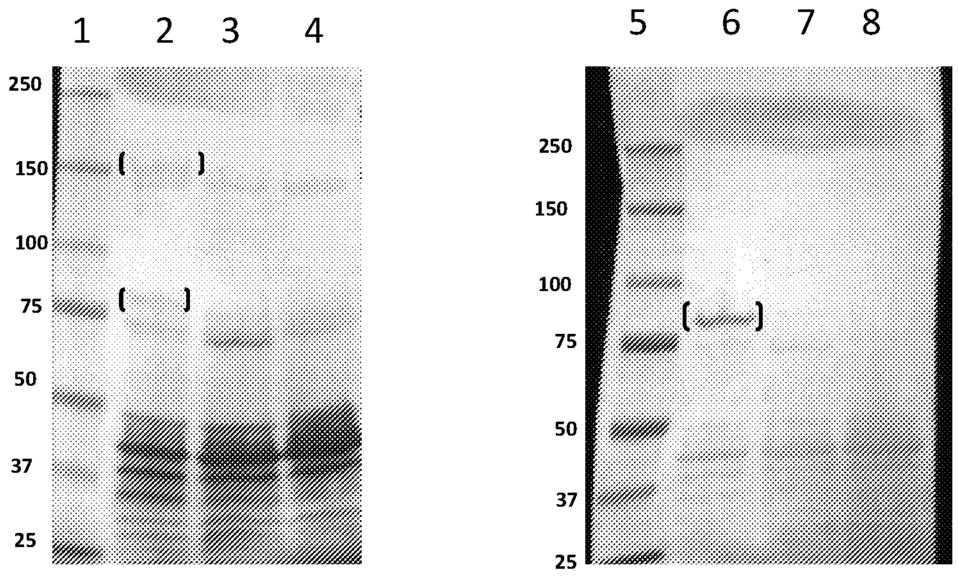
FIG. 13. Western Blots showing the sero-reactivity of the *Fusobacterium necrophorum* rHemin proteins and filamentous hemagglutinin 150 kDa protein grown under iron deplete growth conditions and probed with the convalescent calf serum of example 7 (lanes 1-4) and the rHemin mouse sera as described in example 16 taken 24 hours prior to challenge (lanes 5-8). Lane 1, Molecular Weight Marker; Lane 2, Fuso iron-restricted and hemin supplemented SRP Extract; Lane 3, Fuso iron restricted SRP extract; Lane 4, Iron replete SRP Extract; Lane 5, Molecular Weight Marker; Lane 6, Fuso iron-restricted and hemin supplemented SRP Extract; Lane 7, Fuso iron restricted SRP extract; Lane 8, Iron replete SRP Extract. Note the strong serologic response of the 84 kDa and 150 kDa proteins (shown in brackets in lane 2) to convalescent calf sera when grown in iron restriction plus hemin, and the lack of serologic response when the SRP extract is grown in iron limiting conditions alone, or in iron replete conditions. Also note in the brackets in lane 6 the very strong serologic response at 84 kDa (shown in brackets) to sera from mice vaccinated with the rHemin protein. This is also not present in Fuso SRP grown in iron deplete media or iron replete media as shown in lanes 7 and 8 respectively.

In addition to the upregulation of the rHemin protein, a protein of ~150 kDa by SDS-PAGE was shown to be upregulated in the presence of hemin in an otherwise iron deplete media (FIG. 12, Lane 2). This protein was shown to be immuno-reactive in a western blot against convalescent sera from an experimentally challenged calf of Example 7 as illustrated in FIG. 13 at Lane 2. The closest outer membrane protein found in the annotated genome of 1694 was a hypothetical protein of 154 kDa. This sequence was used to BLAST known sequences, and was a 100% match to filamentous hemagglutinin. The nucleotide sequence and amino acid sequence identified is shown in FIG. 47 (SEQ ID NOs: 78 and 53, respectively).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term “about.” Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising:

an isolated polypeptide having a molecular weight of 131 kDa to 121 kDa, an isolated polypeptide having a molecular weight of 79 kDa to 69 kDa, and an isolated polypeptide having a molecular weight of 33 kDa to 23 kDa, wherein the polypeptides are isolated from a *Fusobacterium necrophorum* subsp. *necrophorum*, wherein the polypeptides are expressed when incubated in media comprising a copper chelator and not expressed at a detectable level when grown in the media without the copper chelator, wherein the copper chelator is quercetin added to the media at a concentration of 50 mM, and wherein molecular weight is as determined by 10% SDS-PAGE under reducing and denaturing conditions, and an isolated polypeptide having a molecular weight of 93 kDa to 83 kDa and an isolated polypeptide having a molecular weight of 52 kDa to 42 kDa, wherein the polypeptides are isolated from the *Fusobacterium necrophorum* subsp. *necrophorum* when incubated in media comprising a copper chelator, wherein the polypeptides are expressed by the *Fusobacterium necrophorum* subsp. *necrophorum* when incubated in media without the copper chelator and are expressed at an enhanced level during growth in media comprising the copper chelator, wherein the copper chelator is quercetin added to the media at a concentration of 50 mM, and wherein molecular weight is as determined by 10% SDS-PAGE under reducing and denaturing conditions, and a pharmaceutically acceptable adjuvant.

2. The composition of claim 1 further comprising:

a polypeptide having at least 85% similarity to amino acids 63-714 of SEQ ID NO:4, a polypeptide having at least 85% similarity to amino acids 63-736 of SEQ ID NO:6, a polypeptide having at least 85% similarity to amino acids 63 to 638 of SEQ ID NO:34, a polypeptide having at least 85% similarity to amino acids 63-1420 of SEQ ID NO:53, or a combination thereof.

3. A method comprising:

administering to a subject an amount of the composition of claim 1 effective to induce the subject to produce antibody that specifically binds to at least one polypeptide of the composition.

4. A method for treating an infection in a subject, the method comprising:

administering an effective amount of the composition of claim 1 to a subject having or at risk of having an infection caused by a *Fusobacterium* spp.

5. A method for treating a symptom in a subject, the method comprising:

administering an effective amount of the composition of claim 1 to a subject having or at risk of having an infection caused by a *Fusobacterium* spp.

6. A method for decreasing colonization in a subject, the method comprising:

administering an effective amount of the composition of claim 1 to a subject colonized by or at risk of being colonized by a *Fusobacterium* spp.

7. The method of claim 3 wherein the subject is a mammal.

8. The method of claim 7 wherein the mammal is a human, a bovine, or an ovine.

9. The method of claim 4 wherein the *Fusobacterium* spp. is *F. necrophorum.*

10. The method of claim 3 wherein at least 10 micrograms (μg) and no greater than 2000 μg of polypeptide is administered.

11. The method of claim 4 wherein the infection causes a condition selected from metritis, hepatic abscesses, and foot rot.

12. A kit for detecting antibody that specifically binds a polypeptide, comprising in separate containers:

the composition of claim 1; and a reagent that detects an antibody that specifically binds to a polypeptide of the composition.

13. The composition of claim 1 further comprising:

a polypeptide comprising an amino acid sequence having at least 85% similarity to amino acids 63-714 of SEQ ID NO:4, a polypeptide comprising an amino acid sequence having at least 85% similarity to amino acids 63-736 of SEQ ID NO:6, a polypeptide comprising an amino acid sequence having at least 85% similarity to amino acids 63 to 638 of SEQ ID NO:34, a polypeptide having comprising an amino acid sequence at least 85% similarity to amino acids 63-1420 of SEQ ID NO:53, or a combination thereof.

14. The composition of claim 1, wherein the three isolated polypeptides that are expressed when incubated in media comprising a copper chelator and not expressed at a detectable level when grown in the media without the copper chelator have molecular weights of 126 kDa, 74 kDa, and 28 kDa, and wherein the two polypeptides that are expressed by the *Fusobacterium necrophorum* subsp. *necrophorum* when incubated in media without the copper chelator and expressed at an enhanced level during growth in media comprising the copper chelator have molecular weights of 88 kDa, and 48 kDa.

15. The composition of claim 1, wherein the polypeptide having a molecular weight of 52 kDa to 42 kDa has at least 85% similarity to amino acids 63-423 of SEQ ID NO:2.

* * * * *

SEQUENCE LISTING

```
<160> NUMBER OF SEQ ID NOS: 85

<210> SEQ ID NO 1
<211> LENGTH: 1272
<212> TYPE: DNA
<213> ORGANISM: Fusobacterium necrophorum

<400> SEQUENCE: 1

atgaaaaagc tatggatatt atttttcctg ctggggagtg ttgcttttgg aagagaagtt      60

actttggaag aagcgattca agcgtcaatg gagaatagca aggcggtcaa aatttcagat     120

aagcagttag aaatttcaaa actaaaaatg aatcaggcaa ttaaaaaagc actgccaagc     180

gtagtgtaca gtgccaacta tcaacgtgga gaatatgaga gaaatattta taagaataaa     240

tcttctatgg aatcggaaaa aggcggttac aaacaatcga ttacaatcag ccaacctatt     300

tttcaaggag gagccattct tgccggaatt caaggggcaa aagcctataa aaccatagca     360

gatttgtcct atgttcaaga gacactaaat actcgtttga agacgattcg aactttttcg     420

aatattgtca acagcaaaag aaatttacaa gctttggaat attccgagaa acaattgcaa     480

aatcgatata aaaagcagga agctcaattg gagttgcgac tgattacgaa gacggattta     540

ttgaaaacgg aatactcttt attggaagta caatctttaa tttccaaagc gaaaagtaat     600

attgaagtac agacggaaga tttaaaattt caaatgggag tggacaaaaa agaagcattg     660

gaagtcaagg aatttatcgt tcccaatcat ttgacagaac gtattacatt tgaaaaagat     720

aaagagaggg cattggaatc cagtattcag gctttgattg caaaatctca agtgaagata     780

gcaaaggcac aggaaacggc agcactggga aatatgcttc ctaaggtaaa tgcctttgtg     840

agttatggag tggcttcgga gagaacacat tggaaacaaa cgaaagaaga tgcggaatgg     900

atgggaggtt tgtctgtttc ttggaatgtc ttttcttttg ggagtgacta tgatgcttat     960
```

```
caaattgcaa aattggaaaa agagtccaaa gagttatcag aaacgacagc tcaggacaat   1020

atagctttga gccttaagac agcttatttg gaattgcaaa gattggaaat tttaagagag   1080

tccagaaaga gaggattgga agcggcagaa ttgaatttta caatggatca agaaaaattt   1140

gatgcaggct tgctttccac agtggattat ttatcatcgg aaacacaatt gcgggaagca   1200

agagtgaatt attaccaagc agaattagat tattactatg cttttgaata ttatagatcg   1260

ttgttagtat aa                                                       1272
```

```
<210> SEQ ID NO 2
<211> LENGTH: 423
<212> TYPE: PRT
<213> ORGANISM: Fusobacterium necrophorum

<400> SEQUENCE: 2

Met Lys Lys Leu Trp Ile Leu Phe Phe Leu Leu Gly Ser Val Ala Phe
1               5                   10                  15

Gly Arg Glu Val Thr Leu Glu Glu Ala Ile Gln Ala Ser Met Glu Asn
            20                  25                  30

Ser Lys Ala Val Lys Ile Ser Asp Lys Gln Leu Glu Ile Ser Lys Leu
        35                  40                  45

Lys Met Asn Gln Ala Ile Lys Lys Ala Leu Pro Ser Val Val Tyr Ser
    50                  55                  60

Ala Asn Tyr Gln Arg Gly Glu Tyr Glu Arg Asn Ile Tyr Lys Asn Lys
65                  70                  75                  80

Ser Ser Met Glu Ser Glu Lys Gly Gly Tyr Lys Gln Ser Ile Thr Ile
                85                  90                  95

Ser Gln Pro Ile Phe Gln Gly Gly Ala Ile Leu Ala Gly Ile Gln Gly
            100                 105                 110

Ala Lys Ala Tyr Lys Thr Ile Ala Asp Leu Ser Tyr Val Gln Glu Thr
        115                 120                 125

Leu Asn Thr Arg Leu Lys Thr Ile Arg Thr Phe Ser Asn Ile Val Asn
    130                 135                 140

Ser Lys Arg Asn Leu Gln Ala Leu Glu Tyr Ser Glu Lys Gln Leu Gln
145                 150                 155                 160

Asn Arg Tyr Lys Lys Gln Glu Ala Gln Leu Glu Leu Arg Leu Ile Thr
                165                 170                 175

Lys Thr Asp Leu Leu Lys Thr Glu Tyr Ser Leu Leu Glu Val Gln Ser
            180                 185                 190

Leu Ile Ser Lys Ala Lys Ser Asn Ile Glu Val Gln Thr Glu Asp Leu
        195                 200                 205

Lys Phe Gln Met Gly Val Asp Lys Lys Glu Ala Leu Glu Val Lys Glu
    210                 215                 220

Phe Ile Val Pro Asn His Leu Thr Glu Arg Ile Thr Phe Glu Lys Asp
225                 230                 235                 240

Lys Glu Arg Ala Leu Glu Ser Ser Ile Gln Ala Leu Ile Ala Lys Ser
                245                 250                 255

Gln Val Lys Ile Ala Lys Ala Gln Glu Thr Ala Ala Leu Gly Asn Met
            260                 265                 270

Leu Pro Lys Val Asn Ala Phe Val Ser Tyr Gly Val Ala Ser Glu Arg
        275                 280                 285

Thr His Trp Lys Gln Thr Lys Glu Asp Ala Glu Trp Met Gly Gly Leu
    290                 295                 300

Ser Val Ser Trp Asn Val Phe Ser Phe Gly Ser Asp Tyr Asp Ala Tyr
```

-continued

```
305                 310                 315                 320

Gln Ile Ala Lys Leu Glu Lys Glu Ser Lys Glu Leu Ser Glu Thr Thr
                325                 330                 335

Ala Gln Asp Asn Ile Ala Leu Ser Leu Lys Thr Ala Tyr Leu Glu Leu
            340                 345                 350

Gln Arg Leu Glu Ile Leu Arg Glu Ser Arg Lys Arg Gly Leu Glu Ala
        355                 360                 365

Ala Glu Leu Asn Phe Thr Met Asp Gln Glu Lys Phe Asp Ala Gly Leu
    370                 375                 380

Leu Ser Thr Val Asp Tyr Leu Ser Ser Glu Thr Gln Leu Arg Glu Ala
385                 390                 395                 400

Arg Val Asn Tyr Tyr Gln Ala Glu Leu Asp Tyr Tyr Tyr Ala Phe Glu
                405                 410                 415

Tyr Tyr Arg Ser Leu Leu Val
            420


<210> SEQ ID NO 3
<211> LENGTH: 2145
<212> TYPE: DNA
<213> ORGANISM: Fusobacterium necrophorum

<400> SEQUENCE: 3

atgaaaaaag tggtatttgg gatttacagt atcttaatgt cctctgctat gcttggagca     60

gaaattgatc ttggaacaca gaatatctat tcggaaaccg gatttgaaac gagtcttcga    120

agctctgttt cttctcctta tatcgttact tcaaaagaaa tcaaagaaaa acattatacc    180

cgtgtttctg aaattttgag agatattccg catatctaca tcggtcccgg tggcagtgta    240

gatatgcgtg gtcagggaag tgctcatgcc agaacaacag ttcaactgtt aattgatgga    300

gttcctgcca atttttgga tacttcccac atcaatcttc ctatcgatac tttaaatcca    360

gaagatatta agagaattga agtcatccct ggaggaggag ctgtttttata tggaagtgga    420

acttccggag gagtgatcaa catcattacc aaaaaataca cgggaaacta tgcaaaggca    480

agctatcaaa taggaagcta tcacaatcat aaatatgacg tagctgccgg aacttctttg    540

ggaaattttg acattaacct aagttattca aaaaataata gggatggata tcgtaaaaaa    600

gccttttccg attccgattt cttctccgga aaattacgtt atcacttcaa tcccacagac    660

agtcttgaat tcaaatatag ctattttgat aataagttca gaggtgttaa atccctaacc    720

agagaacaag tcgagaaaga tcgaaggcaa agtggtcttt ctcctgaaga caatttgaaa    780

aataccatcc gaaaagaaga atggaattta acttacgatg caaaatggac aagctggctg    840

gaacacaaat ccaatctttt ctatcagtcc acagaaataa aatctagtga atatgaagat    900

gctcttcctt tctatcaata tcaaatttct tcttatcaaa aaatgcttac tatgccaggg    960

attcctccta tgatgcaagc acaattgaaa aagcagataa aagccctaca aaatttgata   1020

acgagtaatc caaggatgga attacatcaa ggaagtcgtt tcaaagatca aaaattcggt   1080

tttaaaatga agaataaatt taagtatgga gaaaatagtg attttatttt aggtttggga   1140

tacattcaca acaaaatgga tcgagattct tgggcttata cgaaaaatac gcaaacgaat   1200

caaacaatag caactcttac aaatactaaa attcctttaa ataagaaaac attcgaaatt   1260

ttcggattaa atacctatcg tcataataat tgggaatttg ttcagggctt acgctttgaa   1320

aaagcgaaat ataatggaaa aagacaatat aaaaatctgg aatatccttt aaaagatcgt   1380

agcatgaata atgttgcggc aaatctggct gtcaattatc tctattccga tacaggaaat   1440
```

-continued

```
gtctatgtaa aatatgaaag aggatttact tctcctgctc ctgcacagtt aatggataaa   1500

atcagaaaag gaggagtgaa cgattatgtc aataatgatt taaaatctga aaaatcaaac   1560

tcctttgaag ttggatggaa tgactatctc ttccattctt tagtcagtgc tgatgttttt   1620

ttcagtgaaa cgaaagatga aatttctacc atattctcgg gagggcatgg gacaacattc   1680

agcaatttga accttggtca aacgaaacga tatggttttg atctaaaagc cagtcaagtt   1740

tttgaaaagt ggacattctc ggaagcttac agttatatcc atgcaaaaat catgaaagat   1800

aaaacaaagg cttatgaagg aaaatatatc agttatgttc caaggcataa attttctttg   1860

aatgctgatt atgcaatcac tccaaaatgg actcttgggg gagaatatca atacagttct   1920

tccgtatatc tggacaatgc aaataaaaat ggaaaagatg gagcgagatc tgtttttaat   1980

cttcaaacct cttatgagtt caattcacat ttttctatct atgcaggaat taaaaatgtg   2040

ttaaatcata agtattatga atctgtcagt gcaggttcca gtcaaaagta ttatagtccg   2100

gctccggaaa gaaattacta tgccggattc cgttatcaat tttaa                   2145
```

```
<210> SEQ ID NO 4
<211> LENGTH: 714
<212> TYPE: PRT
<213> ORGANISM: Fusobacterium necrophorum

<400> SEQUENCE: 4

Met Lys Lys Val Val Phe Gly Ile Tyr Ser Ile Leu Met Ser Ser Ala
1               5                   10                  15

Met Leu Gly Ala Glu Ile Asp Leu Gly Thr Gln Asn Ile Tyr Ser Glu
            20                  25                  30

Thr Gly Phe Glu Thr Ser Leu Arg Ser Ser Val Ser Ser Pro Tyr Ile
        35                  40                  45

Val Thr Ser Lys Glu Ile Lys Glu Lys His Tyr Thr Arg Val Ser Glu
    50                  55                  60

Ile Leu Arg Asp Ile Pro His Ile Tyr Ile Gly Pro Gly Gly Ser Val
65                  70                  75                  80

Asp Met Arg Gly Gln Gly Ser Ala His Ala Arg Thr Thr Val Gln Leu
                85                  90                  95

Leu Ile Asp Gly Val Pro Ala Asn Phe Leu Asp Thr Ser His Ile Asn
            100                 105                 110

Leu Pro Ile Asp Thr Leu Asn Pro Glu Asp Ile Lys Arg Ile Glu Val
        115                 120                 125

Ile Pro Gly Gly Gly Ala Val Leu Tyr Gly Ser Gly Thr Ser Gly Gly
    130                 135                 140

Val Ile Asn Ile Ile Thr Lys Lys Tyr Thr Gly Asn Tyr Ala Lys Ala
145                 150                 155                 160

Ser Tyr Gln Ile Gly Ser Tyr His Asn His Lys Tyr Asp Val Ala Ala
                165                 170                 175

Gly Thr Ser Leu Gly Asn Phe Asp Ile Asn Leu Ser Tyr Ser Lys Asn
            180                 185                 190

Asn Arg Asp Gly Tyr Arg Lys Lys Ala Phe Ser Asp Ser Asp Phe Phe
        195                 200                 205

Ser Gly Lys Leu Arg Tyr His Phe Asn Pro Thr Asp Ser Leu Glu Phe
    210                 215                 220

Lys Tyr Ser Tyr Phe Asp Asn Lys Phe Arg Gly Val Lys Ser Leu Thr
225                 230                 235                 240

Arg Glu Gln Val Glu Lys Asp Arg Arg Gln Ser Gly Leu Ser Pro Glu
                245                 250                 255
```

-continued

```
Asp Asn Leu Lys Asn Thr Ile Arg Lys Glu Glu Trp Asn Leu Thr Tyr
            260                 265                 270

Asp Ala Lys Trp Thr Ser Trp Leu Glu His Lys Ser Asn Leu Phe Tyr
        275                 280                 285

Gln Ser Thr Glu Ile Lys Ser Ser Glu Tyr Glu Asp Ala Leu Pro Phe
    290                 295                 300

Tyr Gln Tyr Gln Ile Ser Ser Tyr Gln Lys Met Leu Thr Met Pro Gly
305                 310                 315                 320

Ile Pro Pro Met Met Gln Ala Gln Leu Lys Lys Gln Ile Lys Ala Leu
                325                 330                 335

Gln Asn Leu Ile Thr Ser Asn Pro Arg Met Glu Leu His Gln Gly Ser
            340                 345                 350

Arg Phe Lys Asp Gln Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asp Arg Asp Ser Trp Ala Tyr Thr Lys Asn Thr Gln Thr Asn
385                 390                 395                 400

Gln Thr Ile Ala Thr Leu Thr Asn Thr Lys Ile Pro Leu Asn Lys Lys
                405                 410                 415

Thr Phe Glu Ile Phe Gly Leu Asn Thr Tyr Arg His Asn Asn Trp Glu
            420                 425                 430

Phe Val Gln Gly Leu Arg Phe Glu Lys Ala Lys Tyr Asn Gly Lys Arg
        435                 440                 445

Gln Tyr Lys Asn Leu Glu Tyr Pro Leu Lys Asp Arg Ser Met Asn Asn
    450                 455                 460

Val Ala Ala Asn Leu Ala Val Asn Tyr Leu Tyr Ser Asp Thr Gly Asn
465                 470                 475                 480

Val Tyr Val Lys Tyr Glu Arg Gly Phe Thr Ser Pro Ala Pro Ala Gln
                485                 490                 495

Leu Met Asp Lys Ile Arg Lys Gly Gly Val Asn Asp Tyr Val Asn Asn
            500                 505                 510

Asp Leu Lys Ser Glu Lys Ser Asn Ser Phe Glu Val Gly Trp Asn Asp
        515                 520                 525

Tyr Leu Phe His Ser Leu Val Ser Ala Asp Val Phe Phe Ser Glu Thr
    530                 535                 540

Lys Asp Glu Ile Ser Thr Ile Phe Ser Gly Gly His Gly Thr Thr Phe
545                 550                 555                 560

Ser Asn Leu Asn Leu Gly Gln Thr Lys Arg Tyr Gly Phe Asp Leu Lys
                565                 570                 575

Ala Ser Gln Val Phe Glu Lys Trp Thr Phe Ser Glu Ala Tyr Ser Tyr
            580                 585                 590

Ile His Ala Lys Ile Met Lys Asp Lys Thr Lys Ala Tyr Glu Gly Lys
        595                 600                 605

Tyr Ile Ser Tyr Val Pro Arg His Lys Phe Ser Leu Asn Ala Asp Tyr
    610                 615                 620

Ala Ile Thr Pro Lys Trp Thr Leu Gly Gly Glu Tyr Gln Tyr Ser Ser
625                 630                 635                 640

Ser Val Tyr Leu Asp Asn Ala Asn Lys Asn Gly Lys Asp Gly Ala Arg
                645                 650                 655

Ser Val Phe Asn Leu Gln Thr Ser Tyr Glu Phe Asn Ser His Phe Ser
            660                 665                 670
```

-continued

```
Ile Tyr Ala Gly Ile Lys Asn Val Leu Asn His Lys Tyr Tyr Glu Ser
        675                 680                 685

Val Ser Ala Gly Ser Ser Gln Lys Tyr Tyr Ser Pro Ala Pro Glu Arg
    690                 695                 700

Asn Tyr Tyr Ala Gly Phe Arg Tyr Gln Phe
705                 710
```

```
<210> SEQ ID NO 5
<211> LENGTH: 2211
<212> TYPE: DNA
<213> ORGANISM: Fusobacterium necrophorum

<400> SEQUENCE: 5

atgaaaaaaa ttttgttttt agttggggct ttgttttcta tttctgcttt tgcggagcag     60

actatagaat taggaagtac ttccataaaa ggaaatagaa agacagatta tactttaaca    120

ccaaaagagt ataaaaatac atataccatt acgcaagaaa aaattcaaga acgaaactat    180

aaaaatgtag aagatgtttt acgagatgct cctggtattg ttgttcaaaa tacagcattt    240

ggacctcgaa ttgatatgag agggagtggg gagaaatctt tgtcaagagt aaaggttctt    300

gtggatggaa ttagtatcaa tcctacagag gaaacgatgg cgagtttacc aattaattcg    360

attcccattg aaagtgttaa aaagattgaa attattccag gaggaggagc tactttatat    420

ggaagtggct ctgtaggagg agttgtcagt atttctacga attccaatgt aacgaagaat    480

aatttcttta tggatttgaa ctatggttct tttgataata gaaactttgg atttgcagga    540

ggatataatg taagtgacaa attatatgtg aactatggtt ttaattattt gaacagtgaa    600

gattatagag aacatgagga gaaggaaaat aaaatttatt tgttgggttt tgactataaa    660

atcaacccaa agaatcgttt cagagtacaa acaagatata gtaaaatgaa gcatgatgga    720

agtaactggc taagtcagga ggaattaaag atttcgcgaa agaaagctgg attgaatttg    780

gacctagata caacagataa aagttacact ttcgattatg agtatagatc tagtcaaaat    840

ttaacgctag ccgctactgc ctataaacaa caacaagata gagacattac aaccgatgat    900

attcgagata ttgaaattat agcttctaac cgaaactaca ctgatttaaa agaatatatg    960

actttttatg atgtaaaatc tactttaaag gcaaagttta aagaaaaaaa atatggacta   1020

aaattaaaag gaaaatacga gtatggaaga ggggaagtta ttttcgggta tgattatcaa   1080

gattctaaca ataaaagaaa ctctcttgta caatcagaga ctttaaaaac ttataatgac   1140

aaaatcagtg acttaaattt atctcctgaa gatagaaagc caatcatcaa tagagtcaac   1200

attgatttaa caaagaaatc tcacggtttt tatgtgttta ataagttaga attaacagat   1260

aaatgggatt ttacgacagg atttagaacc gaaattacaa aatataatgg atatcgaaaa   1320

aatgggccaa ataccatgcc aatcgtctct ccgaaagtaa atgaaatcag aacagacgag   1380

aagatgacaa actatgcggg agaagcagga atgttgtaca agtatagtga cacaggaaga   1440

gcctttgttc gatatgaaag aggatttgta acaccgtttg caaaccagtt gacagataaa   1500

attcatgata caaaattaaa aagtccagct ggatttttca ccccaccaat tgtgaacgtt   1560

tcttctttgt atgtagcaaa taacttgaaa tcagaaatca cagatactat agaagtggga   1620

ttccgagatt atatttttaa ttccttaatc agtgcttcct tctttgcaac ggacactacc   1680

gatgaaatta cacttatcag ttccggaatt acgaatccgg cagtcaatag atggaaattt   1740

cgaaatatag gaaaaacaag aagattagga attgaattgg aagcggaaca aaaatgggga   1800

aaatttgatt tcagtcaatc gctaactttt gtagatacaa aagtattaaa aacagatgca   1860
```

-continued

```
gaatccagaa tttttagagg agataaggtt ccaatggttc ctagaatcaa agcaacatta   1920

ggattaaaat ataatgtgac agataacttg gctttgattg gaacttatac gtatttgagt   1980

aaacgggaaa ccagagaatt ggatgaaaaa gataaggtat ataaacatac tatcaaagga   2040

tatggaacag cggatttggg aatattgtat aaggtggaca agtattcaaa ctttaaagtg   2100

ggggcaaaga atatttttgg aaagaaatat aatttacgag agacaaaatt agaagcattg   2160

ccagcaccgg aaagaaatta ctatttagaa tttaatgtca aatttaacta a            2211


<210> SEQ ID NO 6
<211> LENGTH: 736
<212> TYPE: PRT
<213> ORGANISM: Fusobacterium necrophorum

<400> SEQUENCE: 6

Met Lys Lys Ile Leu Phe Leu Val Gly Ala Leu Phe Ser Ile Ser Ala
1               5                   10                  15

Phe Ala Glu Gln Thr Ile Glu Leu Gly Ser Thr Ser Ile Lys Gly Asn
            20                  25                  30

Arg Lys Thr Asp Tyr Thr Leu Thr Pro Lys Glu Tyr Lys Asn Thr Tyr
        35                  40                  45

Thr Ile Thr Gln Glu Lys Ile Gln Glu Arg Asn Tyr Lys Asn Val Glu
    50                  55                  60

Asp Val Leu Arg Asp Ala Pro Gly Ile Val Val Gln Asn Thr Ala Phe
65                  70                  75                  80

Gly Pro Arg Ile Asp Met Arg Gly Ser Gly Glu Lys Ser Leu Ser Arg
                85                  90                  95

Val Lys Val Leu Val Asp Gly Ile Ser Ile Asn Pro Thr Glu Glu Thr
            100                 105                 110

Met Ala Ser Leu Pro Ile Asn Ser Ile Pro Ile Glu Ser Val Lys Lys
        115                 120                 125

Ile Glu Ile Ile Pro Gly Gly Gly Ala Thr Leu Tyr Gly Ser Gly Ser
    130                 135                 140

Val Gly Gly Val Val Ser Ile Ser Thr Asn Ser Asn Val Thr Lys Asn
145                 150                 155                 160

Asn Phe Phe Met Asp Leu Asn Tyr Gly Ser Phe Asp Asn Arg Asn Phe
                165                 170                 175

Gly Phe Ala Gly Gly Tyr Asn Val Ser Asp Lys Leu Tyr Val Asn Tyr
            180                 185                 190

Gly Phe Asn Tyr Leu Asn Ser Glu Asp Tyr Arg Glu His Glu Glu Lys
        195                 200                 205

Glu Asn Lys Ile Tyr Leu Leu Gly Phe Asp Tyr Lys Ile Asn Pro Lys
    210                 215                 220

Asn Arg Phe Arg Val Gln Thr Arg Tyr Ser Lys Met Lys His Asp Gly
225                 230                 235                 240

Ser Asn Trp Leu Ser Gln Glu Glu Leu Lys Ile Ser Arg Lys Lys Ala
                245                 250                 255

Gly Leu Asn Leu Asp Leu Asp Thr Thr Asp Lys Ser Tyr Thr Phe Asp
            260                 265                 270

Tyr Glu Tyr Arg Ser Ser Gln Asn Leu Thr Leu Ala Ala Thr Ala Tyr
        275                 280                 285

Lys Gln Gln Gln Asp Arg Asp Ile Thr Thr Asp Asp Ile Arg Asp Ile
    290                 295                 300

Glu Ile Ile Ala Ser Asn Arg Asn Tyr Thr Asp Leu Lys Glu Tyr Met
305                 310                 315                 320
```

-continued

```
Thr Phe Tyr Asp Val Lys Ser Thr Leu Lys Ala Lys Phe Lys Glu Lys
                325                 330                 335

Lys Tyr Gly Leu Lys Leu Lys Gly Lys Tyr Glu Tyr Gly Arg Gly Glu
            340                 345                 350

Val Ile Phe Gly Tyr Asp Tyr Gln Asp Ser Asn Asn Lys Arg Asn Ser
        355                 360                 365

Leu Val Gln Ser Glu Thr Leu Lys Thr Tyr Asn Asp Lys Ile Ser Asp
    370                 375                 380

Leu Asn Leu Ser Pro Glu Asp Arg Lys Pro Ile Ile Asn Arg Val Asn
385                 390                 395                 400

Ile Asp Leu Thr Lys Lys Ser His Gly Phe Tyr Val Phe Asn Lys Leu
                405                 410                 415

Glu Leu Thr Asp Lys Trp Asp Phe Thr Thr Gly Phe Arg Thr Glu Ile
            420                 425                 430

Thr Lys Tyr Asn Gly Tyr Arg Lys Asn Gly Pro Asn Thr Met Pro Ile
        435                 440                 445

Val Ser Pro Lys Val Asn Glu Ile Arg Thr Asp Glu Lys Met Thr Asn
    450                 455                 460

Tyr Ala Gly Glu Ala Gly Met Leu Tyr Lys Tyr Ser Asp Thr Gly Arg
465                 470                 475                 480

Ala Phe Val Arg Tyr Glu Arg Gly Phe Val Thr Pro Phe Ala Asn Gln
                485                 490                 495

Leu Thr Asp Lys Ile His Asp Thr Lys Leu Lys Ser Pro Ala Gly Phe
            500                 505                 510

Phe Thr Pro Pro Ile Val Asn Val Ser Ser Leu Tyr Val Ala Asn Asn
        515                 520                 525

Leu Lys Ser Glu Ile Thr Asp Thr Ile Glu Val Gly Phe Arg Asp Tyr
    530                 535                 540

Ile Phe Asn Ser Leu Ile Ser Ala Ser Phe Phe Ala Thr Asp Thr Thr
545                 550                 555                 560

Asp Glu Ile Thr Leu Ile Ser Ser Gly Ile Thr Asn Pro Ala Val Asn
                565                 570                 575

Arg Trp Lys Phe Arg Asn Ile Gly Lys Thr Arg Arg Leu Gly Ile Glu
            580                 585                 590

Leu Glu Ala Glu Gln Lys Trp Gly Lys Phe Asp Phe Ser Gln Ser Leu
        595                 600                 605

Thr Phe Val Asp Thr Lys Val Leu Lys Thr Asp Ala Glu Ser Arg Ile
    610                 615                 620

Phe Arg Gly Asp Lys Val Pro Met Val Pro Arg Ile Lys Ala Thr Leu
625                 630                 635                 640

Gly Leu Lys Tyr Asn Val Thr Asp Asn Leu Ala Leu Ile Gly Thr Tyr
                645                 650                 655

Thr Tyr Leu Ser Lys Arg Glu Thr Arg Glu Leu Asp Glu Lys Asp Lys
            660                 665                 670

Val Tyr Lys His Thr Ile Lys Gly Tyr Gly Thr Ala Asp Leu Gly Ile
        675                 680                 685

Leu Tyr Lys Val Asp Lys Tyr Ser Asn Phe Lys Val Gly Ala Lys Asn
    690                 695                 700

Ile Phe Gly Lys Lys Tyr Asn Leu Arg Glu Thr Lys Leu Glu Ala Leu
705                 710                 715                 720

Pro Ala Pro Glu Arg Asn Tyr Tyr Leu Glu Phe Asn Val Lys Phe Asn
                725                 730                 735
```

<210> SEQ ID NO 7
<211> LENGTH: 2097
<212> TYPE: DNA
<213> ORGANISM: Fusobacterium necrophorum

<400> SEQUENCE: 7

```
atgaaaacaa acattttatt tttaacattt ttattttgta atactgtttc ttttgcagaa     60
acaaccattc atctaccaga aagcaatatt caatccgatt atgtggaaat caataagatg    120
aaaaatctca aaaatataat tgtgattgaa aaaaaagaaa ttcaggagaa agggtataca    180
aatttatccg ccgtattgca agatatccca aatattcatg tcggaacaac cggttgggga    240
gaaattgata ttcgaggtca gggagaagga aatgcagcaa aaaatttgca ggtgttaatc    300
gatggagctc cgattaccac tttggtaaac catcctttgc aaacgaatta cgacgtagtt    360
ccggtagaaa atattgaaag aattgaaatt attcccggag gaggttccat catttatggt    420
tccgggacag ctggaggagt tatcaatatt actaccaatc taagtcgttt acacagacca    480
ataaacattg tagaagtttc cgccggaacc ggtggagaaa aatataatct tgcctttggt    540
catagagtta ctaagaaact aaacgtacaa ttatcatatc ttcgaaataa tcagaatcta    600
tatttcaaag atacctatcg acatagcaac tatttcacgg caggattaca ttatcaaatc    660
tccgacagac aaaatttgtc tctgcgatat agtactctca cagaagacgg aaaatttgtt    720
cgaaatattt tatataaaaa attgaatcag gatggaaaaa attatcgacc ggaaaagaaa    780
aaagtaaccg ccggtttgga caaagacgga cataaaattg aaaaatggat ggacggatat    840
tccaatgcca agagaaatat ggacagcttc aatctaagtt atcgtttccg acttggggaa    900
aactcaactt atcttatgga tgccttttac aataagggac atttttccaa tatggctttg    960
agtgatcaga ccatgtatca tcatacctac ggagttaaaa ataaattgga ctttttctat   1020
gcaaagaata gtgcttttga cggaagtagc ttgttgattg gattggattc ttaccaacag   1080
gatgcaaaat tggaatacaa tgattacaaa tttttagatt acaaaaagaa aacttattac   1140
atcagaccgc tttcctttaa atataaaaag aaaaccaatg ctttttatct attgaatact   1200
ctaaaatatg gaaattggga gtcttcacaa ggaattcgaa gagattatac ctattggcat   1260
tttgacaagg ttacttccaa aaatgaagga aaagaaacca gccatcgtca caataccaat   1320
tacgaattca gtcttgccta taaatatcgt gataccggaa ggatctatgc tcgttacgaa   1380
agaggcttta cttcccctga tggtctagaa attacagatg acttttccaa acaagacatt   1440
aagcctacaa aaggaaaaga tgaaatctat gacttatatg aaatcggttg gagagaatac   1500
ttcggattta ctaccataaa cttaactgca ttctattctt ttacagacaa tgaaatgagc   1560
cgaaattatg ttttcaatga actaggattc ggaaggaaaa ccatcaacat tctaaaaacc   1620
aaaagaaaag gaatagaatt aagtctattc caaaaattag gaaatttgga attaaaagaa   1680
agttacgctt atttaaaagg aaaaagaact tacaacggaa aagaatctca attcttagat   1740
ccggatgact atgtagattg gtccaatacg ggacttccca aagtcccaaa acagtctcta   1800
accttggaag caaaatatca ttttagccca aaaatttcag tcggtttacg atataaatac   1860
aatggaaaat atagtaattt cagtgattta agacaaaaag aagaagaagg atacatcaaa   1920
tctcattctg taacggactt atctttacat tatcaaaatg aaaaaggatt tcatctgtat   1980
ggaggaatca ataatgtatt caatgaaaaa tattttgaat ataccggttc taaaatgtat   2040
accatcatcc ctgcggaaga aagaacattc tttgtgggag cgaaatatca attttaa      2097
```

-continued

<210> SEQ ID NO 8
<211> LENGTH: 698
<212> TYPE: PRT
<213> ORGANISM: Fusobacterium necrophorum

<400> SEQUENCE: 8

```
Met Lys Thr Asn Ile Leu Phe Leu Thr Phe Leu Phe Cys Asn Thr Val
1               5                   10                  15

Ser Phe Ala Glu Thr Thr Ile His Leu Pro Glu Ser Asn Ile Gln Ser
            20                  25                  30

Asp Tyr Val Glu Ile Asn Lys Met Lys Asn Leu Lys Asn Ile Ile Val
        35                  40                  45

Ile Glu Lys Lys Glu Ile Gln Glu Lys Gly Tyr Thr Asn Leu Ser Ala
    50                  55                  60

Val Leu Gln Asp Ile Pro Asn Ile His Val Gly Thr Thr Gly Trp Gly
65                  70                  75                  80

Glu Ile Asp Ile Arg Gly Gln Gly Glu Gly Asn Ala Ala Lys Asn Leu
                85                  90                  95

Gln Val Leu Ile Asp Gly Ala Pro Ile Thr Thr Leu Val Asn His Pro
            100                 105                 110

Leu Gln Thr Asn Tyr Asp Val Val Pro Val Glu Asn Ile Glu Arg Ile
        115                 120                 125

Glu Ile Ile Pro Gly Gly Gly Ser Ile Ile Tyr Gly Ser Gly Thr Ala
    130                 135                 140

Gly Gly Val Ile Asn Ile Thr Thr Asn Leu Ser Arg Leu His Arg Pro
145                 150                 155                 160

Ile Asn Ile Val Glu Val Ser Ala Gly Thr Gly Gly Glu Lys Tyr Asn
                165                 170                 175

Leu Ala Phe Gly His Arg Val Thr Lys Lys Leu Asn Val Gln Leu Ser
            180                 185                 190

Tyr Leu Arg Asn Asn Gln Asn Leu Tyr Phe Lys Asp Thr Tyr Arg His
        195                 200                 205

Ser Asn Tyr Phe Thr Ala Gly Leu His Tyr Gln Ile Ser Asp Arg Gln
    210                 215                 220

Asn Leu Ser Leu Arg Tyr Ser Thr Leu Thr Glu Asp Gly Lys Phe Val
225                 230                 235                 240

Arg Asn Ile Leu Tyr Lys Lys Leu Asn Gln Asp Gly Lys Asn Tyr Arg
                245                 250                 255

Pro Glu Lys Lys Lys Val Thr Ala Gly Leu Asp Lys Asp Gly His Lys
            260                 265                 270

Ile Glu Lys Trp Met Asp Gly Tyr Ser Asn Ala Lys Arg Asn Met Asp
        275                 280                 285

Ser Phe Asn Leu Ser Tyr Arg Phe Arg Leu Gly Glu Asn Ser Thr Tyr
    290                 295                 300

Leu Met Asp Ala Phe Tyr Asn Lys Gly His Phe Ser Asn Met Ala Leu
305                 310                 315                 320

Ser Asp Gln Thr Met Tyr His His Thr Tyr Gly Val Lys Asn Lys Leu
                325                 330                 335

Asp Phe Phe Tyr Ala Lys Asn Ser Ala Phe Asp Gly Ser Ser Leu Leu
            340                 345                 350

Ile Gly Leu Asp Ser Tyr Gln Gln Asp Ala Lys Leu Glu Tyr Asn Asp
        355                 360                 365

Tyr Lys Phe Leu Asp Tyr Lys Lys Lys Thr Tyr Tyr Ile Arg Pro Leu
    370                 375                 380
```

-continued

```
Ser Phe Lys Tyr Lys Lys Lys Thr Asn Ala Phe Tyr Leu Leu Asn Thr
385                 390                 395                 400

Leu Lys Tyr Gly Asn Trp Glu Ser Ser Gln Gly Ile Arg Arg Asp Tyr
                405                 410                 415

Thr Tyr Trp His Phe Asp Lys Val Thr Ser Lys Asn Glu Gly Lys Glu
            420                 425                 430

Thr Ser His Arg His Asn Thr Asn Tyr Glu Phe Ser Leu Ala Tyr Lys
        435                 440                 445

Tyr Arg Asp Thr Gly Arg Ile Tyr Ala Arg Tyr Glu Arg Gly Phe Thr
    450                 455                 460

Ser Pro Asp Gly Leu Glu Ile Thr Asp Asp Phe Ser Lys Gln Asp Ile
465                 470                 475                 480

Lys Pro Thr Lys Gly Lys Asp Glu Ile Tyr Asp Leu Tyr Glu Ile Gly
                485                 490                 495

Trp Arg Glu Tyr Phe Gly Phe Thr Thr Ile Asn Leu Thr Ala Phe Tyr
            500                 505                 510

Ser Phe Thr Asp Asn Glu Met Ser Arg Asn Tyr Val Phe Asn Glu Leu
        515                 520                 525

Gly Phe Gly Arg Lys Thr Ile Asn Ile Leu Lys Thr Lys Arg Lys Gly
    530                 535                 540

Ile Glu Leu Ser Leu Phe Gln Lys Leu Gly Asn Leu Glu Leu Lys Glu
545                 550                 555                 560

Ser Tyr Ala Tyr Leu Lys Gly Lys Arg Thr Tyr Asn Gly Lys Glu Ser
                565                 570                 575

Gln Phe Leu Asp Pro Asp Asp Tyr Val Asp Trp Ser Asn Thr Gly Leu
            580                 585                 590

Pro Lys Val Pro Lys Gln Ser Leu Thr Leu Glu Ala Lys Tyr His Phe
        595                 600                 605

Ser Pro Lys Ile Ser Val Gly Leu Arg Tyr Lys Tyr Asn Gly Lys Tyr
    610                 615                 620

Ser Asn Phe Ser Asp Leu Arg Gln Lys Glu Glu Glu Gly Tyr Ile Lys
625                 630                 635                 640

Ser His Ser Val Thr Asp Leu Ser Leu His Tyr Gln Asn Glu Lys Gly
                645                 650                 655

Phe His Leu Tyr Gly Gly Ile Asn Asn Val Phe Asn Glu Lys Tyr Phe
            660                 665                 670

Glu Tyr Thr Gly Ser Lys Met Tyr Thr Ile Ile Pro Ala Glu Glu Arg
        675                 680                 685

Thr Phe Phe Val Gly Ala Lys Tyr Gln Phe
    690                 695


<210> SEQ ID NO 9
<211> LENGTH: 1965
<212> TYPE: DNA
<213> ORGANISM: Fusobacterium necrophorum

<400> SEQUENCE: 9

atgaaaaagt actttgttgc agtgtcgatt tccttagcac tttcgtatca gatttttgca      60

gaggaaaatc ctgttatcaa attaaatgaa actgttataa cttctgaaag ttttggaaca     120

aatattttga gaactccaaa gaatattaca gtaattactg caagaaatat taaaattcaa     180

ggagcaaaga atatagaaga tgctttaaga ggggttgcag gcttaactgc ttataataat     240

atgggcggct ctgatcccaa aatttctctt cgaggaatgg ctccgggaaa agaagaacaa     300

agtattctgt ttttattaga tggaatcccc tataacagta cagtagatac tggagcggta     360
```

-continued

```
aatctgaatt tgattcctat tgacatcgta gagagaattg aaattattcc taatggggga    420

aacgtagttt atggagaagg agctgtcgga ggagttatca atattatcac taaaaaagga    480

aaaaataaaa aatattacgg ttctttttca atagatggag gatcttatga tttaaaggag    540

tataaggtaa atttggggag caacctgacg gagcagcttt ctctagattt gaaatataat    600

aatagaaggc aaaaaaatta ccgggatcac cacacaagag acattgaata tatcaatttg    660

ggaatggaat ataaagaaaa tgagcacagt atttatttcg attttcagaa ttcagaaaca    720

gaatatcgtt ttcctggtta tctgacaaag aaacaaatag aagagggtaa gattaaaaaa    780

tcaacaggaa atataaaggg aaaagaaaaa ttaagaattt accgtgcaaa atacgaggga    840

aaatgggcta aaaatttatt ttttaatatt gcaggagatt ttaaagataa attatataag    900

tccattgatg aaaaaacaaa taccgtcagt accataagag atacggaatc tttttacatc    960

agtccacaaa tcaaatatca atatatgccg aattcttact ttatactagg aggagatttc   1020

ctgaaaggga aatcaaaata tagatataaa aaagacatta aaacagaaac aagcagaaaa   1080

tctgtcggag tgtttcttac caataatata aaatgggaaa attttatatt tacacaggga   1140

tatcgacatc aaaaaatcaa gtatgatgta aaggataagt tgtatccttc cccaaaccat   1200

aaacaaaaaa ttctattgga taaaactttc caacaggatt cctatgaact gacagcaaat   1260

tatcttttgt cggatacagg tagtatatac gcttcttaca caaaagcttt cagagcccct   1320

actgcagatg aagcaggtag atggcgaaaa ggatacgatg taaaaataca agaagcggat   1380

acttttgaag ttggaggaaa gcttgcttgg aagaactggt atatatctgg ttctatcttt   1440

cataccagaa ccgaaaatga gattctatat attgcctatg aagatggaaa gctgggtaaa   1500

aattataact tgcccggaaa gaatataaga cagggaattg agctttctct ggaacaatac   1560

ttagaaaaat taacgttacg ggaaagtttc cattatttaa aacataaaat caaaaaagga   1620

actttcgccg gaaataagat tccaggagtc cctcagtaca tttatagttt aggtatggat   1680

tatagaatat tagatcatgt tatctggagt aattcttttc attattatgg aagtgcctat   1740

ggaaattatg attatcataa taaatttgga aaacagaaag ggcatacgga attaaacacc   1800

agtcttcgct atgaaatgaa aaacggcttg agtttttatg gagggattca caatcttctg   1860

gataaggaat attttactcc aaaattaaat gcggccggaa cagggatgaa ttattattat   1920

ggcagcagaa gaaattacta tattggattc cagtatacct tctaa                   1965
```

<210> SEQ ID NO 10
<211> LENGTH: 651
<212> TYPE: PRT
<213> ORGANISM: Fusobacterium necrophorum

<400> SEQUENCE: 10

```
Met Lys Lys Tyr Phe Val Ala Val Ser Ile Ser Leu Ala Leu Ser Tyr
1               5                   10                  15

Gln Ile Phe Ala Glu Glu Asn Pro Val Ile Lys Leu Asn Glu Thr Val
            20                  25                  30

Ile Thr Ser Glu Ser Phe Gly Thr Asn Ile Leu Arg Thr Pro Lys Asn
        35                  40                  45

Ile Thr Val Ile Thr Ala Arg Asn Ile Lys Ile Gln Gly Ala Lys Asn
    50                  55                  60

Ile Glu Asp Ala Leu Arg Gly Val Ala Gly Leu Thr Ala Tyr Asn Asn
65                  70                  75                  80

Met Gly Gly Ser Asp Pro Lys Ile Ser Leu Arg Gly Met Ala Pro Gly
```

-continued

```
                85                  90                  95

Lys Glu Glu Gln Ser Ile Leu Phe Leu Leu Asp Gly Ile Pro Tyr Asn
            100                 105                 110

Ser Thr Val Asp Thr Gly Ala Val Asn Leu Asn Leu Ile Pro Ile Asp
        115                 120                 125

Ile Val Glu Arg Ile Glu Ile Ile Pro Asn Gly Gly Asn Val Val Tyr
    130                 135                 140

Gly Glu Gly Ala Val Gly Gly Val Ile Asn Ile Ile Thr Lys Lys Gly
145                 150                 155                 160

Lys Asn Lys Lys Tyr Tyr Gly Ser Phe Ser Ile Asp Gly Gly Ser Tyr
                165                 170                 175

Asp Leu Lys Glu Tyr Lys Val Asn Leu Gly Ser Asn Leu Thr Glu Gln
            180                 185                 190

Leu Ser Leu Asp Leu Lys Tyr Asn Asn Arg Arg Gln Lys Asn Tyr Arg
        195                 200                 205

Asp His His Thr Arg Asp Ile Glu Tyr Ile Asn Leu Gly Met Glu Tyr
    210                 215                 220

Lys Glu Asn Glu His Ser Ile Tyr Phe Asp Phe Gln Asn Ser Glu Thr
225                 230                 235                 240

Glu Tyr Arg Phe Pro Gly Tyr Leu Thr Lys Lys Gln Ile Glu Glu Gly
                245                 250                 255

Lys Ile Lys Lys Ser Thr Gly Asn Ile Lys Gly Lys Glu Lys Leu Arg
            260                 265                 270

Ile Tyr Arg Ala Lys Tyr Glu Gly Lys Trp Ala Lys Asn Leu Phe Phe
        275                 280                 285

Asn Ile Ala Gly Asp Phe Lys Asp Lys Leu Tyr Lys Ser Ile Asp Glu
    290                 295                 300

Lys Thr Asn Thr Val Ser Thr Ile Arg Asp Thr Glu Ser Phe Tyr Ile
305                 310                 315                 320

Ser Pro Gln Ile Lys Tyr Gln Tyr Met Pro Asn Ser Tyr Phe Ile Leu
                325                 330                 335

Gly Gly Asp Phe Leu Lys Gly Lys Ser Lys Tyr Arg Tyr Lys Lys Asp
            340                 345                 350

Ile Lys Thr Glu Thr Ser Arg Lys Ser Val Gly Val Phe Leu Thr Asn
        355                 360                 365

Asn Ile Lys Trp Glu Asn Phe Ile Phe Thr Gln Gly Tyr Arg His Gln
    370                 375                 380

Lys Ile Lys Tyr Asp Val Lys Asp Lys Leu Tyr Pro Ser Pro Asn His
385                 390                 395                 400

Lys Gln Lys Ile Leu Leu Asp Lys Thr Phe Gln Gln Asp Ser Tyr Glu
                405                 410                 415

Leu Thr Ala Asn Tyr Leu Leu Ser Asp Thr Gly Ser Ile Tyr Ala Ser
            420                 425                 430

Tyr Thr Lys Ala Phe Arg Ala Pro Thr Ala Asp Glu Ala Gly Arg Trp
        435                 440                 445

Arg Lys Gly Tyr Asp Val Lys Ile Gln Glu Ala Asp Thr Phe Glu Val
    450                 455                 460

Gly Gly Lys Leu Ala Trp Lys Asn Trp Tyr Ile Ser Gly Ser Ile Phe
465                 470                 475                 480

His Thr Arg Thr Glu Asn Glu Ile Leu Tyr Ile Ala Tyr Glu Asp Gly
                485                 490                 495

Lys Leu Gly Lys Asn Tyr Asn Leu Pro Gly Lys Asn Ile Arg Gln Gly
            500                 505                 510
```

```
Ile Glu Leu Ser Leu Glu Gln Tyr Leu Glu Lys Leu Thr Leu Arg Glu
        515                 520                 525

Ser Phe His Tyr Leu Lys His Lys Ile Lys Lys Gly Thr Phe Ala Gly
    530                 535                 540

Asn Lys Ile Pro Gly Val Pro Gln Tyr Ile Tyr Ser Leu Gly Met Asp
545                 550                 555                 560

Tyr Arg Ile Leu Asp His Val Ile Trp Ser Asn Ser Phe His Tyr Tyr
                565                 570                 575

Gly Ser Ala Tyr Gly Asn Tyr Asp Tyr His Asn Lys Phe Gly Lys Gln
            580                 585                 590

Lys Gly His Thr Glu Leu Asn Thr Ser Leu Arg Tyr Glu Met Lys Asn
        595                 600                 605

Gly Leu Ser Phe Tyr Gly Gly Ile His Asn Leu Leu Asp Lys Glu Tyr
    610                 615                 620

Phe Thr Pro Lys Leu Asn Ala Ala Gly Thr Gly Met Asn Tyr Tyr Tyr
625                 630                 635                 640

Gly Ser Arg Arg Asn Tyr Tyr Ile Gly Phe Gln
                645                 650


<210> SEQ ID NO 11
<211> LENGTH: 2001
<212> TYPE: DNA
<213> ORGANISM: Fusobacterium necrophorum

<400> SEQUENCE: 11

atgaaaaaaa tttttatggt aacagcaatt ttagcaacag cttccggtct tggttttgca      60

aaggagattt ctcctattga actggagcaa acagtcgtaa cttctgaatc tttcggaaca     120

tcaactcata ggacagccaa aaatatacag gtaattacag caaaggaaat ggaagaaaaa     180

ggggcattaa cagtagatga agcattaaag ggagtacccg gagttatggt aagaaaaatg     240

gatggaggaa ctcctgttat tgatttacgg gggtcaggag cggcatccag tttcagttcc     300

agcatactct tgttggatgg agttccgtta aacggtttgg tgaaattgga catcaattcc     360

attcctctaa gtgaaatcag tcgtatcgaa attattcaag gaggaggagc tgttatgtat     420

ggggatggct ccacaggagg ggttgttaat attattacga agagtccgaa atacaaaaaa     480

cattatggaa gtgcaggctt ggaatacggt tcttggaaaa caagtcgggc aagcttacat     540

tacggaacgg ctttaacaga taaattatcc gtcagtgctt cctattccgg atatgcttct     600

atggaatacc gagatcgagg acatggaaaa acttggagcg gagaaagttt cgattacaga     660

aataaaaaag ataagaaata ttccctttgg ttacaaggaa aatatcaatt ggaagacgga     720

agtatcggct tcaagtataa tcataacgaa agaaaggatt attacaccgg atatttggaa     780

aagaaacagt atgaagaaaa tcctaaacaa ataggaagtt attcaggtaa aatacaggat     840

gtgacggata tttataatct ttcttatcaa acaaagttga cagatacctt ggaattttta     900

gtttacggag gatattatcg aggaaagagc atcgaccaaa atcagcttac cagtgaatat     960

tttataaaac ctcaattcaa atatacttac ggagaaaaca gctatgttat tttaggtggg    1020

gattaccgag atggaaagcg ggaattcaaa gaaaaagttc tggtaaacgg aaggatgcaa    1080

aaagctccca acgatgaaag agaatccaaa gcaatctatg ttatgaataa aacttctttg    1140

ggaaactggg aattttctca aggatatcgt tatgaaaagg tggattataa atacagttcc    1200

aaaatttatg gaccaggctg gtcattatcc gaaattaaac cgatgaattc aaaatattct    1260

cataatgaca gctttgaatt gggagtgaat tatctatatt ccgatacggg aaatgtatat    1320
```

```
ttcaattata ccaaagcgat gagaactccg acaattggag aggcaggagc ttggtacgga   1380

gatgtaaaga cacagaaaaa tgatattttt gaaataggat taagggatta tttcaaaaat   1440

acacaaatct cttcttctat tttctatatt acttccaaaa atgaagtcta ctatgataaa   1500

acgaatccga ataattcaaa taacagaaac tttgacggaa gggtaagaag aacgggggca   1560

caattgtctt tgacccatta tttggataaa ttaagtgtaa gagaaagaat ttcttacatc   1620

catccaaaag tatccagtgg aatttatagc ggaaaaactt ttgcaggagt tccaaaatgg   1680

actttaaatc taggggcaac ttatcatgtt acggataagt ttttagtaaa tacagattta   1740

tattatcaat ccaaagctta tgcagaagat gattttgaca actattttaa gaaggataat   1800

tcttatgcaa ctttggatat caatacttct tatgcgtttg aaaatggaat ggaagtatac   1860

ggaggagtca aaaatgtatt tgataaaaaa tatgccaata cgataacttc tagcagaagc   1920

acatggtctc cgggacctag aactgtgttc tatcctgcag atggaaagag tgtttatgta   1980

ggattcaaat atcattttta a                                             2001
```

<210> SEQ ID NO 12
<211> LENGTH: 666
<212> TYPE: PRT
<213> ORGANISM: Fusobacterium necrophorum

<400> SEQUENCE: 12

```
Met Lys Lys Ile Phe Met Val Thr Ala Ile Leu Ala Thr Ala Ser Gly
1               5                   10                  15

Leu Gly Phe Ala Lys Glu Ile Ser Pro Ile Glu Leu Glu Gln Thr Val
            20                  25                  30

Val Thr Ser Glu Ser Phe Gly Thr Ser Thr His Arg Thr Ala Lys Asn
        35                  40                  45

Ile Gln Val Ile Thr Ala Lys Glu Met Glu Glu Lys Gly Ala Leu Thr
    50                  55                  60

Val Asp Glu Ala Leu Lys Gly Val Pro Gly Val Met Val Arg Lys Met
65                  70                  75                  80

Asp Gly Gly Thr Pro Val Ile Asp Leu Arg Gly Ser Gly Ala Ala Ser
                85                  90                  95

Ser Phe Ser Ser Ser Ile Leu Leu Leu Asp Gly Val Pro Leu Asn Gly
            100                 105                 110

Leu Val Lys Leu Asp Ile Asn Ser Ile Pro Leu Ser Glu Ile Ser Arg
        115                 120                 125

Ile Glu Ile Ile Gln Gly Gly Gly Ala Val Met Tyr Gly Asp Gly Ser
    130                 135                 140

Thr Gly Gly Val Val Asn Ile Ile Thr Lys Ser Pro Lys Tyr Lys Lys
145                 150                 155                 160

His Tyr Gly Ser Ala Gly Leu Glu Tyr Gly Ser Trp Lys Thr Ser Arg
                165                 170                 175

Ala Ser Leu His Tyr Gly Thr Ala Leu Thr Asp Lys Leu Ser Val Ser
            180                 185                 190

Ala Ser Tyr Ser Gly Tyr Ala Ser Met Glu Tyr Arg Asp Arg Gly His
        195                 200                 205

Gly Lys Thr Trp Ser Gly Glu Ser Phe Asp Tyr Arg Asn Lys Lys Asp
    210                 215                 220

Lys Lys Tyr Ser Leu Trp Leu Gln Gly Lys Tyr Gln Leu Glu Asp Gly
225                 230                 235                 240

Ser Ile Gly Phe Lys Tyr Asn His Asn Glu Arg Lys Asp Tyr Tyr Thr
```

-continued

```
                245                 250                 255

Gly Tyr Leu Glu Lys Lys Gln Tyr Glu Glu Asn Pro Lys Gln Ile Gly
            260                 265                 270

Ser Tyr Ser Gly Lys Ile Gln Asp Val Thr Asp Ile Tyr Asn Leu Ser
        275                 280                 285

Tyr Gln Thr Lys Leu Thr Asp Thr Leu Glu Phe Leu Val Tyr Gly Gly
    290                 295                 300

Tyr Tyr Arg Gly Lys Ser Ile Asp Gln Asn Gln Leu Thr Ser Glu Tyr
305                 310                 315                 320

Phe Ile Lys Pro Gln Phe Lys Tyr Thr Tyr Gly Glu Asn Ser Tyr Val
                325                 330                 335

Ile Leu Gly Gly Asp Tyr Arg Asp Gly Lys Arg Glu Phe Lys Glu Lys
            340                 345                 350

Val Leu Val Asn Gly Arg Met Gln Lys Ala Pro Asn Asp Glu Arg Glu
        355                 360                 365

Ser Lys Ala Ile Tyr Val Met Asn Lys Thr Ser Leu Gly Asn Trp Glu
    370                 375                 380

Phe Ser Gln Gly Tyr Arg Tyr Glu Lys Val Asp Tyr Lys Tyr Ser Ser
385                 390                 395                 400

Lys Ile Tyr Gly Pro Gly Trp Ser Leu Ser Glu Ile Lys Pro Met Asn
                405                 410                 415

Ser Lys Tyr Ser His Asn Asp Ser Phe Glu Leu Gly Val Asn Tyr Leu
            420                 425                 430

Tyr Ser Asp Thr Gly Asn Val Tyr Phe Asn Tyr Thr Lys Ala Met Arg
        435                 440                 445

Thr Pro Thr Ile Gly Glu Ala Gly Ala Trp Tyr Gly Asp Val Lys Thr
    450                 455                 460

Gln Lys Asn Asp Ile Phe Glu Ile Gly Leu Arg Asp Tyr Phe Lys Asn
465                 470                 475                 480

Thr Gln Ile Ser Ser Ser Ile Phe Tyr Ile Thr Ser Lys Asn Glu Val
                485                 490                 495

Tyr Tyr Asp Lys Thr Asn Pro Asn Asn Ser Asn Asn Arg Asn Phe Asp
            500                 505                 510

Gly Arg Val Arg Arg Thr Gly Ala Gln Leu Ser Leu Thr His Tyr Leu
        515                 520                 525

Asp Lys Leu Ser Val Arg Glu Arg Ile Ser Tyr Ile His Pro Lys Val
    530                 535                 540

Ser Ser Gly Ile Tyr Ser Gly Lys Thr Phe Ala Gly Val Pro Lys Trp
545                 550                 555                 560

Thr Leu Asn Leu Gly Ala Thr Tyr His Val Thr Asp Lys Phe Leu Val
                565                 570                 575

Asn Thr Asp Leu Tyr Tyr Gln Ser Lys Ala Tyr Ala Glu Asp Asp Phe
            580                 585                 590

Asp Asn Tyr Phe Lys Lys Asp Asn Ser Tyr Ala Thr Leu Asp Ile Asn
        595                 600                 605

Thr Ser Tyr Ala Phe Glu Asn Gly Met Glu Val Tyr Gly Gly Val Lys
    610                 615                 620

Asn Val Phe Asp Lys Lys Tyr Ala Asn Thr Ile Thr Ser Ser Arg Ser
625                 630                 635                 640

Thr Trp Ser Pro Gly Pro Arg Thr Val Phe Tyr Pro Ala Asp Gly Lys
                645                 650                 655

Ser Val Tyr Val Gly Phe Lys Tyr His Phe
            660                 665
```

<210> SEQ ID NO 13
<211> LENGTH: 2382
<212> TYPE: DNA
<213> ORGANISM: Fusobacterium necrophorum

<400> SEQUENCE: 13
atggaagaaa acaatggaac gattgtcatc acggaagaaa tgatacaaaa gaagcattat 60
gacagcgttg ccaaaatttt tgaagattct ccggtttccg tcgtaagaca tacggcattc 120
ggaccgattg tcgatttgcg aggaagcgga gagagaacca tcagtcgagt gaaagtgatg 180
attgatggca caccgatcaa ccctttagaa gaaactcacg gaaccatccc ttttgatacc 240
attccggtgg aatccattgc caagatagaa attgttccgg gaacaggaac gacaaaatat 300
ggaggaggaa ccacaggagg gtatatcaac attcatacga aaaaacagaa acagaataat 360
tacattacga tcaatgcgga caatgcctct tataatgcca agagtattgg aattgctgcg 420
ggaatgaatg taaccaagaa attatttgtt tatgcgggag aagcctatca aagaaaagac 480
ggctatcgaa agaaagacca ttcggacaga aacaattttt taggaggctt tgattatcaa 540
atcaatgcaa aacataggat caaaggacaa ggaaatctct accgagagga tttaaaatcc 600
acaacggaag taactcatga agaattgaaa gaagatagaa gaaaagcggg agaagataca 660
aagatagaaa tggatcgaga ttttgcttct ttggactatg aatacacacc tacttcccat 720
tttaaattaa gaaccaatgt caatcgagct cattttacaa gagatgtatc tatgaatgcg 780
aagcaggatc aacttgttct tgcttttatg ccaagagatg aacaaggata ttttttgcat 840
tttgatgcag gattattggc agatcctaag ttatctgatg taaggccggt tcttctggat 900
tttgaatcta ctatggaagg aaaattcaag gaaaaaaatc aggagggaaa gctggacgga 960
gaatggaaat acaatcaagg aaaagggcat ttacaatttg gatatagtta taatgagaag 1020
aaattgaatc aagatttaaa atcaatttcc aaacctttta ctttaaaaaa tcaattggga 1080
tatttgattc aaggtgaccc ggctccgaaa ggatatgaag attacaccgg aaaaattatt 1140
gccccggaag aaatgtttaa aataaaattt aaagattttc ctcaaatact ggaaactttt 1200
ttaggactta ggagagaagg cgtcgaaaag gaaaaaattg attttcaaaa ttataataaa 1260
attgatgctt ttaaggatac tcatgccttg tatttgttaa atgattacaa attaactcca 1320
aaatttaatt ttagagcagg tttaagatgg gaacattcag aatatggttc tgatagaaaa 1380
aatagaatga ttttgggagt tcataatgca caatcatcag gaatggcaaa tagaatggca 1440
attgcgggtc ttcttaatga gtatcaaatg gaggcttatg tacaaggaaa attatcctac 1500
ttggatgttg atttatcttt gaaagaaact catgtcaaag ataggagtga taatttcgga 1560
ggagagcttg gatttactta tcaatatcat cgaaaaggaa gtgtattttt ccgatatgaa 1620
agaggatttt tatctccatt gccttcccaa cttaccaata aggatttctt aacaggaatt 1680
tattatccaa gtcatgtcaa atcggaaaaa gtagacacta ttgaaatggg aatcaaacat 1740
tctctatgga acaatactca tatcgaagcc actactttct tttctttgac aaaagatgaa 1800
attacaaata tgcgatacaa tgcgaacaac catatgaata tgcgttgggc atatgccaat 1860
atttctaaaa caagaagatt gggattggaa ttgaatgcgg aacatatttt cgacaaatta 1920
aagattcgag agtccttcag ttatgtggat gctaagatag caaaagatac cggattcaaa 1980
gattactatc attccgatta caaagtgaaa tcggaaaaag aatttaaaga cgccccccta 2040
tattataaaa aaggacaaca agtacctctt gtttctaagg tcaaagtgac ggtaggagca 2100

-continued

```
gaatatcaat ttacagataa attgagttta ggaggaaact ataactatgt cagtggctat   2160

gatacccgag aaccgggcga aggcttccaa gcaaagacct ataaagtaaa aggccatgga   2220

actttggacc tgtttggaag atattctttc acagactatg cctatgtacg atttggagtg   2280

aataatgtgc taggagaaaa atacaattta cgagaagact ctcactatgc agtaccggct   2340

ccaaaacaaa attattatgc aggatttagt tataagttct aa                      2382


<210> SEQ ID NO 14
<211> LENGTH: 793
<212> TYPE: PRT
<213> ORGANISM: Fusobacterium necrophorum

<400> SEQUENCE: 14

Met Glu Glu Asn Asn Gly Thr Ile Val Ile Thr Glu Glu Met Ile Gln
1               5                   10                  15

Lys Lys His Tyr Asp Ser Val Ala Lys Ile Phe Glu Asp Ser Pro Val
            20                  25                  30

Ser Val Val Arg His Thr Ala Phe Gly Pro Ile Val Asp Leu Arg Gly
        35                  40                  45

Ser Gly Glu Arg Thr Ile Ser Arg Val Lys Val Met Ile Asp Gly Thr
    50                  55                  60

Pro Ile Asn Pro Leu Glu Glu Thr His Gly Thr Ile Pro Phe Asp Thr
65                  70                  75                  80

Ile Pro Val Glu Ser Ile Ala Lys Ile Glu Ile Val Pro Gly Thr Gly
                85                  90                  95

Thr Thr Lys Tyr Gly Gly Gly Thr Thr Gly Gly Tyr Ile Asn Ile His
            100                 105                 110

Thr Lys Lys Gln Lys Gln Asn Asn Tyr Ile Thr Ile Asn Ala Asp Asn
        115                 120                 125

Ala Ser Tyr Asn Ala Lys Ser Ile Gly Ile Ala Ala Gly Met Asn Val
    130                 135                 140

Thr Lys Lys Leu Phe Val Tyr Ala Gly Glu Ala Tyr Gln Arg Lys Asp
145                 150                 155                 160

Gly Tyr Arg Lys Lys Asp His Ser Asp Arg Asn Asn Phe Leu Gly Gly
                165                 170                 175

Phe Asp Tyr Gln Ile Asn Ala Lys His Arg Ile Lys Gly Gln Gly Asn
            180                 185                 190

Leu Tyr Arg Glu Asp Leu Lys Ser Thr Thr Glu Val Thr His Glu Glu
        195                 200                 205

Leu Lys Glu Asp Arg Arg Lys Ala Gly Glu Asp Thr Lys Ile Glu Met
    210                 215                 220

Asp Arg Asp Phe Ala Ser Leu Asp Tyr Glu Tyr Thr Pro Thr Ser His
225                 230                 235                 240

Phe Lys Leu Arg Thr Asn Val Asn Arg Ala His Phe Thr Arg Asp Val
                245                 250                 255

Ser Met Asn Ala Lys Gln Asp Gln Leu Val Leu Ala Phe Met Pro Arg
            260                 265                 270

Asp Glu Gln Gly Tyr Phe Leu His Phe Asp Ala Gly Leu Leu Ala Asp
        275                 280                 285

Pro Lys Leu Ser Asp Val Arg Pro Val Leu Leu Asp Phe Glu Ser Thr
    290                 295                 300

Met Glu Gly Lys Phe Lys Glu Lys Asn Gln Glu Gly Lys Leu Asp Gly
305                 310                 315                 320

Glu Trp Lys Tyr Asn Gln Gly Lys Gly His Leu Gln Phe Gly Tyr Ser
```

-continued

```
                325                 330                 335

Tyr Asn Glu Lys Lys Leu Asn Gln Asp Leu Lys Ser Ile Ser Lys Pro
            340                 345                 350

Phe Thr Leu Lys Asn Gln Leu Gly Tyr Leu Ile Gln Gly Asp Pro Ala
        355                 360                 365

Pro Lys Gly Tyr Glu Asp Tyr Thr Gly Lys Ile Ile Ala Pro Glu Glu
    370                 375                 380

Met Phe Lys Ile Lys Phe Lys Asp Phe Pro Gln Ile Leu Glu Thr Phe
385                 390                 395                 400

Leu Gly Leu Arg Arg Glu Gly Val Glu Lys Glu Lys Ile Asp Phe Gln
                405                 410                 415

Asn Tyr Asn Lys Ile Asp Ala Phe Lys Asp Thr His Ala Leu Tyr Leu
            420                 425                 430

Leu Asn Asp Tyr Lys Leu Thr Pro Lys Phe Asn Phe Arg Ala Gly Leu
        435                 440                 445

Arg Trp Glu His Ser Glu Tyr Gly Ser Asp Arg Lys Asn Arg Met Ile
    450                 455                 460

Leu Gly Val His Asn Ala Gln Ser Ser Gly Met Ala Asn Arg Met Ala
465                 470                 475                 480

Ile Ala Gly Leu Leu Asn Glu Tyr Gln Met Glu Ala Tyr Val Gln Gly
                485                 490                 495

Lys Leu Ser Tyr Leu Asp Val Asp Leu Ser Leu Lys Glu Thr His Val
            500                 505                 510

Lys Asp Arg Ser Asp Asn Phe Gly Gly Glu Leu Gly Phe Thr Tyr Gln
        515                 520                 525

Tyr His Arg Lys Gly Ser Val Phe Phe Arg Tyr Glu Arg Gly Phe Leu
    530                 535                 540

Ser Pro Leu Pro Ser Gln Leu Thr Asn Lys Asp Phe Leu Thr Gly Ile
545                 550                 555                 560

Tyr Tyr Pro Ser His Val Lys Ser Glu Lys Val Asp Thr Ile Glu Met
                565                 570                 575

Gly Ile Lys His Ser Leu Trp Asn Asn Thr His Ile Glu Ala Thr Thr
            580                 585                 590

Phe Phe Ser Leu Thr Lys Asp Glu Ile Thr Asn Met Arg Tyr Asn Ala
        595                 600                 605

Asn Asn His Met Asn Met Arg Trp Ala Tyr Ala Asn Ile Ser Lys Thr
    610                 615                 620

Arg Arg Leu Gly Leu Glu Leu Asn Ala Glu His Ile Phe Asp Lys Leu
625                 630                 635                 640

Lys Ile Arg Glu Ser Phe Ser Tyr Val Asp Ala Lys Ile Ala Lys Asp
                645                 650                 655

Thr Gly Phe Lys Asp Tyr Tyr His Ser Asp Tyr Lys Val Lys Ser Glu
            660                 665                 670

Lys Glu Phe Lys Asp Ala Pro Leu Tyr Tyr Lys Lys Gly Gln Gln Val
        675                 680                 685

Pro Leu Val Ser Lys Val Lys Val Thr Val Gly Ala Glu Tyr Gln Phe
    690                 695                 700

Thr Asp Lys Leu Ser Leu Gly Gly Asn Tyr Asn Tyr Val Ser Gly Tyr
705                 710                 715                 720

Asp Thr Arg Glu Pro Gly Glu Gly Phe Gln Ala Lys Thr Tyr Lys Val
                725                 730                 735

Lys Gly His Gly Thr Leu Asp Leu Phe Gly Arg Tyr Ser Phe Thr Asp
            740                 745                 750
```

```
Tyr Ala Tyr Val Arg Phe Gly Val Asn Asn Val Leu Gly Glu Lys Tyr
        755                 760                 765

Asn Leu Arg Glu Asp Ser His Tyr Ala Val Pro Ala Pro Lys Gln Asn
    770                 775                 780

Tyr Tyr Ala Gly Phe Ser Tyr Lys Phe
785                 790


<210> SEQ ID NO 15
<211> LENGTH: 2934
<212> TYPE: DNA
<213> ORGANISM: Fusobacterium necrophorum

<400> SEQUENCE: 15

atgaaaaaag aaaatacggg tatgtggcaa aggattttga aaatcggtat gttaagtata     60

atactcttat actggacaga ctctctatat gcaatagaga ctagcgagaa tatgcagtcg    120

acaacgatgt cggtttccgg agaaacggta aacttcaaaa tggaaggaat taccgtggag    180

gcaaaaagac cggattggga atcgaaatta tcaccgggaa cagtgacggt cattcgtccg    240

gatgattata aaggagagca aaaagattta cctgattttt tgaaaatggt tcccggagtt    300

catgtgcggg aaatcaatgg aaaagggcag tacaccacag tcagtgttcg tggttccact    360

gcggctcagg tcggagtgtt tgtagacgga gttcttttta atctcggagg agatgcggca    420

gctgatattt caacaattcc cgtgcataat gtggaaagaa ttgaagtgta tcgtggatat    480

attcctgcac gtttcggtgg aacttttatg ggaggagtta tcaatatcgt taccaaaaaa    540

ccgaatcgag gaaatgtgag cgcaagcgtc ggacgaagtt cttttggcgg taaaaaagca    600

aatttgcagt ttgatcttcc cttgggaagc ggaactttaa tggtcggaat caatcatgat    660

gaaagcaaag gaaatttcaa atataaaaac ttctcctatg atagagataa agagtatcaa    720

aaggaagtgg aaaatgcaaa aagttcggaa cgaggagcaa tagataatta taataaggca    780

tttaaagaat taaaaaaata cgattttaca gatgatagcg gaaatatatt taaggttgat    840

actctggaag aagcaactca gattgtcaaa aataatcagg atcgttggga aaagtctttg    900

caggaagcta aaaatgacat tgataataat tttttaaaaa agaaacatat tatagcaaga    960

ttcccgggaa ttcccaaaga agagattctt cctcttctta gaagtactca tattgatgca   1020

gagcaagctc tttatgaatc tgcttttaaa gaatactctg taaatcaagg caataatttt   1080

attccaaaat ggaaagattc cagtggtaac tgggttgtcc ctgatagagt ggaagattat   1140

gttgaagctt ataataagag tcatgaaata ggatatcaac attttcaaca gattatagca   1200

aagggtgtgc agggagatat agaaagatgg atagcaaaat atggaaaaag ctatgctgtt   1260

aattatgcac aacaggcgga gtatagtgtc aaagaaatgg aaaaacataa aaaacaggcg   1320

gaagcggtga aagaccacta tagacgaaga aaagccaatg attataaaaa tatggatatt   1380

attttaaaat ggcaggatga acattggatg gcgaaggcaa cttggaaaag aatcaaaaga   1440

catctgccgt ttcctattga tgagaactat ggtaatgcac catatataga taccgacctt   1500

atggcaaata atccgctctc tatcttttat catcgaaatc agaaattgac cgttcaggaa   1560

tttcttttcg gaagacggga tactttcagg aatcttgaat ggggctggag tgttaattat   1620

ctaaaacaag agaaagatta ctatgttgat gattgggaat ggttggaaaa aaatacggga   1680

agtctcttaa acagctatcg tccaaacact ctgtggagta aatatgacag tcatcgctgg   1740

ggtgcaaaat tggatggaag ctacaaagcg ggagaacgtc atatcataga atttatggta   1800

aacgcttcca aagaaaaaat ggatattgac ggctggcgta tgaaggattt cagttctcac   1860
```

-continued

```
agttcagata cacttgccag atggagaaat tattatgagc aggatatttt caatgcacag   1920

cttcaggata ccatcacttt aaatcggaaa ggagatctgt ggttaacccc gagcattcgt   1980

tataatcgtt ctacaatact cggacgcagt gaacgctacg ataaaaagaa agatccgcaa   2040

aagtggaaat ttttcagccg ggaagacaaa caaaccgatg ataaagtgac ttggcaagtc   2100

gcaatcaaaa aacaattcaa tgagcatttc accttgcgtg ctaccggagg aagctattat   2160

cgtctgttga atatgtatga aattgccgga gacggagcag gaattatccc tatgcccaat   2220

atcaaagggg atggaagtat cgaagaagga gggaaaactc atgtttttcc tatgccggaa   2280

gaaggaaaac aatgggatgt cagtgctatc tgggacggag ctgcattggg agcaaaggcg   2340

gccaagcttc aactgacata tttcggacga gattccaaaa gaattttgga actgggttcc   2400

tggaatcgtt ttttctttgt ttataccaat gccatcagtg ccaaggttca cggagcggaa   2460

atacaggcgg atttatcttg gaaaaaatgg gatctcaacc tacaggcaac ttataccaga   2520

cccagaaatg tagtgtatga caatagtgct ctgccggaag ctatattctg gaatggagga   2580

gtctttaagg gctttctgac atatcagccg aaatgggaag ggacggcaag aattacctat   2640

cgtccgaatc cacgttggag tatcttttct caatttcgtt atgtcggaga aatgattacg   2700

agcagaattc ctttggcaac gggagatttt atgcatcagt cttcactgac agcttgggat   2760

ttgggaatca agtgtaaact aacggaacat tttcaaatcg ctcttggagt gaatgatcta   2820

ttcaataaag caaacgatat gtatcataaa tataaaagca tcaattatca gaccaacatt   2880

caatatccta ttcagggaag aagctactat gcaagctttc aatacaaatt ttaa         2934
```

<210> SEQ ID NO 16
<211> LENGTH: 977
<212> TYPE: PRT
<213> ORGANISM: Fusobacterium necrophorum

<400> SEQUENCE: 16

```
Met Lys Lys Glu Asn Thr Gly Met Trp Gln Arg Ile Leu Lys Ile Gly
1               5                   10                  15

Met Leu Ser Ile Ile Leu Leu Tyr Trp Thr Asp Ser Leu Tyr Ala Ile
            20                  25                  30

Glu Thr Ser Glu Asn Met Gln Ser Thr Thr Met Ser Val Ser Gly Glu
        35                  40                  45

Thr Val Asn Phe Lys Met Glu Gly Ile Thr Val Glu Ala Lys Arg Pro
    50                  55                  60

Asp Trp Glu Ser Lys Leu Ser Pro Gly Thr Val Thr Val Ile Arg Pro
65                  70                  75                  80

Asp Asp Tyr Lys Gly Glu Gln Lys Asp Leu Pro Asp Phe Leu Lys Met
                85                  90                  95

Val Pro Gly Val His Val Arg Glu Ile Asn Gly Lys Gly Gln Tyr Thr
            100                 105                 110

Thr Val Ser Val Arg Gly Ser Thr Ala Ala Gln Val Gly Val Phe Val
        115                 120                 125

Asp Gly Val Leu Phe Asn Leu Gly Gly Asp Ala Ala Ala Asp Ile Ser
    130                 135                 140

Thr Ile Pro Val His Asn Val Glu Arg Ile Glu Val Tyr Arg Gly Tyr
145                 150                 155                 160

Ile Pro Ala Arg Phe Gly Gly Thr Phe Met Gly Gly Val Ile Asn Ile
                165                 170                 175

Val Thr Lys Lys Pro Asn Arg Gly Asn Val Ser Ala Ser Val Gly Arg
```

-continued

```
            180                 185                 190

Ser Ser Phe Gly Gly Lys Lys Ala Asn Leu Gln Phe Asp Leu Pro Leu
        195                 200                 205

Gly Ser Gly Thr Leu Met Val Gly Ile Asn His Asp Glu Ser Lys Gly
    210                 215                 220

Asn Phe Lys Tyr Lys Asn Phe Ser Tyr Asp Arg Asp Lys Glu Tyr Gln
225                 230                 235                 240

Lys Glu Val Glu Asn Ala Lys Ser Ser Glu Arg Gly Ala Ile Asp Asn
                245                 250                 255

Tyr Asn Lys Ala Phe Lys Glu Leu Lys Lys Tyr Asp Phe Thr Asp Asp
            260                 265                 270

Ser Gly Asn Ile Phe Lys Val Asp Thr Leu Glu Glu Ala Thr Gln Ile
        275                 280                 285

Val Lys Asn Asn Gln Asp Arg Trp Glu Lys Ser Leu Gln Glu Ala Lys
    290                 295                 300

Asn Asp Ile Asp Asn Asn Phe Leu Lys Lys Lys His Ile Ile Ala Arg
305                 310                 315                 320

Phe Pro Gly Ile Pro Lys Glu Glu Ile Leu Pro Leu Leu Arg Ser Thr
                325                 330                 335

His Ile Asp Ala Glu Gln Ala Leu Tyr Glu Ser Ala Phe Lys Glu Tyr
            340                 345                 350

Ser Val Asn Gln Gly Asn Asn Phe Ile Pro Lys Trp Lys Asp Ser Ser
        355                 360                 365

Gly Asn Trp Val Val Pro Asp Arg Val Glu Asp Tyr Val Glu Ala Tyr
    370                 375                 380

Asn Lys Ser His Glu Ile Gly Tyr Gln His Phe Gln Gln Ile Ile Ala
385                 390                 395                 400

Lys Gly Val Gln Gly Asp Ile Glu Arg Trp Ile Ala Lys Tyr Gly Lys
                405                 410                 415

Ser Tyr Ala Val Asn Tyr Ala Gln Gln Ala Glu Tyr Ser Val Lys Glu
            420                 425                 430

Met Glu Lys His Lys Lys Gln Ala Glu Ala Val Lys Asp His Tyr Arg
        435                 440                 445

Arg Arg Lys Ala Asn Asp Tyr Lys Asn Met Asp Ile Ile Leu Lys Trp
    450                 455                 460

Gln Asp Glu His Trp Met Ala Lys Ala Thr Trp Lys Arg Ile Lys Arg
465                 470                 475                 480

His Leu Pro Phe Pro Ile Asp Glu Asn Tyr Gly Asn Ala Pro Tyr Ile
                485                 490                 495

Asp Thr Asp Leu Met Ala Asn Asn Pro Leu Ser Ile Phe Tyr His Arg
            500                 505                 510

Asn Gln Lys Leu Thr Val Gln Glu Phe Leu Phe Gly Arg Arg Asp Thr
        515                 520                 525

Phe Arg Asn Leu Glu Trp Gly Trp Ser Val Asn Tyr Leu Lys Gln Glu
    530                 535                 540

Lys Asp Tyr Tyr Val Asp Asp Trp Glu Trp Leu Glu Lys Asn Thr Gly
545                 550                 555                 560

Ser Leu Leu Asn Ser Tyr Arg Pro Asn Thr Leu Trp Ser Lys Tyr Asp
                565                 570                 575

Ser His Arg Trp Gly Ala Lys Leu Asp Gly Ser Tyr Lys Ala Gly Glu
            580                 585                 590

Arg His Ile Ile Glu Phe Met Val Asn Ala Ser Lys Glu Lys Met Asp
        595                 600                 605
```

```
Ile Asp Gly Trp Arg Met Lys Asp Phe Ser Ser His Ser Ser Asp Thr
    610                 615                 620

Leu Ala Arg Trp Arg Asn Tyr Tyr Glu Gln Asp Ile Phe Asn Ala Gln
625                 630                 635                 640

Leu Gln Asp Thr Ile Thr Leu Asn Arg Lys Gly Asp Leu Trp Leu Thr
                645                 650                 655

Pro Ser Ile Arg Tyr Asn Arg Ser Thr Ile Leu Gly Arg Ser Glu Arg
            660                 665                 670

Tyr Asp Lys Lys Lys Asp Pro Gln Lys Trp Lys Phe Phe Ser Arg Glu
        675                 680                 685

Asp Lys Gln Thr Asp Asp Lys Val Thr Trp Gln Val Ala Ile Lys Lys
    690                 695                 700

Gln Phe Asn Glu His Phe Thr Leu Arg Ala Thr Gly Gly Ser Tyr Tyr
705                 710                 715                 720

Arg Leu Leu Asn Met Tyr Glu Ile Ala Gly Asp Gly Ala Gly Ile Ile
                725                 730                 735

Pro Met Pro Asn Ile Lys Gly Asp Gly Ser Ile Glu Glu Gly Gly Lys
            740                 745                 750

Thr His Val Phe Pro Met Pro Glu Glu Gly Lys Gln Trp Asp Val Ser
        755                 760                 765

Ala Ile Trp Asp Gly Ala Ala Leu Gly Ala Lys Ala Ala Lys Leu Gln
    770                 775                 780

Leu Thr Tyr Phe Gly Arg Asp Ser Lys Arg Ile Leu Glu Leu Gly Ser
785                 790                 795                 800

Trp Asn Arg Phe Phe Phe Val Tyr Thr Asn Ala Ile Ser Ala Lys Val
                805                 810                 815

His Gly Ala Glu Ile Gln Ala Asp Leu Ser Trp Lys Lys Trp Asp Leu
            820                 825                 830

Asn Leu Gln Ala Thr Tyr Thr Arg Pro Arg Asn Val Val Tyr Asp Asn
        835                 840                 845

Ser Ala Leu Pro Glu Ala Ile Phe Trp Asn Gly Gly Val Phe Lys Gly
    850                 855                 860

Phe Leu Thr Tyr Gln Pro Lys Trp Glu Gly Thr Ala Arg Ile Thr Tyr
865                 870                 875                 880

Arg Pro Asn Pro Arg Trp Ser Ile Phe Ser Gln Phe Arg Tyr Val Gly
                885                 890                 895

Glu Met Ile Thr Ser Arg Ile Pro Leu Ala Thr Gly Asp Phe Met His
            900                 905                 910

Gln Ser Ser Leu Thr Ala Trp Asp Leu Gly Ile Lys Cys Lys Leu Thr
        915                 920                 925

Glu His Phe Gln Ile Ala Leu Gly Val Asn Asp Leu Phe Asn Lys Ala
    930                 935                 940

Asn Asp Met Tyr His Lys Tyr Lys Ser Ile Asn Tyr Gln Thr Asn Ile
945                 950                 955                 960

Gln Tyr Pro Ile Gln Gly Arg Ser Tyr Tyr Ala Ser Phe Gln Tyr Lys
                965                 970                 975

Phe


<210> SEQ ID NO 17
<211> LENGTH: 1986
<212> TYPE: DNA
<213> ORGANISM: Fusobacterium necrophorum

<400> SEQUENCE: 17
```

```
atgagaaaaa attttttatt ggcaagtttt ttggtatttg gagtaaatat agcttttgcg     60
gaagaaaacc cggtgttgac attggaacaa acgattgtga gtacggaatc ctttggaaca    120
tctgctcgaa agacaccaag aaatgtaaga gtgatgacag agaaagaaat taaagagaaa    180
ggagccttga ccatagagga agctctcaaa ggacttccgg gagtgatagt cagaagaata    240
gatggctctg ctcctattat tgacttaaga ggaacaggta tggcttccag tatcagttcc    300
agtcttcttc ttttaaacgg agttccttta aatggactta ttgtatttga tattaattcc    360
attcctatca acgaagtgga aagaattgaa attattcaag gaggaggagc tctgatgtat    420
ggggatggtg ccgttggtgg aatgataaat atcatcacaa aatctcctaa gaataagaaa    480
tattttggaa gtgtcaatct ggaacttggt tcttggaaga ctaaacgagc caatatcaat    540
tatggaatga aagtgggaga aaaattatcg gtgaatgctt cctattctgg atattcctct    600
atggattatc gggacaggta tcatggaatg gattggacag gacagtacct tgattaccga    660
aatcgagcgg ataagaaata ttctgtttgg tttagcggaa agtatgactt acaagatgga    720
aatatagaat tacgctacaa tcatactgaa aatagagaca tctttgccgg ttctttggat    780
aaaaaacaat ttcaagacaa tccaaaacaa accggcggtt ttggaaggga agtgaaaaat    840
atatctgatg tttggaatct atcttatcag aaagcattga aagaaaattt agaattttca    900
cttattggag gacatcacca agacaagagt atccttttga atcaaatttc ttccgagtat    960
tttatcaaac cacaattaaa atatcgctat ggaaaaaata gttatcttat ttttggagga   1020
gattataaaa atggaaaacg tgtctttaag acacccctta ttacaaatca taaaaaagcc   1080
ccagatgata agagaaaagc tatggcattc tattttatga ataaattttc caatggaaaa   1140
tgggaatttt cacaaggata cagaagagaa agagtagaat atgattatac ttccaaagcc   1200
tatagaaatc tttactattt atcagaagca aatccagttt cttcgcgttc ttctaataac   1260
aatagttttg aattgggagt aaattattta tattctgata caggaaatat gtatttcaat   1320
tacacaaggg ctgttagaac tccaacaata gaagatgcta aatttggtat tggagaggta   1380
aagagtaaaa aaagtgatat ttttgagata ggaatgagag actatttcaa aaatacctta   1440
atctcctcct ctatttttta tatgaatgca aaaaatgaag tttattatga tacgagagat   1500
atgttgcgta tcaaaagtag aaattttgat ggaacagtaa gacggattgg ggcacagtta   1560
gcattaagcc attatcttgg gaaattcgtt ttgaaagaaa atatttctta tgttaatccc   1620
aaaattgtga gtggacccta taaaggaaaa agctttgtta cggtgccaaa ttggattttg   1680
aatctggggg cagcttatcg tttttcagaa caatttttaa taaatgcaga cttatattat   1740
caatccaaaa tgtatgcaga agatgatttc gagaatattc ttggaaaaga taattcctat   1800
gtaactttga atatgaacgc atcctataag tttgataatg gaattgagat ttatggagga   1860
attaaaaatc tgttgaatga aagatatgcg gatacgatag cgataaatcc ttatccaagc   1920
cctaaaatag catattatcc gggagatggg agaaattttt atatgggatt tcgatatcag   1980
ttttag                                                              1986
```

```
<210> SEQ ID NO 18
<211> LENGTH: 661
<212> TYPE: PRT
<213> ORGANISM: Fusobacterium necrophorum

<400> SEQUENCE: 18

Met Arg Lys Asn Phe Leu Leu Ala Ser Phe Leu Val Phe Gly Val Asn
1               5                   10                  15
```

-continued

```
Ile Ala Phe Ala Glu Glu Asn Pro Val Leu Thr Leu Glu Gln Thr Ile
            20                  25                  30

Val Ser Thr Glu Ser Phe Gly Thr Ser Ala Arg Lys Thr Pro Arg Asn
        35                  40                  45

Val Arg Val Met Thr Glu Lys Glu Ile Lys Glu Lys Gly Ala Leu Thr
    50                  55                  60

Ile Glu Glu Ala Leu Lys Gly Leu Pro Gly Val Ile Val Arg Arg Ile
65                  70                  75                  80

Asp Gly Ser Ala Pro Ile Ile Asp Leu Arg Gly Thr Gly Met Ala Ser
                85                  90                  95

Ser Ile Ser Ser Ser Leu Leu Leu Leu Asn Gly Val Pro Leu Asn Gly
            100                 105                 110

Leu Ile Val Phe Asp Ile Asn Ser Ile Pro Ile Asn Glu Val Glu Arg
        115                 120                 125

Ile Glu Ile Ile Gln Gly Gly Gly Ala Leu Met Tyr Gly Asp Gly Ala
    130                 135                 140

Val Gly Gly Met Ile Asn Ile Ile Thr Lys Ser Pro Lys Asn Lys Lys
145                 150                 155                 160

Tyr Phe Gly Ser Val Asn Leu Glu Leu Gly Ser Trp Lys Thr Lys Arg
                165                 170                 175

Ala Asn Ile Asn Tyr Gly Met Lys Val Gly Glu Lys Leu Ser Val Asn
            180                 185                 190

Ala Ser Tyr Ser Gly Tyr Ser Ser Met Asp Tyr Arg Asp Arg Tyr His
        195                 200                 205

Gly Met Asp Trp Thr Gly Gln Tyr Leu Asp Tyr Arg Asn Arg Ala Asp
    210                 215                 220

Lys Lys Tyr Ser Val Trp Phe Ser Gly Lys Tyr Asp Leu Gln Asp Gly
225                 230                 235                 240

Asn Ile Glu Leu Arg Tyr Asn His Thr Glu Asn Arg Asp Ile Phe Ala
                245                 250                 255

Gly Ser Leu Asp Lys Lys Gln Phe Gln Asp Asn Pro Lys Gln Thr Gly
            260                 265                 270

Gly Phe Gly Arg Glu Val Lys Asn Ile Ser Asp Val Trp Asn Leu Ser
        275                 280                 285

Tyr Gln Lys Ala Leu Lys Glu Asn Leu Glu Phe Ser Leu Ile Gly Gly
    290                 295                 300

His His Gln Asp Lys Ser Ile Leu Leu Asn Gln Ile Ser Ser Glu Tyr
305                 310                 315                 320

Phe Ile Lys Pro Gln Leu Lys Tyr Arg Tyr Gly Lys Asn Ser Tyr Leu
                325                 330                 335

Ile Phe Gly Gly Asp Tyr Lys Asn Gly Lys Arg Val Phe Lys Thr Pro
            340                 345                 350

Leu Ile Thr Asn His Lys Lys Ala Pro Asp Asp Lys Arg Lys Ala Met
        355                 360                 365

Ala Phe Tyr Phe Met Asn Lys Phe Ser Asn Gly Lys Trp Glu Phe Ser
    370                 375                 380

Gln Gly Tyr Arg Arg Glu Arg Val Glu Tyr Asp Tyr Thr Ser Lys Ala
385                 390                 395                 400

Tyr Arg Asn Leu Tyr Tyr Leu Ser Glu Ala Asn Pro Val Ser Ser Arg
                405                 410                 415

Ser Ser Asn Asn Asn Ser Phe Glu Leu Gly Val Asn Tyr Leu Tyr Ser
            420                 425                 430
```

```
Asp Thr Gly Asn Met Tyr Phe Asn Tyr Thr Arg Ala Val Arg Thr Pro
        435                 440                 445

Thr Ile Glu Asp Ala Lys Ile Trp Tyr Gly Glu Val Lys Ser Lys Lys
    450                 455                 460

Ser Asp Ile Phe Glu Ile Gly Met Arg Asp Tyr Phe Lys Asn Thr Leu
465                 470                 475                 480

Ile Ser Ser Ser Ile Phe Tyr Met Asn Ala Lys Asn Glu Val Tyr Tyr
                485                 490                 495

Asp Thr Arg Asp Met Leu Arg Ile Lys Ser Arg Asn Phe Asp Gly Thr
            500                 505                 510

Val Arg Arg Ile Gly Ala Gln Leu Ala Leu Ser His Tyr Leu Gly Lys
        515                 520                 525

Phe Val Leu Lys Glu Asn Ile Ser Tyr Val Asn Pro Lys Ile Val Ser
    530                 535                 540

Gly Pro Tyr Lys Gly Lys Ser Phe Val Thr Val Pro Asn Trp Ile Leu
545                 550                 555                 560

Asn Leu Gly Ala Ala Tyr Arg Phe Ser Glu Gln Phe Leu Ile Asn Ala
                565                 570                 575

Asp Leu Tyr Tyr Gln Ser Lys Met Tyr Ala Glu Asp Asp Phe Glu Asn
            580                 585                 590

Ile Leu Gly Lys Asp Asn Ser Tyr Val Thr Leu Asn Met Asn Ala Ser
        595                 600                 605

Tyr Lys Phe Asp Asn Gly Ile Glu Ile Tyr Gly Gly Ile Lys Asn Leu
    610                 615                 620

Leu Asn Glu Arg Tyr Ala Asp Thr Ile Ala Ile Asn Pro Tyr Pro Ser
625                 630                 635                 640

Pro Lys Ile Ala Tyr Tyr Pro Gly Asp Gly Arg Asn Phe Tyr Met Gly
                645                 650                 655

Phe Arg Tyr Gln Phe
            660


<210> SEQ ID NO 19
<211> LENGTH: 2907
<212> TYPE: DNA
<213> ORGANISM: Fusobacterium necrophorum

<400> SEQUENCE: 19

atgagagtga aagtattggt agacggaaac tcgatgactt cgattgatga aagtatggga     60

gtgattcctt tcaattccat tcccgcagga agcattaaga gaattgaaat cattccgggg    120

ggaggaatca ctttatacgg aagcggaagt tccagtggag tcatcaatat tgtgaccaaa    180

atgggagaac ttaaaaatta tggaagcgta agcgtttcca caggttcctt tgacacctac    240

aaggcggaaa tcacaaaagg gatccgtatc aatcgatatt tgtttagtaa tctttcttta    300

gaggcgaaaa aaggaaaagg ataccgggac cgggagcaag ataaaagaat caatgcactt    360

ctcggactta acatcaattt tcatcccaaa catcgaatga aaattcaagg aagccatttt    420

caagaggacg cggaagggac caatgaattg tatttgacag aattacaaaa aaatcgtagg    480

ggagcgggag attctttttc taccatagat tcaaaacgaa ctgccctttc tattgattat    540

gaatacagtc cgacagaaaa ttggactcta actgccaatg tcaatcaatc gaaatttaca    600

cgggacattc gccaagattc tcacccttat ttgacttttt tgccttccat tgatttgagt    660

ttttatggag tgcctcaagg atatacagcg gaaatggttt ctgtgaatac tcccatggaa    720

ttaaaaggaa acatggaaga gaagattaag ggagcaagaa tcaaatcgga atatcgttat    780
```

-continued

```
gcggaacaaa aaggaaaatt tacatttgga gcggaacata gtgagcatag cctacaccga    840
gatatgaata tggaagtgaa accttttcat ccttttaaca gtatggcttt tttgattcat    900
aaagaagacg ataaaatttt tacggaagaa agattgaaaa atagtcatga acttatggat    960
attaattcag tttttttacc ttttattatt gagaaaaata atacacctac tttaaaggaa   1020
gagaaaataa ataaatggaa agaaaatttt ttatatcaaa aagctagtga agaagaaaaa   1080
aaagcttatg atgcgggggg aggaatagca gctttggcta attcttggta tgaaaaccaa   1140
ggaattatga attatgaatt ttcacatttc aagataaaag attattttga tttggtggaa   1200
aaagatggga aaaaaggaat ttattatatt tttagagaga aaaaaaaggt agaaataact   1260
ttgccaaatg ggaaaaaaag aaaaaagaca gttactgtgg aaagacctga atttatggaa   1320
gtgaatgatg aaagtcgatt aaaagatatt cttaatttta tacaaaagga taaagtagat   1380
ccctctttaa cagtaaatac tttgatacaa tcaaaaatag atgtaaaaaa gaaaacagat   1440
tctttctatt tacataacag ctatccgcta accgagaaat taactgtcaa tgcaggactt   1500
cgttatgaaa aggcaaagta tcatggaaat cgggaaacac agacaataca acgaattaca   1560
ggaaatgcgg ataagaaaga aacacaggat gctgtaaatt tatatatttc cgtttcggat   1620
gtggaatatt tgaaaaaaga tccaagaatc aattggaatg ctaatatcaa tgcagaaaca   1680
caggcaaagt taaaagaatt gaaagaaaca ggaagcacac agattgtcat gtcacaatta   1740
ttccgaaaag aaaagagaga agaggaaaat ttgggtggag aaattggctt tgattataaa   1800
atcaatgata gtgatttggc atatgtgaaa tatgaaagag ctttcaattc tcctttacca   1860
aatcaactaa ccaataaaac ctatgacccg attcataaag tgaagacata ttgggaaagt   1920
gatttgaaaa cggagaaaat ggataatttt gaaattggaa ttcgtggggc ttggaatgag   1980
catattacct acggattggc aggatttttg agtacaacct atgatgaaat tgtttctgtg   2040
gtaaaagatg gaaattccca tatgtcaaga gaatggagat ttatcaattt ggacaaaacg   2100
agaagaatgg gaatagaatt gcaatcggaa caagtctttg ataaatggag attacgccaa   2160
tctttgactt atgtggatcc gaaagtgttg tccaatgatt ataaaaaaca agtggcaaga   2220
atcgcacagg agcagtccga tgcgatgata gacagtcatg agaaaattat gagaaacaat   2280
gtatatccaa ttcgtttaga cattgctgca tggaagggaa agatatccga agctgagttt   2340
caaaaattga aacctcaaat tatggcatta acagatcatg gtttagaggg aaagatttca   2400
caagtggaaa tgaacgcaca gttggaaaaa ttattggaaa gtctttctaa tatggcgaag   2460
aaggaaatca aggaaacggt caaggcaaga tttacagacc gagatattta caaagagcga   2520
gtggaaaagc aatttagaga acagtatcaa actgagggag gaagctttat taaaaaagga   2580
gatagaattc ctttggcacc gaaaatcaaa gcgacttttg gagcggatta ccaatttaca   2640
aatcatttaa aaatgggaac aaatgtcact tatgtaggaa attatatgac agcggaacca   2700
agtaagggct atgaaattgt acaagtgaaa gttccttctc acttgctaac ggatttttat   2760
ggaagttatg agtttgacag cggcttttct ataaaattcg gaattaacaa tgtcttcaat   2820
cataagtact atttaagaca agattccaga acggcaacac ctgcaccggg aagaacttac   2880
agtgcaggat ttagttatcg tttttaa                                       2907
```

<210> SEQ ID NO 20
<211> LENGTH: 968
<212> TYPE: PRT
<213> ORGANISM: Fusobacterium necrophorum

<400> SEQUENCE: 20

-continued

```
Met Arg Val Lys Val Leu Val Asp Gly Asn Ser Met Thr Ser Ile Asp
1               5                   10                  15

Glu Ser Met Gly Val Ile Pro Phe Asn Ser Ile Pro Ala Gly Ser Ile
            20                  25                  30

Lys Arg Ile Glu Ile Ile Pro Gly Gly Gly Ile Thr Leu Tyr Gly Ser
        35                  40                  45

Gly Ser Ser Ser Gly Val Ile Asn Ile Val Thr Lys Met Gly Glu Leu
    50                  55                  60

Lys Asn Tyr Gly Ser Val Ser Val Ser Thr Gly Ser Phe Asp Thr Tyr
65                  70                  75                  80

Lys Ala Glu Ile Thr Lys Gly Ile Arg Ile Asn Arg Tyr Leu Phe Ser
                85                  90                  95

Asn Leu Ser Leu Glu Ala Lys Lys Gly Lys Gly Tyr Arg Asp Arg Glu
            100                 105                 110

Gln Asp Lys Arg Ile Asn Ala Leu Leu Gly Leu Asn Ile Asn Phe His
        115                 120                 125

Pro Lys His Arg Met Lys Ile Gln Gly Ser His Phe Gln Glu Asp Ala
    130                 135                 140

Glu Gly Thr Asn Glu Leu Tyr Leu Thr Glu Leu Gln Lys Asn Arg Arg
145                 150                 155                 160

Gly Ala Gly Asp Ser Phe Ser Thr Ile Asp Ser Lys Arg Thr Ala Leu
                165                 170                 175

Ser Ile Asp Tyr Glu Tyr Ser Pro Thr Glu Asn Trp Thr Leu Thr Ala
            180                 185                 190

Asn Val Asn Gln Ser Lys Phe Thr Arg Asp Ile Arg Gln Asp Ser His
        195                 200                 205

Pro Tyr Leu Thr Phe Leu Pro Ser Ile Asp Leu Ser Phe Tyr Gly Val
    210                 215                 220

Pro Gln Gly Tyr Thr Ala Glu Met Val Ser Val Asn Thr Pro Met Glu
225                 230                 235                 240

Leu Lys Gly Asn Met Glu Glu Lys Ile Lys Gly Ala Arg Ile Lys Ser
                245                 250                 255

Glu Tyr Arg Tyr Ala Glu Gln Lys Gly Lys Phe Thr Phe Gly Ala Glu
            260                 265                 270

His Ser Glu His Ser Leu His Arg Asp Met Asn Met Glu Val Lys Pro
        275                 280                 285

Phe His Pro Phe Asn Ser Met Ala Phe Leu Ile His Lys Glu Asp Asp
    290                 295                 300

Lys Ile Phe Thr Glu Glu Arg Leu Lys Asn Ser His Glu Leu Met Asp
305                 310                 315                 320

Ile Asn Ser Val Phe Leu Pro Phe Ile Ile Glu Lys Asn Asn Thr Pro
                325                 330                 335

Thr Leu Lys Glu Glu Lys Ile Asn Lys Trp Lys Glu Asn Phe Leu Tyr
            340                 345                 350

Gln Lys Ala Ser Glu Glu Glu Lys Lys Ala Tyr Asp Ala Gly Gly Gly
        355                 360                 365

Ile Ala Ala Leu Ala Asn Ser Trp Tyr Glu Asn Gln Gly Ile Met Asn
    370                 375                 380

Tyr Glu Phe Ser His Phe Lys Ile Lys Asp Tyr Phe Asp Leu Val Glu
385                 390                 395                 400

Lys Asp Gly Lys Lys Gly Ile Tyr Tyr Ile Phe Arg Glu Lys Lys Lys
                405                 410                 415
```

```
Val Glu Ile Thr Leu Pro Asn Gly Lys Lys Arg Lys Lys Thr Val Thr
            420                 425                 430

Val Glu Arg Pro Glu Phe Met Glu Val Asn Asp Glu Ser Arg Leu Lys
        435                 440                 445

Asp Ile Leu Asn Phe Ile Gln Lys Asp Lys Val Asp Pro Ser Leu Thr
    450                 455                 460

Val Asn Thr Leu Ile Gln Ser Lys Ile Asp Val Lys Lys Lys Thr Asp
465                 470                 475                 480

Ser Phe Tyr Leu His Asn Ser Tyr Pro Leu Thr Glu Lys Leu Thr Val
                485                 490                 495

Asn Ala Gly Leu Arg Tyr Glu Lys Ala Lys Tyr His Gly Asn Arg Glu
            500                 505                 510

Thr Gln Thr Ile Gln Arg Ile Thr Gly Asn Ala Asp Lys Lys Glu Thr
        515                 520                 525

Gln Asp Ala Val Asn Leu Tyr Ile Ser Val Ser Asp Val Glu Tyr Leu
    530                 535                 540

Lys Lys Asp Pro Arg Ile Asn Trp Asn Ala Asn Ile Asn Ala Glu Thr
545                 550                 555                 560

Gln Ala Lys Leu Lys Glu Leu Lys Glu Thr Gly Ser Thr Gln Ile Val
                565                 570                 575

Met Ser Gln Leu Phe Arg Lys Glu Lys Arg Glu Glu Glu Asn Leu Gly
            580                 585                 590

Gly Glu Ile Gly Phe Asp Tyr Lys Ile Asn Asp Ser Asp Leu Ala Tyr
        595                 600                 605

Val Lys Tyr Glu Arg Ala Phe Asn Ser Pro Leu Pro Asn Gln Leu Thr
    610                 615                 620

Asn Lys Thr Tyr Asp Pro Ile His Lys Val Lys Thr Tyr Trp Glu Ser
625                 630                 635                 640

Asp Leu Lys Thr Glu Lys Met Asp Asn Phe Glu Ile Gly Ile Arg Gly
                645                 650                 655

Ala Trp Asn Glu His Ile Thr Tyr Gly Leu Ala Gly Phe Leu Ser Thr
            660                 665                 670

Thr Tyr Asp Glu Ile Val Ser Val Val Lys Asp Gly Asn Ser His Met
        675                 680                 685

Ser Arg Glu Trp Arg Phe Ile Asn Leu Asp Lys Thr Arg Arg Met Gly
    690                 695                 700

Ile Glu Leu Gln Ser Glu Gln Val Phe Asp Lys Trp Arg Leu Arg Gln
705                 710                 715                 720

Ser Leu Thr Tyr Val Asp Pro Lys Val Leu Ser Asn Asp Tyr Lys Lys
                725                 730                 735

Gln Val Ala Arg Ile Ala Gln Glu Gln Ser Asp Ala Met Ile Asp Ser
            740                 745                 750

His Glu Lys Ile Met Arg Asn Asn Val Tyr Pro Ile Arg Leu Asp Ile
        755                 760                 765

Ala Ala Trp Lys Gly Lys Ile Ser Glu Ala Glu Phe Gln Lys Leu Lys
    770                 775                 780

Pro Gln Ile Met Ala Leu Thr Asp His Gly Leu Glu Gly Lys Ile Ser
785                 790                 795                 800

Gln Val Glu Met Asn Ala Gln Leu Glu Lys Leu Leu Glu Ser Leu Ser
                805                 810                 815

Asn Met Ala Lys Lys Glu Ile Lys Glu Thr Val Lys Ala Arg Phe Thr
            820                 825                 830

Asp Arg Asp Ile Tyr Lys Glu Arg Val Glu Lys Gln Phe Arg Glu Gln
```

```
        835                 840                 845

Tyr Gln Thr Glu Gly Gly Ser Phe Ile Lys Lys Gly Asp Arg Ile Pro
    850                 855                 860

Leu Ala Pro Lys Ile Lys Ala Thr Phe Gly Ala Asp Tyr Gln Phe Thr
865                 870                 875                 880

Asn His Leu Lys Met Gly Thr Asn Val Thr Tyr Val Gly Asn Tyr Met
                885                 890                 895

Thr Ala Glu Pro Ser Lys Gly Tyr Glu Ile Val Gln Val Lys Val Pro
            900                 905                 910

Ser His Leu Leu Thr Asp Phe Tyr Gly Ser Tyr Glu Phe Asp Ser Gly
        915                 920                 925

Phe Ser Ile Lys Phe Gly Ile Asn Asn Val Phe Asn His Lys Tyr Tyr
    930                 935                 940

Leu Arg Gln Asp Ser Arg Thr Ala Thr Pro Ala Pro Gly Arg Thr Tyr
945                 950                 955                 960

Ser Ala Gly Phe Ser Tyr Arg Phe
                965


<210> SEQ ID NO 21
<211> LENGTH: 3315
<212> TYPE: DNA
<213> ORGANISM: Fusobacterium necrophorum

<400> SEQUENCE: 21

atgagaaaag aaatgctttt gacattgttg tgttttgttt ctttgcatgc tatggcagca      60

acacaggaag tggagttgaa cccgacaaaa attcgaggag ggggggcgac ctataatggc     120

tcggttctct ccaatgaaaa gaaaaatgta atcatcatta cgaaagcaga tattgaaaag     180

aaaaattata gagatttgga atctattttt aaggattctc cggttacttc tgtcgtttat     240

acggaggcgg gtcctttggt caccttaaga ggaagtggac aaaagacggc aatgagagtt     300

aaagtactct tagatggcgt ttccatcaat accgtggatg attctatggg agtgattcct     360

ttcaacgcca ttccggttgc cagtattgaa aaaattgaaa ttattccggg aggagggatt     420

actcttcacg gttccggaac ttccagcgga gtcatcaaca tcgtgacggg aaaatcgagt     480

aagaaagatt atggagagct tggttttact gtaagttctt tcaatactta caatacaacc     540

ttcaataagg gaatttcctt tggagataag ctgtattgga atattggagt ggaagcggaa     600

aaaggaaagg catatcgaga gaaagaggat agtaaaaaga taaatctgct gtccggaatc     660

aactataaaa tcaatgaaaa acatcaaatt aaattacatg gaagtaaata ttggtcggat     720

tttaacggaa caaatgaatt ggatcttatc agtttgcaaa aaaatcgaag aggggcagga     780

aaatcagatg ccgaagtaaa gtcaaatcga tattcccttt ctttcgatta tgaatataaa     840

cctacagaag atttgaccgt tacttccgga tacaatcaac aaaaatttcg aaggaatttt     900

acacagaaca acaaacctta tcttactttc ttatcgtcgg aatgggtgga agatatgttt     960

ggaattcccg acggaatgaa tgcagattta gtcattaaaa atgtaaataa ccatttaacg    1020

ggacgtattg aagaaaaaat aaaaaatgga aaagtcaaag tggactggaa acacagtaac    1080

aatcgtggaa aattaacttt tggatatgat tattcttctc atgaattaaa acgaagaatg    1140

aatgtacaag ttgatgcttt taatccgatc gataataatt acttttttt gagaaaaaaa     1200

gaggagagaa ttatcaatga agaaatttta gaacaacatc cggatcagtt aatgcatttt    1260

ttcgataaca ctttagcggc aattctaata tttgatcctg attctatgga tagttatggg    1320

ctagattctg ttaaactaaa gaaaaaaata gacgaactct attatcattt gactacttcg    1380
```

gaaaaagata agaaaaaata tgaaaatgga gaagaaaatc cttgggatta ttgggaaacc 1440
atcaaaccga atatgtggaa aatgatttat catttgacag aagaaaagat tcaagagtat 1500
gcaaaagacg gaaaaaatat tcttaagaga gaagatgaaa atgattggga ttctgaacca 1560
agcgttcagg ttccgattga ggggaaaaaa tttaaagaat ttttaagatt gattattcct 1620
agtatgtatg accccgattt tagtatgaca ccaatcacgc aaagtatggt agatgtgaag 1680
aagacaacga attcctttta tctatttgac agctataaac ttactgatcg tttagaaatc 1740
aatggaggtt tgcgatatga aaaagcaaaa tactccggaa atcgttatac aaaaacggaa 1800
caatttatca aaggaaatgc ggagaataaa tctaccaact ctatgatagc gatgtatacg 1860
gaattgtcag aagcggaatc ggcaaagaaa aacataggag atactcatca ctggaatgga 1920
aatgatactt ccaaagaaaa aataaaagaa ctgaaagaaa aaggatatac taccatttta 1980
atgacggatt taactcgaaa agagaaaaga gaagaggaaa atctgggagg agaaattggg 2040
attaattacc gtttcaatga tacagacaca gtatatttaa aatatgaaag aggctttaat 2100
actcctcttc ctacacaatt gaccaataaa acctttgatc cgaaaaccaa gataaaagca 2160
tattgggaaa gcaatataaa gacagaaaaa atagacaatg tagaactggg aattcgagga 2220
atgttacacc caaaagtgac ctattctttg acaggattta tcagtgatac tcaaaatgaa 2280
attctatcca ttgtgaagaa tggaagttct catatgctcc gagaatggag atttatcaat 2340
attgataaaa cgagaagaat gggactggag ttccaatctc aacaaaattt tgataaattg 2400
actttaaaag aatctcttac ttatgtggat ccaaagattc tatccaatga ttatgaaaaa 2460
caggttcata aaattggagt ggacagagcg gaggaaatgt accaaaacaa tcaaaaagta 2520
cgagattgga caattgaaaa tatcagattt catgaaaatg gctttacaat tccggcagga 2580
acttcggaag aagaaattgt aaaaatgaag gcggagtcca agcgattggg aaaagaagcg 2640
gttaaaatca ttcaaaaact aagagagaca ggagtaaaag tggactatag tgcacgagat 2700
gccaaactga aagaaattgt tccgggaatg tcttctgccg aacaatctaa gattagaatg 2760
gaagcttcaa aattagcaca agaagctgaa aatagagctg tggcagaacc tagaaaagcc 2820
ttggaagatc ttcttgcaaa ctcagcttat cctgacattt ttaaagaaaa attgcgttca 2880
ttcaataacc ataccttaat tcaggaagga acgatgaaag aaattattta tgaacatttt 2940
gaaaaagaga taaagtcttc ttatacgaaa ggaaccttag aaaagggaag cagaatcccg 3000
ctttctccaa aatggaaagg aactttcagt gcggactatc aattcacgga taggttaaaa 3060
ttaggaatga atactactta tataggaagc tatgattccg cggaaccggg aaaaggatat 3120
gaaattgtaa tgacaaaagt accgcatcat atggtagccg atttctatgg aagttatgat 3180
attcaggaag atttttccat taaattcgga attaacaatg tatttaatca tcaatattat 3240
ttacgacaag attccagaac ggcaactccg gcacccggaa gaacctacag tgcgggattc 3300
agttatcgat tttaa 3315

<210> SEQ ID NO 22
<211> LENGTH: 1104
<212> TYPE: PRT
<213> ORGANISM: Fusobacterium necrophorum

<400> SEQUENCE: 22

Met Arg Lys Glu Met Leu Leu Thr Leu Leu Cys Phe Val Ser Leu His
1 5 10 15

Ala Met Ala Ala Thr Gln Glu Val Glu Leu Asn Pro Thr Lys Ile Arg

```
            20                  25                  30

Gly Gly Gly Ala Thr Tyr Asn Gly Ser Val Leu Ser Asn Glu Lys Lys
        35                  40                  45

Asn Val Ile Ile Ile Thr Lys Ala Asp Ile Glu Lys Lys Asn Tyr Arg
    50                  55                  60

Asp Leu Glu Ser Ile Phe Lys Asp Ser Pro Val Thr Ser Val Val Tyr
65                  70                  75                  80

Thr Glu Ala Gly Pro Leu Val Thr Leu Arg Gly Ser Gly Gln Lys Thr
                85                  90                  95

Ala Met Arg Val Lys Val Leu Leu Asp Gly Val Ser Ile Asn Thr Val
            100                 105                 110

Asp Asp Ser Met Gly Val Ile Pro Phe Asn Ala Ile Pro Val Ala Ser
        115                 120                 125

Ile Glu Lys Ile Glu Ile Ile Pro Gly Gly Gly Ile Thr Leu His Gly
    130                 135                 140

Ser Gly Thr Ser Ser Gly Val Ile Asn Ile Val Thr Gly Lys Ser Ser
145                 150                 155                 160

Lys Lys Asp Tyr Gly Glu Leu Gly Phe Thr Val Ser Ser Phe Asn Thr
                165                 170                 175

Tyr Asn Thr Thr Phe Asn Lys Gly Ile Ser Phe Gly Asp Lys Leu Tyr
            180                 185                 190

Trp Asn Ile Gly Val Glu Ala Glu Lys Gly Lys Ala Tyr Arg Glu Lys
        195                 200                 205

Glu Asp Ser Lys Lys Ile Asn Leu Leu Ser Gly Ile Asn Tyr Lys Ile
    210                 215                 220

Asn Glu Lys His Gln Ile Lys Leu His Gly Ser Lys Tyr Trp Ser Asp
225                 230                 235                 240

Phe Asn Gly Thr Asn Glu Leu Asp Leu Ile Ser Leu Gln Lys Asn Arg
                245                 250                 255

Arg Gly Ala Gly Lys Ser Asp Ala Glu Val Lys Ser Asn Arg Tyr Ser
            260                 265                 270

Leu Ser Phe Asp Tyr Glu Tyr Lys Pro Thr Glu Asp Leu Thr Val Thr
        275                 280                 285

Ser Gly Tyr Asn Gln Gln Lys Phe Arg Arg Asn Phe Thr Gln Asn Asn
    290                 295                 300

Lys Pro Tyr Leu Thr Phe Leu Ser Ser Glu Trp Val Glu Asp Met Phe
305                 310                 315                 320

Gly Ile Pro Asp Gly Met Asn Ala Asp Leu Val Ile Lys Asn Val Asn
                325                 330                 335

Asn His Leu Thr Gly Arg Ile Glu Glu Lys Ile Lys Asn Gly Lys Val
            340                 345                 350

Lys Val Asp Trp Lys His Ser Asn Asn Arg Gly Lys Leu Thr Phe Gly
        355                 360                 365

Tyr Asp Tyr Ser Ser His Glu Leu Lys Arg Arg Met Asn Val Gln Val
    370                 375                 380

Asp Ala Phe Asn Pro Ile Asp Asn Asn Tyr Phe Phe Leu Arg Lys Lys
385                 390                 395                 400

Glu Glu Arg Ile Ile Asn Glu Glu Ile Leu Glu Gln His Pro Asp Gln
                405                 410                 415

Leu Met His Phe Phe Asp Asn Thr Leu Ala Ala Ile Leu Ile Phe Asp
            420                 425                 430

Pro Asp Ser Met Asp Ser Tyr Gly Leu Asp Ser Val Lys Leu Lys Lys
        435                 440                 445
```

-continued

```
Lys Ile Asp Glu Leu Tyr Tyr His Leu Thr Thr Ser Glu Lys Asp Lys
    450                 455                 460

Lys Lys Tyr Glu Asn Gly Glu Glu Asn Pro Trp Asp Tyr Trp Glu Thr
465                 470                 475                 480

Ile Lys Pro Asn Met Trp Lys Met Ile Tyr His Leu Thr Glu Glu Lys
                485                 490                 495

Ile Gln Glu Tyr Ala Lys Asp Gly Lys Asn Ile Leu Lys Arg Glu Asp
            500                 505                 510

Glu Asn Asp Trp Asp Ser Glu Pro Ser Val Gln Val Pro Ile Glu Gly
        515                 520                 525

Lys Lys Phe Lys Glu Phe Leu Arg Leu Ile Ile Pro Ser Met Tyr Asp
    530                 535                 540

Pro Asp Phe Ser Met Thr Pro Ile Thr Gln Ser Met Val Asp Val Lys
545                 550                 555                 560

Lys Thr Thr Asn Ser Phe Tyr Leu Phe Asp Ser Tyr Lys Leu Thr Asp
                565                 570                 575

Arg Leu Glu Ile Asn Gly Gly Leu Arg Tyr Glu Lys Ala Lys Tyr Ser
            580                 585                 590

Gly Asn Arg Tyr Thr Lys Thr Glu Gln Phe Ile Lys Gly Asn Ala Glu
        595                 600                 605

Asn Lys Ser Thr Asn Ser Met Ile Ala Met Tyr Thr Glu Leu Ser Glu
    610                 615                 620

Ala Glu Ser Ala Lys Lys Asn Ile Gly Asp Thr His His Trp Asn Gly
625                 630                 635                 640

Asn Asp Thr Ser Lys Glu Lys Ile Lys Glu Leu Lys Glu Lys Gly Tyr
                645                 650                 655

Thr Thr Ile Leu Met Thr Asp Leu Thr Arg Lys Glu Lys Arg Glu Glu
            660                 665                 670

Glu Asn Leu Gly Gly Glu Ile Gly Ile Asn Tyr Arg Phe Asn Asp Thr
        675                 680                 685

Asp Thr Val Tyr Leu Lys Tyr Glu Arg Gly Phe Asn Thr Pro Leu Pro
    690                 695                 700

Thr Gln Leu Thr Asn Lys Thr Phe Asp Pro Lys Thr Lys Ile Lys Ala
705                 710                 715                 720

Tyr Trp Glu Ser Asn Ile Lys Thr Glu Lys Ile Asp Asn Val Glu Leu
                725                 730                 735

Gly Ile Arg Gly Met Leu His Pro Lys Val Thr Tyr Ser Leu Thr Gly
            740                 745                 750

Phe Ile Ser Asp Thr Gln Asn Glu Ile Leu Ser Ile Val Lys Asn Gly
        755                 760                 765

Ser Ser His Met Leu Arg Glu Trp Arg Phe Ile Asn Ile Asp Lys Thr
    770                 775                 780

Arg Arg Met Gly Leu Glu Phe Gln Ser Gln Gln Asn Phe Asp Lys Leu
785                 790                 795                 800

Thr Leu Lys Glu Ser Leu Thr Tyr Val Asp Pro Lys Ile Leu Ser Asn
                805                 810                 815

Asp Tyr Glu Lys Gln Val His Lys Ile Gly Val Asp Arg Ala Glu Glu
            820                 825                 830

Met Tyr Gln Asn Asn Gln Lys Val Arg Asp Trp Thr Ile Glu Asn Ile
        835                 840                 845

Arg Phe His Glu Asn Gly Phe Thr Ile Pro Ala Gly Thr Ser Glu Glu
    850                 855                 860
```

-continued

```
Glu Ile Val Lys Met Lys Ala Glu Ser Lys Arg Leu Gly Lys Glu Ala
865                 870                 875                 880

Val Lys Ile Ile Gln Lys Leu Arg Glu Thr Gly Val Lys Val Asp Tyr
                885                 890                 895

Ser Ala Arg Asp Ala Lys Leu Lys Glu Ile Val Pro Gly Met Ser Ser
            900                 905                 910

Ala Glu Gln Ser Lys Ile Arg Met Glu Ala Ser Lys Leu Ala Gln Glu
        915                 920                 925

Ala Glu Asn Arg Ala Val Ala Glu Pro Arg Lys Ala Leu Glu Asp Leu
    930                 935                 940

Leu Ala Asn Ser Ala Tyr Pro Asp Ile Phe Lys Glu Lys Leu Arg Ser
945                 950                 955                 960

Phe Asn Asn His Thr Leu Ile Gln Glu Gly Thr Met Lys Glu Ile Ile
                965                 970                 975

Tyr Glu His Phe Glu Lys Glu Ile Lys Ser Ser Tyr Thr Lys Gly Thr
            980                 985                 990

Leu Glu Lys Gly Ser Arg Ile Pro  Leu Ser Pro Lys Trp  Lys Gly Thr
        995                 1000                1005

Phe Ser  Ala Asp Tyr Gln Phe  Thr Asp Arg Leu Lys  Leu Gly Met
    1010                1015                1020

Asn Thr  Thr Tyr Ile Gly Ser  Tyr Asp Ser Ala Glu  Pro Gly Lys
    1025                1030                1035

Gly Tyr  Glu Ile Val Met Thr  Lys Val Pro His His  Met Val Ala
    1040                1045                1050

Asp Phe  Tyr Gly Ser Tyr Asp  Ile Gln Glu Asp Phe  Ser Ile Lys
    1055                1060                1065

Phe Gly  Ile Asn Asn Val Phe  Asn His Gln Tyr Tyr  Leu Arg Gln
    1070                1075                1080

Asp Ser  Arg Thr Ala Thr Pro  Ala Pro Gly Arg Thr  Tyr Ser Ala
    1085                1090                1095

Gly Phe  Ser Tyr Arg Phe
    1100
```

<210> SEQ ID NO 23
<211> LENGTH: 1941
<212> TYPE: DNA
<213> ORGANISM: Fusobacterium necrophorum

<400> SEQUENCE: 23

```
atgaaaaaaa agttaatgat tttggcaatt ttaagtattt cagtttcagc atttgctatg      60

aaggaggaaa ttcctgtgca aagattaaat gaaacagtaa taacaactcc tgaaagattc     120

ggtacaaagg ttagaaatat atcaaaaaat atacaaataa ttacaaaaaa agatatgaag     180

gaaaaggggg caaaaaacct ttttgaggca ttgagaggac tcccaggagt agttatacgt     240

agagatggag gaggacatat agatcttcgt ggttctggag aaaatgataa aaaaaatatg     300

atatttttaa tagatggaat accctatagt ggattaagta tatttgacat taattctatc     360

tcaatggaag aaattgaaag aattgaaatt atccaaagtg gtggtgtttt atatggagat     420

ggagctatag gaggagttat aaatttagtt actaagccta ttactactgg aaaatacagc     480

aatagcattg gtttggaata cggctcttgg gaaacggcta aattaaatgt aaatgtcgga     540

actaaattaa cagataattt tgttgtaagt gtttcttact ctggtgaaca aactgaagaa     600

tataaaaata gaagcataga tttcaaagat aaaaaagata gccgggaatc tatttggtta     660

aaaactaaat ataatttaaa tgatggggaa attgagttaa aatataatca tttgaaaaac     720
```

aatgactaca tcacaggact tctatcagca aaagacttta aagaaaatcc taaaaaagca 780
ggtacaacaa atgcttcttt taaagctgaa tcagatttat ggaacctatc ttttaataaa 840
aaattaaata gtaagtttga agttttctta caaggtggat attatactga tgaaacaaaa 900
tactatgaaa taggtccagg atatgcagat ttttcaaaaa atggaaataa aagtcatttt 960
ataagacctc aaataaaata taattatatg gaagatagtt gcatcatatt aggaggagat 1020
agaaaaaaag aaactgttac taataaatta tctccaaatt ctcctaaaac tataaggaaa 1080
aaagaatcta tttacttatt aaatagtaat aagataggaa actttgaaat tacagaagga 1140
tatagaatag aaaaaattga tttaaaaaga aagaatagag ctaaagactt taaagaagat 1200
ggaatggaat taggaataaa ctatctttat tcagatactg gaaatcttta ttttaattac 1260
acaaaaggat ttagagtacc tacattgggt gaaatgaata gttgggttgg tgatatgaaa 1320
tcacataaaa atcatacttt tgaattaggt ttaagagatg tatatgaaaa tacttctata 1380
aatacttcta ttttcacatt gtattccaaa gatgaaatct tttatgatag tttagttgca 1440
aacccttcac caaaaaatcc taatagaaaa ggagcaaata gaaactttga aggtaaggtt 1500
agaagaatag gtgcacagtt agctttagaa cacaatattg gtaaattatc attaagagaa 1560
aaaatttctt acatggatcc taaaataatt gatggatatt ataaagagaa agttttcccg 1620
ggagttccta aattaacagc agcactaggt ttaacttata attttgaaaa ttcccttaaa 1680
ttaaatattg atgggtatta tcaagaaaaa atttatgccg gaactgattt ttttaaataaa 1740 tatggtaaac acaatagtta tacagtagta gatgctaata tttcatatac ttttgaaaat 1800
ggtttggaac tttatggtgg agttaaaaac ttatttgata aaacatatgc tactgccttt 1860
ttcccaagag caacaggaga attaagatat gatccagata atggaagaag tttttacact 1920
gggtttaagt atacttttta a 1941

<210> SEQ ID NO 24
<211> LENGTH: 646
<212> TYPE: PRT
<213> ORGANISM: Fusobacterium necrophorum

<400> SEQUENCE: 24

Met Lys Lys Lys Leu Met Ile Leu Ala Ile Leu Ser Ile Ser Val Ser
1               5                   10                  15

Ala Phe Ala Met Lys Glu Glu Ile Pro Val Gln Arg Leu Asn Glu Thr
            20                  25                  30

Val Ile Thr Thr Pro Glu Arg Phe Gly Thr Lys Val Arg Asn Ile Ser
        35                  40                  45

Lys Asn Ile Gln Ile Ile Thr Lys Lys Asp Met Lys Glu Lys Gly Ala
    50                  55                  60

Lys Asn Leu Phe Glu Ala Leu Arg Gly Leu Pro Gly Val Val Ile Arg
65                  70                  75                  80

Arg Asp Gly Gly Gly His Ile Asp Leu Arg Gly Ser Gly Glu Asn Asp
                85                  90                  95

Lys Lys Asn Met Ile Phe Leu Ile Asp Gly Ile Pro Tyr Ser Gly Leu
            100                 105                 110

Ser Ile Phe Asp Ile Asn Ser Ile Ser Met Glu Glu Ile Glu Arg Ile
        115                 120                 125

Glu Ile Ile Gln Ser Gly Gly Val Leu Tyr Gly Asp Gly Ala Ile Gly
    130                 135                 140

Gly Val Ile Asn Leu Val Thr Lys Pro Ile Thr Thr Gly Lys Tyr Ser

-continued

```
145                 150                 155                 160

Asn Ser Ile Gly Leu Glu Tyr Gly Ser Trp Glu Thr Ala Lys Leu Asn
                165                 170                 175

Val Asn Val Gly Thr Lys Leu Thr Asp Asn Phe Val Val Ser Val Ser
            180                 185                 190

Tyr Ser Gly Glu Gln Thr Glu Glu Tyr Lys Asn Arg Ser Ile Asp Phe
        195                 200                 205

Lys Asp Lys Lys Asp Ser Arg Glu Ser Ile Trp Leu Lys Thr Lys Tyr
    210                 215                 220

Asn Leu Asn Asp Gly Glu Ile Glu Leu Lys Tyr Asn His Leu Lys Asn
225                 230                 235                 240

Asn Asp Tyr Ile Thr Gly Leu Leu Ser Ala Lys Asp Phe Lys Glu Asn
                245                 250                 255

Pro Lys Lys Ala Gly Thr Thr Asn Ala Ser Phe Lys Ala Glu Ser Asp
            260                 265                 270

Leu Trp Asn Leu Ser Phe Asn Lys Lys Leu Asn Ser Lys Phe Glu Val
        275                 280                 285

Phe Leu Gln Gly Gly Tyr Tyr Thr Asp Glu Thr Lys Tyr Tyr Glu Ile
    290                 295                 300

Gly Pro Gly Tyr Ala Asp Phe Ser Lys Asn Gly Asn Lys Ser His Phe
305                 310                 315                 320

Ile Arg Pro Gln Ile Lys Tyr Asn Tyr Met Glu Asp Ser Cys Ile Ile
                325                 330                 335

Leu Gly Gly Asp Arg Lys Lys Glu Thr Val Thr Asn Lys Leu Ser Pro
            340                 345                 350

Asn Ser Pro Lys Thr Ile Arg Lys Lys Glu Ser Ile Tyr Leu Leu Asn
        355                 360                 365

Ser Asn Lys Ile Gly Asn Phe Glu Ile Thr Glu Gly Tyr Arg Ile Glu
    370                 375                 380

Lys Ile Asp Leu Lys Arg Lys Asn Arg Ala Lys Asp Phe Lys Glu Asp
385                 390                 395                 400

Gly Met Glu Leu Gly Ile Asn Tyr Leu Tyr Ser Asp Thr Gly Asn Leu
                405                 410                 415

Tyr Phe Asn Tyr Thr Lys Gly Phe Arg Val Pro Thr Leu Gly Glu Met
            420                 425                 430

Asn Ser Trp Val Gly Asp Met Lys Ser His Lys Asn His Thr Phe Glu
        435                 440                 445

Leu Gly Leu Arg Asp Val Tyr Glu Asn Thr Ser Ile Asn Thr Ser Ile
    450                 455                 460

Phe Thr Leu Tyr Ser Lys Asp Glu Ile Phe Tyr Asp Ser Leu Val Ala
465                 470                 475                 480

Asn Pro Ser Pro Lys Asn Pro Asn Arg Lys Gly Ala Asn Arg Asn Phe
                485                 490                 495

Glu Gly Lys Val Arg Arg Ile Gly Ala Gln Leu Ala Leu Glu His Asn
            500                 505                 510

Ile Gly Lys Leu Ser Leu Arg Glu Lys Ile Ser Tyr Met Asp Pro Lys
        515                 520                 525

Ile Ile Asp Gly Tyr Tyr Lys Glu Lys Val Phe Pro Gly Val Pro Lys
    530                 535                 540

Leu Thr Ala Ala Leu Gly Leu Thr Tyr Asn Phe Glu Asn Ser Leu Lys
545                 550                 555                 560

Leu Asn Ile Asp Gly Tyr Tyr Gln Glu Lys Ile Tyr Ala Gly Thr Asp
                565                 570                 575
```

-continued

```
Phe Leu Asn Lys Tyr Gly Lys His Asn Ser Tyr Thr Val Val Asp Ala
            580                 585                 590

Asn Ile Ser Tyr Thr Phe Glu Asn Gly Leu Glu Leu Tyr Gly Gly Val
        595                 600                 605

Lys Asn Leu Phe Asp Lys Thr Tyr Ala Thr Ala Phe Phe Pro Arg Ala
    610                 615                 620

Thr Gly Glu Leu Arg Tyr Asp Pro Asp Asn Gly Arg Ser Phe Tyr Thr
625                 630                 635                 640

Gly Phe Lys Tyr Thr Phe
                645


<210> SEQ ID NO 25
<211> LENGTH: 1992
<212> TYPE: DNA
<213> ORGANISM: Fusobacterium necrophorum

<400> SEQUENCE: 25

atgaaaaaaa atttttactt actgtctatt ttcatgttgg caactgttca aacagttttt      60

ggaaaagagg atcccactgt gacattggag caaacaattg tcagtatgga ttcttttgga     120

agttctcccc acaggactgc aaaaaatgtt cgtgtggtta ccaaagaaga aataaaagaa     180

aaaggagctt tgaatgtaga agatgctttg aagggaattc cggggcttct catacggaac     240

ttggatggag ctcctccggt cattgattta aggggagccg gaatggcttc cagtttgact     300

tccactctgt tgcttctcaa tggagttccc ttaagtggag ttcgagtttt tgatgtcaat     360

tccattcctg tttctgaaat tgagagaatt gaaatcattc agggaggagg agctttgatg     420

tatggagacg gtgctgcggg aggagttgtc aacattatca cacagacgat gaagaataaa     480

aaatattatg gaaatgtcga tttggaatat ggttcttgga aaacgggaag aattcatttg     540

ggaataggag gtcaaatgga gaaaaacttt tctctccaag cttcctattc aggatattct     600

tctatggatt ggagagatag agcacatggg attgacatga gcggaaagac tttcgactac     660

agacataaaa aagataggaa agacagtttt tggttgagtg ggaaaaagga agggaaagac     720

caaagtattg aattacgtta cagtcatatg aaaagcaaag actattttac cacttttctg     780

aacaaaaaac agtatgaaga aaatccgaaa caagcgggaa tgacaggtaa ctacatagag     840

gatgtcacgg atatctggaa tctatcctat cgtaaaaaat ggaatgataa gcttgatttt     900

ttactttatg gaggctatca tcacggaaaa aatgaaaatc aacattttct aatggaagaa     960

tattttgtga ctccgcagat aaagtatctc tacggaaaca atagctatgt catcgtcggt    1020

ggggacatta gaaacggaaa aagggaatgg aaggatacct tcctatcgaa tggaaaaaag    1080

gctccgaacg ataccagaaa atcgaaggct ctctatctca tgaataaaat taccgttaag    1140

aattgggaat ttacacaagg ctatcgaaga gaaagggtaa attatgatta cacttccaaa    1200

gtttacggtc ctgtttggaa tttgttggaa gcaaatcctg tatcctccac ttcttccaat    1260

aacaacagtt ttgaactggg agtcaattat ctttattccg acagcggaaa cttgtatttc    1320

aattacacaa attcgatgag aactccaagt atcggggata tggaggcatg gaccggagat    1380

gtgaaaacga aaaaagacag tatttatgaa ctgggatggc gagattatct tgcgaacact    1440

cttttctcga cttctatttt ctggatggat actcgaaatg aagtatatta cgataaaacg    1500

ggattgtatc aagtcaaaac aagaaatttt gatgggaaaa caagaagaag gggagctcaa    1560

atctccttga ttcattattt ggataagctg tccctacgag aaaatatctc ctatatccat    1620

cccaagatag aaagtggaat ctatcaaggg aaaacgttcc cggaagttcc gaaatggatt    1680
```

```
gtgaatttgg gagccagcta tcatgttaca gaacaatttc atatcaatac ggatgtatat   1740

tatcaatcga aggcttatgc tgacgacgat tttaaaaatg aattttcaaa agaaaattct   1800

tacacaacat gggaccttca tctttcctac cgttttcaaa atggaatgga aatttatggg   1860

ggagctaaaa acctattcga taaaaaatat gctcacagtg tagcgattat gcgaagtcct   1920

tttgcttctc agaaggtata tcatccggca aatggaagaa atgtctatgt aggatttaaa   1980

tatcgttttt aa                                                       1992
```

```
<210> SEQ ID NO 26
<211> LENGTH: 663
<212> TYPE: PRT
<213> ORGANISM: Fusobacterium necrophorum

<400> SEQUENCE: 26

Met Lys Lys Asn Phe Tyr Leu Leu Ser Ile Phe Met Leu Ala Thr Val
1               5                   10                  15

Gln Thr Val Phe Gly Lys Glu Asp Pro Thr Val Thr Leu Glu Gln Thr
            20                  25                  30

Ile Val Ser Met Asp Ser Phe Gly Ser Ser Pro His Arg Thr Ala Lys
        35                  40                  45

Asn Val Arg Val Val Thr Lys Glu Glu Ile Lys Glu Lys Gly Ala Leu
    50                  55                  60

Asn Val Glu Asp Ala Leu Lys Gly Ile Pro Gly Leu Leu Ile Arg Asn
65                  70                  75                  80

Leu Asp Gly Ala Pro Pro Val Ile Asp Leu Arg Gly Ala Gly Met Ala
                85                  90                  95

Ser Ser Leu Thr Ser Thr Leu Leu Leu Leu Asn Gly Val Pro Leu Ser
            100                 105                 110

Gly Val Arg Val Phe Asp Val Asn Ser Ile Pro Val Ser Glu Ile Glu
        115                 120                 125

Arg Ile Glu Ile Ile Gln Gly Gly Gly Ala Leu Met Tyr Gly Asp Gly
    130                 135                 140

Ala Ala Gly Gly Val Val Asn Ile Ile Thr Gln Thr Met Lys Asn Lys
145                 150                 155                 160

Lys Tyr Tyr Gly Asn Val Asp Leu Glu Tyr Gly Ser Trp Lys Thr Gly
                165                 170                 175

Arg Ile His Leu Gly Ile Gly Gly Gln Met Glu Lys Asn Phe Ser Leu
            180                 185                 190

Gln Ala Ser Tyr Ser Gly Tyr Ser Ser Met Asp Trp Arg Asp Arg Ala
        195                 200                 205

His Gly Ile Asp Met Ser Gly Lys Thr Phe Asp Tyr Arg His Lys Lys
    210                 215                 220

Asp Arg Lys Asp Ser Phe Trp Leu Ser Gly Lys Lys Glu Gly Lys Asp
225                 230                 235                 240

Gln Ser Ile Glu Leu Arg Tyr Ser His Met Lys Ser Lys Asp Tyr Phe
                245                 250                 255

Thr Thr Phe Leu Asn Lys Lys Gln Tyr Glu Glu Asn Pro Lys Gln Ala
            260                 265                 270

Gly Met Thr Gly Asn Tyr Ile Glu Asp Val Thr Asp Ile Trp Asn Leu
        275                 280                 285

Ser Tyr Arg Lys Lys Trp Asn Asp Lys Leu Asp Phe Leu Leu Tyr Gly
    290                 295                 300

Gly Tyr His His Gly Lys Asn Glu Asn Gln His Phe Leu Met Glu Glu
```

-continued

```
305                 310                 315                 320

Tyr Phe Val Thr Pro Gln Ile Lys Tyr Leu Tyr Gly Asn Asn Ser Tyr
                325                 330                 335

Val Ile Val Gly Gly Asp Ile Arg Asn Gly Lys Arg Glu Trp Lys Asp
            340                 345                 350

Thr Phe Leu Ser Asn Gly Lys Lys Ala Pro Asn Asp Thr Arg Lys Ser
        355                 360                 365

Lys Ala Leu Tyr Leu Met Asn Lys Ile Thr Val Lys Asn Trp Glu Phe
    370                 375                 380

Thr Gln Gly Tyr Arg Arg Glu Arg Val Asn Tyr Asp Tyr Thr Ser Lys
385                 390                 395                 400

Val Tyr Gly Pro Val Trp Asn Leu Leu Glu Ala Asn Pro Val Ser Ser
                405                 410                 415

Thr Ser Ser Asn Asn Asn Ser Phe Glu Leu Gly Val Asn Tyr Leu Tyr
            420                 425                 430

Ser Asp Ser Gly Asn Leu Tyr Phe Asn Tyr Thr Asn Ser Met Arg Thr
        435                 440                 445

Pro Ser Ile Gly Asp Met Glu Ala Trp Thr Gly Asp Val Lys Thr Lys
    450                 455                 460

Lys Asp Ser Ile Tyr Glu Leu Gly Trp Arg Asp Tyr Leu Ala Asn Thr
465                 470                 475                 480

Leu Phe Ser Thr Ser Ile Phe Trp Met Asp Thr Arg Asn Glu Val Tyr
                485                 490                 495

Tyr Asp Lys Thr Gly Leu Tyr Gln Val Lys Thr Arg Asn Phe Asp Gly
            500                 505                 510

Lys Thr Arg Arg Arg Gly Ala Gln Ile Ser Leu Ile His Tyr Leu Asp
        515                 520                 525

Lys Leu Ser Leu Arg Glu Asn Ile Ser Tyr Ile His Pro Lys Ile Glu
    530                 535                 540

Ser Gly Ile Tyr Gln Gly Lys Thr Phe Pro Glu Val Pro Lys Trp Ile
545                 550                 555                 560

Val Asn Leu Gly Ala Ser Tyr His Val Thr Glu Gln Phe His Ile Asn
                565                 570                 575

Thr Asp Val Tyr Tyr Gln Ser Lys Ala Tyr Ala Asp Asp Asp Phe Lys
            580                 585                 590

Asn Glu Phe Ser Lys Glu Asn Ser Tyr Thr Thr Trp Asp Leu His Leu
        595                 600                 605

Ser Tyr Arg Phe Gln Asn Gly Met Glu Ile Tyr Gly Gly Ala Lys Asn
    610                 615                 620

Leu Phe Asp Lys Lys Tyr Ala His Ser Val Ala Ile Met Arg Ser Pro
625                 630                 635                 640

Phe Ala Ser Gln Lys Val Tyr His Pro Ala Asn Gly Arg Asn Val Tyr
                645                 650                 655

Val Gly Phe Lys Tyr Arg Phe
            660


<210> SEQ ID NO 27
<211> LENGTH: 1980
<212> TYPE: DNA
<213> ORGANISM: Fusobacterium necrophorum

<400> SEQUENCE: 27

atgaaaaaat tattcttact attttctttg attgcctgtt ccaattcggt ttactccgaa      60

atcatccatt tgggggcaag tgacatttac tctgatactg gttatgcgac caatataaga     120
```

-continued

```
agtacgactt catctccttt tataataact gcaaaagaaa ttcaggaaaa aaggtttgca    180

agtctctctg aaattttggc aagtcttccg ggaatcacta tacgagaggg atacgaacct    240

gaaattgatt tgagaggaca gggatactcg aaagcaaggg caaccattca ggtcatgata    300

gacggtgtgc ctgtcaatat gctggattct tctcatagaa aagttccctt aaatactgta    360

aatccgaatc aaatcgaacg aatcgaagtc attccgggtg gaggagctgt tttatatggg    420

aatggaacgg caggcggtgt catcaatatt cttactaaaa aacatcgagg aaattttgga    480

aatataggct atcgttatgg aagttttgga gatcgtaaat acgatattgc cgcaggaacc    540

agtttaggaa actttgactt tgctcttgat tattccaatg aagataaaaa cggctacaga    600

agaaattctc cttccgattc ggattatttt tctgccagaa ttgcttataa cttcaataaa    660

aatgatacaa ttgctctaaa atacagagga tatagaacag agtataaaca gtacaacggt    720

ttaagcaaaa agcaagtaca ggaagacaga agacagaacg gaatggcccc cggacaaaaa    780

ggttccactg atagaaagtt ggatgaatac agtttcaatt ttcataaaag agtaggaaaa    840

aacaacgatc ttagtttcca tgcctataaa ctagaaagcg atataaaaac aagatcacaa    900

actccaaaat taacgagaat tgtaaaagcg gaagataata gatcaggagt aaaaatcaaa    960

gataaattga attatggaaa tggtaacaac attattatcg gtgcaggtta taccaatcat   1020

accatgtttt taagcaacat aaaagtagag aaaaagactc tggaaagctt cgccttgaac   1080

acattgaaat tcggaaaact tgaattttca caaggattga gatttgaaaa atccaaatat   1140

caaggagatg ccgccaaagc tttcggatta aaaagtggag aaacttctaa aacactggag   1200

aactatggtg cttccctagc tcttaattat ttgtattctc atgcaggaaa tgtatatgtg   1260

aaatatgaga gagcttttaa tactcctgcc cctttacaaa ccataaaaaa tattaactgg   1320

caaacctata acagtgatgc aaaatcagaa aaaagtaata cctatgaaat cggcttccga   1380

gactatattc taaattccat agtcagtgct tccgcttatt atagtgaaac cgcaaatgaa   1440

ttaaaaacag tttggttagg tagccatttc catgatcttt ccaattttaa taccatcaac   1500

tatggaaaga caaagagata cggattcgat ttgaaggcgg aacagaaatt tgaaaaattc   1560

agaatttcag aatcctattc ctttgtaaat gctaaaatca taaaaagtgg ggaaactgcc   1620

agtcaaaaag caacggaagg aaaatatatt cctgatgttc cgaaacacaa gtttgtactt   1680

tcgactgatt atgattttaa tgaaaaattc tctattggag caagctatca ataccaagct   1740

gctgcatata ttgactctcg aaacagcttg ggaaaagaag ggaaaaaatc aattgtgaat   1800

ttgagagcaa actataaatt caatgatcat ttccacattt atgccggaat taaaaatcta   1860

tttaatgcaa aatactatga ttctgtgggt tatactactg ccaaaccaaa taggatatat   1920

aaggtttaca accctgcacc aagcagaaat tactatatgg gatttgatta taaattctaa   1980
```

<210> SEQ ID NO 28
<211> LENGTH: 659
<212> TYPE: PRT
<213> ORGANISM: Fusobacterium necrophorum

<400> SEQUENCE: 28

```
Met Lys Lys Leu Phe Leu Leu Phe Ser Leu Ile Ala Cys Ser Asn Ser
1               5                   10                  15

Val Tyr Ser Glu Ile Ile His Leu Gly Ala Ser Asp Ile Tyr Ser Asp
            20                  25                  30

Thr Gly Tyr Ala Thr Asn Ile Arg Ser Thr Thr Ser Ser Pro Phe Ile
        35                  40                  45
```

-continued

```
Ile Thr Ala Lys Glu Ile Gln Glu Lys Arg Phe Ala Ser Leu Ser Glu
    50                  55                  60

Ile Leu Ala Ser Leu Pro Gly Ile Thr Ile Arg Glu Gly Tyr Glu Pro
65                  70                  75                  80

Glu Ile Asp Leu Arg Gly Gln Gly Tyr Ser Lys Ala Arg Ala Thr Ile
                85                  90                  95

Gln Val Met Ile Asp Gly Val Pro Val Asn Met Leu Asp Ser Ser His
            100                 105                 110

Arg Lys Val Pro Leu Asn Thr Val Asn Pro Asn Gln Ile Glu Arg Ile
        115                 120                 125

Glu Val Ile Pro Gly Gly Gly Ala Val Leu Tyr Gly Asn Gly Thr Ala
    130                 135                 140

Gly Gly Val Ile Asn Ile Leu Thr Lys Lys His Arg Gly Asn Phe Gly
145                 150                 155                 160

Asn Ile Gly Tyr Arg Tyr Gly Ser Phe Gly Asp Arg Lys Tyr Asp Ile
                165                 170                 175

Ala Ala Gly Thr Ser Leu Gly Asn Phe Asp Phe Ala Leu Asp Tyr Ser
            180                 185                 190

Asn Glu Asp Lys Asn Gly Tyr Arg Arg Asn Ser Pro Ser Asp Ser Asp
        195                 200                 205

Tyr Phe Ser Ala Arg Ile Ala Tyr Asn Phe Asn Lys Asn Asp Thr Ile
    210                 215                 220

Ala Leu Lys Tyr Arg Gly Tyr Arg Thr Glu Tyr Lys Gln Tyr Asn Gly
225                 230                 235                 240

Leu Ser Lys Lys Gln Val Gln Glu Asp Arg Arg Gln Asn Gly Met Ala
                245                 250                 255

Pro Gly Gln Lys Gly Ser Thr Asp Arg Lys Leu Asp Glu Tyr Ser Phe
            260                 265                 270

Asn Phe His Lys Arg Val Gly Lys Asn Asn Asp Leu Ser Phe His Ala
        275                 280                 285

Tyr Lys Leu Glu Ser Asp Ile Lys Thr Arg Ser Gln Thr Pro Lys Leu
    290                 295                 300

Thr Arg Ile Val Lys Ala Glu Asp Asn Arg Ser Gly Val Lys Ile Lys
305                 310                 315                 320

Asp Lys Leu Asn Tyr Gly Asn Gly Asn Asn Ile Ile Ile Gly Ala Gly
                325                 330                 335

Tyr Thr Asn His Thr Met Phe Leu Ser Asn Ile Lys Val Glu Lys Lys
            340                 345                 350

Thr Leu Glu Ser Phe Ala Leu Asn Thr Leu Lys Phe Gly Lys Leu Glu
        355                 360                 365

Phe Ser Gln Gly Leu Arg Phe Glu Lys Ser Lys Tyr Gln Gly Asp Ala
    370                 375                 380

Ala Lys Ala Phe Gly Leu Lys Ser Gly Glu Thr Ser Lys Thr Leu Glu
385                 390                 395                 400

Asn Tyr Gly Ala Ser Leu Ala Leu Asn Tyr Leu Tyr Ser His Ala Gly
                405                 410                 415

Asn Val Tyr Val Lys Tyr Glu Arg Ala Phe Asn Thr Pro Ala Pro Leu
            420                 425                 430

Gln Thr Ile Lys Asn Ile Asn Trp Gln Thr Tyr Asn Ser Asp Ala Lys
        435                 440                 445

Ser Glu Lys Ser Asn Thr Tyr Glu Ile Gly Phe Arg Asp Tyr Ile Leu
    450                 455                 460
```

```
Asn Ser Ile Val Ser Ala Ser Ala Tyr Tyr Ser Glu Thr Ala Asn Glu
465                 470                 475                 480

Leu Lys Thr Val Trp Leu Gly Ser His Phe His Asp Leu Ser Asn Phe
                485                 490                 495

Asn Thr Ile Asn Tyr Gly Lys Thr Lys Arg Tyr Gly Phe Asp Leu Lys
            500                 505                 510

Ala Glu Gln Lys Phe Glu Lys Phe Arg Ile Ser Glu Ser Tyr Ser Phe
        515                 520                 525

Val Asn Ala Lys Ile Ile Lys Ser Gly Glu Thr Ala Ser Gln Lys Ala
    530                 535                 540

Thr Glu Gly Lys Tyr Ile Pro Asp Val Pro Lys His Lys Phe Val Leu
545                 550                 555                 560

Ser Thr Asp Tyr Asp Phe Asn Glu Lys Phe Ser Ile Gly Ala Ser Tyr
                565                 570                 575

Gln Tyr Gln Ala Ala Ala Tyr Ile Asp Ser Arg Asn Ser Leu Gly Lys
            580                 585                 590

Glu Gly Lys Lys Ser Ile Val Asn Leu Arg Ala Asn Tyr Lys Phe Asn
        595                 600                 605

Asp His Phe His Ile Tyr Ala Gly Ile Lys Asn Leu Phe Asn Ala Lys
    610                 615                 620

Tyr Tyr Asp Ser Val Gly Tyr Thr Thr Ala Lys Pro Asn Arg Ile Tyr
625                 630                 635                 640

Lys Val Tyr Asn Pro Ala Pro Ser Arg Asn Tyr Tyr Met Gly Phe Asp
                645                 650                 655

Tyr Lys Phe


<210> SEQ ID NO 29
<211> LENGTH: 2145
<212> TYPE: DNA
<213> ORGANISM: Fusobacterium necrophorum

<400> SEQUENCE: 29

atgaaaaaag tggtatttgg gatttacagt atcttaatgt cctctgctat gcttggagca      60

gaaattgatc ttggaacaca gaatatctat tcggaaaccg gatttgaaac gagtcttcga     120

agctctgttt cttctcctta tatcgttact tcaaaagaaa tcaaagaaaa acattatacc     180

cgtgtttctg aaattttgag agatattccg catatctaca tcggtcccgg tggcagtgta     240

gatatgcgtg gtcagggaag tgctcatgcc agaacaacag ttcaactgtt aattgatgga     300

gttcctgcca attttttgga tacttcccac atcaatcttc ctatcgatac tttaaatcca     360

gaagatatta agagaattga agtcatccct ggaggaggag ctgttttata tggaagtgga     420

acttccggag gagtgatcaa catcattacc aaaaaataca cgggaaacta tgcaaaggca     480

agctatcaaa taggaagcta tcacaatcat aaatatgacg tagctgccgg aacttctttg     540

ggaaattttg acattaacct aagttattca aaaaataata gggatggata tcgtaaaaaa     600

gcctttttccg attccgattt cttctccgga aaattacgtt atcacttcaa tcccacagac     660

agtcttgaat tcaaatatag ctattttgat aataagttca gaggtgttaa atccctaacc     720

agagaacaag tcgagaaaga tcgaaggcaa agtggtcttt ctcctgaaga caatttgaaa     780

aataccatcc gaaaagaaga atggaattta acttacgatg caaaatggac aagctggctg     840

gaacacaaat ccaatctttt ctatcagtcc acagaaataa aatctagtga atatgaagat     900

gctcttcctt tctatcaata tcaaatttct tcttatcaaa aaatgcttac tatgccaggg     960

attcctccta tgatgcaagc acaattgaaa aagcagataa aagccctaca aaatttgata    1020
```

acgagtaatc caaggatgga attacatcaa ggaagtcgtt tcaaagatca aaaattcggt 1080
tttaaaatga agaataaatt taagtatgga gaaaatagtg attttatttt aggtttggga 1140
tacattcaca acaaaatgga tcgagattct tgggcttata cgaaaaatac gcaaacgaat 1200
caaacaatag caactcttac aaatactaaa attcctttaa ataagaaaac attcgaaatt 1260
ttcggattaa atacctatcg tcataataat tgggaatttg ttcagggctt acgctttgaa 1320
aaagcgaaat ataatggaaa aagacaatat aaaaatctgg aatatccttt aaaagatcgt 1380
agcatgaata atgttgcggc aaatctggct gtcaattatc tctattccga tacaggaaat 1440
gtctatgtaa aatatgaaag aggatttact tctcctgctc ctgcacagtt aatggataaa 1500
atcagaaaag gaggagtgaa cgattatgtc aataatgatt taaaatctga aaaatcaaac 1560
tcctttgaag ttggatggaa tgactatctc ttccattctt tagtcagtgc tgatgttttt 1620
ttcagtgaaa cgaaagatga aatttctacc atattctcgg gagggcatgg gacaacattc 1680
agcaatttga accttggtca aacgaaacga tatggttttg atctaaaagc cagtcaagtt 1740
tttgaaaagt ggacattctc ggaagcttac agttatatcc atgcaaaaat catgaaagat 1800
aaaacaaagg cttatgaagg aaaatatatc agttatgttc caaggcataa attttctttg 1860
aatgctgatt atgcaatcac tccaaaatgg actcttgggg gagaatatca atacagttct 1920
tccgtatatc tggacaatgc aaataaaaat ggaaaagatg gagcgagatc tgtttttaat 1980
cttcaaacct cttatgagtt caattcacat ttttctatct atgcaggaat taaaaatgtg 2040
ttaaatcata agtattatga atctgtcagt gcaggttcca gtcaaaagta ttatagtccg 2100
gctccggaaa gaaattacta tgccggattc cgttatcaat tttaa 2145

<210> SEQ ID NO 30
<211> LENGTH: 714
<212> TYPE: PRT
<213> ORGANISM: Fusobacterium necrophorum

<400> SEQUENCE: 30

Met Lys Lys Val Val Phe Gly Ile Tyr Ser Ile Leu Met Ser Ser Ala
1 5 10 15

Met Leu Gly Ala Glu Ile Asp Leu Gly Thr Gln Asn Ile Tyr Ser Glu
20 25 30

Thr Gly Phe Glu Thr Ser Leu Arg Ser Ser Val Ser Ser Pro Tyr Ile
35 40 45

Val Thr Ser Lys Glu Ile Lys Glu Lys His Tyr Thr Arg Val Ser Glu
50 55 60

Ile Leu Arg Asp Ile Pro His Ile Tyr Ile Gly Pro Gly Gly Ser Val
65 70 75 80

Asp Met Arg Gly Gln Gly Ser Ala His Ala Arg Thr Thr Val Gln Leu
85 90 95

Leu Ile Asp Gly Val Pro Ala Asn Phe Leu Asp Thr Ser His Ile Asn
100 105 110

Leu Pro Ile Asp Thr Leu Asn Pro Glu Asp Ile Lys Arg Ile Glu Val
115 120 125

Ile Pro Gly Gly Gly Ala Val Leu Tyr Gly Ser Gly Thr Ser Gly Gly
130 135 140

Val Ile Asn Ile Ile Thr Lys Lys Tyr Thr Gly Asn Tyr Ala Lys Ala
145 150 155 160

Ser Tyr Gln Ile Gly Ser Tyr His Asn His Lys Tyr Asp Val Ala Ala
165 170 175

-continued

```
Gly Thr Ser Leu Gly Asn Phe Asp Ile Asn Leu Ser Tyr Ser Lys Asn
            180                 185                 190

Asn Arg Asp Gly Tyr Arg Lys Lys Ala Phe Ser Asp Ser Asp Phe Phe
        195                 200                 205

Ser Gly Lys Leu Arg Tyr His Phe Asn Pro Thr Asp Ser Leu Glu Phe
    210                 215                 220

Lys Tyr Ser Tyr Phe Asp Asn Lys Phe Arg Gly Val Lys Ser Leu Thr
225                 230                 235                 240

Arg Glu Gln Val Glu Lys Asp Arg Arg Gln Ser Gly Leu Ser Pro Glu
                245                 250                 255

Asp Asn Leu Lys Asn Thr Ile Arg Lys Glu Glu Trp Asn Leu Thr Tyr
            260                 265                 270

Asp Ala Lys Trp Thr Ser Trp Leu Glu His Lys Ser Asn Leu Phe Tyr
        275                 280                 285

Gln Ser Thr Glu Ile Lys Ser Ser Glu Tyr Glu Asp Ala Leu Pro Phe
    290                 295                 300

Tyr Gln Tyr Gln Ile Ser Ser Tyr Gln Lys Met Leu Thr Met Pro Gly
305                 310                 315                 320

Ile Pro Pro Met Met Gln Ala Gln Leu Lys Lys Gln Ile Lys Ala Leu
                325                 330                 335

Gln Asn Leu Ile Thr Ser Asn Pro Arg Met Glu Leu His Gln Gly Ser
            340                 345                 350

Arg Phe Lys Asp Gln Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asp Arg Asp Ser Trp Ala Tyr Thr Lys Asn Thr Gln Thr Asn
385                 390                 395                 400

Gln Thr Ile Ala Thr Leu Thr Asn Thr Lys Ile Pro Leu Asn Lys Lys
                405                 410                 415

Thr Phe Glu Ile Phe Gly Leu Asn Thr Tyr Arg His Asn Asn Trp Glu
            420                 425                 430

Phe Val Gln Gly Leu Arg Phe Glu Lys Ala Lys Tyr Asn Gly Lys Arg
        435                 440                 445

Gln Tyr Lys Asn Leu Glu Tyr Pro Leu Lys Asp Arg Ser Met Asn Asn
    450                 455                 460

Val Ala Ala Asn Leu Ala Val Asn Tyr Leu Tyr Ser Asp Thr Gly Asn
465                 470                 475                 480

Val Tyr Val Lys Tyr Glu Arg Gly Phe Thr Ser Pro Ala Pro Ala Gln
                485                 490                 495

Leu Met Asp Lys Ile Arg Lys Gly Gly Val Asn Asp Tyr Val Asn Asn
            500                 505                 510

Asp Leu Lys Ser Glu Lys Ser Asn Ser Phe Glu Val Gly Trp Asn Asp
        515                 520                 525

Tyr Leu Phe His Ser Leu Val Ser Ala Asp Val Phe Phe Ser Glu Thr
    530                 535                 540

Lys Asp Glu Ile Ser Thr Ile Phe Ser Gly Gly His Gly Thr Thr Phe
545                 550                 555                 560

Ser Asn Leu Asn Leu Gly Gln Thr Lys Arg Tyr Gly Phe Asp Leu Lys
                565                 570                 575

Ala Ser Gln Val Phe Glu Lys Trp Thr Phe Ser Glu Ala Tyr Ser Tyr
            580                 585                 590
```

-continued

```
Ile His Ala Lys Ile Met Lys Asp Lys Thr Lys Ala Tyr Glu Gly Lys
        595                 600                 605

Tyr Ile Ser Tyr Val Pro Arg His Lys Phe Ser Leu Asn Ala Asp Tyr
    610                 615                 620

Ala Ile Thr Pro Lys Trp Thr Leu Gly Gly Glu Tyr Gln Tyr Ser Ser
625                 630                 635                 640

Ser Val Tyr Leu Asp Asn Ala Asn Lys Asn Gly Lys Asp Gly Ala Arg
                645                 650                 655

Ser Val Phe Asn Leu Gln Thr Ser Tyr Glu Phe Asn Ser His Phe Ser
            660                 665                 670

Ile Tyr Ala Gly Ile Lys Asn Val Leu Asn His Lys Tyr Tyr Glu Ser
        675                 680                 685

Val Ser Ala Gly Ser Ser Gln Lys Tyr Tyr Ser Pro Ala Pro Glu Arg
    690                 695                 700

Asn Tyr Tyr Ala Gly Phe Arg Tyr Gln Phe
705                 710


<210> SEQ ID NO 31
<211> LENGTH: 1410
<212> TYPE: DNA
<213> ORGANISM: Fusobacterium necrophorum

<400> SEQUENCE: 31

atgaatttaa aattaaaatg tatattactt agtagtctac taagcatgac agcatatgga      60

gcatccatag accatattca aacgtatgca ccagaatatt taggaaatca agctcaaaat     120

ggagcaatta acggagtttc tccttattac aatcctgccg gaactactca gctagaagaa     180

ggattctata tcaatggtgg attacaaata gcagctggac atgagcaatc agaatacaaa     240

gagaaagaat ataaagctat ttttatacaa cctgttccaa gtattgcatt gacgaaagta     300

aacaaagata gttcgactta ttttactttt agtgctattg cgggaggagg aacattaaac     360

tataaacatg gagtagtagg aactgcaatt attcctgatt tagtggcaaa tttaaaagtc     420

ggatatttaa attcagctgc ttttggtatg ccaacaattc catctacatt agctggaaaa     480

aaagtggcag ttcaagtttt agatggaaca agagcaaaag gaagtaatct atacagtcaa     540

atgacattag gaaaagcatt tcaagtgaat gataaattat ctctttctgc aggaattcga     600

tttgtacatg gaagaagaga tttagaggga aacattaaat taaaagcata ttccccagat     660

tctccaaatt tggatcctgt tttagcaaaa ttgcctttag aagcagaaat tgattctaaa     720

agaagagcaa aaggatttgg atttgtattg ggagcgaact acaaggtaaa tgataagtgg     780

aatgttggaa tgagatacga ttctagagta aaattaaatt tcaaagcttc tacaagcgaa     840

aaagaaatta gcattcctac agtaggggga ataaagcata tcggatttac ttctgattta     900

tattatcctc aatataaaga tggaaagaaa gtaagaaggg atttaccagc tattttagca     960

ttaggaacaa cttatcaggt atcagataca tggaaaactg gtctatctgt aaattattat    1020

ttcaataaaa atgctaaaat ggatggacaa aaatacaaaa atggctttga agtggctttc    1080

ggaaatgaat ataaattaaa tgaaaaatgg actttgctag cttctattaa ctatgcaaaa    1140

acaggagcat taaaggaaag ttatagtgat gtggaatatg ctttggattc tatcatgtta    1200

ggaacaggag tgaaatatca atatagccct actttagaat taacagcaac tgtaggacac    1260

tatttttata gatcggaaga gggagatatc aaaggaagag ttgctaaaaa gacggattcc    1320

atgataaaac aattgcaaaa tgtaaatgaa caacaaaaat acagaaaaag tattactgct    1380

tttgggcttg gctttaccaa aaaattctag                                     1410
```

<210> SEQ ID NO 32
<211> LENGTH: 469
<212> TYPE: PRT
<213> ORGANISM: Fusobacterium necrophorum

<400> SEQUENCE: 32

```
Met Asn Leu Lys Leu Lys Cys Ile Leu Leu Ser Ser Leu Leu Ser Met
1               5                   10                  15

Thr Ala Tyr Gly Ala Ser Ile Asp His Ile Gln Thr Tyr Ala Pro Glu
            20                  25                  30

Tyr Leu Gly Asn Gln Ala Gln Asn Gly Ala Ile Asn Gly Val Ser Pro
        35                  40                  45

Tyr Tyr Asn Pro Ala Gly Thr Thr Gln Leu Glu Glu Gly Phe Tyr Ile
    50                  55                  60

Asn Gly Gly Leu Gln Ile Ala Ala Gly His Glu Gln Ser Glu Tyr Lys
65                  70                  75                  80

Glu Lys Glu Tyr Lys Ala Ile Phe Ile Gln Pro Val Pro Ser Ile Ala
                85                  90                  95

Leu Thr Lys Val Asn Lys Asp Ser Ser Thr Tyr Phe Thr Phe Ser Ala
            100                 105                 110

Ile Ala Gly Gly Gly Thr Leu Asn Tyr Lys His Gly Val Val Gly Thr
        115                 120                 125

Ala Ile Ile Pro Asp Leu Val Ala Asn Leu Lys Val Gly Tyr Leu Asn
    130                 135                 140

Ser Ala Ala Phe Gly Met Pro Thr Ile Pro Ser Thr Leu Ala Gly Lys
145                 150                 155                 160

Lys Val Ala Val Gln Val Leu Asp Gly Thr Arg Ala Lys Gly Ser Asn
                165                 170                 175

Leu Tyr Ser Gln Met Thr Leu Gly Lys Ala Phe Gln Val Asn Asp Lys
            180                 185                 190

Leu Ser Leu Ser Ala Gly Ile Arg Phe Val His Gly Arg Arg Asp Leu
        195                 200                 205

Glu Gly Asn Ile Lys Leu Lys Ala Tyr Ser Pro Asp Ser Pro Asn Leu
    210                 215                 220

Asp Pro Val Leu Ala Lys Leu Pro Leu Glu Ala Glu Ile Asp Ser Lys
225                 230                 235                 240

Arg Arg Ala Lys Gly Phe Gly Phe Val Leu Gly Ala Asn Tyr Lys Val
                245                 250                 255

Asn Asp Lys Trp Asn Val Gly Met Arg Tyr Asp Ser Arg Val Lys Leu
            260                 265                 270

Asn Phe Lys Ala Ser Thr Ser Glu Lys Glu Ile Ser Ile Pro Thr Val
        275                 280                 285

Gly Gly Ile Lys His Ile Gly Phe Thr Ser Asp Leu Tyr Tyr Pro Gln
    290                 295                 300

Tyr Lys Asp Gly Lys Lys Val Arg Arg Asp Leu Pro Ala Ile Leu Ala
305                 310                 315                 320

Leu Gly Thr Thr Tyr Gln Val Ser Asp Thr Trp Lys Thr Gly Leu Ser
                325                 330                 335

Val Asn Tyr Tyr Phe Asn Lys Asn Ala Lys Met Asp Gly Gln Lys Tyr
            340                 345                 350

Lys Asn Gly Phe Glu Val Ala Phe Gly Asn Glu Tyr Lys Leu Asn Glu
        355                 360                 365

Lys Trp Thr Leu Leu Ala Ser Ile Asn Tyr Ala Lys Thr Gly Ala Leu
```

-continued

```
    370                 375                 380

Lys Glu Ser Tyr Ser Asp Val Glu Tyr Ala Leu Asp Ser Ile Met Leu
385                 390                 395                 400

Gly Thr Gly Val Lys Tyr Gln Tyr Ser Pro Thr Leu Glu Leu Thr Ala
                405                 410                 415

Thr Val Gly His Tyr Phe Tyr Arg Ser Glu Glu Gly Asp Ile Lys Gly
            420                 425                 430

Arg Val Ala Lys Lys Thr Asp Ser Met Ile Lys Gln Leu Gln Asn Val
        435                 440                 445

Asn Glu Gln Gln Lys Tyr Arg Lys Ser Ile Thr Ala Phe Gly Leu Gly
    450                 455                 460

Phe Thr Lys Lys Phe
465


<210> SEQ ID NO 33
<211> LENGTH: 1917
<212> TYPE: DNA
<213> ORGANISM: Fusobacterium necrophorum

<400> SEQUENCE: 33

atggggaatt ttaatttaaa attttttacc atatctttat taattttatt ggtacaaaat      60

tcttttgcag aagatccggt aataaaaaga ggaaataacc aagatagtat agtagccggt     120

ctccataaca aagctgtaaa cggatattcc ttagcttatg gagatgctaa tgaggccact     180

ggagatgcag ccagtgtagc ttttggctta aaaaatgtgg caagtgggaa aagtgcaaca     240

gcctttggta atgccaataa ggcgggtgga gatacagcag cagcttttgg gaacaataac     300

acagcaggcg gtcgttttag cttagctttt ggtaataaaa atgaggtcag tggaacaagc     360

agtgcagctt ttggtttcca aaataaggct aaatctaaag aaagtgttgc tgtaggtcat     420

gagaatgagg tagaagcgga ctacggcatt gctttgggta atggaaatga agtaaaatca     480

caaaaaggtg tagcagtagg atatcaaaat gaagcaaaag gtttttcaaa ttctgttttc     540

ggtattgaaa gtagagtcag tgggacaagc agtacagttg taggaaattc ttatgaagtt     600

tcaggaacta aatcgggtgc ctttggagtg ggagaagccg gactaaagtc ttcaggaata     660

agctacaaat ataaaaatga aggtaatgaa tcttacacta taggaaatag aaacagtata     720

gcaacaagga cgaataataa ctttatattg ggaaatgatg ttactatagg tgacggaata     780

aacggtgctg tagttttagg taaaagttct aaggtaacgg aaagcaatac agtttctgtc     840

ggttctgaaa acgaaagaag aagaatagta tttgtggcgg atggaactca ggatacagat     900

gcggctactg tagggcaagt caagaaacta atttcttcaa gtacagtact gggagctgga     960

atgggaaatg tttatacaaa ggctgagagt gatgctaaat ttgctactaa agatgcaggt    1020

aatttgtcgg caagtgatgt tgatgcttgg agaagtaagt taggagttat tgctaacaca    1080

gcagcagatc caaaaagtac aagtatagga aataataata aagtgaccgg aacttattca    1140

acagcggttg gttacaaaaa tgaagttagc ggaaataaat ctggagcttt tggagatcca    1200

aatatagtta cagggaatcg ttcctatgcc tttggcaatg ataatactat tgcaggggat    1260

gataattttg ttttaggttc taatgtaaat ataggagtgg gaatatcaaa ttctgttgcg    1320

cttggaaata actcaaaagt aaaagcttct aatgaagttt ctgtaggttc ggtaggaaat    1380

gaaagaaaga taacgaatat ggcagatgga gaagtttcat ctacatcgac agatgcaatt    1440

acaggtagac aactatatca tgtaatgcaa aattcaggaa caacaggaat agaaaattta    1500

agaaatgaag taaatgaaaa gttctcagat gttaaaaatg aagtgaacca tgtaggttcc    1560
```

```
ttgagcgcgg cactttctgc attaaatcct atgcagtatg atccgaaagc tcctaatcaa   1620

atcatggcag gcttgggaca ttatagaaat aaacaggctg ttgcagtagg actaagccat   1680

catttcaata atagtgcgat gatgacagca gggcttgcct tagggaatga gtcaaagata   1740

aaagctatgg caaatcttgg atttacaata agattgggaa gaggcggaga aacttcggct   1800

gaaattcctc aaagtgtaat tcaaaatgaa atggcaagat tagctagaga gaatcaagaa   1860

ctaaaaaaag agttatttat cataagagag cagttagaag aattaataaa caaataa      1917


<210> SEQ ID NO 34
<211> LENGTH: 638
<212> TYPE: PRT
<213> ORGANISM: Fusobacterium necrophorum

<400> SEQUENCE: 34

Met Gly Asn Phe Asn Leu Lys Phe Phe Thr Ile Ser Leu Leu Ile Leu
1               5                   10                  15

Leu Val Gln Asn Ser Phe Ala Glu Asp Pro Val Ile Lys Arg Gly Asn
            20                  25                  30

Asn Gln Asp Ser Ile Val Ala Gly Leu His Asn Lys Ala Val Asn Gly
        35                  40                  45

Tyr Ser Leu Ala Tyr Gly Asp Ala Asn Glu Ala Thr Gly Asp Ala Ala
    50                  55                  60

Ser Val Ala Phe Gly Leu Lys Asn Val Ala Ser Gly Lys Ser Ala Thr
65                  70                  75                  80

Ala Phe Gly Asn Ala Asn Lys Ala Gly Gly Asp Thr Ala Ala Ala Phe
                85                  90                  95

Gly Asn Asn Asn Thr Ala Gly Gly Arg Phe Ser Leu Ala Phe Gly Asn
            100                 105                 110

Lys Asn Glu Val Ser Gly Thr Ser Ser Ala Ala Phe Gly Phe Gln Asn
        115                 120                 125

Lys Ala Lys Ser Lys Glu Ser Val Ala Val Gly His Glu Asn Glu Val
    130                 135                 140

Glu Ala Asp Tyr Gly Ile Ala Leu Gly Asn Gly Asn Glu Val Lys Ser
145                 150                 155                 160

Gln Lys Gly Val Ala Val Gly Tyr Gln Asn Glu Ala Lys Gly Phe Ser
                165                 170                 175

Asn Ser Val Phe Gly Ile Glu Ser Arg Val Ser Gly Thr Ser Ser Thr
            180                 185                 190

Val Val Gly Asn Ser Tyr Glu Val Ser Gly Thr Lys Ser Gly Ala Phe
        195                 200                 205

Gly Val Gly Glu Ala Gly Leu Lys Ser Ser Gly Ile Ser Tyr Lys Tyr
    210                 215                 220

Lys Asn Glu Gly Asn Glu Ser Tyr Thr Ile Gly Asn Arg Asn Ser Ile
225                 230                 235                 240

Ala Thr Arg Thr Asn Asn Asn Phe Ile Leu Gly Asn Asp Val Thr Ile
                245                 250                 255

Gly Asp Gly Ile Asn Gly Ala Val Val Leu Gly Lys Ser Ser Lys Val
            260                 265                 270

Thr Glu Ser Asn Thr Val Ser Val Gly Ser Glu Asn Glu Arg Arg Arg
        275                 280                 285

Ile Val Phe Val Ala Asp Gly Thr Gln Asp Thr Asp Ala Ala Thr Val
    290                 295                 300

Gly Gln Val Lys Lys Leu Ile Ser Ser Ser Thr Val Leu Gly Ala Gly
```

-continued 305 310 315 320

Met Gly Asn Val Tyr Thr Lys Ala Glu Ser Asp Ala Lys Phe Ala Thr
325 330 335

Lys Asp Ala Gly Asn Leu Ser Ala Ser Asp Val Asp Ala Trp Arg Ser
340 345 350

Lys Leu Gly Val Ile Ala Asn Thr Ala Ala Asp Pro Lys Ser Thr Ser
355 360 365

Ile Gly Asn Asn Asn Lys Val Thr Gly Thr Tyr Ser Thr Ala Val Gly
370 375 380

Tyr Lys Asn Glu Val Ser Gly Asn Lys Ser Gly Ala Phe Gly Asp Pro
385 390 395 400

Asn Ile Val Thr Gly Asn Arg Ser Tyr Ala Phe Gly Asn Asp Asn Thr
405 410 415

Ile Ala Gly Asp Asp Asn Phe Val Leu Gly Ser Asn Val Asn Ile Gly
420 425 430

Val Gly Ile Ser Asn Ser Val Ala Leu Gly Asn Asn Ser Lys Val Lys
435 440 445

Ala Ser Asn Glu Val Ser Val Gly Ser Val Gly Asn Glu Arg Lys Ile
450 455 460

Thr Asn Met Ala Asp Gly Glu Val Ser Ser Thr Ser Thr Asp Ala Ile
465 470 475 480

Thr Gly Arg Gln Leu Tyr His Val Met Gln Asn Ser Gly Thr Thr Gly
485 490 495

Ile Glu Asn Leu Arg Asn Glu Val Asn Glu Lys Phe Ser Asp Val Lys
500 505 510

Asn Glu Val Asn His Val Gly Ser Leu Ser Ala Ala Leu Ser Ala Leu
515 520 525

Asn Pro Met Gln Tyr Asp Pro Lys Ala Pro Asn Gln Ile Met Ala Gly
530 535 540

Leu Gly His Tyr Arg Asn Lys Gln Ala Val Ala Val Gly Leu Ser His
545 550 555 560

His Phe Asn Asn Ser Ala Met Met Thr Ala Gly Leu Ala Leu Gly Asn
565 570 575

Glu Ser Lys Ile Lys Ala Met Ala Asn Leu Gly Phe Thr Ile Arg Leu
580 585 590

Gly Arg Gly Gly Glu Thr Ser Ala Glu Ile Pro Gln Ser Val Ile Gln
595 600 605

Asn Glu Met Ala Arg Leu Ala Arg Glu Asn Gln Glu Leu Lys Lys Glu
610 615 620

Leu Phe Ile Ile Arg Glu Gln Leu Glu Glu Leu Ile Asn Lys
625 630 635

<210> SEQ ID NO 35
<211> LENGTH: 507
<212> TYPE: PRT
<213> ORGANISM: Fusobacterium necrophorum

<400> SEQUENCE: 35

Leu Gly Ile Phe Ser Phe Leu Gly Ile Ile Gln Phe Leu Ile Arg Asn
1 5 10 15

Ser Ser Asp Gln Lys Met Leu Ile Leu Gly Ile Phe Phe Leu Tyr Leu
20 25 30

Ser Ser Leu Leu Phe Val Tyr Ser Phe Gln Ser Ile Leu Lys Glu Lys
35 40 45

-continued

```
Asp Met Gly Leu Phe Phe Phe Leu Gly Ile Leu Phe Pro Tyr Tyr Phe
    50                  55                  60

Gln Lys His Pro Tyr Val Phe Lys Asp Leu Met Arg Glu Ser His Asn
65                  70                  75                  80

Ile Arg Asn Ile Asn Tyr Val Tyr Ile Phe Ile Phe Ser Ile Phe Phe
                85                  90                  95

Leu Lys Tyr Phe Phe Tyr Asn Thr Lys Lys Asn Trp Lys Glu Tyr Leu
            100                 105                 110

Glu Val Glu Asn Ile Arg Asn Tyr Leu Leu Tyr Leu Met Pro Phe Phe
        115                 120                 125

Ile Leu Arg Ala Lys Asp Ile Lys Met Ile Gly Phe Phe Tyr Gly Ile
    130                 135                 140

Val Val Phe Val Phe Cys Tyr Lys Lys Asp Trp Asn Ile Leu Leu Glu
145                 150                 155                 160

Lys Arg Lys Lys Ile Cys Leu Leu Phe Leu Val Leu Leu Phe Leu Phe
                165                 170                 175

Phe Ser Tyr Met Ser Asn Tyr Val Trp Gly Ile Pro Asn Gln Phe Gly
            180                 185                 190

Glu Gln Leu Leu Gly Asn Tyr Val Tyr Asn Tyr Phe Leu Leu Leu Ile
        195                 200                 205

Leu Leu Leu Ile Pro Ile Ser Glu Glu Met Met Lys Lys Ile Lys Met
    210                 215                 220

Ser Ile Ala Ile Ser Leu Phe Tyr Pro Ile Leu Leu Ile Val Leu Glu
225                 230                 235                 240

Trp Met Gln Asn His Tyr Thr Leu Glu Ile Ala Met Gly Thr Glu Glu
                245                 250                 255

Trp Thr Ser Ile Trp Ala Val Arg Ala Gly Leu Val Ser Leu Ile Ser
            260                 265                 270

Leu Phe Phe Tyr Leu Ser Glu Lys Arg Lys Val Tyr Leu Phe Gly Val
        275                 280                 285

Ile Phe Ser Leu Leu Ser Leu Phe Leu Gly Gln Gly Arg Gly Pro Ile
    290                 295                 300

Leu Ser Phe Ile Ala Ser Phe Cys Ile Leu Phe Phe Phe Phe Tyr Glu
305                 310                 315                 320

Lys Lys Thr Asp Arg Lys Lys Val Phe Thr Ser Leu Gly Ile Val Leu
                325                 330                 335

Leu Leu Leu Phe Val Ile Tyr Asn Thr Glu Asn Tyr Ile Ile Lys Lys
            340                 345                 350

Phe Gln Leu Val Phe Leu Gly Ala Asp Ser Ser Thr Asn Thr Arg Ile
        355                 360                 365

Glu Leu Tyr His Gly Ala Ile Glu Gln Trp Lys Ser Gln Lys Trp Ile
    370                 375                 380

Gly Tyr Gly Leu Gly Ser Tyr Lys Glu Thr Val Glu Leu Leu Lys Gln
385                 390                 395                 400

Glu Tyr Leu Glu Lys Tyr Asp Leu Ile Arg Ile Pro His Ala His Asn
                405                 410                 415

Asn Ile Leu Glu Leu Leu Arg Ser Leu Gly Ile Leu Gly Thr Phe Ile
            420                 425                 430

Tyr Ile Phe Leu Asn Gly Tyr Leu Cys Phe Trp Leu Leu Gly Lys Tyr
        435                 440                 445

Trp Lys Thr Arg Glu Lys Leu Tyr Ile Leu Pro Phe Val Leu Ile Val
    450                 455                 460

Asn Phe Glu Leu Ser Gly Ile Thr Asp Phe Ser Leu Met Met Tyr Lys
```

465 470 475 480

Ser Gln Leu Leu Leu Phe Phe Ile Cys Ser Leu Ser Leu Ser Tyr Thr
485 490 495

Val Ser Met Ser Thr Asp Val Glu Tyr Lys Ile
500 505

<210> SEQ ID NO 36
<211> LENGTH: 225
<212> TYPE: PRT
<213> ORGANISM: Fusobacterium necrophorum

<400> SEQUENCE: 36

Val Glu Met Phe Val Leu Phe Gly Thr Ser His Met Ile Met Ile Leu
1 5 10 15

Ile Gly Val Ile Ser Val Leu Leu Leu Ile Ile Leu Gly Phe Leu Ile
20 25 30

Arg Pro Gln Leu Leu Ala Lys Trp Ile Ser Val Ser Val Leu Val Ile
35 40 45

Lys Leu Ala Glu Met Tyr Tyr Arg His Arg Val Leu Gly Glu Glu Ile
50 55 60

Tyr Arg Met Leu Pro Phe His Leu Cys Asn Leu Thr Ile Ile Leu Ser
65 70 75 80

Leu Phe Met Met Phe Phe His Ser Lys Phe Leu Phe Gln Leu Val Tyr
85 90 95

Phe Trp Phe Val Gly Ala Ile Phe Ala Ile Leu Thr Pro Asp Ile Ile
100 105 110

Phe Ala Tyr Pro Asn Phe Trp Thr Ile Ser Phe Phe Ile Thr His Phe
115 120 125

Tyr Leu Val Phe Ser Ala Leu Phe Ala Leu Ile His Phe His Phe Arg
130 135 140

Pro Thr Lys Arg Gly Met Leu Met Ala Phe Leu Phe Ile Asn Leu Trp
145 150 155 160

Ala Val Leu Met Tyr Phe Val Asn Gln Glu Leu Gly Thr Asn Tyr Leu
165 170 175

Phe Val Asn Arg Ile Pro Glu Thr Thr Thr Leu Leu Ser Tyr Phe Gly
180 185 190

Ala Trp Pro Tyr Tyr Leu Leu Pro Val Glu Gly Ile Tyr Ile Ile Glu
195 200 205

Ser Ile Leu Leu Tyr Leu Pro Phe Arg Lys Ser Asn Ile Lys Phe His
210 215 220

Phe
225

<210> SEQ ID NO 37
<211> LENGTH: 166
<212> TYPE: PRT
<213> ORGANISM: Fusobacterium necrophorum

<400> SEQUENCE: 37

Met Arg Ala Asn Ser Ile Arg Ile Asn Ala Leu Glu Ile Asn Ile Ile
1 5 10 15

Glu Ala Leu Lys Glu Glu Leu Pro Glu Glu Met Thr Ile Val Leu Asp
20 25 30

Asp Arg Ala Leu Asn Phe Asp Phe Asp Lys Ser Val Val Lys Pro Lys
35 40 45

Tyr Asn Glu Met Leu Thr Asn Leu Lys Glu Phe Ile Thr Lys Asn Asn 50 55 60

Tyr Glu Val Thr Ile Glu Gly His Thr Asp Tyr Ile Ala Ser Asn Glu
65 70 75 80

Tyr Asn Met Gly Leu Ser Lys Arg Arg Ala Glu Ala Val Lys Ala Lys
85 90 95

Leu Ile Glu Leu Gly Leu Glu Pro Ser Arg Ile Val Ala Ile Leu Pro
100 105 110

Lys Gly Glu Glu Glu Pro Ile Ala Asp Asn Lys Thr Thr Glu Gly Arg
115 120 125

Ala Lys Asn Arg Arg Val Glu Phe Lys Leu Val Lys Arg Asp Ser Val
130 135 140

Gly Glu Val Asn Ser Glu Glu Ser Arg Ile Ile Asp Val Lys Lys Gly
145 150 155 160

Val Val Glu Ala Glu Asn
165

<210> SEQ ID NO 38
<211> LENGTH: 183
<212> TYPE: PRT
<213> ORGANISM: Fusobacterium necrophorum

<400> SEQUENCE: 38

Met Lys Lys Tyr Leu Gly Met Thr Val Leu Leu Ala Ser Phe Val Leu
1 5 10 15

Ala Ala Cys Gly Lys Thr Ser Asn Thr Ser Val Arg Asp Leu Ser Thr
20 25 30

Glu Gly Asn Gln Asn Phe Ala Ile Glu Asp Ile Asp Thr Ala Lys Lys
35 40 45

Pro Leu Glu Asp Ile Ile Val Phe Asn Gln Asp Gly Val Thr Ile Arg
50 55 60

Arg Glu Gly Asn Asn Leu Ile Leu Ser Met Pro Glu Leu Ile Leu Phe
65 70 75 80

Asp Phe Asp Lys Tyr Glu Val Lys Asp Gly Ile Lys Pro Ser Leu Arg
85 90 95

Thr Leu Ala Asn Ala Leu Gly Ala Asn Ser Asp Ile Lys Ile Lys Ile
100 105 110

Asp Gly Tyr Thr Asp Phe Ile Gly Ser Glu Gly Tyr Asn Leu Glu Leu
115 120 125

Ser Val Asn Arg Ala Lys Ala Ile Lys Ser Tyr Leu Val Asn His Gly
130 135 140

Ala Ile Glu Asn Asn Ile Ser Ile Glu Gly Tyr Gly Lys Gln Asn Pro
145 150 155 160

Val Ala Ser Asn Ala Thr Glu Ser Gly Arg Ala Arg Asn Arg Arg Val
165 170 175

Glu Phe Ile Ile Ser Arg Ser
180

<210> SEQ ID NO 39
<211> LENGTH: 172
<212> TYPE: PRT
<213> ORGANISM: Fusobacterium necrophorum

<400> SEQUENCE: 39

Val Gly Arg Lys Ser Thr Lys Ile Gly Ile Leu Phe Phe Leu Phe Leu
1 5 10 15

Phe Ser Leu Pro Ser Phe Ala Val Gln Lys Leu Thr Thr Thr Gln Met 20 25 30

Arg Glu Asn Ser Ile Arg Ile Asn Ala Leu Glu Leu Lys Glu Met Asp
35 40 45

Ile His Leu Lys Lys Val Thr Val Val Leu Asp Glu Arg Ala Leu Asn
50 55 60

Phe Asp Phe Asp Lys Trp Asn Ile Lys Glu Gln Tyr Tyr Glu Val Leu
65 70 75 80

Glu Asn Leu Lys Glu Tyr Ile Leu Ala Asn Asp Tyr Glu Val Val Ile
85 90 95

Glu Gly His Thr Asp Ser Ile Gly Thr Asn Ala Tyr Asn Ile Gly Leu
100 105 110

Ser Phe Lys Arg Ala Asn Ser Thr Lys Glu Lys Leu Ile Glu Phe Gly
115 120 125

Leu Pro Ala Asp Arg Ile Val Gly Ile Ser Gly Lys Gly Glu Glu Ser
130 135 140

Pro Ile Ala Thr Asn Glu Thr Pro Glu Gly Arg Ser Gln Asn Arg Arg
145 150 155 160

Val Glu Phe His Leu Glu Lys Ile Gly Asp Lys Glu
165 170

<210> SEQ ID NO 40
<211> LENGTH: 789
<212> TYPE: PRT
<213> ORGANISM: Fusobacterium necrophorum

<400> SEQUENCE: 40

Met Glu Glu Asn Asn Gly Thr Ile Val Ile Thr Glu Glu Met Ile Gln
1 5 10 15

Lys Lys His Tyr Asp Ser Val Ala Lys Ile Phe Glu Asp Ser Pro Val
20 25 30

Ser Val Val Arg His Thr Ala Phe Gly Pro Ile Val Asp Leu Arg Gly
35 40 45

Ser Gly Glu Arg Thr Ile Ser Arg Val Lys Val Met Ile Asp Gly Thr
50 55 60

Pro Ile Asn Pro Leu Glu Glu Thr His Gly Thr Ile Pro Phe Asp Thr
65 70 75 80

Ile Pro Val Glu Ser Ile Ala Lys Ile Glu Ile Val Pro Gly Thr Gly
85 90 95

Thr Thr Lys Tyr Gly Gly Gly Thr Thr Gly Gly Tyr Ile Asn Ile His
100 105 110

Thr Lys Lys Asp Lys Gln Lys Asn Tyr Ile Thr Ile Asn Ala Asp His
115 120 125

Ala Ser Tyr His Ala Asn Ser Ile Gly Ile Ala Ala Gly Met Asn Ala
130 135 140

Ser Lys Lys Leu Phe Val Tyr Ala Gly Glu Ala Tyr Gln Arg Lys Asp
145 150 155 160

Gly Tyr Arg Lys Lys Asp His Ser Asp Arg Asn Asn Phe Leu Gly Gly
165 170 175

Phe Asp Tyr Gln Ile Asn Ala Lys His Arg Ile Lys Gly Gln Gly Asn
180 185 190

Leu Tyr Arg Glu Asp Leu Lys Ser Thr Thr Glu Val Thr His Glu Glu
195 200 205

Leu Lys Gln Asp Arg Arg Lys Ala Gly Glu Asp Thr Lys Ile Glu Met
210 215 220

-continued

```
Asp Arg Asp Phe Ala Ser Leu Asp Tyr Glu Tyr Thr Pro Thr Ser His
225                 230                 235                 240

Phe Thr Leu Arg Ala Asn Val Asn Arg Ala His Phe Thr Arg Asp Val
                245                 250                 255

Ser Met Asp Ala Lys Gln Glu Gln Leu Thr Leu Val Asn Ala Phe Arg
            260                 265                 270

Phe Thr His Asn Met Ser Met Val Asp Asp Glu Val Lys Thr Leu Lys
        275                 280                 285

Pro Val Leu Lys Asp Phe Gln Ser Thr Met Glu Gly Lys Phe Lys Glu
    290                 295                 300

Glu Asn Gln Glu Gly Lys Val Asp Gly Glu Trp Lys Tyr Asn Gln Gly
305                 310                 315                 320

Lys Gly His Leu Gln Phe Gly Tyr Ala Tyr Asn Lys Lys Ser Leu Asp
                325                 330                 335

Gln Asn Leu Lys Ile Gln Ser Lys Pro Phe Asn Leu Gly Lys Ser Leu
            340                 345                 350

Tyr Tyr Leu Phe Pro Gly Asp Pro Ala Pro His Pro Phe Glu Asp Tyr
        355                 360                 365

Ala Gly Lys Val Leu Asp Gln Glu Thr Met Trp Arg Val Ile Phe Asn
    370                 375                 380

Asp Leu Gly Tyr Ser Gln Glu Tyr Ile Asp Thr His Ala Pro Ser Met
385                 390                 395                 400

Ala Gly Asp Asn Ser Gly Glu Ile Leu Asp Leu Gln Asn Tyr Asn Gln
                405                 410                 415

Val Asp Ser Phe Arg Asn Thr His Ser Leu Tyr Leu Leu Asn Asp Tyr
            420                 425                 430

Lys Ile Thr Pro Lys Leu Asn Phe Arg Ser Gly Leu Arg Trp Glu Tyr
        435                 440                 445

Ser Lys Tyr Gly Ser Lys Arg Lys Asn Tyr Met Ala Ile Gly Ile His
    450                 455                 460

Lys Ala Gln His Ser Asp Leu Ala Ala Ser Ala Gly Leu Ala Gly Leu
465                 470                 475                 480

Leu Asp Ser Tyr Glu Lys Glu Ala Leu Leu Leu Gly Lys Leu Asp Tyr
                485                 490                 495

Val Asp Ile Glu Leu Ser Ile Lys Asp Thr Asp Met Lys Asp Ser Ser
            500                 505                 510

His Asn Phe Gly Gly Glu Val Gly Phe Ser Tyr Gln Tyr His Lys Lys
        515                 520                 525

Gly Asn Leu Tyr Phe Arg Tyr Glu Arg Gly Phe Leu Ser Pro Leu Pro
    530                 535                 540

Ser Gln Leu Thr Asn Lys Asp Phe Leu Thr Gly Asn Tyr Tyr Pro Ser
545                 550                 555                 560

Gly Val Lys Ser Glu Lys Val Asp Thr Ile Glu Ile Gly Ile Lys His
                565                 570                 575

Ser Leu Trp Asn Asn Thr His Ile Glu Ala Asn Thr Phe Phe Ser Leu
            580                 585                 590

Thr Lys Asp Glu Ile Thr Asn Met Arg Tyr Asn Ala Asn Asn His Met
        595                 600                 605

Asn Met Arg Trp Ala Tyr Ala Asn Ile Ser Lys Thr Arg Arg Leu Gly
    610                 615                 620

Phe Glu Leu Asn Ala Glu His Ile Phe Asp Lys Leu Lys Ile Arg Glu
625                 630                 635                 640

Ser Phe Ser Tyr Val Asp Ala Lys Ile Ala Lys Asp Thr Gly Phe Lys
```

-continued

```
                645                 650                 655

Asp Tyr Tyr His Ser Asp Tyr Lys Glu Gly Thr Lys Asn Glu Phe Lys
            660                 665                 670

Asp Ala Pro Leu Tyr Tyr Lys Lys Gly Gln Thr Val Pro Leu Val Ser
        675                 680                 685

Lys Val Lys Val Thr Val Gly Ala Glu Tyr Gln Cys Thr Asp Lys Leu
    690                 695                 700

Ser Leu Gly Gly Asn Tyr Asn Tyr Val Ser Gly Tyr Asp Thr Arg Glu
705                 710                 715                 720

Pro Gly Glu Gly Phe Gln Ala Lys Thr Tyr Lys Val Lys Gly His Gly
                725                 730                 735

Thr Leu Asp Leu Phe Gly Arg Tyr Tyr Phe Thr Asp Tyr Ala Tyr Val
            740                 745                 750

Arg Phe Gly Val Asn Asn Val Leu Gly Glu Lys Tyr Asn Leu Arg Glu
        755                 760                 765

Asp Ser His Tyr Ala Val Pro Ala Pro Lys Gln Asn Tyr Tyr Ala Gly
    770                 775                 780

Phe Ser Tyr Lys Phe
785


<210> SEQ ID NO 41
<211> LENGTH: 159
<212> TYPE: PRT
<213> ORGANISM: Fusobacterium necrophorum

<400> SEQUENCE: 41

Met Lys Lys Met Leu Leu Val Leu Gly Leu Val Ser Ala Phe Ser Met
1               5                   10                  15

Ser Ala Phe Ala Asp Lys Ile Ala Val Val Asp Ser Gln Glu Val Ile
            20                  25                  30

Gly Arg Tyr Ser Gly Thr Lys Gly Val Glu Ala Thr Leu Gln Lys Glu
        35                  40                  45

Val Lys Arg Ile Glu Asn Asp Val Asn Gln Arg Gln Val Ala Leu Gln
    50                  55                  60

Lys Glu Glu Val Ala Leu Gln Ala Lys Gly Asp Lys Leu Thr Asp Ala
65                  70                  75                  80

Glu Lys Lys Ala Phe Gln Ala Lys Val Glu Gly Phe Tyr Lys Tyr Val
                85                  90                  95

Asn Thr Ser Arg Glu Ser Leu Ala Lys Met Glu Gln Thr Lys Met Ser
            100                 105                 110

Ala Ile Phe Thr Lys Ala Asn Lys Ala Val Gln Ala Val Ala Ala Glu
        115                 120                 125

Gly Lys Tyr Asp Tyr Val Leu Asp Arg Gly Ala Val Leu Val Gly Gly
    130                 135                 140

Glu Asp Ile Thr Asp Lys Val Ile Lys Lys Met Glu Thr Ile Lys
145                 150                 155


<210> SEQ ID NO 42
<211> LENGTH: 377
<212> TYPE: PRT
<213> ORGANISM: Fusobacterium necrophorum

<400> SEQUENCE: 42

Met Lys Lys Leu Ala Leu Val Leu Gly Ser Leu Leu Val Ile Gly Ser
1               5                   10                  15

Ala Ala Ser Ala Lys Glu Val Met Pro Ala Pro Met Pro Glu Pro Glu
```

```
                20                  25                  30

Val Lys Ile Val Glu Lys Pro Val Glu Val Ile Val Tyr Arg Asp Arg
        35                  40                  45

Val Val Gln Ala Pro Ala Lys Trp Lys Pro Asn Gly Ser Val Gly Val
    50                  55                  60

Glu Leu Arg Thr Gln Gly Lys Val Glu Asn Lys Gly Lys Lys Ala Thr
65                  70                  75                  80

Glu Glu Asn Ala Arg Lys Gly Trp Ala Gly Lys Glu Pro Asn Val Arg
                85                  90                  95

Leu Glu Thr Lys Ala Ser Val Asn Phe Thr Glu Asn Gln Asn Leu Glu
            100                 105                 110

Val Arg Thr Arg Gln Thr His Val Leu Thr Lys Thr Asp Ser Asp Lys
        115                 120                 125

Glu Glu Ser Asn His Lys Asp Thr Gln Val Arg Ile Arg His Thr Tyr
    130                 135                 140

Asn Phe Gly Lys Leu Gly Ser Ser Lys Val Gly Phe Lys Val Ala Ser
145                 150                 155                 160

Gln Tyr Leu His Asp Asp His Val Asp Ser Leu Arg Thr Arg Ala Val
                165                 170                 175

Phe Asp Phe Ala Asp Tyr Ile Tyr Ser Asn Ser Leu Phe Lys Thr Thr
            180                 185                 190

Ala Leu Glu Ile Gly Pro Ser Tyr Lys Tyr Val Trp Gly Gly Asn Asp
        195                 200                 205

Asp Arg Tyr Tyr Asn Ala Leu Gly Leu Tyr Ala Asn Ala Glu Phe Glu
    210                 215                 220

Leu Pro Tyr Gly Phe Gly Phe Gln Ala Glu Phe Glu Asp Ala Phe Thr
225                 230                 235                 240

Tyr Thr Ser Thr Gly Lys Gly Asp Gly Lys Arg Asp Lys Ala Lys Leu
                245                 250                 255

Gly His Ala Asp Phe Val Leu Ser His Ser Leu Asp Leu Tyr Lys Glu
            260                 265                 270

Gly Lys His Ser Leu Ala Phe Leu Asn Glu Leu Glu Tyr Glu Thr Phe
        275                 280                 285

Trp Ala Trp Asp Lys Lys Asp Ala Ser Met Glu Glu Trp Pro His Val
    290                 295                 300

Asp Gly His Gly Arg Val Asn Ser Glu Gly Lys Asn Lys Lys Trp Gly
305                 310                 315                 320

Ala Tyr Glu Leu Thr Tyr Thr Pro Lys Leu Gln Tyr Asn Tyr Gln Ala
                325                 330                 335

Thr Glu Phe Val Lys Leu Tyr Ala Ala Ile Gly Gly Glu Tyr Val Asn
            340                 345                 350

Arg Glu Asn Asn Lys Ser Thr Ala Arg Tyr Trp Arg Trp Asn Pro Thr
        355                 360                 365

Ala Trp Ala Gly Met Lys Val Thr Phe
    370                 375


<210> SEQ ID NO 43
<211> LENGTH: 246
<212> TYPE: PRT
<213> ORGANISM: Fusobacterium necrophorum

<400> SEQUENCE: 43

Met Lys Lys Asn Phe Ile Ile Ala Ile Phe Cys Ser Phe Ala Ala Phe
1               5                   10                  15
```

Ser Tyr Ala Glu Glu Lys Met Ser Gly Val Asn Leu Gly Ile Thr Ala
20 25 30

Ser His Ala Lys Glu Ile Tyr Lys Val Ser Ala Lys Glu Lys Tyr Ser
35 40 45

Val Leu Pro Leu Ile Ser Val Asn Tyr Lys Asp Phe Tyr Ile Asn Gln
50 55 60

Ser Glu Leu Gly Tyr Gln Phe Gln Val His Asp Asn Phe Leu Ile Ser
65 70 75 80

Gly Tyr Phe Asp Phe Leu Asp Gly Tyr Pro Val Lys Gly Lys Glu Met
85 90 95

Gln Lys Glu Tyr Lys Ser Ile Gln Thr Arg Arg Ser Gln Ile Val Gly
100 105 110

Gly Gly Arg Ile Thr Tyr Phe Lys Asp Asn Phe Gln Thr Ser Ile Phe
115 120 125

Ala Gln Gly Gly Lys Arg Gly Ser Ser Thr Gly Ala Asp Leu Ser Leu
130 135 140

Ser Phe Pro Leu Thr Glu Lys Leu Phe Phe Thr Thr Gly Leu Asn Tyr
145 150 155 160

Thr Ile Tyr Ser Lys Asn Phe Thr Asn Tyr Tyr Phe Gly Val His Lys
165 170 175

Glu Asp Phe Gly Gly Lys Leu Thr Lys Val Tyr Ser Pro Lys Ala Ser
180 185 190

Tyr Ser Tyr Gly Ala Glu Ala Ser Leu Glu Tyr Gln Ile Thr Glu Pro
195 200 205

Phe Ser Ile Phe Thr Ser Val Ser Ala Thr Asn Tyr Ser Lys Glu Ile
210 215 220

Thr Asn Ser Pro Leu Val Lys Asp Lys Thr Asn Ile Ser Thr Thr Ile
225 230 235 240

Gly Leu Gln Tyr Ser Phe
245

<210> SEQ ID NO 44
<211> LENGTH: 476
<212> TYPE: PRT
<213> ORGANISM: Fusobacterium necrophorum

<400> SEQUENCE: 44

Met Lys Gln Lys Trp Ser Phe Phe Leu Cys Leu Leu Phe Leu Ser Ser
1 5 10 15

Cys Ser Ser Val Asn Lys Glu Ile Ser Glu Thr Ser Leu Leu Gln Glu
20 25 30

Leu Lys Arg Lys Glu Thr Glu Thr Gln Arg Ile Leu Thr Glu Gln Arg
35 40 45

Leu Ser Leu Glu Glu Ala Ile Gln Ile Ala Lys Glu Arg Asn Leu Glu
50 55 60

Leu Lys Thr Lys Gln Leu Glu Arg Glu Ile Ser Lys Ile Asp Ser Lys
65 70 75 80

Ile Ala Phe Gly Asn Phe Leu Pro Arg Ile Ser Ala Phe Tyr Thr Arg
85 90 95

Ser Phe Trp Glu Glu Ala Leu Ser Gly Gln Val Asp Leu Pro Ala Ser
100 105 110

Leu Ser Gln Phe Pro Leu Ile Gly Pro Met Leu Pro Lys Glu Ile Gln
115 120 125

Gly Arg Leu Leu Asp Lys Ser Tyr Ser Val Tyr Gly Leu Gln Ala Ser
130 135 140

-continued

Met Pro Ile Phe Ala Pro Ala Thr Trp Phe Leu Tyr Ser Ala Arg Arg
145 150 155 160

Lys Gly Glu Glu Ile Gln Ser Leu Val Leu Thr Leu Thr Glu Lys Met
165 170 175

Ile Ser Ile Gln Val Ile Gln Gln Tyr Tyr Trp Ile Leu Ala Leu Glu
180 185 190

Ala Glu Glu Ile Gln Leu Lys Ala Ser Leu Lys Ser Ala Glu Gln Leu
195 200 205

Leu His Asn Met Lys Ile Ala Leu Asp Thr Gln Ser Ile Leu Glu Trp
210 215 220

Gln Tyr Gln Lys Ala Gln Ala Tyr Tyr Lys Gln Lys Lys Leu Ala Leu
225 230 235 240

Ala Gln Asn Gln Arg Asp Leu Lys Leu Ala Lys Met Gly Leu Leu Ser
245 250 255

Thr Leu Asn Leu Ser Pro Leu Ser Ser Val Arg Leu Gln Lys Thr Gln
260 265 270

Asn Ile Thr Lys Arg Lys Glu Asp Asn Tyr Glu Glu Val Ile Tyr Gln
275 280 285

Ala Leu Val His Asn Asp Ala Leu Gly Ile Gln Glu Lys Val Leu Glu
290 295 300

Val Glu Lys Glu Lys Leu Lys Ile Ser Phe Ser Arg Phe Leu Pro Val
305 310 315 320

Ile Gly Leu Gln Gly Phe Tyr Gly Glu His Ser Leu Ser Leu Leu Ser
325 330 335

Ser Ser His Tyr Leu Leu Gly Ile Leu Gly Gly Val Phe Ser Ile Phe
340 345 350

Asn Gly Phe Gln Asp Ile Ser Ala Tyr Gln Lys Ala Lys Ile Glu Gln
355 360 365

Arg Lys Ala Met Leu Lys Lys Glu Ser Leu Ile Leu Gln Ser Ile Ala
370 375 380

Glu Thr Thr Asn Val Tyr Gln Lys Leu Gln Ser Ser Ile Glu Glu Glu
385 390 395 400

Glu Ile Ala Glu Ile Asn Glu Lys Ala Glu Arg Gly Lys Phe His Gln
405 410 415

Lys Ser Leu Glu Arg Lys Val Gly Met Ile Asp Glu Leu Ser Tyr Leu
420 425 430

Gln Ala Val Gln Ser Tyr Glu Glu Ala Lys Ser Leu Ala Leu Lys Ala
435 440 445

Glu Tyr Gln Ser Ala Val Leu Gln Glu Ile Leu Asp Thr Leu Val Gly
450 455 460

Arg Gly Arg Phe Val Glu Glu Gly Glu Asn Asn Asp
465 470 475

<210> SEQ ID NO 45
<211> LENGTH: 465
<212> TYPE: PRT
<213> ORGANISM: Fusobacterium necrophorum

<400> SEQUENCE: 45

Met Lys Lys Asn Val Phe Met Leu Gly Gly Phe Ile Leu Leu Thr Ser
1 5 10 15

Ser Val Leu Ala Lys Glu Ala Leu Val Val Pro Glu Gln Lys Pro Glu
20 25 30

Ile Leu Val Val Glu Lys Pro Val Glu Val Ile Val Tyr Arg Asp Arg

-continued

```
        35                  40                  45

Val Leu Glu Thr Pro Ala Lys Trp Arg Pro Asn Gly Ser Ile Asp Ile
    50                  55                  60

Gln Tyr Arg Val Tyr Gly Lys Thr Glu Asn Lys Val Ala Ser Pro Arg
65                  70                  75                  80

Thr Val Pro Pro Ile Pro Ile Glu Pro Pro Arg Ile Pro Leu Val Pro
                85                  90                  95

Leu Glu Pro Pro His Ile Pro Leu Val Pro Leu Glu Pro Pro His Ile
            100                 105                 110

Pro Leu Val Pro Leu Leu Pro Pro Pro Thr Leu Glu Glu Asp Asp Gly
        115                 120                 125

Glu Thr His Trp Gln Ala Ala Ser Leu Leu Glu Gly Glu Gly Glu Val
    130                 135                 140

Tyr Asp Asp Glu Asp Val Asp Asp Leu Ser Glu Thr Val Glu Ile Pro
145                 150                 155                 160

Pro Met Gln Ala Ala Glu Ala Leu Glu Glu Lys Glu Asp Glu Lys Thr
                165                 170                 175

Ser Lys Trp Ala Arg Lys Lys Arg Tyr Asn Thr Gly Arg Leu Gln Val
            180                 185                 190

Glu Ala Lys Leu Asn Phe Thr Glu Lys Gln Ser Leu Glu Ile Arg Glu
        195                 200                 205

Arg Val Tyr His Ala Leu Arg Thr Thr Lys Val Asp Glu Asn Glu Arg
    210                 215                 220

Tyr Gly Lys Ala Ala Ala Asp Glu Asp Glu Leu Arg Leu Arg His Phe
225                 230                 235                 240

Tyr Arg Phe Gly Asn Leu Gly Asn Ser Lys Val Asn Ala Ser Ser Arg
                245                 250                 255

Leu Glu Tyr Asn Thr Leu His Asn Ser Glu Lys Met Ser Gly Ser Ala
            260                 265                 270

Tyr Leu Ala Phe Asp Ile Ser Ser Tyr Leu Phe Gln Asn Asn Phe Ile
        275                 280                 285

Lys Thr Asp Tyr Phe Arg Val Gly Pro Thr Tyr Thr Tyr Ala Met Lys
    290                 295                 300

Asn Lys Thr Asn Tyr Ser Asn Gln Ile Gly Leu Leu Leu Glu Ser Tyr
305                 310                 315                 320

Phe Ser Leu Pro Tyr Asn Phe Gly Leu Glu Leu Asn Val His Pro Lys
                325                 330                 335

Tyr Met Ala Tyr Asn Lys Glu Phe Glu Ile Gly Glu Gly Lys Thr Lys
            340                 345                 350

Lys His Glu Phe Tyr Ala Glu Val Glu Ala Lys Leu Phe His Ser Leu
        355                 360                 365

Asn Leu Tyr Lys Asn Asn Lys Trp Arg Leu Asp Leu Asn Thr Glu Gly
    370                 375                 380

Gly Tyr Asp Pro Tyr Gln Phe His Gln Tyr Lys Val Val Lys Asn Arg
385                 390                 395                 400

Glu Lys Lys Val Glu Lys Arg Ala Tyr Ser Leu Tyr Ala Leu Pro Thr
                405                 410                 415

Phe Gln Val Ser Tyr Gln Ala Thr Glu Tyr Val Asn Val Tyr Ala Thr
            420                 425                 430

Ala Gly Ala Glu Tyr Arg Asn Trp Val Asp Thr Ala Glu Ser Thr Ala
        435                 440                 445

Ser His Trp Arg Trp Gln Pro Thr Ala Trp Ala Gly Met Lys Val Thr
    450                 455                 460
```

```
Phe
465


<210> SEQ ID NO 46
<211> LENGTH: 423
<212> TYPE: PRT
<213> ORGANISM: Fusobacterium necrophorum

<400> SEQUENCE: 46

Met Lys Lys Ile Ala Ala Ile Phe Phe Leu Thr Gly Thr Val Leu Phe
1               5                   10                  15

Ala Gly Glu Ile Thr Leu Glu Glu Ala Ile Ala Arg Ala Leu Lys His
            20                  25                  30

Ser Arg Glu Val Gln Ile Ala Glu Lys Lys Phe Leu Ser Ser Lys Ile
        35                  40                  45

Lys Ala Lys Gln Ala Ile Lys Lys Ala Leu Pro Ser Leu Val Tyr Ser
    50                  55                  60

Gly Ser Tyr Gln Gln Ser Glu Tyr Glu Arg Met Gln Ala Lys Asn Arg
65                  70                  75                  80

Thr Glu Lys Gln Gly Glu Lys Ile Gly Tyr Arg Gln Ser Val Thr Leu
                85                  90                  95

Thr Gln Pro Leu Phe Gln Gly Gly Ser Ile Val Ala Glu Ile Gln Gly
            100                 105                 110

Ala Lys Tyr Tyr Glu Ser Leu Phe Glu Ile Glu Tyr Leu Gln Lys Lys
        115                 120                 125

Ile Glu Thr Arg Leu Lys Thr Ile Gln Ile Tyr Ser His Ile Ile Arg
    130                 135                 140

Ala Lys Lys Glu Leu Glu Ala Leu Arg Tyr Ser Lys Lys Gln Leu Glu
145                 150                 155                 160

Gln Arg Tyr Glu Lys Gln Lys Val Gln Leu Glu Leu Gln Leu Ile Thr
                165                 170                 175

Arg Thr Asp Leu Leu Lys Thr Glu Tyr His Leu Leu Ser Val Glu Ser
            180                 185                 190

Gln Met Glu Lys Ala Lys Asn Glu Ile Glu Val Gln Met Glu Asn Leu
        195                 200                 205

Lys Ile Gln Met Gly Leu Phe Lys Asp Glu Lys Ile Glu Ile Gln Glu
    210                 215                 220

Phe Phe Val Pro Lys Gln Cys Ser Ala Lys Ile Asp Phe Asp Lys Asp
225                 230                 235                 240

Arg Lys Gln Ala Met Glu Thr Ser Met Ser Val Leu Ser Ala Lys Tyr
                245                 250                 255

Arg Leu Glu Ile Ala Lys Ala Glu Gln Arg Gly Arg Ala Gly Glu Met
            260                 265                 270

Leu Pro Glu Ile Asn Leu Phe Ala Ser Tyr Glu Asn Val Gly Glu Arg
        275                 280                 285

Arg Thr Phe Asn Gln Ser Arg Lys Asp Met Glu Trp Ile Gly Gly Val
    290                 295                 300

Glu Val Arg Trp Lys Leu Phe Ser Phe Gly Arg Glu Tyr Asp Ser Tyr
305                 310                 315                 320

Lys Val Ala Thr Leu Glu Lys Glu Thr Gln Glu Leu Ser Gln Glu Lys
                325                 330                 335

Ile Gln Asp Ser Leu Arg Leu Lys Leu Arg Glu Ala Tyr Leu Asp Leu
            340                 345                 350

Cys Arg Leu Glu Ile Leu Arg Asp Ser Lys Thr Lys Ala Leu Glu Thr
```

```
        355                 360                 365

Ala Glu Leu Asn Phe Gln Met Glu Gln Glu Lys Tyr Asp Ala Gly Leu
    370                 375                 380

Ile Ser Val Val Asp Tyr Leu Asp Ser Glu Lys Gln Leu Arg Glu Ala
385                 390                 395                 400

Lys Val Ser Tyr Tyr Gln Thr Glu Leu Glu Tyr Tyr Tyr Ala Phe Glu
                405                 410                 415

Tyr Tyr Gln Ser Leu Leu Val
            420


<210> SEQ ID NO 47
<211> LENGTH: 172
<212> TYPE: PRT
<213> ORGANISM: Fusobacterium necrophorum

<400> SEQUENCE: 47

Val Gly Arg Lys Ser Thr Lys Ile Gly Ile Leu Phe Phe Leu Phe Leu
1               5                   10                  15

Phe Ser Leu Pro Ser Phe Ala Val Gln Lys Leu Thr Thr Thr Gln Met
            20                  25                  30

Arg Glu Asn Ser Ile Arg Ile Asn Ala Leu Glu Leu Lys Glu Met Asp
        35                  40                  45

Ile His Leu Lys Lys Val Thr Val Val Leu Asp Glu Arg Ala Leu Asn
    50                  55                  60

Phe Asp Phe Asp Lys Trp Asn Ile Lys Glu Gln Tyr Tyr Glu Val Leu
65                  70                  75                  80

Glu Asn Leu Lys Glu Tyr Ile Leu Ala Asn Asp Tyr Glu Val Val Ile
                85                  90                  95

Glu Gly His Thr Asp Ser Ile Gly Thr Asn Ala Tyr Asn Ile Gly Leu
            100                 105                 110

Ser Phe Lys Arg Ala Asn Ser Thr Lys Glu Lys Leu Ile Glu Phe Gly
        115                 120                 125

Leu Pro Ala Asp Arg Ile Val Gly Ile Ser Gly Lys Gly Glu Glu Ser
    130                 135                 140

Pro Ile Ala Thr Asn Glu Thr Pro Glu Gly Arg Ser Gln Asn Arg Arg
145                 150                 155                 160

Val Glu Phe His Leu Glu Lys Ile Gly Asp Lys Glu
                165                 170


<210> SEQ ID NO 48
<211> LENGTH: 385
<212> TYPE: PRT
<213> ORGANISM: Fusobacterium necrophorum

<400> SEQUENCE: 48

Met Lys Lys Leu Ala Leu Val Leu Gly Ser Leu Leu Val Ile Gly Ser
1               5                   10                  15

Ala Ala Ser Ala Lys Glu Val Met Pro Ala Pro Met Pro Glu Pro Glu
            20                  25                  30

Val Lys Ile Val Glu Lys Pro Val Glu Val Ile Val Tyr Arg Asp Arg
        35                  40                  45

Val Val Gln Ala Pro Ala Lys Trp Lys Pro Asn Gly Ser Val Asp Val
    50                  55                  60

Gln Tyr Arg Trp Tyr Gly Glu Thr Glu Asn Lys Val Asp Gly Gln Leu
65                  70                  75                  80

Lys Gln Glu Gly Leu Ala Glu Gly Glu His Asp Trp Ala Asn Asp Glu
```

-continued

```
                85                  90                  95

Asn Asn Tyr Gly Arg Leu Gln Thr Glu Ala Lys Ile Asn Phe Thr Glu
            100                 105                 110

Asn Gln Arg Leu Glu Ile Arg Thr Arg Asn Phe His Thr Trp Ala Gln
        115                 120                 125

Gly Lys Asn Thr Lys Asp Tyr Ser Lys Ala Lys Ala Glu Asp Asp Lys
    130                 135                 140

Ile Arg Leu Arg His Phe Tyr Asn Phe Gly Lys Ile Ala Asn Thr Lys
145                 150                 155                 160

Val Asn Ala Thr Ser Arg Leu Glu Trp Asp Gln Lys Ser Gly Asp Gly
                165                 170                 175

Ala Lys Lys Leu Glu Ala Ser Val Gly Phe Asn Phe Ala Asp Tyr Leu
            180                 185                 190

Phe Asn Asn Asp Phe Val Lys Thr Thr Asn Phe Thr Val Arg Pro Leu
        195                 200                 205

Tyr Ala His Lys Trp Thr Ala His Arg Gly Gly Gly Arg Lys Gly Ala
    210                 215                 220

Glu Val Leu Gly Leu Asn Leu Glu Ser Asn Phe Glu Phe Pro Tyr Gly
225                 230                 235                 240

Phe Glu Leu Glu Phe Lys Leu Glu Pro Thr Tyr Thr Phe Tyr Gly Thr
                245                 250                 255

Lys Gln Thr Ile Ser Asp Lys Asp Gly Glu Asn Gln Arg Glu Lys Lys
            260                 265                 270

Arg Ala Phe Asp Met Asp Val Thr Leu Ile Leu Ser Asn Ser Val Asn
        275                 280                 285

Leu Tyr Thr Gln Asp Lys Phe Ala Leu Asp Phe Asn Phe Glu Gly Gly
    290                 295                 300

Tyr Asp Pro Tyr Ser Phe His Gln Tyr Arg Ile Tyr Asp Lys Glu Glu
305                 310                 315                 320

Lys Glu Val Gly Val Lys Arg Ser Tyr Ser Leu Tyr Ala Leu Pro Thr
                325                 330                 335

Leu Glu Ala Asn Tyr Gln Ala Thr Glu Phe Val Lys Leu Tyr Ala Gly
            340                 345                 350

Ala Gly Ala Glu Tyr Arg Asn Trp Lys Ile Glu Asp Glu Asp Tyr Ala
        355                 360                 365

Thr Arg Trp Arg Trp Gln Pro Thr Ala Tyr Ala Gly Met Lys Val Asn
    370                 375                 380

Phe
385


<210> SEQ ID NO 49
<211> LENGTH: 338
<212> TYPE: PRT
<213> ORGANISM: Fusobacterium necrophorum

<400> SEQUENCE: 49

Val Lys Thr Lys Asn Phe Val Leu Glu Ser Lys Gln Asp Thr Ser Glu
1               5                   10                  15

Arg Lys Asp Ser Ser Tyr Gly Gly Ser Phe Ser Ile Asp Leu Gly Asn
            20                  25                  30

Pro Ser Asn Leu Ser Val Thr Met Asn Gly Arg Lys Gly Asn Gly Glu
        35                  40                  45

Lys Glu Trp Val Glu Lys Gln Thr Ser Phe Ile Ala Arg Asn Gly Gly
    50                  55                  60
```

-continued

Lys Ile Asp Thr Asp Ser Leu Thr Asn Ile Gly Ala Val Ile Gly Ser
65 70 75 80

Glu Ser Glu Thr Glu Lys Leu Lys Val Ser Ala Asn Gln Val Ile Val
85 90 95

Lys Asp Leu Glu Asp Lys Asn Gln Tyr Glu Asn Met Gly Gly Gly Ile
100 105 110

Ser Ile Gly Thr Ser Ile Pro Asn Ile Ser Ile Lys His Asp Lys Ile
115 120 125

Glu Lys Glu Gln Ile Asn Arg Ala Thr Ala Ala Asn Thr Glu Phe Gly
130 135 140

Ile Ser Gly Lys Lys Thr Ser Ala Glu Asp Leu Gly Phe Asn Thr Asp
145 150 155 160

Ile Asn Lys Thr Gln Glu Val Thr Lys Asn Glu Glu Lys His Leu Asp
165 170 175

Ala Glu Leu His Ala Asp Leu Ile Gly Glu Asp Lys Arg Asn Glu Ile
180 185 190

Lys Tyr Ala Phe Lys Lys Leu Gly Ser Leu His Glu Ile Leu Asp Gln
195 200 205

Lys Lys Phe Lys Glu Ser Met Glu Gly Val Leu Val Asp Lys Phe Lys
210 215 220

Asp Glu His Gln Lys Glu Phe His Leu Ile Lys Asp Glu Asn Leu Ser
225 230 235 240

Leu Glu Asp Lys Gln Lys Leu Ala Gln Asn Leu Val Glu Lys Tyr Leu
245 250 255

Arg Glu Asn Gly Tyr Gln Gly Ile Ile Pro Glu Val Leu Leu Thr Glu
260 265 270

Glu Ala His Ser Phe Thr Val Asp Ser Lys Asp Lys Thr Thr Gly Ala
275 280 285

Lys Arg Gly Glu Lys Ile Tyr Phe Ser Ile His Asp Ile Ala Asn Pro
290 295 300

Asp Leu Ala Phe Ser Gln Leu Phe Gly His Glu Lys Ala His Met Asn
305 310 315 320

Thr Tyr Asp Glu Gly Lys Tyr Gly Glu Glu Thr Ser Phe His Cys Lys
325 330 335

Leu Gln

<210> SEQ ID NO 50
<211> LENGTH: 559
<212> TYPE: PRT
<213> ORGANISM: Fusobacterium necrophorum

<400> SEQUENCE: 50

Val Lys Gly Ser Val Asn Asn Ser Lys Thr Ile Glu Ala Thr Asn Ile
1 5 10 15

Asp Ile Thr Gly Glu Asn Leu Val Asn Ser Ser Ser Ile Lys Ala Asp
20 25 30

Asn Ile Leu Ala Thr Val Lys Thr Thr Lys Asn Asp Gly Asp Ile Leu
35 40 45

Ala Leu Lys Asp Ile Thr Leu Asn Thr Lys Lys Leu Asp Asn Thr Lys
50 55 60

Lys Ile Ala Ala Leu Gln Asn Ile Thr Ala Asn Asn Thr Ala Leu Thr
65 70 75 80

Asn Ser Gly Glu Ile Val Ser Asn His Lys Ile Glu Leu Asn His Ser
85 90 95

-continued

```
Asn Ile Ser Asn Thr Asn Lys Ile Leu Ser Asn Thr Ile Asp Met Lys
            100                 105                 110

Asn Thr Ser Asn Phe Asn Asn Thr Gly Thr Ile Ser Gly Thr Asp Val
        115                 120                 125

Thr Leu Thr Ser Val Asn Asp Ile His Leu Ile Ala Asn Leu His Gly
    130                 135                 140

Glu Asn Ser Leu Ile Ile Glu Gly Lys Asn Ile Val Asn Glu Asn Ser
145                 150                 155                 160

Ile Ser Ala Asn Asp Leu His Met Asn Ala Lys Asn Leu Thr Asn His
                165                 170                 175

Asp Leu Ile Ala Ala Glu Asn Asn Ala Asn Ile Asn Val Lys Asn Lys
            180                 185                 190

Val Thr Asn Thr Glu Asn Ser Ser Ile Tyr Ala Gly Asn Lys Leu Asn
        195                 200                 205

Ile Gln Ala Ser Glu Leu Phe Asn Asp Ser Ala Glu Ile Leu Gly Thr
    210                 215                 220

Asp Val Lys Leu Glu Ala Asn Gln Ile Thr Asn His Ile Gly Thr Leu
225                 230                 235                 240

Gln Ala Leu Asn Thr Met His Ile Lys Ala Gly Lys Phe Glu Asn Ile
                245                 250                 255

Gly Lys Val Glu Asp Leu Asp Arg Tyr Glu Ser Tyr Tyr Glu Thr Trp
            260                 265                 270

Asp Gly Gln Arg Ile Glu Ala Asn Gln Ile Glu Asp Trp Lys Val His
        275                 280                 285

Phe Ser Lys Ser Ser Ser Lys Arg Ser Asn Gly Ser Ala Gly Lys Thr
    290                 295                 300

Ile Arg Lys Arg Gln Arg Glu Ala Tyr His Glu Ile Ser Glu Lys Met
305                 310                 315                 320

Lys Asn Asp Lys Tyr Ala Ser Leu Leu Phe Pro Lys Tyr Asp Lys Leu
                325                 330                 335

Met Arg Gly Tyr Leu Gly Asp Arg Gly Glu Tyr Thr Glu Lys Thr Gly
            340                 345                 350

Ser Ala Arg Ile Gln Thr Val Pro Leu Gln Glu Lys Leu Arg Ser Leu
        355                 360                 365

Gly Lys Thr Thr His Ala Lys Val Leu Ala Gly Asn Asn Ile Leu Ile
    370                 375                 380

Glu Lys Lys Ser Asp Ser Asn Asn Glu Val Met Asn Lys Asp Gly Ile
385                 390                 395                 400

Leu Ser Ala Gly Asn Thr Ile Lys Ile Asp Ala Asn Gln Val Gln Asn
                405                 410                 415

Leu Val Ser Val Gly Asp Glu Lys Ile Lys Val Lys Thr Gly Glu Glu
            420                 425                 430

Ser Met Tyr Ile Lys Leu Glu Arg Thr Gly Lys Lys Pro Arg Lys Lys
        435                 440                 445

Val Lys Met Glu Val Ser Tyr Asp Arg Asp Phe Ala Asn Asp Tyr Ile
    450                 455                 460

Thr Lys Lys Ile Pro Lys Leu Asp Glu Lys Gly Arg Gln Val Tyr Gln
465                 470                 475                 480

Lys Lys Phe Gly Gly Arg Lys Lys Pro Val Tyr Glu Tyr Val Thr Glu
                485                 490                 495

Tyr Val Gly Arg Tyr Ala Tyr Val Thr Gly Gln Pro Ser Val Ile Glu
            500                 505                 510

Gly Lys Asn Val Val Ile Asp Asn Ala Ser Leu Val Arg Gln Gly Ile
```

```
        515                 520                 525

Glu Glu Ala Asn Gly Tyr Ile Lys Ser Gly Lys Asp Val Asn Ile Gln
    530                 535                 540

Asn Phe Thr Ser Lys Asn Phe His Thr Gly Leu Ser Asn Gly Asn
545                 550                 555


<210> SEQ ID NO 51
<211> LENGTH: 172
<212> TYPE: PRT
<213> ORGANISM: Fusobacterium necrophorum

<400> SEQUENCE: 51

Val Gly Arg Lys Ser Thr Lys Ile Gly Ile Leu Phe Phe Leu Phe Leu
1               5                   10                  15

Phe Ser Leu Pro Ser Phe Ala Val Gln Lys Leu Thr Thr Thr Gln Met
            20                  25                  30

Arg Glu Asn Ser Ile Arg Ile Asn Ala Leu Glu Leu Lys Glu Met Asp
        35                  40                  45

Ile His Leu Lys Lys Val Thr Val Val Leu Asp Glu Arg Ala Leu Asn
    50                  55                  60

Phe Asp Phe Asp Lys Trp Asn Ile Lys Glu Gln Tyr Tyr Glu Val Leu
65                  70                  75                  80

Glu Asn Leu Lys Glu Tyr Ile Leu Ala Asn Asp Tyr Glu Val Val Ile
                85                  90                  95

Glu Gly His Thr Asp Ser Ile Gly Thr Asn Ala Tyr Asn Ile Gly Leu
            100                 105                 110

Ser Phe Lys Arg Ala Asn Ser Thr Lys Glu Lys Leu Ile Glu Phe Gly
        115                 120                 125

Leu Pro Ala Asp Arg Ile Val Gly Ile Ser Gly Lys Gly Glu Glu Ser
    130                 135                 140

Pro Ile Ala Thr Asn Glu Thr Pro Glu Gly Arg Ser Gln Asn Arg Arg
145                 150                 155                 160

Val Glu Phe His Leu Glu Lys Ile Gly Asp Lys Glu
                165                 170


<210> SEQ ID NO 52
<211> LENGTH: 261
<212> TYPE: PRT
<213> ORGANISM: Fusobacterium necrophorum
<220> FEATURE:
<221> NAME/KEY: misc_feature
<222> LOCATION: (229)..(232)
<223> OTHER INFORMATION: Xaa can be any naturally occurring amino acid

<400> SEQUENCE: 52

Leu Glu Lys Lys Lys Lys Gly Leu Ser Leu Ser Ile Ser Lys Asn Ser
1               5                   10                  15

Phe Lys Val Ala Tyr Gly Lys Asn Gln Phe Asn Tyr Asp Glu Lys Asp
            20                  25                  30

Lys Thr Asn Ile Lys Ser Asn Leu Val Leu Gly Asp Gly Thr Val Leu
        35                  40                  45

Asn Lys Gly Ala Glu Ile Thr Ala Thr Asn Phe Asn His Gly Asp Ile
    50                  55                  60

Thr Ile Asn Asn Gly Asp Val Ile Tyr Gly Ala Arg Lys Asp Glu Arg
65                  70                  75                  80

Asp Val Lys Thr Ser Thr Lys Lys Ser Ser Phe Gly Ile Ser Ala Asn
                85                  90                  95
```

-continued

```
Val Ser Ser Pro Ala Leu Glu Arg Ile Lys Gln Gly Ala Asn Ala Leu
            100                 105                 110

Glu Gln Ile Gly Asn Gly Asp Ala Leu Gly Gly Leu Val Asn Val Gly
        115                 120                 125

Asn Val Val Thr Gly Thr Val Asp Gly Leu Ala Ser Asn Ile Lys Thr
    130                 135                 140

Lys Asp Gly Lys Gln Ala Thr Ala Lys Asp Val Lys Asp Asn Lys Phe
145                 150                 155                 160

Thr Ser Asn Asn Ser Phe Tyr Val Gln Ala Gly Gly Ser Ala Gly Tyr
                165                 170                 175

Ser Lys Ser Lys Gln Lys Thr Lys Ser His Thr Glu Lys Ala Val Val
            180                 185                 190

Thr Asn Ile Thr Gly Leu Asp Glu Asn Ala Lys Ile Thr Tyr Asn Asp
        195                 200                 205

Asn Lys Asn Val Lys Tyr Gln Gly Thr Gln Thr Gln Asn Thr Thr Phe
    210                 215                 220

Val Tyr Asn Asn Xaa Xaa Xaa Xaa Asp Ser Tyr Ile Asp Gly Lys Leu
225                 230                 235                 240

Thr Thr Asp Ser Lys Ala Ile Tyr Asn Lys Tyr Ile Leu Glu Ser Ile
                245                 250                 255

Gly Ile Phe Phe Phe
            260
```

<210> SEQ ID NO 53
<211> LENGTH: 1420
<212> TYPE: PRT
<213> ORGANISM: Fusobacterium necrophorum

<400> SEQUENCE: 53

```
Met Lys Lys Leu Lys Asn Phe Glu Asn Val Leu Lys Ser His Leu Lys
1               5                   10                  15

Gln Arg Val Arg Ile Thr Thr Ala Phe Ile Val Ala Phe Leu Ile His
            20                  25                  30

Gly Met Leu Ser Phe Asp Val Glu Ala Arg Asp Leu Arg Val Arg Asn
        35                  40                  45

Gln Ile Thr Pro Ser Asn Ser Asn Asn Gly Leu Arg Ile Thr Ser Ser
    50                  55                  60

Gln Asn Gly Thr Asp Val Ile Asn Ile Val Asp Pro Asn Asn Gly Ile
65                  70                  75                  80

Ser His Asn Lys Tyr Val Asp Phe Asn Val Gly Asp Lys Asn Asn Val
                85                  90                  95

Ile Phe Asn Asn Ser Gln Lys Asn Gly Thr Ser Val Thr Gly Gly Glu
            100                 105                 110

Val Ser Ala Asn Pro Asn Leu Thr Asn Ser Ala Ser Val Ile Leu Asn
        115                 120                 125

Glu Ile Gln Gly Asn Ser Ala Ser Glu Leu Asn Gly Gly Leu Glu Val
    130                 135                 140

Phe Gly Lys Arg Ala Asp Leu Val Ile Ala Asn Glu Asn Gly Ile Asn
145                 150                 155                 160

Val Asn Gly Ala Arg Phe Ile Asn Thr Ser Ala Leu Thr Leu Ser Thr
                165                 170                 175

Gly Lys Val Ser Val Asp Asn Lys Lys Ile Ser Phe Asn Thr Ala Thr
            180                 185                 190

Asn Asn Ala Lys Ile Ala Val Lys Glu Lys Gly Ile Glu Thr Asp Ser
        195                 200                 205
```

-continued

```
Asp Tyr Leu Asn Ile Leu Ser Arg Arg Ala Glu Leu Asp Gly Ala Ile
    210                 215                 220

Asn Ser Glu His Asn Lys Asn Leu Asn Ile Asn Val Ile Ala Gly Ala
225                 230                 235                 240

Asn Thr Val Thr Ala Val Asn Asp Thr Phe Glu Leu Asn Ala Glu Asn
                245                 250                 255

Ala Lys Asp Gly Ile Thr Asn Val Glu Ala Ile Ser Ala Ser Lys Phe
            260                 265                 270

Gly Ala Met Tyr Gly Asn Asn Ile Phe Ile Leu Ser Thr Asn Lys Gly
        275                 280                 285

Glu Gly Ile Lys Tyr Glu Gly Ser Leu Lys Ala Lys Asp Glu Val Glu
    290                 295                 300

Ile Ile Ser Glu Gly Lys Val Val Ser Ser Asp Ile Asn Gly Lys Asp
305                 310                 315                 320

Ile Lys Ile Ser Ser Lys Glu Glu Ile Asn Asn Ile Gly Lys Met Lys
                325                 330                 335

Ala Asp Lys Asn Val Ser Leu Asn Ala Pro Ile Val Lys Asn Met Ser
            340                 345                 350

Arg Leu Glu Gly Ser Val Arg Leu Lys Ser Asn Glu His Asn Lys Lys
        355                 360                 365

Tyr Gln Asn Arg Glu Arg Gly Ile Ile Tyr Tyr Asp Tyr Tyr Leu Asn
    370                 375                 380

Val Lys Asn Met Ser Glu Val Glu Asn Glu Leu Lys Leu Val Lys Ser
385                 390                 395                 400

Ser Ile Glu Ala Gly Asn Asn Ile Glu Ile Asn Asn Asn Leu Glu Asn
                405                 410                 415

Gly Ser Phe Glu Asn Leu Ser Gly Asp Leu Lys Ala Gly Asn Asp Ile
            420                 425                 430

Lys Val Lys Gly Asn Phe Lys Thr Lys His Leu Ser Glu Gly Ile Lys
        435                 440                 445

Leu Glu Asp Leu Leu Lys Arg Ile Lys Val Asp Leu Arg Trp Glu His
    450                 455                 460

Arg Ser Leu Val Asp Asn Ala Tyr Phe Asn Gly Asn Ser Ser Leu Thr
465                 470                 475                 480

Asp Gly Ser Leu Leu Asp Ala Leu Lys Ile Met Thr Gln Lys Lys Asn
                485                 490                 495

Lys Glu Tyr Tyr Thr Ala Leu Lys Gln Ile Asp Asp Pro Gln Leu Asn
            500                 505                 510

Lys Val Leu Ser Gly Leu Leu Gly Ala Asp Trp Arg Thr Arg Glu Arg
        515                 520                 525

Ile Lys Asp Glu Lys Asp Trp Asn Lys Glu Ala Ala Ile Ser Phe Thr
    530                 535                 540

Asn Gly Thr Tyr Ser Ile Glu Ala Gly Asn Asp Leu Lys Ala Ser Gly
545                 550                 555                 560

Lys Val Ile Glu Leu Gly Gly Ser Asn Val Met Thr Lys Lys Glu Ile
                565                 570                 575

Phe Glu Val Ala Ser Thr Lys Thr Glu Ser Leu Gln Ser Thr Ile Ser
            580                 585                 590

Asp Val Lys Asn Ala Asn Ile Lys Ala Lys Asn Val Tyr Met Glu Ala
        595                 600                 605

Asp Asn Ile Thr Asn Val Asn Ala Asp Ile Ala Ala Glu Asp Ser Ala
    610                 615                 620
```

Ile Leu Tyr Ser Lys Asn Asn Ile Asp Val Lys Gly Ala Lys Val Ser
625 630 635 640

Ala Asp Lys Ile Leu Leu Glu Ala Gly Lys Asp Ile Asn Leu Ser Ser
645 650 655

Glu Leu Gly Phe Lys Ser Ser Gly Glu His Ala Ile Ile Lys Glu Thr
660 665 670

Asp Val Thr Ala Asn Lys Ala Val Gly Ile Lys Ser Lys Asn Leu Asn
675 680 685

Ile Tyr Gly Ala Asp Val Glu Ala Lys Asp Gly Leu Ile Lys Ile Asp
690 695 700

Ser Asp Lys Leu Asn Val Lys Asp Ile Ser Thr Ile Asn Ala Asn Tyr
705 710 715 720

Lys Ala Glu Leu Ile Glu Gly Lys Lys Tyr Ile Leu Arg Asp His Gln
725 730 735

Tyr Thr Lys Ala Leu Gln Ala Lys Val Glu Ser Thr Pro Ser Lys Ile
740 745 750

Ile Ala Asn Lys Ile Phe Ile Thr Ala Lys Asp Gly Ala Ala Ile Glu
755 760 765

Gly Ser Leu Ile Ser Gly Lys Asn Ala Asp Ser Ile Ile Gln Ile Ile
770 775 780

Ser Glu Gly Asn Val Asn Ile Lys Asn Ser Asn Asn Ile Asp Tyr Ser
785 790 795 800

Asn Phe Tyr Ser Asp Ser Arg Gly Lys Asn Lys Lys Gly Val Tyr Lys
805 810 815

Leu Leu Lys Ile Asp Lys Ala Ser Lys Glu Asn Leu Asp Ile Val Gly
820 825 830

Ser Asn Leu Lys Ser Glu Gly Asn Ile Asn Ile Lys Ser Lys Asn Leu
835 840 845

Thr Val Val Ser Ser Lys Ile Lys Ala Gly Lys Lys Val Asn Leu Glu
850 855 860

Ala Glu Glu Asp Ile Lys Leu Leu Ala Ser Leu Asn Ser Lys Lys Glu
865 870 875 880

Glu Leu Asn Lys Met Glu Trp Gly Ser Gly Ala Ile Asn Ser Tyr Lys
885 890 895

Lys Ser Leu Glu Lys Lys Asp Val Val Ser Thr Met Ile Glu Ala Gly
900 905 910

Glu Lys Ala Asn Val His Ala Lys Arg Asp Leu Tyr Lys Gln Ser Val
915 920 925

Phe Val Lys Ala Gly Ser Val Thr Met Asn Gly Glu Ala Asn Asn Tyr
930 935 940

Ser Asp Ala Leu Ala Ser Thr Glu Ile Lys Lys Glu Thr Asp Val Lys
945 950 955 960

Ala Gly Phe Gly Val Glu Gly Lys Ile Ala Phe Ala Gly Met Gly Ala
965 970 975

Ala Gly Glu Ala Asn Thr Leu Asp Asn Thr Ala Thr Gly Lys Thr Ser
980 985 990

Gly Ile Lys Gly Leu Leu Glu Lys Glu Asn Glu Phe Lys Lys Ala Glu
995 1000 1005

Ala Arg Ala Lys Val Tyr Ala Lys Met Glu Val Asn Lys Ser Ile
1010 1015 1020

Lys Glu Ser Lys Asn Tyr Val Asn Asn Asn Ile Thr Ser Glu Ser
1025 1030 1035

Gly Asp Val Thr Ile Gly Ser Asn Gly Val Thr Asp Ile Gly Asn

```
    1040                1045                1050

Thr Asp  Ile Asn Ser Gln Asn  Asp Val Asn Leu Arg  Gly Lys Lys
    1055                1060                1065

Val Glu  Thr Thr Thr Lys Glu  Asn Val Thr Lys Glu  Val Asn His
    1070                1075                1080

Lys Leu  Asp Leu Ser Val Lys  Gly Asp Ile Ala Phe  Ser Asn Glu
    1085                1090                1095

Asn Val  Asn Lys Leu Asn Asp  Leu Ala Asn Asp Val  Leu Lys Ser
    1100                1105                1110

Lys Glu  Met Leu Glu Lys Lys  Asp Ile Leu Gly Leu  Ala Gln Lys
    1115                1120                1125

Ala Glu  Glu Thr Ile Lys Asp  Leu Lys Glu Thr Ile  Pro Asn Leu
    1130                1135                1140

Thr Lys  Lys Asp Ile Leu Gly  Ile Lys Ser Ser Gln  Gly Val Gly
    1145                1150                1155

Val Glu  Tyr Thr Asn Lys Thr  Ser Thr Thr Thr Glu  Thr Thr Ala
    1160                1165                1170

Ser Ser  Leu Lys Ala Lys Gly  Lys Leu Asn Ile Lys  Ala Asp Glu
    1175                1180                1185

Gly Asp  Ile Thr Leu Lys Asn  Thr Tyr Leu Lys Ala  Gln Glu Phe
    1190                1195                1200

Asn Thr  Glu Thr Pro Gly Lys  Val Asn Leu Leu Ala  Gly Lys Lys
    1205                1210                1215

Thr Ile  His Lys Glu Glu Asn  Ser Leu Lys Val Gly  Val Ser Val
    1220                1225                1230

Asn Glu  Asn Val Gly Val Asn  Ile Ala Asp Gly Ala  Asn Ala Lys
    1235                1240                1245

Ile Gly  Val Gly Val Gln Ala  Ser Tyr Asn Gly Gly  Thr Asp Leu
    1250                1255                1260

Asn Lys  Lys Ser Leu Asn Thr  Thr Val Glu Val Gly  Lys Val Asn
    1265                1270                1275

His Lys  Ala Ala Ala Val Asn  Glu Asp Asn Lys Thr  Asp Phe Tyr
    1280                1285                1290

Tyr Lys  Asp Lys Arg Gly Ala  Gly Val Asp Val Asp  Leu Lys Ile
    1295                1300                1305

Gly Val  Ser Ser Asn His Ile  Val Ala Ala Asp Gly  Asn Val Gly
    1310                1315                1320

Gly Asn  Val Asn Tyr Ser Phe  Ala Ala Gly Lys Ser  Thr Thr Asp
    1325                1330                1335

Val Val  Thr Asn Lys Thr Glu  Ser Thr Asp Val Lys  Ala Gly Val
    1340                1345                1350

Gly Leu  Lys Ala Ser Val Gly  Ile Asp Gly Lys Ser  Pro Asp Phe
    1355                1360                1365

Ser Ile  Ser Thr Asp Gln Ile  Glu Tyr Lys Lys Asp  Gly Lys Val
    1370                1375                1380

Leu Val  Asn Ile Asp Ala Lys  Asp Lys Met Ile Thr  Lys Glu Arg
    1385                1390                1395

Ile Glu  Gln Met Arg Asp Lys  Val Lys Asn Trp Arg  Thr Pro Thr
    1400                1405                1410

Asn Ser  Ala Glu Lys Leu Ile
    1415                1420
```

<210> SEQ ID NO 54

```
<211> LENGTH: 707
<212> TYPE: PRT
<213> ORGANISM: Fusobacterium necrophorum

<400> SEQUENCE: 54

Met Lys Arg Thr Leu Val Ala Met Leu Leu Phe Leu Val Ser Met Val
1               5                   10                  15

Ser Phe Ala Ala Gly Gly Ser Leu Ile Val Lys Lys Val Glu Val Leu
            20                  25                  30

Asn Asn Gln Glu Val Pro Ala Ser Ile Ile Leu Asn Gln Met Asp Leu
        35                  40                  45

Lys Glu Gly Lys Pro Phe Ser Thr Glu Ile Met Leu His Asp Phe Gln
    50                  55                  60

Thr Leu Lys Lys Ser Lys Tyr Leu Glu Asp Val Leu Ile Gln Pro Gln
65                  70                  75                  80

Ala Tyr Glu Gly Gly Val Asn Val Val Val Asn Val Ile Glu Lys Lys
                85                  90                  95

Asp Val Gln Ser Leu Leu Arg Glu Asp Gly Val Ile Ser Met Ser Glu
            100                 105                 110

Gln Ala Asn Val Asp Lys Ser Leu Ile Leu Ser Asp Ile Ile Ile Ser
        115                 120                 125

Gly Asn Gln Phe Val Ser Thr Ala Asp Leu Lys Lys Val Leu Ser Val
    130                 135                 140

Lys Gln Gly Gly Tyr Phe Ser Lys Thr Ala Ile Glu Asp Gly Gln Lys
145                 150                 155                 160

Ala Leu Leu Ala Thr Gly Tyr Phe Arg Glu Val Thr Pro Asn Thr Gln
                165                 170                 175

Lys Asn Gly Asn Gly Val Lys Ile Ile Tyr Thr Val Val Glu Asn Pro
            180                 185                 190

Val Ile Gln Gly Ile Asn Ile His Gly Asn Thr Leu Phe Ser Thr Pro
        195                 200                 205

Asp Ile Leu Lys Val Leu Lys Thr Lys Ile Gly Glu Val Leu Asn Ile
    210                 215                 220

Asn Ser Leu Arg Glu Asp Arg Asp Thr Ile Met Asn Leu Tyr Gln Asp
225                 230                 235                 240

Gln Gly Tyr Thr Leu Ser Glu Ile Ser Asp Met Gly Leu Asn Asp Arg
                245                 250                 255

Gly Glu Leu Glu Val Val Ile Ser Glu Gly Ile Ile Arg Asn Val Ser
            260                 265                 270

Phe Gln Lys Met Val Thr Lys Gln Lys Gly Asn Arg Arg Lys Pro Thr
        275                 280                 285

Asp Asp Ile Leu Lys Thr Gln Asp Tyr Val Ile Gln Arg Glu Ile Glu
    290                 295                 300

Leu Gln Glu Gly Lys Ile Tyr Asn Ala Lys Asp Tyr Asp Asn Thr Val
305                 310                 315                 320

Gln Asn Leu Met Arg Leu Gly Val Phe Lys Asn Ile Lys Ser Glu Ile
                325                 330                 335

Arg Arg Val Pro Gly Asp Pro Asn Gly Arg Asp Ile Val Leu Leu Ile
            340                 345                 350

Asp Glu Asp Arg Thr Ala Ile Leu Gln Gly Ala Ile Ser Tyr Gly Ser
        355                 360                 365

Glu Thr Gly Leu Met Gly Thr Leu Ser Leu Lys Asp Asn Asn Trp Lys
    370                 375                 380

Gly Arg Ala Gln Glu Phe Gly Val Asn Phe Glu Lys Ser Asn Lys Asp
```

385 390 395 400

Tyr Thr Gly Phe Thr Ile Asp Phe Phe Asp Pro Trp Ile Arg Asp Thr
405 410 415

Asp Arg Ile Ser Trp Gly Trp Ser Leu Tyr Lys Thr Ser Tyr Gly Asp
420 425 430

Ser Asp Ser Ala Leu Phe Asn Asp Ile Asp Thr Ile Gly Ala Lys Ile
435 440 445

Asn Val Gly Lys Gly Phe Ala Arg Asn Trp Arg Phe Ser Leu Gly Phe
450 455 460

Lys Gly Glu Tyr Val Lys Glu Lys Ala Asn Lys Gly Asn Phe Arg Gln
465 470 475 480

Leu Pro Asp Gly Thr Trp Tyr Tyr Thr Gly Lys Asn Lys Asn Asp Ala
485 490 495

Ser Asn Thr Pro Leu Pro Lys Asp Ala Val Asn Asp Lys Tyr Met Val
500 505 510

Phe Ser Ile Phe Pro Tyr Leu Thr Tyr Asp Thr Arg Asn Asn Pro Trp
515 520 525

Asn Ala Thr Thr Gly Glu Tyr Ala Lys Leu Gln Leu Glu Thr Gly Tyr
530 535 540

Ala Gly Gly Tyr Lys Ser Gly Ser Phe Ser Asn Val Thr Leu Glu Leu
545 550 555 560

Arg Lys Tyr His Arg Gly Phe Trp Lys Lys Asn Thr Phe Ala Tyr Lys
565 570 575

Val Val Gly Gly Val Met Thr Gln Ser Thr Lys Glu Gly Gln Arg Phe
580 585 590

Trp Val Gly Gly Gly Asn Thr Leu Arg Gly Tyr Asp Gly Gly Thr Phe
595 600 605

Arg Gly Thr Gln Lys Leu Ala Ala Thr Ile Glu Asn Arg Thr Gln Ile
610 615 620

Asn Asp Ile Leu Gly Ile Val Phe Phe Ala Asp Ala Gly Arg Ala Trp
625 630 635 640

Lys Gln Asn Gly Arg Asp Pro Glu Tyr Gly Asn Asp Glu Lys Phe Ser
645 650 655

Lys Gly Ile Ala Thr Thr Ala Gly Val Gly Leu Arg Leu Asn Thr Pro
660 665 670

Met Gly Pro Leu Arg Phe Asp Phe Gly Trp Pro Val Gly Lys Ser Gln
675 680 685

Asp Lys Tyr Ser Asn Asp Arg Gly Met Lys Phe Tyr Phe Asn Met Gly
690 695 700

Gln Ser Phe
705

<210> SEQ ID NO 55
<211> LENGTH: 39
<212> TYPE: DNA
<213> ORGANISM: Artificial
<220> FEATURE:
<223> OTHER INFORMATION: primer

<400> SEQUENCE: 55
tcaatttgct aggggatctg ccgaaatcga tctgggcac 39

<210> SEQ ID NO 56
<211> LENGTH: 36
<212> TYPE: DNA
<213> ORGANISM: Artificial

<220> FEATURE:
<223> OTHER INFORMATION: primer

<400> SEQUENCE: 56
ccatggctag ctagctagtg gtggtggtgg tggtgc 36

<210> SEQ ID NO 57
<211> LENGTH: 23
<212> TYPE: DNA
<213> ORGANISM: Artificial
<220> FEATURE:
<223> OTHER INFORMATION: primer

<400> SEQUENCE: 57
tagctagcta gccatggcat cac 23

<210> SEQ ID NO 58
<211> LENGTH: 31
<212> TYPE: DNA
<213> ORGANISM: Artificial
<220> FEATURE:
<223> OTHER INFORMATION: primer

<400> SEQUENCE: 58
agatccccta gcaaattgaa gagaaagatc t 31

<210> SEQ ID NO 59
<211> LENGTH: 39
<212> TYPE: DNA
<213> ORGANISM: Artificial
<220> FEATURE:
<223> OTHER INFORMATION: primer

<400> SEQUENCE: 59
tactgttata gatctttctg aacaaacgat tgaactggg 39

<210> SEQ ID NO 60
<211> LENGTH: 36
<212> TYPE: DNA
<213> ORGANISM: Artificial
<220> FEATURE:
<223> OTHER INFORMATION: primer

<400> SEQUENCE: 60
tccctgcctc tgtcacttcc tttcgggctt tgttag 36

<210> SEQ ID NO 61
<211> LENGTH: 18
<212> TYPE: DNA
<213> ORGANISM: Artificial
<220> FEATURE:
<223> OTHER INFORMATION: primer

<400> SEQUENCE: 61
tgacagaggc agggagtg 18

<210> SEQ ID NO 62
<211> LENGTH: 32
<212> TYPE: DNA
<213> ORGANISM: Artificial
<220> FEATURE:
<223> OTHER INFORMATION: primer

<400> SEQUENCE: 62
agaaagatct ataacagtag ccatatttaa ac 32

<210> SEQ ID NO 63
<211> LENGTH: 423
<212> TYPE: PRT
<213> ORGANISM: F. necrophorum

<400> SEQUENCE: 63

```
Met Lys Lys Leu Trp Ile Leu Phe Phe Leu Leu Gly Ser Val Ala Phe
1               5                   10                  15

Gly Arg Glu Val Thr Leu Glu Glu Ala Ile Gln Ala Ser Met Glu Asn
            20                  25                  30

Ser Lys Ala Val Lys Ile Ser Asp Lys Gln Leu Glu Ile Ser Lys Leu
        35                  40                  45

Lys Met Asn Gln Ala Ile Lys Lys Ala Leu Pro Ser Val Val Tyr Ser
    50                  55                  60

Ala Asn Tyr Gln Arg Gly Glu Tyr Glu Arg Asn Ile Tyr Lys Asn Lys
65                  70                  75                  80

Ser Ser Met Glu Ser Glu Lys Gly Gly Tyr Lys Gln Ser Ile Thr Ile
                85                  90                  95

Ser Gln Pro Ile Phe Gln Gly Gly Ala Ile Leu Ala Gly Ile Gln Gly
            100                 105                 110

Ala Lys Ala Tyr Lys Thr Ile Ala Asp Leu Ser Tyr Val Gln Glu Thr
        115                 120                 125

Leu Asn Thr Arg Leu Lys Thr Ile Arg Thr Phe Ser Asn Ile Val Asn
    130                 135                 140

Ser Lys Arg Asn Leu Gln Ala Leu Glu Tyr Ser Glu Lys Gln Leu Gln
145                 150                 155                 160

Asn Arg Tyr Lys Lys Gln Glu Ala Gln Leu Glu Leu Arg Leu Ile Thr
                165                 170                 175

Lys Thr Asp Leu Leu Lys Thr Glu Tyr Ser Leu Leu Glu Val Gln Ser
            180                 185                 190

Leu Ile Ser Lys Ala Lys Ser Asn Ile Glu Val Gln Thr Glu Asp Leu
        195                 200                 205

Lys Phe Gln Met Gly Val Asp Lys Lys Glu Ala Leu Glu Val Lys Glu
    210                 215                 220

Phe Ile Val Pro Asn His Leu Thr Glu Arg Ile Thr Phe Glu Lys Asp
225                 230                 235                 240

Lys Glu Arg Ala Leu Glu Ser Ser Ile Gln Ala Leu Ile Ala Lys Ser
                245                 250                 255

Gln Val Lys Ile Ala Lys Ala Gln Glu Thr Ala Ala Leu Gly Asn Met
            260                 265                 270

Leu Pro Lys Val Asn Ala Phe Val Ser Tyr Gly Val Ala Ser Glu Arg
        275                 280                 285

Thr His Trp Lys Gln Thr Arg Glu Asp Ala Glu Trp Met Gly Gly Leu
    290                 295                 300

Ser Val Ser Trp Asn Val Phe Ser Phe Gly Ser Asp Tyr Asp Ala Tyr
305                 310                 315                 320

Gln Ile Ala Lys Leu Glu Lys Glu Ser Lys Glu Leu Ser Glu Thr Thr
                325                 330                 335

Ala Gln Asp Asn Ile Ala Leu Ser Leu Lys Thr Ala Tyr Leu Glu Leu
            340                 345                 350

Gln Arg Leu Glu Ile Leu Arg Glu Ser Arg Lys Arg Gly Leu Glu Ala
        355                 360                 365

Ala Glu Leu Asn Phe Thr Met Asp Gln Glu Lys Phe Asp Ala Gly Leu
    370                 375                 380
```

```
Leu Ser Thr Val Asp Tyr Leu Ser Ser Glu Thr Gln Leu Arg Glu Ala
385                 390                 395                 400

Arg Val Asn Tyr Tyr Gln Ala Glu Leu Asp Tyr Tyr Tyr Ala Phe Glu
                405                 410                 415

Tyr Tyr Arg Ser Leu Leu Val
            420


<210> SEQ ID NO 64
<211> LENGTH: 423
<212> TYPE: PRT
<213> ORGANISM: F. necrophorum

<400> SEQUENCE: 64

Met Lys Lys Leu Trp Ile Leu Phe Phe Leu Leu Gly Ser Val Ala Phe
1               5                   10                  15

Gly Arg Glu Val Thr Leu Glu Glu Ala Ile Gln Ala Ser Met Glu Asn
            20                  25                  30

Ser Lys Ala Val Lys Ile Ser Asp Lys Gln Leu Glu Ile Ser Lys Leu
        35                  40                  45

Lys Met Asn Gln Ala Ile Lys Lys Ala Leu Pro Ser Val Val Tyr Ser
    50                  55                  60

Ala Asn Tyr Gln Arg Gly Glu Tyr Glu Arg Asn Ile Tyr Lys Asn Lys
65                  70                  75                  80

Ser Ser Met Glu Ser Glu Lys Gly Gly Tyr Lys Gln Ser Ile Thr Ile
                85                  90                  95

Ser Gln Pro Ile Phe Gln Gly Gly Ala Ile Leu Ala Gly Ile Gln Gly
            100                 105                 110

Ala Lys Ala Tyr Lys Thr Ile Ala Asp Leu Ser Tyr Val Gln Glu Thr
        115                 120                 125

Leu Asn Thr Arg Leu Lys Thr Ile Arg Thr Phe Ser Asn Ile Val Asn
    130                 135                 140

Ser Lys Arg Asn Leu Gln Ala Leu Glu Tyr Ser Glu Lys Gln Leu Gln
145                 150                 155                 160

Asn Arg Tyr Lys Lys Gln Glu Ala Gln Leu Glu Leu Arg Leu Ile Thr
                165                 170                 175

Lys Thr Asp Leu Leu Lys Thr Glu Tyr Ser Leu Leu Glu Val Gln Ser
            180                 185                 190

Leu Ile Ser Lys Ala Lys Ser Asn Ile Glu Val Gln Thr Glu Asp Leu
        195                 200                 205

Lys Phe Gln Met Gly Val Asn Lys Lys Glu Ala Leu Glu Val Lys Glu
    210                 215                 220

Phe Ile Val Pro Asn His Leu Thr Glu Arg Ile Thr Phe Glu Lys Asp
225                 230                 235                 240

Lys Glu Arg Ala Leu Glu Ser Ser Ile Gln Ala Leu Ile Ala Lys Ser
                245                 250                 255

Gln Val Lys Ile Ala Lys Ala Gln Glu Thr Ala Ala Leu Gly Asn Met
            260                 265                 270

Leu Pro Lys Val Asn Ala Phe Val Ser Tyr Gly Val Ala Ser Glu Arg
        275                 280                 285

Thr His Trp Lys Gln Thr Arg Glu Asp Ala Glu Trp Met Gly Gly Leu
    290                 295                 300

Ser Val Ser Trp Asn Val Phe Ser Phe Gly Ser Asp Tyr Asp Ala Tyr
305                 310                 315                 320

Gln Ile Ala Lys Leu Glu Lys Glu Ser Lys Glu Leu Ser Glu Thr Thr
```

```
                325                 330                 335

Ala Gln Asp Asn Ile Ala Leu Ser Leu Lys Thr Ala Tyr Leu Glu Leu
            340                 345                 350

Gln Arg Leu Glu Ile Leu Arg Glu Ser Arg Lys Arg Gly Leu Glu Ala
        355                 360                 365

Ala Glu Leu Asn Phe Thr Met Asp Gln Glu Lys Phe Asp Ala Gly Leu
    370                 375                 380

Leu Ser Thr Val Asp Tyr Leu Ser Ser Glu Thr Gln Leu Arg Glu Ala
385                 390                 395                 400

Arg Val Asn Tyr Tyr Gln Ala Glu Leu Asp Tyr Tyr Tyr Ala Phe Glu
                405                 410                 415

Tyr Tyr Arg Ser Leu Leu Val
            420


<210> SEQ ID NO 65
<211> LENGTH: 423
<212> TYPE: PRT
<213> ORGANISM: F. necrophorum

<400> SEQUENCE: 65

Met Lys Lys Leu Trp Ile Leu Phe Phe Leu Leu Gly Asn Val Ala Phe
1               5                   10                  15

Gly Arg Glu Val Thr Leu Glu Glu Ala Ile Gln Ala Ser Met Glu Asn
            20                  25                  30

Ser Lys Ala Val Lys Ile Ser Asp Lys Gln Leu Glu Ile Ser Lys Leu
        35                  40                  45

Lys Met Asn Gln Ala Ile Lys Lys Ala Leu Pro Ser Val Val Tyr Ser
    50                  55                  60

Thr Asn Tyr Gln Arg Gly Glu Tyr Glu Arg Asn Ile Tyr Lys Asn Lys
65                  70                  75                  80

Ser Ser Met Glu Ser Glu Lys Gly Gly Tyr Lys Gln Ser Ile Thr Ile
                85                  90                  95

Ser Gln Pro Ile Phe Gln Gly Gly Ala Ile Leu Ala Gly Ile Gln Gly
            100                 105                 110

Ala Lys Ala Tyr Lys Thr Ile Ala Asp Leu Ser Tyr Val Gln Glu Thr
        115                 120                 125

Leu Asn Thr Arg Leu Lys Ala Ile Arg Thr Phe Ser Asn Ile Val Asn
    130                 135                 140

Ser Lys Arg Asn Leu Gln Ala Leu Glu Tyr Ser Glu Lys Gln Leu Gln
145                 150                 155                 160

Asn Arg Tyr Lys Lys Gln Glu Ala Gln Leu Glu Leu Arg Leu Ile Thr
                165                 170                 175

Lys Thr Asp Leu Leu Lys Thr Glu Tyr Ser Leu Leu Glu Val Gln Ser
            180                 185                 190

Leu Ile Ser Lys Ala Lys Ser Asn Ile Glu Val Gln Thr Glu Asp Leu
        195                 200                 205

Lys Phe Gln Met Gly Val Asp Lys Lys Glu Val Leu Glu Val Lys Glu
    210                 215                 220

Phe Ile Val Pro Asn His Leu Thr Glu Arg Ile Thr Phe Glu Lys Asp
225                 230                 235                 240

Lys Glu Lys Ala Leu Glu Ser Ser Ile Gln Ala Leu Ile Ala Lys Ser
                245                 250                 255

Gln Val Lys Ile Ala Lys Ala Gln Glu Thr Ala Ala Leu Gly Asn Met
            260                 265                 270
```

-continued

```
Leu Pro Lys Val Asn Ala Phe Val Ser Tyr Gly Val Ala Ser Glu Arg
        275                 280                 285

Thr His Trp Lys Gln Thr Arg Glu Asp Ala Glu Trp Met Gly Gly Leu
    290                 295                 300

Ser Val Ser Trp Asn Val Phe Ser Phe Gly Ser Asp Tyr Asp Ala Tyr
305                 310                 315                 320

Gln Ile Ala Lys Leu Glu Lys Glu Ser Lys Glu Leu Ser Glu Met Thr
                325                 330                 335

Ala Gln Asp Ser Ile Ala Leu Ser Leu Lys Thr Ala Tyr Leu Glu Leu
            340                 345                 350

Gln Arg Leu Glu Ile Leu Arg Glu Ser Arg Lys Arg Gly Leu Glu Ala
        355                 360                 365

Ala Glu Leu Asn Phe Thr Met Asp Gln Glu Lys Phe Asp Ala Gly Leu
    370                 375                 380

Leu Ser Thr Val Asp Tyr Leu Ser Ser Glu Thr Gln Leu Arg Glu Ala
385                 390                 395                 400

Arg Val Asn Tyr Tyr Gln Ala Glu Leu Asp Tyr Tyr Tyr Ala Phe Glu
                405                 410                 415

Tyr Tyr Arg Ser Leu Leu Val
            420


<210> SEQ ID NO 66
<211> LENGTH: 423
<212> TYPE: PRT
<213> ORGANISM: F. gonidiaformans

<400> SEQUENCE: 66

Met Lys Lys Ile Trp Thr Met Phe Phe Leu Val Gly Ser Leu Ala Phe
1               5                   10                  15

Ala Arg Glu Ile Thr Leu Glu Glu Ala Ile Gln Glu Ser Met Asn His
            20                  25                  30

Ser Lys Thr Leu Lys Ile Ser Glu Lys Lys Leu Gln Ile Ser Lys Leu
        35                  40                  45

Asn Arg Ser Gln Ala Ile Lys Lys Ala Leu Pro Ser Val Leu Tyr Asn
    50                  55                  60

Thr Ser Tyr Gln Arg Thr Glu Tyr Glu Arg Asn Ile Ser Lys Asn Lys
65                  70                  75                  80

Ser Ser Met Gln Leu Glu Lys Gly Gly Tyr Lys Gln Ser Ile Thr Ile
                85                  90                  95

Ser Gln Pro Ile Phe Gln Gly Gly Ala Ile Ile Ala Gly Ile Gln Gly
            100                 105                 110

Ala Lys Ala Tyr Glu Thr Ile Ala Asp Leu Ser Tyr Val Gln Glu Gly
        115                 120                 125

Leu Asn Thr Arg Leu Lys Thr Ile Arg Thr Phe Ser Asn Ile Val Asn
    130                 135                 140

Ser Lys Arg Asn Leu Gln Ala Leu Glu Asn Ser Glu Lys Gln Leu Gln
145                 150                 155                 160

Lys Arg Tyr Gln Lys Gln Glu Ala Gln Leu Glu Leu Arg Leu Ile Thr
                165                 170                 175

Lys Thr Asp Leu Leu Lys Thr Lys Tyr Asn Leu Leu Glu Ile Gln Ser
            180                 185                 190

Leu Ile Ala Lys Ala Lys Ser Asn Ile Glu Val Gln Thr Glu Asp Leu
        195                 200                 205

Lys Phe Gln Met Gly Ile Asp Lys Glu Glu Gln Leu Glu Val Lys Glu
    210                 215                 220
```

```
Phe Asn Val Pro Asn His Leu Thr Asp Thr Ile Asp Phe Gln Lys Asp
225                 230                 235                 240

Lys Glu Lys Ala Leu Glu Ser Ser Ile Gln Ser Leu Ile Ala Lys Ser
                245                 250                 255

Gln Val Glu Ile Ala Lys Ala Gln Glu Thr Ala Ala Leu Gly Asn Met
            260                 265                 270

Leu Pro Lys Ile Asn Ala Phe Ala Ser Tyr Gly Val Ala Thr Glu Arg
        275                 280                 285

Thr Lys Trp Lys Gln Thr Arg Glu Asp Ala Glu Trp Met Gly Gly Leu
    290                 295                 300

Ser Val Ser Trp Asn Val Phe Ser Phe Gly Ser Asp Tyr Asp Asn Tyr
305                 310                 315                 320

Gln Ile Ala Lys Leu Glu Lys Glu Asn Lys Glu Leu Ser Glu Met Thr
                325                 330                 335

Ala Gln Asp Thr Ile Glu Leu Thr Leu Lys Thr Ala Tyr Ser Glu Leu
            340                 345                 350

Gln Arg Leu Glu Ile Leu Arg Glu Ser Arg Lys Arg Gly Leu Glu Ala
        355                 360                 365

Ala Glu Leu Asn Phe Ser Met Asp Gln Glu Lys Phe Asp Ser Gly Leu
    370                 375                 380

Ile Ser Thr Ile Asp Tyr Leu Leu Ser Glu Thr Gln Leu Arg Glu Ala
385                 390                 395                 400

Arg Val Asn Tyr Tyr Gln Ala Glu Leu Asp Tyr Tyr Tyr Ala Phe Glu
                405                 410                 415

Tyr Tyr Arg Ser Leu Leu Val
            420


<210> SEQ ID NO 67
<211> LENGTH: 423
<212> TYPE: PRT
<213> ORGANISM: F. ulcerans

<400> SEQUENCE: 67

Met Lys Lys Ile Leu Gly Leu Leu Leu Ile Leu Ser Ser Ser Val Phe
1               5                   10                  15

Ala Arg Glu Ile Thr Leu Asp Gln Ala Ile Gln Met Ser Leu Glu Asn
            20                  25                  30

Ser Lys Glu Ile Lys Ile Ser Glu Lys Asp Val Glu Val Ser Lys Leu
        35                  40                  45

Arg Val Gly Met Ala Phe Lys Asp Ala Leu Pro Ser Val Val Tyr Ser
    50                  55                  60

Gly Thr Tyr Thr Arg Gly Glu Ser Asp Arg Lys Met Tyr Arg His Gly
65                  70                  75                  80

Trp Glu Asp Gln Val Glu Arg Lys Gly Gly Tyr Thr Gln Thr Ile Ser
                85                  90                  95

Ile Ser Gln Pro Leu Phe Gln Gly Gly Ala Val Leu Gly Gly Ile Lys
            100                 105                 110

Gly Ala Lys Ala Tyr Lys Thr Ile Ala Asn Leu Leu Tyr Leu Gly Glu
        115                 120                 125

Arg Arg Asp Thr Arg Leu Lys Thr Ile Gln Asn Tyr Ser Asn Ile Val
    130                 135                 140

Lys Tyr Glu Lys Asp Leu Glu Ala Leu Glu Ser Ser Lys Arg Glu Leu
145                 150                 155                 160

Gln Ala Arg Tyr Asn Lys Gln Lys Ala Gln Leu Asp Leu Arg Leu Ile
```

```
                165                 170                 175

Thr Lys Thr Asp Leu Leu Lys Thr Glu Tyr Ser Leu Leu Glu Val Glu
            180                 185                 190

Ser Gln Ile Ile Gly Thr Lys Asn Gly Ile Thr Ile Glu Lys Glu Asn
        195                 200                 205

Leu Lys Ile Lys Thr Gly Ile Pro Lys Gln Glu Asp Val Thr Val Val
    210                 215                 220

Asp Phe Asn Val Pro Met Tyr Leu Ser Arg Asn Ile Asn Phe Lys Ala
225                 230                 235                 240

Asp Leu Asp Gln Ala Met Asn Glu Ser Ile Asn Ala Leu Val Ala Lys
                245                 250                 255

Asn Tyr Val Glu Ala Ala Asp Ala Ser Lys Met Val Ser Arg Ala Asp
            260                 265                 270

Met Leu Pro Lys Val Asn Ala Phe Ala Ser Tyr Gly Thr Ser Glu Arg
        275                 280                 285

Thr Lys Tyr Asn Pro Thr Ile Asp Glu Ala Glu Trp Arg Gly Gly Val
    290                 295                 300

Gln Val Thr Trp Asn Val Phe Glu Phe Gly Lys Asn Tyr Asp Ser Tyr
305                 310                 315                 320

Lys Val Ala Ala Ile Gly Lys Glu Gln Glu Ile Leu Arg Glu Lys Ile
                325                 330                 335

Ser Lys Asp Ser Ile Asp Ile Ser Val Thr Asp Ala Tyr Leu Glu Leu
            340                 345                 350

Ile Arg Met Glu Lys Glu Arg Asp Ser Lys Glu Arg Ala Met Glu Ala
        355                 360                 365

Ala Ile Glu Asn Phe Arg Met Asp Gln Glu Arg Tyr Asp Ala Gly Leu
    370                 375                 380

Ile Ser Thr Val Asp Tyr Leu Leu Ser Glu Ser Gln Glu Arg Glu Ala
385                 390                 395                 400

Lys Val Ser Tyr Asn Gln Ile Val Ile Asp Tyr Leu Tyr Ala Phe Glu
                405                 410                 415

Lys Tyr Arg Ser Leu Leu Ile
            420


<210> SEQ ID NO 68
<211> LENGTH: 423
<212> TYPE: PRT
<213> ORGANISM: F. varium

<400> SEQUENCE: 68

Met Lys Lys Ile Leu Gly Leu Leu Leu Ile Leu Ser Ser Ser Leu Phe
1               5                   10                  15

Ala Arg Glu Ile Thr Leu Asp Gln Ala Ile Gln Met Ala Leu Glu Asn
            20                  25                  30

Ser Lys Glu Ile Lys Val Ser Glu Lys Asp Val Glu Val Ser Lys Leu
        35                  40                  45

Lys Val Gly Ile Ala Phe Lys Asp Ala Leu Pro Ser Val Val Tyr Asn
    50                  55                  60

Gly Lys Tyr Thr Arg Gly Glu Tyr Glu Arg Lys Met Tyr Lys His Gly
65                  70                  75                  80

Trp Glu Glu Gln Val Asp Arg Lys Gly Gly Tyr Thr Gln Thr Ile Ser
                85                  90                  95

Ile Ser Gln Pro Leu Phe Gln Gly Gly Ala Ile Leu Gly Gly Ile Lys
            100                 105                 110
```

Gly Ala Lys Ala Tyr Lys Ser Ile Ala Asn Leu Leu Tyr Leu Gly Glu
115 120 125

Arg Arg Asp Thr Arg Leu Arg Thr Ile Gln Asn Tyr Ser Asn Ile Val
130 135 140

Lys Tyr Gln Lys Asp Leu Glu Ala Leu Glu Ala Ser Lys Lys Glu Leu
145 150 155 160

Gln Ala Arg Tyr Asn Lys Gln Lys Ala Gln Leu Asp Leu Arg Leu Ile
165 170 175

Thr Lys Thr Asp Leu Leu Lys Thr Glu Tyr Ser Leu Leu Asp Val Glu
180 185 190

Ser Gln Ile Ile Gly Thr Lys Asn Gly Ile Thr Ile Glu Lys Glu Asn
195 200 205

Leu Lys Ile Lys Thr Gly Ile Pro Lys His Glu Asp Val Ser Val Val
210 215 220

Glu Phe Glu Val Pro Met Tyr Leu Ser Arg Asn Ile Asn Phe Lys Ala
225 230 235 240

Asp Leu Asp Gln Ala Met Asn Glu Ser Ile Asn Ala Leu Val Ala Lys
245 250 255

Asn Tyr Val Glu Ala Ala Asp Ala Ser Arg Ile Val Ser Arg Ala Asp
260 265 270

Met Leu Pro Lys Val Asn Ala Phe Ala Ser Tyr Gly Thr Ser Glu Arg
275 280 285

Thr Lys Tyr Asn Pro Thr Ile Asp Glu Ala Glu Trp Arg Gly Gly Ile
290 295 300

Glu Val Thr Trp Asn Val Phe Glu Phe Gly Lys Asn Tyr Asp Asn Tyr
305 310 315 320

Arg Val Ala Ala Ile Gly Lys Glu Gln Glu Met Leu Arg Glu Lys Ile
325 330 335

Ser Lys Asp Ser Ile Asp Ile Asn Val Thr Asp Ala Tyr Leu Glu Leu
340 345 350

Ile Lys Met Glu Lys Glu Arg Asp Ser Lys Glu Arg Ala Met Glu Ala
355 360 365

Ala Ile Glu Asn Phe Arg Met Asp Gln Glu Arg Tyr Asp Ala Gly Leu
370 375 380

Ile Ser Thr Val Asp Tyr Leu Leu Ser Glu Ser Gln Val Arg Glu Ala
385 390 395 400

Thr Val Ala Tyr Asn Gln Ile Val Ile Asp Tyr Leu Tyr Ala Phe Glu
405 410 415

Lys Tyr Arg Ser Leu Leu Ile
420

<210> SEQ ID NO 69
<211> LENGTH: 423
<212> TYPE: PRT
<213> ORGANISM: F. nucleatum

<400> SEQUENCE: 69

Met Lys Lys Ile Leu Thr Ile Phe Met Leu Met Ala Ser Val Ala Leu
1 5 10 15

Ala Arg Asp Leu Thr Leu Glu Gln Ala Ile Asp Leu Ser Leu Asn Asn
20 25 30

Ser Lys Glu Met Arg Ile Ser Glu Lys Asn Leu Glu Ile Ser Lys Leu
35 40 45

Asn Val Ser Lys Ala Phe Lys Asn Ala Leu Pro Ser Val Thr Tyr Ser
50 55 60

Gly Thr Tyr Ala Val Gly Glu His Glu Arg Gln Ile Leu Thr Gln Ser
65 70 75 80

Glu Arg Asn Tyr Ala Ser Lys Lys Arg Gly Tyr Thr Gln Asn Leu Arg
85 90 95

Leu Thr Gln Pro Leu Phe Thr Gly Gly Thr Ile Thr Ala Gly Ile Lys
100 105 110

Gly Ala Lys Ala Tyr Glu Asn Ile Ala Ser Tyr Ser Tyr Leu Gln Ser
115 120 125

Lys Ile Gln Asn Arg Leu Asp Thr Ile Lys Ile Phe Ser Asp Ile Ile
130 135 140

Asn Ala Glu Arg Asn Leu Glu Ala Leu Glu Tyr Ser Glu Asn Ile Leu
145 150 155 160

Gln Lys Arg Tyr Gln Lys Gln Glu Glu Gln Leu Asn Leu Arg Leu Ile
165 170 175

Thr Arg Thr Asp Ile Leu Gln Thr Glu Tyr Ser Ile Glu Asp Ile Arg
180 185 190

Ala Gln Met Ile Asn Ala Lys Asn Thr Ile Asp Thr Asn Met Glu Lys
195 200 205

Leu Tyr Ile Arg Thr Gly Ile Asn Lys Ser Glu Ser Leu Asn Leu Ile
210 215 220

Pro Phe Asp Ile Pro Asn Asn Phe Ser Glu Lys Ile Asn Leu Asn Asn
225 230 235 240

Asp Leu Lys Gln Ala Ile Asn Glu Ser Leu Ser Ala Lys Val Ala Glu
245 250 255

Glu Gln Val Lys Val Ala Ser Ala Thr Arg Met Ala Ala Val Gly Asp
260 265 270

Leu Leu Pro Gln Val Asn Ala Tyr Ala Ser Tyr Gly Thr Gly Glu Arg
275 280 285

Thr Ser Phe Glu Arg Ser Tyr Lys Asp Gly Glu Trp Thr Gly Gly Ile
290 295 300

Glu Val Ser Trp Lys Val Phe Ser Phe Gly Ser Asp Leu Asp Ser Tyr
305 310 315 320

Arg Val Ala Lys Leu Gln Glu Glu Gln Glu Glu Leu Arg Glu Thr Ser
325 330 335

Thr Lys Glu Asp Ile Glu Val Asn Val Arg Ser Ala Tyr Leu Asn Val
340 345 350

Leu Ser Leu Glu Lys Gln Ile Asp Ser Gln Ala Lys Ala Leu Glu Ala
355 360 365

Ala Lys Val Asn Phe Glu Leu Asn Gln Glu Lys Tyr Asp Ala Gly Leu
370 375 380

Ile Ser Thr Val Asp Tyr Leu Asp Phe Glu Asn Thr Tyr Arg Gln Ala
385 390 395 400

Arg Ile Ala Tyr Asn Lys Val Leu Leu Asp Tyr Tyr Tyr Ala Phe Glu
405 410 415

Thr Tyr Arg Ser Leu Leu Ile
420

<210> SEQ ID NO 70
<211> LENGTH: 433
<212> TYPE: PRT
<213> ORGANISM: F. mortiferum

<400> SEQUENCE: 70

Met Lys Lys Thr Leu Gly Leu Leu Leu Leu Leu Ser Ser Ser Val Phe

-continued

```
1               5                   10                  15

Ala Arg Glu Leu Thr Leu Asp Gln Ala Ile Gln Met Ala Leu Asp Asn
            20                  25                  30

Ser Lys Glu Met Gln Ile Ser Gln Arg Asp Val Glu Thr Ala Lys Leu
        35                  40                  45

Asn Val Gly Ile Ala Phe Lys Asn Ala Leu Pro Ser Val Val Tyr Thr
    50                  55                  60

Gly Ser Tyr Thr Arg Ser Glu Tyr Asp Arg Lys Ile Thr Ala Glu Glu
65                  70                  75                  80

Arg Pro Asn His Arg Leu Glu Lys Asn Gly Ser Arg Glu Val Glu Ala
                85                  90                  95

Lys Gly Gly Tyr Thr Gln Lys Ile Thr Ile Ser Gln Pro Ile Phe Gln
            100                 105                 110

Gly Gly Ala Ile Leu Gly Gly Ile Gln Tyr Ala Lys Ala Tyr Lys Ser
        115                 120                 125

Val Ala Asn Leu Met Tyr Leu Ser Ser Gln Arg Asp Val Arg Leu Glu
    130                 135                 140

Thr Ile Gln Ile Tyr Ser Asp Ile Val Lys Ser Glu Lys Asp Leu Glu
145                 150                 155                 160

Ala Leu Met Ser Ser Lys Glu Glu Leu Lys Ala Thr Tyr Asp Lys Gln
                165                 170                 175

Lys Ala Gln Leu Asp Leu Arg Leu Ile Thr Lys Ala Asp Leu Leu Lys
            180                 185                 190

Thr Glu Tyr Ser Met Leu Glu Val Asp Ser Gln Ile Ile Gly Thr Gln
        195                 200                 205

Asn Gln Ile Thr Val Gln Lys Glu Asn Leu Lys Leu Lys Leu Gly Leu
    210                 215                 220

Pro Lys Thr Glu Asp Leu Thr Val Val Glu Phe Asp Val Pro Met Tyr
225                 230                 235                 240

Leu Ser Arg Asn Ile Asp Phe Gln Ala Asp Leu Asn Gln Ala Leu Thr
                245                 250                 255

Glu Ser Ile Asp Ala Met Val Ala Asn Lys Tyr Val Asp Met Ala Asp
            260                 265                 270

Ala Gln Arg Lys Val Ala Arg Ala Asp Met Leu Pro Gln Val Ser Ala
        275                 280                 285

Phe Ala Ser Tyr Gly Val Asp Ser Asp Arg Arg Lys Tyr Asn Ala Thr
    290                 295                 300

Met Asp Asp Ala Glu Trp Arg Gly Gly Val Gln Val Thr Trp Asn Val
305                 310                 315                 320

Phe Glu Phe Gly Lys Asn Tyr Asp Thr Tyr Lys Thr Ala Ala Ile Ala
                325                 330                 335

Lys Glu Gln Glu Glu Leu Arg Glu Lys Ile Ser Lys Asp Thr Ile Asp
            340                 345                 350

Ile Asn Val Thr Asp Ala Tyr Leu Glu Leu Val Arg Met Glu Lys Asp
        355                 360                 365

Arg Asp Ser Lys Gly Arg Ala Leu Glu Ala Ala Met Glu Asn Tyr Lys
    370                 375                 380

Ile Asp Lys Glu Lys Tyr Thr Ala Gly Leu Ile Ser Thr Ile Asp Phe
385                 390                 395                 400

Leu Ala Ser Glu Thr Gln Leu Arg Glu Ala Lys Val Ala Tyr Asn Gln
                405                 410                 415

Val Val Ile Asp Tyr Leu Tyr Ala Phe Glu Lys Tyr Arg Ser Met Leu
            420                 425                 430
```

Ile

<210> SEQ ID NO 71
<211> LENGTH: 422
<212> TYPE: PRT
<213> ORGANISM: F. russii

<400> SEQUENCE: 71

Met Lys Lys Leu Leu Ser Ile Phe Phe Leu Leu Thr Gly Ser Leu Phe
1 5 10 15

Ala Arg Glu Leu Thr Leu Asp Glu Ala Ile Asn Leu Ser Leu Thr Asn
20 25 30

Ser Lys Asp Ile Gln Ile Ser Glu Lys Asn Leu Glu Ile Ser Glu Ile
35 40 45

Asn Leu Gln Lys Ala Phe Lys Leu Ala Leu Pro Thr Val Thr Tyr Asn
50 55 60

Gly Lys Tyr Ser Arg Thr Asn Tyr Asp Arg Lys Ile Ala Ile Asp Asp
65 70 75 80

His Ser Ser Glu Lys Gly Arg Gly Ser Tyr Ser Gln Ser Ile Thr Ile
85 90 95

Ala Gln Pro Leu Phe Ala Gly Gly Thr Ile Phe Ala Gly Ile Lys Gly
100 105 110

Ala Gln Ala Tyr Glu Asn Ile Ala Asn Tyr Asn Phe Leu Asn Ser Lys
115 120 125

Ile Lys Met Arg Ile Glu Thr Ile Ala Ala Tyr Phe Ser Leu Leu Asn
130 135 140

Ala Glu Lys Asp Leu Asn Ala Leu Lys Asn Ser Lys Ser Ile Leu Gln
145 150 155 160

Lys Arg Tyr Asp Lys Gln Lys Val Gln Leu Glu Leu Arg Leu Ile Arg
165 170 175

Lys Ser Asp Ile Ser Gln Thr Glu Tyr Ser Leu Leu Asn Val Glu Ser
180 185 190

Asn Ile Ile Ala Ile Lys Ser Gln Ile Asp Thr Tyr Arg Glu Gln Leu
195 200 205

Arg Ile Lys Thr Gly Leu Ala Lys Asn Glu Phe Ile Thr Val Val Asp
210 215 220

Phe Asn Val Pro Met Asn Leu Ser Lys Asn Ile Asn Ile Asp Lys Asp
225 230 235 240

Leu Glu Gln Ala Ile Asn Glu Ser Leu Asn Ala Lys Ile Ala Glu Glu
245 250 255

Met Tyr Lys Ile Ser Glu Ala Gln Thr Ile Ala Ala Ala Gly Ser Ile
260 265 270

Leu Pro Lys Val Ser Ala Phe Ala Thr Tyr Gly Thr Thr Glu Arg Thr
275 280 285

Lys Phe Glu Asn Ser Tyr Arg Asp Ala Lys Trp Val Gly Gly Ile Gln
290 295 300

Val Thr Trp Asn Val Phe Ser Phe Gly Ser Asp Ile Asp Glu Tyr Arg
305 310 315 320

Ile Ala Lys Leu Glu Glu Glu Gln Gln Lys Leu Lys Glu Ile Ser Thr
325 330 335

Lys Glu Asn Ile Glu Ile Ala Val Lys Ser Ala Tyr Phe Asp Leu Leu
340 345 350

Arg Leu Glu Lys Leu Arg Glu Ser Lys Ser Lys Ala Leu Glu Val Ala
355 360 365

Lys Leu Asn Phe Glu Met Asp Gln Glu Arg Tyr Asp Ala Gly Leu Ile
370 375 380

Ser Thr Ile Asp Tyr Leu Asp Thr Glu Asn Thr Tyr Arg Asn Ala Asn
385 390 395 400

Ile Asp Tyr Asn Lys Thr Leu Met Asp Tyr Tyr Leu Ala Phe Glu Lys
405 410 415

Tyr Arg Ser Leu Ile Ile
420

<210> SEQ ID NO 72
<211> LENGTH: 714
<212> TYPE: PRT
<213> ORGANISM: F. necrophorum

<400> SEQUENCE: 72

Met Lys Lys Val Val Phe Gly Ile Cys Ser Ile Leu Ile Ser Ser Ala
1 5 10 15

Met Leu Gly Ala Glu Ile Asp Leu Gly Thr Gln Asn Ile Tyr Ser Glu
20 25 30

Thr Gly Phe Glu Thr Ser Leu Arg Ser Ser Val Ser Ser Pro Tyr Ile
35 40 45

Val Thr Ser Lys Glu Ile Lys Glu Lys His Tyr Thr Arg Val Ser Glu
50 55 60

Ile Leu Arg Asp Ile Pro His Ile Tyr Ile Gly Pro Gly Gly Ser Val
65 70 75 80

Asp Met Arg Gly Gln Gly Ser Ala His Ala Arg Thr Thr Val Gln Leu
85 90 95

Leu Ile Asp Gly Val Pro Ala Asn Phe Leu Asp Thr Ser His Ile Asn
100 105 110

Leu Pro Ile Asp Thr Leu Asn Pro Glu Asp Ile Lys Arg Ile Glu Val
115 120 125

Ile Pro Gly Gly Gly Ala Val Leu Tyr Gly Ser Gly Thr Ser Gly Gly
130 135 140

Val Ile Asn Ile Ile Thr Lys Lys Tyr Thr Gly Asn Tyr Ala Lys Ala
145 150 155 160

Ser Tyr Gln Ile Gly Ser Tyr His Asn His Lys Tyr Asp Val Ala Ala
165 170 175

Gly Thr Ser Leu Gly Asn Phe Asp Ile Asn Leu Ser Tyr Ser Lys Asn
180 185 190

Asn Arg Asp Gly Tyr Arg Lys Lys Ala Phe Ser Asp Ser Asp Phe Phe
195 200 205

Ser Gly Lys Leu Arg Tyr His Phe Asn Pro Thr Asp Ser Leu Glu Phe
210 215 220

Lys Tyr Ser Tyr Phe Asp Asn Lys Phe Arg Gly Val Lys Ser Leu Thr
225 230 235 240

Arg Glu Gln Val Glu Lys Asp Arg Arg Gln Ser Gly Leu Ser Pro Glu
245 250 255

Asp Asn Leu Lys Asn Thr Ile Arg Lys Glu Glu Trp Asn Leu Thr Tyr
260 265 270

Asp Ala Lys Trp Thr Ser Trp Leu Glu His Lys Ser Asn Leu Phe Tyr
275 280 285

Gln Ser Thr Glu Ile Lys Ser Ser Glu Tyr Glu Asp Ala Leu Pro Phe
290 295 300

Tyr Gln Tyr Gln Ile Ser Ser Tyr Gln Lys Met Leu Thr Met Pro Gly

-continued

```
305                 310                 315                 320

Ile Pro Pro Met Met Gln Ala Gln Leu Lys Lys Gln Ile Lys Ala Leu
                325                 330                 335

Gln Asn Leu Ile Thr Ser Asn Pro Arg Met Glu Leu His Gln Gly Ser
            340                 345                 350

Arg Phe Lys Asp Gln Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asp Arg Asp Ser Trp Ala Tyr Thr Lys Asn Thr Gln Thr Asn
385                 390                 395                 400

Gln Thr Ile Ala Thr Leu Thr Asn Thr Lys Ile Pro Leu Asn Lys Lys
                405                 410                 415

Thr Phe Glu Ile Phe Gly Leu Asn Thr Tyr Arg His Asn Asn Trp Glu
            420                 425                 430

Phe Val Gln Gly Leu Arg Phe Glu Lys Ala Lys Tyr Asn Gly Lys Arg
        435                 440                 445

Gln Tyr Lys Asn Leu Glu Tyr Pro Leu Lys Asp Arg Ser Met Asn Asn
    450                 455                 460

Val Ala Ala Asn Leu Ala Val Asn Tyr Leu Tyr Ser Asp Thr Gly Asn
465                 470                 475                 480

Val Tyr Val Lys Tyr Glu Arg Gly Phe Thr Ser Pro Ala Pro Ala Gln
                485                 490                 495

Leu Met Asp Lys Ile Arg Lys Gly Gly Val Asn Asp Tyr Val Asn Asn
            500                 505                 510

Asp Leu Lys Ser Glu Lys Ser Asn Ser Phe Glu Val Gly Trp Asn Asp
        515                 520                 525

Tyr Leu Phe His Ser Leu Val Ser Ala Asp Val Phe Phe Ser Glu Thr
    530                 535                 540

Lys Asp Glu Ile Ser Thr Ile Phe Ser Gly Gly His Gly Thr Thr Phe
545                 550                 555                 560

Ser Asn Leu Asn Leu Gly Gln Thr Lys Arg Tyr Gly Phe Asp Leu Lys
                565                 570                 575

Ala Ser Gln Val Phe Glu Lys Trp Thr Phe Ser Glu Ala Tyr Ser Tyr
            580                 585                 590

Ile His Ala Lys Ile Met Lys Asp Lys Thr Lys Ala Tyr Glu Gly Lys
        595                 600                 605

Tyr Ile Ser Tyr Val Pro Arg His Lys Phe Ser Leu Asn Ala Asp Tyr
    610                 615                 620

Ala Ile Thr Pro Lys Trp Thr Leu Gly Gly Glu Tyr Gln Tyr Ser Ser
625                 630                 635                 640

Ser Val Tyr Leu Asp Asn Ala Asn Lys Asn Gly Lys Asp Gly Ala Arg
                645                 650                 655

Ser Val Phe Asn Leu Gln Thr Ser Tyr Glu Phe Asn Ser His Phe Ser
            660                 665                 670

Ile Tyr Ala Gly Ile Lys Asn Val Leu Asn His Lys Tyr Tyr Glu Ser
        675                 680                 685

Val Ser Ala Gly Ser Ser Gln Lys Tyr Tyr Ser Pro Ala Pro Glu Arg
    690                 695                 700

Asn Tyr Tyr Ala Gly Phe Arg Tyr Gln Phe
705                 710
```

<210> SEQ ID NO 73

<211> LENGTH: 714
<212> TYPE: PRT
<213> ORGANISM: F. necrophorum

<400> SEQUENCE: 73

Met Lys Lys Val Val Phe Gly Ile Cys Ser Ile Leu Ile Ser Ser Ala
1               5                   10                  15

Met Leu Gly Ala Glu Ile Asp Leu Gly Thr Gln Asn Ile Tyr Ser Glu
            20                  25                  30

Thr Gly Phe Glu Thr Ser Leu Arg Ser Ser Val Ser Ser Pro Tyr Ile
        35                  40                  45

Val Thr Ser Lys Glu Ile Lys Glu Lys His Tyr Thr Arg Val Ser Glu
    50                  55                  60

Ile Leu Arg Asp Ile Pro His Ile Tyr Ile Gly Pro Gly Gly Ser Val
65                  70                  75                  80

Asp Met Arg Gly Gln Gly Ser Ala His Ala Arg Thr Thr Val Gln Leu
                85                  90                  95

Leu Ile Asp Gly Val Pro Ala Asn Phe Leu Asp Thr Ser His Ile Asn
            100                 105                 110

Leu Pro Ile Asp Thr Leu Asn Pro Glu Asp Ile Lys Arg Ile Glu Val
        115                 120                 125

Ile Pro Gly Gly Gly Ala Val Leu Tyr Gly Ser Gly Thr Ser Gly Gly
    130                 135                 140

Val Ile Asn Ile Ile Thr Lys Lys Tyr Thr Gly Asn Tyr Ala Lys Ala
145                 150                 155                 160

Ser Tyr Gln Ile Gly Ser Tyr His Asn His Lys Tyr Asp Val Ala Ala
                165                 170                 175

Gly Thr Ser Leu Gly Asn Phe Asp Ile Asn Leu Ser Tyr Ser Lys Asn
            180                 185                 190

Asn Arg Asp Gly Tyr Arg Lys Lys Ala Phe Ser Asp Ser Asp Phe Phe
        195                 200                 205

Ser Gly Lys Leu Arg Tyr His Phe Asn Pro Thr Asp Ser Leu Glu Phe
    210                 215                 220

Lys Tyr Ser Tyr Phe Asp Asn Lys Phe Arg Gly Val Lys Ser Leu Thr
225                 230                 235                 240

Arg Glu Gln Val Glu Lys Asp Arg Arg Gln Ser Gly Leu Ser Pro Glu
                245                 250                 255

Asp Asn Leu Lys Asn Thr Ile Arg Lys Glu Glu Trp Asn Leu Thr Tyr
            260                 265                 270

Asp Ala Lys Trp Thr Ser Trp Leu Glu His Lys Ser Asn Leu Phe Tyr
        275                 280                 285

Gln Ser Thr Glu Ile Lys Ser Ser Glu Tyr Glu Asp Ala Leu Pro Phe
    290                 295                 300

Tyr Gln Tyr Gln Ile Ser Ser Tyr Gln Lys Met Leu Thr Met Pro Gly
305                 310                 315                 320

Ile Pro Pro Met Met Gln Ala Gln Leu Lys Lys Gln Ile Lys Ala Leu
                325                 330                 335

Gln Asn Leu Ile Thr Ser Asn Pro Arg Met Glu Leu His Gln Gly Ser
            340                 345                 350

Arg Phe Lys Asp Gln Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asp Arg Asp Ser Trp Ala Tyr Thr Lys Asn Thr Gln Thr Asn

-continued 385 390 395 400

Gln Thr Ile Ala Thr Leu Thr Asn Thr Lys Ile Pro Leu Asn Lys Lys
405 410 415

Thr Phe Glu Ile Phe Gly Leu Asn Thr Tyr Arg His Asn Asn Trp Glu
420 425 430

Phe Val Gln Gly Leu Arg Phe Glu Lys Ala Lys Tyr Asn Gly Lys Arg
435 440 445

Gln Tyr Lys Asn Leu Glu Tyr Pro Leu Lys Asp Arg Ser Met Asn Asn
450 455 460

Val Ala Ala Asn Leu Ala Val Asn Tyr Leu Tyr Ser Asp Thr Gly Asn
465 470 475 480

Val Tyr Val Lys Tyr Glu Arg Gly Phe Thr Ser Pro Ala Pro Ala Gln
485 490 495

Leu Met Asp Lys Ile Arg Lys Gly Gly Val Asn Asp Tyr Val Asn Asn
500 505 510

Asp Leu Lys Ser Glu Lys Ser Asn Ser Phe Glu Val Gly Trp Asn Asp
515 520 525

Tyr Leu Phe His Ser Leu Val Ser Ala Asp Val Phe Phe Ser Glu Thr
530 535 540

Lys Asp Glu Ile Ser Thr Ile Phe Ser Gly Gly His Gly Thr Ala Phe
545 550 555 560

Ser Asn Leu Asn Leu Gly Gln Thr Lys Arg Tyr Gly Phe Asp Leu Lys
565 570 575

Ala Ser Gln Val Phe Gln Lys Trp Thr Phe Ser Glu Ala Tyr Ser Tyr
580 585 590

Ile His Ala Lys Ile Val Lys Asp Lys Asn Lys Ala Tyr Glu Gly Lys
595 600 605

Tyr Ile Ser Tyr Val Pro Arg His Lys Phe Ser Leu Asn Ala Asp Tyr
610 615 620

Ala Ile Thr Pro Lys Trp Thr Leu Gly Gly Glu Tyr Gln Tyr Ser Ser
625 630 635 640

Ser Val Tyr Leu Asp Asn Ala Asn Lys Asn Gly Lys Asp Gly Ala Arg
645 650 655

Ala Val Phe Asn Leu Gln Thr Ser Tyr Glu Phe Asn Ser His Phe Ser
660 665 670

Ile Tyr Ala Gly Ile Lys Asn Val Leu Asn His Lys Tyr Tyr Glu Ser
675 680 685

Val Thr Ala Gly Ser Gly Gln Lys Tyr Tyr Ser Pro Ala Pro Glu Arg
690 695 700

Asn Tyr Tyr Ala Gly Phe Arg Tyr Gln Phe
705 710

<210> SEQ ID NO 74
<211> LENGTH: 714
<212> TYPE: PRT
<213> ORGANISM: F. necrophorum

<400> SEQUENCE: 74

Met Lys Lys Val Val Phe Gly Ile Cys Ser Ile Leu Met Ser Ser Ala
1 5 10 15

Met Leu Gly Ala Glu Ile Asp Leu Gly Thr Gln Asn Ile Tyr Ser Glu
20 25 30

Thr Gly Phe Glu Thr Ser Leu Arg Ser Ser Val Ser Ser Pro Tyr Ile
35 40 45

-continued

```
Val Thr Ser Lys Lys Ile Lys Glu Lys His Tyr Thr Arg Val Ser Glu
    50                  55                  60

Ile Leu Arg Asp Ile Pro Asn Ile Tyr Ile Gly Ser Gly Gly Ser Val
65                  70                  75                  80

Asp Met Arg Gly Gln Gly Ser Ile His Ser Arg Thr Thr Val Gln Leu
                85                  90                  95

Leu Ile Asp Gly Val Pro Ala Asn Phe Leu Asp Thr Ser His Ile Asn
            100                 105                 110

Leu Pro Ile Asp Thr Leu Asn Pro Glu Asp Ile Glu Arg Ile Glu Val
        115                 120                 125

Ile Pro Gly Gly Gly Ala Val Leu Tyr Gly Ser Gly Thr Ser Gly Gly
    130                 135                 140

Val Ile Asn Ile Ile Thr Lys Lys Tyr Thr Gly Asn Tyr Ala Lys Ala
145                 150                 155                 160

Gly Tyr Gln Ile Gly Ser Tyr His Asn His Lys Tyr Asp Val Ala Ala
                165                 170                 175

Gly Thr Ser Leu Gly Lys Phe Asp Ile Asn Leu Ser Tyr Ser Lys Asn
            180                 185                 190

Asn Arg Asp Gly Tyr Arg Lys Lys Ala Phe Ser Asp Ser Asp Phe Phe
        195                 200                 205

Ser Gly Lys Leu Arg Tyr His Phe Asn Pro Thr Asp Ser Leu Glu Phe
    210                 215                 220

Lys Tyr Ser Tyr Phe Asp Asn Lys Phe Arg Gly Val Lys Ser Leu Thr
225                 230                 235                 240

Arg Glu Gln Val Glu Lys Asp Arg Arg Gln Ser Asp Leu Ser Pro Glu
                245                 250                 255

Asp Asn Leu Lys Asn Thr Ile Arg Lys Glu Glu Trp Asn Leu Thr Tyr
            260                 265                 270

Asp Ala Lys Trp Thr Ser Trp Leu Glu His Lys Ser Asn Leu Phe Tyr
        275                 280                 285

Gln Ser Thr Glu Ile Lys Ser Ser Glu Tyr Glu Asp Ala Leu Pro Phe
    290                 295                 300

Tyr Gln Tyr Gln Ile Ser Ser Tyr Gln Lys Met Leu Thr Met Pro Gly
305                 310                 315                 320

Ile Pro Pro Met Met Gln Ala Gln Leu Lys Lys Gln Ile Lys Ala Leu
                325                 330                 335

Gln Asn Leu Ile Met Ser Asn Pro Arg Met Glu Leu His Gln Gly Ser
            340                 345                 350

Arg Phe Lys Asp Gln Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asp Arg Asp Ser Trp Ala Tyr Thr Lys Asn Thr Gln Thr Asn
385                 390                 395                 400

Gln Thr Ile Ala Thr Leu Thr Asn Thr Lys Ile Pro Leu Asn Lys Lys
                405                 410                 415

Thr Phe Glu Ile Phe Gly Leu Asn Thr Tyr Arg His Asn Asn Trp Glu
            420                 425                 430

Phe Val Gln Gly Leu Arg Phe Glu Lys Ala Lys Tyr Asn Gly Lys Arg
        435                 440                 445

Gln Tyr Lys Asn Leu Glu Tyr Pro Leu Lys Asp Arg Ser Met Asn Asn
    450                 455                 460

Val Ala Ala Asn Leu Ala Val Asn Tyr Leu Tyr Ser Asp Thr Gly Asn
```

465 470 475 480

Val Tyr Val Lys Tyr Glu Arg Gly Phe Thr Ser Pro Ala Pro Ala Gln
485 490 495

Leu Met Asp Lys Ile Arg Lys Gly Gly Val Asn Asp Tyr Val Asn Asn
500 505 510

Asp Leu Lys Ser Glu Lys Ser Asn Ser Phe Glu Val Gly Trp Asn Asp
515 520 525

Tyr Leu Phe His Ser Leu Val Ser Ala Asp Val Phe Phe Ser Glu Thr
530 535 540

Lys Asp Glu Ile Ser Thr Ile Phe Ser Gly Gly His Gly Thr Thr Phe
545 550 555 560

Ser Asn Leu Asn Leu Gly Gln Thr Lys Arg Tyr Gly Phe Asp Leu Lys
565 570 575

Ala Ser Gln Val Phe Glu Lys Trp Thr Phe Ser Glu Ala Tyr Ser Tyr
580 585 590

Ile His Ala Lys Ile Met Lys Asp Lys Thr Lys Ala Tyr Glu Gly Lys
595 600 605

Tyr Ile Ser Tyr Val Pro Arg His Lys Phe Ser Leu Asn Ala Asp Tyr
610 615 620

Ala Ile Thr Pro Lys Trp Thr Leu Gly Gly Glu Tyr Gln Tyr Ser Ser
625 630 635 640

Ser Val Tyr Leu Asp Asn Ala Asn Lys Asn Gly Lys Asp Gly Ala Arg
645 650 655

Ser Val Phe Asn Leu Gln Thr Ser Tyr Glu Phe Asn Ser His Phe Ser
660 665 670

Ile Tyr Ala Gly Ile Lys Asn Val Leu Asn His Lys Tyr Tyr Glu Ser
675 680 685

Val Ser Ala Gly Ser Ser Gln Lys Tyr Tyr Ser Pro Ala Pro Glu Arg
690 695 700

Asn Tyr Tyr Ala Gly Phe Arg Tyr Gln Phe
705 710

<210> SEQ ID NO 75
<211> LENGTH: 714
<212> TYPE: PRT
<213> ORGANISM: F. necrophorum

<400> SEQUENCE: 75

Met Lys Lys Val Ile Phe Gly Ile Tyr Ser Ile Leu Leu Ser Ser Ala
1 5 10 15

Met Leu Gly Ala Glu Ile Asp Leu Gly Thr Gln Asn Ile Tyr Ser Glu
20 25 30

Thr Gly Phe Glu Thr Ser Leu Arg Ser Ser Val Ser Ser Pro Tyr Ile
35 40 45

Val Thr Ser Lys Lys Ile Lys Glu Lys His Tyr Thr Arg Val Ser Glu
50 55 60

Ile Leu Arg Asp Ile Pro Asn Ile Tyr Ile Gly Ser Gly Gly Ser Val
65 70 75 80

Asp Met Arg Gly Gln Gly Ser Ile His Ser Arg Thr Thr Val Gln Leu
85 90 95

Leu Ile Asp Gly Val Pro Ala Asn Phe Leu Asp Thr Ser His Ile Asn
100 105 110

Leu Pro Ile Asp Thr Leu Asn Pro Glu Asp Ile Glu Arg Ile Glu Val
115 120 125

-continued

```
Ile Pro Gly Gly Gly Ala Val Leu Tyr Gly Ser Gly Thr Ser Gly Gly
    130                 135                 140

Val Ile Asn Ile Ile Thr Lys Lys Tyr Thr Gly Asn Tyr Ala Lys Ala
145                 150                 155                 160

Gly Tyr Gln Ile Gly Ser Tyr His Asn His Lys Tyr Asp Val Ala Ala
                165                 170                 175

Gly Thr Ser Leu Gly Lys Phe Asp Ile Asn Leu Ser Tyr Ser Lys Asn
            180                 185                 190

Asn Arg Asp Gly Tyr Arg Lys Lys Ala Phe Ser Asp Ser Asp Phe Phe
        195                 200                 205

Ser Gly Lys Leu Arg Tyr His Phe Asn Pro Thr Asp Ser Leu Glu Phe
    210                 215                 220

Lys Tyr Ser Tyr Phe Asp Asn Lys Phe Arg Gly Val Lys Ser Leu Thr
225                 230                 235                 240

Arg Glu Gln Val Glu Glu Asp Arg Arg Gln Ser Gly Leu Ser Pro Glu
                245                 250                 255

Asp Asn Leu Lys Asn Thr Ile Arg Lys Glu Glu Trp Asn Leu Thr Tyr
            260                 265                 270

Asp Ala Lys Trp Thr Asn Trp Leu Glu His Lys Ser Asn Leu Phe Tyr
        275                 280                 285

Gln Ser Ser Glu Ile Lys Ser Ser Asp Tyr Glu Asp Ala Ile Pro Phe
    290                 295                 300

Tyr Gln Ala Arg Ile Ala Met Tyr Gln Gln Met Leu Ala Thr Pro Gly
305                 310                 315                 320

Ile Pro Pro Met Met Leu Glu Lys Leu Lys Lys Gln Ile Gln Ile Trp
                325                 330                 335

Glu Asn Ile Ile Thr Asn Asn Pro Lys Met Glu Leu Arg Gln Gly Ser
            340                 345                 350

Leu Phe Lys Asp Arg Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asn Arg Asn Ser Trp Ala Tyr Thr Lys Asn Thr Gln Thr Asn
385                 390                 395                 400

Gln Thr Ile Glu Thr Ile Thr Asp Thr Lys Ile Pro Leu Asn Lys Lys
                405                 410                 415

Thr Phe Glu Ile Phe Gly Leu Asn Thr Tyr Arg His Asn Asn Trp Glu
            420                 425                 430

Phe Val Gln Gly Leu Arg Phe Glu Lys Ala Lys Tyr Ser Gly Lys Arg
        435                 440                 445

Gln Tyr Lys Asn Leu Glu Tyr Pro Leu Lys Asp Arg Ser Met Asn Asn
    450                 455                 460

Val Ala Ala Asn Leu Ala Val Asn Tyr Leu Tyr Ser Asp Thr Gly Asn
465                 470                 475                 480

Val Tyr Val Lys Tyr Glu Arg Gly Phe Thr Ser Pro Ala Pro Ala Gln
                485                 490                 495

Leu Met Asp Lys Ile Lys Lys Gly Gly Val Asn Asp Tyr Val Asn Asn
            500                 505                 510

Asp Leu Lys Ser Glu Lys Ser Asn Ser Phe Glu Val Gly Trp Asn Asp
        515                 520                 525

Tyr Leu Phe His Ser Leu Val Ser Ala Asp Val Phe Phe Ser Glu Thr
    530                 535                 540

Lys Asp Glu Ile Ser Thr Ile Phe Ser Gly Gly His Gly Thr Ala Phe
```

545 550 555 560

Ser Asn Leu Asn Leu Gly Gln Thr Lys Arg Tyr Gly Phe Asp Leu Lys
565 570 575

Ala Ser Gln Val Phe Arg Lys Trp Thr Phe Ser Glu Ala Tyr Ser Tyr
580 585 590

Ile His Ala Lys Ile Val Lys Asp Lys Asn Lys Ala Tyr Glu Gly Lys
595 600 605

Tyr Ile Ser Tyr Val Pro Arg His Lys Phe Ser Leu Asn Ala Asp Tyr
610 615 620

Ala Ile Thr Pro Lys Trp Thr Leu Gly Gly Glu Tyr Gln Tyr Ser Ser
625 630 635 640

Ser Val Tyr Leu Asp Asn Ala Asn Lys Asn Gly Lys Asp Gly Ala Arg
645 650 655

Ala Val Phe Asn Leu Gln Thr Ser Tyr Glu Phe Asn Ser His Phe Ser
660 665 670

Ile Tyr Ala Gly Ile Lys Asn Val Leu Asn His Lys Tyr Tyr Glu Ser
675 680 685

Val Thr Ala Gly Ser Gly Gln Lys Tyr Tyr Ser Pro Ala Pro Glu Arg
690 695 700

Asn Tyr Tyr Ala Gly Phe His Tyr Gln Phe
705 710

<210> SEQ ID NO 76
<211> LENGTH: 714
<212> TYPE: PRT
<213> ORGANISM: F. necrophorum

<400> SEQUENCE: 76

Met Lys Lys Val Val Phe Gly Ile Tyr Ser Ile Leu Met Ser Ser Ala
1 5 10 15

Met Leu Gly Ala Glu Ile Asp Leu Gly Thr Gln Asn Ile Tyr Ser Glu
20 25 30

Thr Gly Phe Glu Thr Ser Leu Arg Ser Ser Val Ser Ser Pro Tyr Ile
35 40 45

Val Thr Ser Lys Lys Ile Lys Glu Lys His Tyr Thr Arg Val Ser Glu
50 55 60

Ile Leu Arg Asp Ile Pro Asn Ile Tyr Ile Gly Ser Gly Gly Ser Val
65 70 75 80

Asp Met Arg Gly Gln Gly Ser Ile His Ser Arg Thr Thr Val Gln Leu
85 90 95

Leu Ile Asp Gly Val Pro Ala Asn Phe Leu Asp Thr Ser His Ile Asn
100 105 110

Leu Pro Ile Asp Thr Leu Asn Pro Glu Asp Ile Glu Arg Ile Glu Val
115 120 125

Ile Pro Gly Gly Gly Ala Val Leu Tyr Gly Ser Gly Thr Ser Gly Gly
130 135 140

Val Ile Asn Ile Ile Thr Lys Lys Tyr Thr Gly Asn Tyr Ala Lys Ala
145 150 155 160

Gly Tyr Gln Ile Gly Ser Tyr His Asn His Lys Tyr Asp Val Ala Ala
165 170 175

Gly Thr Ser Leu Gly Lys Phe Asp Ile Asn Leu Ser Tyr Ser Lys Asn
180 185 190

Asn Arg Asp Gly Tyr Arg Lys Lys Ala Phe Ser Asp Ser Asp Phe Phe
195 200 205

```
Ser Gly Lys Leu Arg Tyr His Phe Asn Pro Thr Asp Ser Leu Glu Phe
    210                 215                 220

Lys Tyr Ser Tyr Phe Asp Asn Lys Phe Arg Gly Val Lys Ser Leu Thr
225                 230                 235                 240

Gly Glu Gln Val Glu Glu Asp Arg Arg Gln Ser Gly Leu Ser Pro Lys
                245                 250                 255

Asp Asn Leu Lys Asn Thr Ile Arg Lys Glu Glu Trp Asn Leu Thr Tyr
            260                 265                 270

Asp Ala Lys Trp Thr Asn Trp Leu Glu His Lys Ser Asn Leu Phe Tyr
        275                 280                 285

Gln Ser Ser Glu Ile Lys Ser Ser Asp Tyr Glu Asp Ala Ile Pro Phe
    290                 295                 300

Tyr Gln Ala Arg Ile Ala Met Tyr Gln Gln Met Leu Ala Thr Pro Gly
305                 310                 315                 320

Ile Pro Pro Met Met Leu Glu Lys Leu Lys Lys Gln Ile Gln Ile Trp
                325                 330                 335

Glu Asn Ile Ile Thr Asn Asn Pro Lys Met Glu Leu Arg Gln Gly Ser
            340                 345                 350

Leu Phe Lys Asp Arg Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asn Arg Asn Ser Trp Ala Tyr Thr Lys Asn Thr Gln Thr Asn
385                 390                 395                 400

Gln Thr Ile Glu Thr Ile Thr Asp Thr Lys Ile Pro Leu Asn Lys Lys
                405                 410                 415

Thr Phe Glu Ile Phe Gly Leu Asn Thr Tyr Arg His Asn Asn Trp Glu
            420                 425                 430

Phe Val Gln Gly Leu Arg Phe Glu Lys Ala Lys Tyr Ser Gly Lys Arg
        435                 440                 445

Gln Tyr Lys Asn Leu Glu Tyr Pro Leu Lys Asp Arg Ser Met Asn Asn
    450                 455                 460

Val Ala Ala Asn Leu Ala Val Asn Tyr Leu Tyr Ser Asp Thr Gly Asn
465                 470                 475                 480

Val Tyr Val Lys Tyr Glu Arg Gly Phe Thr Ser Pro Ala Pro Ala Gln
                485                 490                 495

Leu Met Asp Lys Val Lys Lys Gly Gly Val Asn Asp Tyr Val Asn Asn
            500                 505                 510

Asp Leu Lys Ser Glu Lys Ser Asn Ser Phe Glu Val Gly Trp Asn Asp
        515                 520                 525

Tyr Leu Phe His Ser Leu Val Ser Ala Asp Val Phe Phe Ser Glu Thr
    530                 535                 540

Lys Asp Glu Ile Ser Thr Ile Phe Ser Gly Gly His Gly Thr Ala Phe
545                 550                 555                 560

Ser Asn Leu Asn Leu Gly Gln Thr Lys Arg Tyr Gly Phe Asp Leu Lys
                565                 570                 575

Ala Ser Gln Val Phe Gln Lys Trp Thr Phe Ser Glu Ala Tyr Ser Tyr
            580                 585                 590

Ile His Ala Lys Ile Val Lys Asp Lys Asn Lys Ala Tyr Glu Gly Lys
        595                 600                 605

Tyr Ile Ser Tyr Val Pro Arg His Lys Phe Ser Leu Asn Ala Asp Tyr
    610                 615                 620

Ala Ile Thr Pro Lys Trp Thr Leu Gly Gly Glu Tyr Gln Tyr Ser Ser
```

```
625                 630                 635                 640

Ser Val Tyr Leu Asp Asn Ala Asn Lys Asn Gly Lys Asp Gly Ala Arg
                645                 650                 655

Ala Val Phe Asn Leu Gln Thr Ser Tyr Glu Phe Asn Ser His Phe Ser
            660                 665                 670

Ile Tyr Ala Gly Ile Lys Asn Val Leu Asn His Lys Tyr Tyr Glu Ser
        675                 680                 685

Val Thr Ala Gly Ser Gly Gln Lys Tyr Tyr Ser Pro Ala Pro Glu Arg
    690                 695                 700

Asn Tyr Tyr Ala Gly Phe Arg Tyr Gln Phe
705                 710


<210> SEQ ID NO 77
<211> LENGTH: 714
<212> TYPE: PRT
<213> ORGANISM: F. gonidiaformans

<400> SEQUENCE: 77

Met Lys Lys Val Val Phe Gly Ile Cys Ser Ile Leu Met Ser Ser Ala
1               5                   10                  15

Met Leu Gly Ala Glu Ile Asp Leu Gly Thr Gln Asn Ile Tyr Ser Glu
            20                  25                  30

Thr Gly Phe Glu Thr Ser Leu Arg Ser Ser Val Ser Ser Pro Tyr Ile
        35                  40                  45

Val Thr Ser Lys Lys Ile Lys Glu Lys His Tyr Thr Arg Val Ser Glu
    50                  55                  60

Ile Leu Arg Asp Ile Pro Asn Ile Tyr Ile Gly Ser Gly Gly Ser Val
65                  70                  75                  80

Asp Met Arg Gly Gln Gly Ser Ile His Ser Arg Thr Thr Val Gln Leu
                85                  90                  95

Leu Ile Asp Gly Val Pro Ala Asn Phe Leu Asp Thr Ser His Ile Asn
            100                 105                 110

Leu Pro Ile Asp Thr Leu Asn Pro Glu Asp Ile Glu Arg Ile Glu Val
        115                 120                 125

Ile Pro Gly Gly Gly Ala Val Leu Tyr Gly Ser Gly Thr Ser Gly Gly
    130                 135                 140

Val Ile Asn Ile Ile Thr Lys Lys Tyr Thr Gly Asn Tyr Ala Lys Ala
145                 150                 155                 160

Gly Tyr Gln Ile Gly Ser Tyr His Asn His Lys Tyr Asp Val Ala Ala
                165                 170                 175

Gly Thr Ser Leu Gly Lys Phe Asp Ile Asn Leu Ser Tyr Ser Lys Asn
            180                 185                 190

Asn Arg Asp Gly Tyr Arg Lys Lys Ala Phe Ser Asp Ser Asp Phe Phe
        195                 200                 205

Ser Gly Lys Leu Arg Tyr His Phe Asn Pro Thr Asp Ser Leu Glu Phe
    210                 215                 220

Lys Tyr Ser Tyr Phe Asp Asn Lys Phe Arg Asp Val Lys Ser Leu Thr
225                 230                 235                 240

Arg Glu Gln Val Glu Glu Asp Arg Arg Gln Ser Gly Leu Ser Pro Lys
                245                 250                 255

Asp Asn Leu Lys Asn Thr Ile Arg Lys Glu Glu Trp Asn Leu Thr Tyr
            260                 265                 270

Asp Ala Lys Trp Thr Asn Trp Leu Glu His Lys Ser Asn Leu Phe Tyr
        275                 280                 285
```

-continued

```
Gln Ser Ser Glu Ile Lys Ser Ser Glu Tyr Glu Asp Ala Ile Pro Phe
    290                 295                 300

Tyr Gln Ala Arg Ile Ala Met Tyr Gln Gln Met Leu Ala Thr Pro Gly
305                 310                 315                 320

Ile Pro Ser Met Met Leu Glu Lys Leu Lys Lys Gln Ile Gln Phe Trp
                325                 330                 335

Glu Asn Ile Ile Thr Asn Asn Pro Lys Met Glu Leu Arg Gln Gly Ser
            340                 345                 350

Leu Phe Lys Asp Arg Lys Phe Gly Phe Lys Met Lys Asn Lys Phe Lys
        355                 360                 365

Tyr Gly Glu Asn Ser Asp Phe Ile Leu Gly Leu Gly Tyr Ile His Asn
    370                 375                 380

Lys Met Asn Arg Asn Ser Trp Ala Tyr Thr Lys Asn Thr Gln Thr Asn
385                 390                 395                 400

Gln Thr Ile Glu Thr Ile Thr Asp Thr Lys Ile Pro Leu Asn Lys Lys
                405                 410                 415

Thr Phe Glu Ile Phe Gly Leu Asn Thr Tyr Arg His Asn Asn Trp Glu
            420                 425                 430

Phe Val Gln Gly Leu Arg Phe Glu Lys Ala Lys Tyr Ser Gly Lys Arg
        435                 440                 445

Gln Tyr Lys Asn Leu Glu Tyr Pro Leu Lys Asp Arg Ser Met Asn Asn
    450                 455                 460

Val Ala Ala Asn Leu Ala Val Asn Tyr Leu Tyr Ser Asp Thr Gly Asn
465                 470                 475                 480

Val Tyr Val Lys Tyr Glu Arg Gly Phe Thr Ser Pro Ala Pro Ala Gln
                485                 490                 495

Leu Met Asp Lys Ile Lys Lys Gly Gly Val Asn Asp Tyr Val Asn Asn
            500                 505                 510

Asp Leu Lys Ser Glu Lys Ser Asn Ser Phe Glu Val Gly Trp Asn Asp
        515                 520                 525

Tyr Leu Phe His Ser Leu Val Ser Ala Asp Val Phe Phe Ser Glu Thr
    530                 535                 540

Lys Asp Glu Ile Ser Thr Ile Phe Ser Gly Gly His Gly Thr Ala Phe
545                 550                 555                 560

Ser Asn Leu Asn Leu Gly Gln Thr Lys Arg Tyr Gly Phe Asp Leu Lys
                565                 570                 575

Ala Ser Gln Val Phe Gln Lys Trp Thr Phe Ser Glu Ala Tyr Ser Tyr
            580                 585                 590

Ile His Ala Lys Ile Val Lys Asp Lys Asn Lys Ala Tyr Glu Gly Lys
        595                 600                 605

Tyr Ile Ser Tyr Val Pro Arg His Lys Phe Ser Leu Asn Ala Asp Tyr
    610                 615                 620

Ala Ile Thr Pro Lys Trp Thr Leu Gly Gly Glu Tyr Gln Tyr Ser Ser
625                 630                 635                 640

Ser Val Tyr Leu Asp Asn Ala Asn Lys Asn Gly Lys Asp Gly Ala Arg
                645                 650                 655

Ala Val Phe Asn Leu Gln Thr Ser Tyr Glu Phe Asn Ser His Phe Ser
            660                 665                 670

Ile Tyr Ala Gly Ile Lys Asn Val Leu Asn His Lys Tyr Tyr Glu Ser
        675                 680                 685

Val Thr Ala Gly Ser Gly Gln Lys Tyr Tyr Ser Pro Ala Pro Glu Arg
    690                 695                 700

Asn Tyr Tyr Ala Gly Phe Arg Tyr Gln Phe
```

705 710

<210> SEQ ID NO 78
<211> LENGTH: 4263
<212> TYPE: DNA
<213> ORGANISM: F. necrophorum

<400> SEQUENCE: 78
atgaaaaaat taaaaaattt tgaaaatgtt ttaaaatcgc atttaaaaca aagagtaaga 60
attacgacag cattcattgt tgcttttttta attcatggga tgctaagctt tgatgttgaa 120
gcaagagatt taagagttag gaatcaaata actccgtcaa attcaaataa tggcttaaga 180
ataacttcaa gccaaaatgg gaccgatgtt attaatattg ttgatcctaa taatggaata 240
tctcacaata agtatgtaga ttttaatgtt ggggacaaaa ataatgttat ttttaacaac 300
agtcaaaaaa atggaacttc tgttacagga ggagaagtca gtgcaaaccc aaatttaaca 360
aactctgctt ctgttatctt gaatgaaatt caaggaaatt ctgcttcaga attaaacgga 420
ggacttgaag tttttgggaa aagagcagat cttgttattg ccaatgaaaa tggaataaat 480
gtaaatggag caagatttat aaacacttca gctctaacat tatcaacagg aaaagtctca 540
gtcgataata aaaaaatttc ttttaacaca gctacaaata atgcaaagat agcagtaaaa 600
gaaaaaggaa tagaaacaga ttctgattac ttgaatatcc tttcaagaag ggctgaacta 660
gatggagcaa tcaactctga acataataaa aatttaaata tcaatgttat agctggtgca 720
aatactgtta cagctgtaaa tgatactttc gaattaaatg ctgaaaacgc caaagatgga 780
attaccaatg tagaagctat ttccgcttca aaatttggag ctatgtatgg aaataacatt 840
tttatcttga gtactaataa aggcgaagga atcaaatatg aaggaagcct aaaagcaaag 900
gatgaagtgg agataatctc tgaaggaaaa gttgtaagtt ctgacataaa tggaaaagat 960
atcaaaatat cgtctaaaga agaaattaac aatattggaa aaatgaaagc ggataaaaat 1020
gtcagtctta atgctcctat cgtaaaaaat atgtccagat tagaaggaag tgttagatta 1080
aaatcaaatg aacataataa aaagtatcaa aatagagaaa gaggaattat ctattatgac 1140
tattatttaa atgtgaaaaa tatgtcagaa gtggaaaatg aattaaaatt agttaaatcg 1200
tctattgaag ccggaaataa tattgaaata aataataatc ttgaaaatgg aagttttgaa 1260
aatttatctg ggatttaaa agcaggaaat gatatcaaag taaaaggaaa ttttaaaaca 1320
aaacatttgt cagaaggaat aaagctagaa gatcttttaa aaagaataaa agtagatctt 1380
cgttgggagc acagaagtct agttgataac gcatatttta atggaaactc ttctttaaca 1440
gatggaagct tgttggatgc tttaaaaata atgactcaaa agaaaaataa agaatattac 1500
acagccttaa aacaaattga tgaccctcaa ttaaataaag ttttaagtgg tttattaggg 1560
gctgattgga gaacaaggga acgaataaaa gatgaaaaag attggaataa agaagcagcc 1620
ataagtttta caaatggaac ttattcaata gaagcaggaa atgacttgaa agcttctgga 1680
aaagtgattg aacttggtgg ttctaatgtt atgactaaaa aagaaatatt tgaagtagca 1740
tctacgaaaa cggaaagttt acaatcaacg atttcagatg ttaaaaatgc taatataaaa 1800
gcgaaaaatg tttatatgga agccgataat ataacaaatg taaatgcaga tattgcagcg 1860
gaagacagtg cgattcttta ttctaaaaac aatattgatg tgaagggagc taaagtttct 1920
gctgataaaa ttcttcttga agctggtaaa gatataaatt tatcttcaga acttggtttc 1980
aaatcttctg ggaacatgc gattattaaa gaaacagatg ttactgcaaa taaggctgtt 2040
ggaatcaaat ccaagaactt aaatatttat ggtgcagatg tagaggcaaa agatggactt 2100

-continued ataaaaatag actctgataa gttaaatgta aaagatatca gtacaatcaa tgcaaattat 2160
aaggccgaat taatagaagg aaaaaaatat attttaagag atcatcaata tacaaaagct 2220
ttacaagcta aagtggaatc tacaccttct aaaataattg ctaataaaat ttttatcact 2280
gcaaaagatg gtgctgctat tgagggttca ctgatttcag gaaaaaatgc tgacagcata 2340
atccaaatca tttctgaggg aaatgtcaat atcaaaaata gcaataatat tgattatagt 2400
aatttttatt cagatagcag aggaaaaaat aaaaaaggag tctacaaatt attaaaaata 2460
gataaggctt caaaagaaaa tcttgacata gtaggaagca acttaaaatc ggaaggaaat 2520
ataaatataa aatcaaaaaa tttaactgtt gtatcaagta aaataaaagc aggaaaaaaa 2580
gttaacttag aagccgaaga agatataaaa ttactagctt ctttgaattc taagaaagag 2640
gaattaaata agatggaatg gggtagcggt gctatcaata gttataaaaa gtctttggag 2700
aaaaaagatg tagtgtctac tatgattgaa gctggagaaa aagcaaatgt acatgcaaaa 2760
agagatttgt ataaacaatc tgtttttgtg aaagctggaa gcgtaactat gaatggtgag 2820
gcaaataatt acagtgatgc tttagcttca acagaaataa aaaaagaaac agatgtgaaa 2880
gctggctttg gtgtagaagg aaagattgct tttgctggaa tgggagcagc tggggaagca 2940
aacactttag ataatacagc aacaggaaaa acttccggga taaaaggtct tttagaaaaa 3000
gagaatgaat ttaaaaaagc ggaagccaga gcgaaagttt acgcaaaaat ggaagttaat 3060
aagagcataa aagaaagtaa aaattatgta aataacaaca ttacctcgga aagtggtgat 3120
gtgactatag gttctaatgg ggtcactgat ataggaaata ccgatatcaa ttctcaaaat 3180
gatgttaact taagaggtaa aaaagtagaa accactacaa aggaaaatgt aacgaaagag 3240
gttaatcata agcttgatct ttctgtaaaa ggtgacatcg ctttttctaa tgaaaatgtc 3300
aataaattga atgatttggc aaatgatgtt ctaaaaagta aagagatgtt agaaaagaaa 3360
gatatactcg ggttagctca aaaagcagaa gaaacaatca aagatttaaa agaaacgatt 3420
ccaaatctaa ctaaaaaaga cattttagga ataaaatcaa gtcagggagt aggggtagaa 3480
tacactaata aaacttctac tactacggaa acaacagctt cttctttgaa agcgaaaggg 3540
aagttaaata taaaggcaga tgaaggagat attactttaa aaaacactta tttaaaagct 3600
caagagttta acacagaaac tcctggaaaa gttaatcttt tagcagggaa gaaaacgatt 3660
cataaagaag aaaattcttt aaaggttggt gtatcagtta acgaaaatgt aggagtcaat 3720
atagcagatg gagccaatgc taaaattggt gtaggtgttc aagctagtta caatggcgga 3780
actgatttga ataaaaaaag tttaaataca actgtagagg taggaaaagt gaatcataaa 3840
gctgcagctg taaatgaaga taataaaaca gacttttatt acaaagataa aagaggtgca 3900
ggagttgatg ttgatttaaa aataggagtt tcttcgaatc atatagtagc ggcagatgga 3960
aatgtaggag gaaatgtgaa ttattctttt gcggctggaa aatcaacaac agatgttgta 4020
acaaataaga cagaaagtac tgatgtaaaa gcaggggttg gactgaaagc ttctgttgga 4080
atagatggaa aaagtccaga tttttcaatt tcaacagacc aaattgaata taaaaaagat 4140
ggaaaagtat tagttaatat tgacgcaaaa gataaaatga tcaccaaaga gagaattgaa 4200
cagatgagag ataaggtaaa aaattggaga actccaacaa atagtgcgga aaaattaatc 4260
taa 4263

<210> SEQ ID NO 79
<211> LENGTH: 736
<212> TYPE: PRT

<213> ORGANISM: F. necrophorum

<400> SEQUENCE: 79

```
Met Lys Lys Ile Leu Phe Leu Val Gly Ala Leu Phe Ser Ile Ser Ala
1               5                   10                  15

Phe Ala Glu Gln Thr Ile Glu Leu Gly Ser Thr Ser Ile Lys Gly Asn
            20                  25                  30

Arg Lys Thr Asp Tyr Thr Leu Thr Pro Lys Glu Tyr Lys Asn Thr Tyr
        35                  40                  45

Thr Ile Thr Gln Glu Lys Ile Arg Glu Arg Asn Tyr Lys Asn Val Glu
    50                  55                  60

Asp Val Leu Arg Asp Ala Pro Gly Val Val Val Gln Asn Thr Ala Phe
65                  70                  75                  80

Gly Pro Arg Ile Asp Met Arg Gly Ser Gly Glu Lys Ser Leu Ser Arg
                85                  90                  95

Val Lys Val Leu Val Asp Gly Ile Ser Ile Asn Pro Thr Glu Glu Thr
            100                 105                 110

Met Ala Ser Leu Pro Ile Asn Ser Ile Pro Ile Glu Ser Val Lys Lys
        115                 120                 125

Ile Glu Ile Ile Pro Gly Gly Gly Ala Thr Leu Tyr Gly Ser Gly Ser
    130                 135                 140

Val Gly Gly Val Val Ser Ile Ser Thr Asn Ser Asn Val Thr Lys Asn
145                 150                 155                 160

Asn Phe Phe Met Asp Leu Asn Tyr Gly Ser Phe Asp Asn Arg Asn Phe
                165                 170                 175

Gly Phe Ala Gly Gly Tyr Asn Val Ser Asp Lys Leu Tyr Val Asn Tyr
            180                 185                 190

Gly Phe Asn Tyr Leu Asn Ser Glu Asp Tyr Arg Glu His Glu Glu Lys
        195                 200                 205

Glu Asn Lys Ile Tyr Leu Leu Gly Phe Asp Tyr Lys Ile Asn Pro Lys
    210                 215                 220

Asn Arg Phe Arg Val Gln Thr Arg Tyr Ser Lys Met Lys His Asp Gly
225                 230                 235                 240

Ser Asn Trp Leu Ser Gln Glu Glu Leu Lys Ile Ser Arg Lys Lys Ala
                245                 250                 255

Gly Leu Asn Leu Asp Leu Asp Thr Thr Asp Lys Ser Tyr Thr Phe Asp
            260                 265                 270

Tyr Glu Tyr Arg Pro Ser Gln Asn Leu Thr Leu Ala Ala Thr Ala Tyr
        275                 280                 285

Lys Gln Gln Gln Asp Arg Asp Ile Thr Thr Asp Asp Ile Arg Asp Ile
    290                 295                 300

Glu Ile Ile Ala Ser Asn Arg Asn Tyr Thr Asp Leu Lys Glu Tyr Met
305                 310                 315                 320

Thr Phe Tyr Asp Val Lys Ser Thr Leu Lys Ala Lys Phe Lys Glu Lys
                325                 330                 335

Lys Tyr Gly Leu Lys Leu Lys Gly Lys Tyr Glu Tyr Gly Arg Gly Glu
            340                 345                 350

Val Ile Phe Gly Tyr Asp Tyr Gln Asp Ser Asn Asn Lys Arg Asn Ser
        355                 360                 365

Leu Val Gln Ser Glu Thr Leu Lys Thr Tyr Asn Asp Lys Ile Ser Asp
    370                 375                 380

Leu Asn Leu Ser Pro Glu Asp Arg Lys Pro Ile Ile Asn Arg Val Asn
385                 390                 395                 400
```

```
Ile Asp Leu Thr Lys Lys Ser His Gly Phe Tyr Val Phe Asn Lys Leu
                405                 410                 415

Glu Leu Thr Asp Lys Trp Asp Phe Thr Thr Gly Phe Arg Thr Glu Ile
            420                 425                 430

Thr Lys Tyr Asn Gly Tyr Arg Lys Asn Gly Pro Asn Thr Met Pro Ile
        435                 440                 445

Val Ser Pro Lys Val Asn Glu Ile Arg Thr Asp Glu Lys Met Thr Asn
    450                 455                 460

Tyr Ala Gly Glu Ala Gly Met Leu Tyr Lys Tyr Ser Asp Thr Gly Arg
465                 470                 475                 480

Ala Phe Val Arg Tyr Glu Arg Gly Phe Val Thr Pro Phe Ala Asn Gln
                485                 490                 495

Leu Thr Asp Lys Ile His Asp Thr Lys Leu Lys Ser Pro Ala Gly Phe
            500                 505                 510

Phe Thr Pro Pro Ile Val Asn Val Ser Ser Leu Tyr Val Ala Asn Asn
        515                 520                 525

Leu Lys Ser Glu Ile Thr Asp Thr Ile Glu Val Gly Phe Arg Asp Tyr
    530                 535                 540

Ile Phe Asn Ser Leu Ile Ser Ala Ser Phe Phe Ala Thr Asp Thr Thr
545                 550                 555                 560

Asp Glu Ile Thr Leu Ile Ser Ser Gly Ile Thr Asn Pro Ala Val Asn
                565                 570                 575

Arg Trp Lys Phe Arg Asn Ile Gly Lys Thr Arg Arg Leu Gly Ile Glu
            580                 585                 590

Leu Glu Ala Glu Gln Lys Trp Gly Lys Phe Asp Phe Ser Gln Ser Leu
        595                 600                 605

Thr Phe Val Asp Thr Lys Val Leu Lys Thr Asp Ala Glu Ser Arg Ile
    610                 615                 620

Phe Arg Gly Asp Lys Val Pro Met Val Pro Arg Ile Lys Ala Thr Leu
625                 630                 635                 640

Gly Leu Lys Tyr Asn Val Thr Asp Asn Leu Ala Leu Ile Gly Thr Tyr
                645                 650                 655

Thr Tyr Leu Ser Lys Arg Glu Thr Arg Glu Leu Asp Glu Lys Asp Lys
            660                 665                 670

Val Tyr Lys His Thr Ile Lys Gly Tyr Gly Thr Ala Asp Leu Gly Ile
        675                 680                 685

Leu Tyr Lys Val Asp Lys Tyr Ser Asn Phe Lys Val Gly Ala Lys Asn
    690                 695                 700

Ile Phe Gly Lys Lys Tyr Asn Leu Arg Glu Thr Lys Leu Glu Ala Leu
705                 710                 715                 720

Pro Ala Pro Glu Arg Asn Tyr Tyr Leu Glu Phe Asn Val Lys Phe Asn
                725                 730                 735


<210> SEQ ID NO 80
<211> LENGTH: 694
<212> TYPE: PRT
<213> ORGANISM: F. necrophorum

<400> SEQUENCE: 80

Leu Lys Val Asn Phe Ile Met Lys Arg Glu Ser Glu Lys Met Lys Lys
1               5                   10                  15

Ile Leu Phe Leu Val Gly Ala Leu Phe Ser Ile Ser Ala Phe Ala Glu
            20                  25                  30

Gln Thr Ile Glu Leu Gly Ser Thr Ser Ile Lys Gly Asn Arg Lys Thr
        35                  40                  45
```

```
Asp Tyr Thr Leu Thr Pro Lys Glu Tyr Lys Asn Thr Tyr Thr Ile Thr
    50                  55                  60

Gln Glu Lys Ile Arg Glu Arg Asn Tyr Lys Asn Val Glu Asp Val Leu
65                  70                  75                  80

Arg Asp Ala Pro Gly Val Val Val Gln Asn Thr Ala Phe Gly Pro Arg
                85                  90                  95

Ile Asp Met Arg Gly Ser Gly Glu Lys Ser Leu Ser Arg Val Lys Val
            100                 105                 110

Leu Val Asp Gly Ile Ser Ile Asn Pro Thr Glu Glu Thr Met Ala Ser
        115                 120                 125

Leu Pro Ile Asn Ser Ile Pro Ile Glu Ser Val Lys Lys Ile Glu Ile
    130                 135                 140

Ile Pro Gly Gly Gly Ala Thr Leu Tyr Gly Ser Gly Ser Val Gly Gly
145                 150                 155                 160

Val Val Ser Ile Ser Thr Asn Ser Asn Val Thr Lys Asn Asn Phe Phe
                165                 170                 175

Met Asp Leu Asn Tyr Gly Ser Phe Asp Asn Arg Asn Phe Gly Phe Ala
            180                 185                 190

Gly Gly Tyr Asn Val Ser Asp Lys Leu Tyr Val Asn Tyr Gly Phe Asn
        195                 200                 205

Tyr Leu Asn Ser Glu Asp Tyr Arg Glu His Glu Glu Lys Glu Asn Lys
    210                 215                 220

Ile Tyr Leu Leu Gly Phe Asp Tyr Lys Ile Asn Pro Lys Asn Arg Phe
225                 230                 235                 240

Arg Val Gln Thr Arg Tyr Ser Lys Met Lys His Asp Gly Ser Asn Trp
                245                 250                 255

Leu Ser Gln Glu Glu Leu Lys Ile Ser Arg Lys Lys Ala Gly Leu Asn
            260                 265                 270

Leu Asp Leu Asp Thr Thr Asp Lys Ser Tyr Thr Phe Asp Tyr Glu Tyr
        275                 280                 285

Arg Pro Ser Gln Asn Leu Thr Leu Ala Ala Thr Ala Tyr Lys Gln Gln
    290                 295                 300

Gln Asp Arg Asp Ile Thr Thr Asp Asp Ile Arg Asp Ile Glu Ile Ile
305                 310                 315                 320

Ala Ser Asn Arg Asn Tyr Thr Asp Leu Lys Glu Tyr Met Thr Phe Tyr
                325                 330                 335

Asp Val Lys Ser Thr Leu Lys Ala Lys Phe Lys Glu Lys Lys Tyr Gly
            340                 345                 350

Leu Lys Leu Lys Gly Asn Ile Asp Leu Thr Lys Lys Ser His Gly Phe
        355                 360                 365

Tyr Val Phe Asn Lys Leu Glu Leu Thr Asp Lys Trp Asp Phe Thr Thr
    370                 375                 380

Gly Phe Arg Thr Glu Ile Thr Lys Tyr Asn Gly Tyr Arg Lys Asn Gly
385                 390                 395                 400

Pro Asn Thr Met Pro Ile Val Ser Pro Lys Val Asn Glu Ile Arg Thr
                405                 410                 415

Asp Glu Lys Met Thr Asn Tyr Ala Gly Glu Ala Gly Met Leu Tyr Lys
            420                 425                 430

Tyr Ser Asp Thr Gly Arg Ala Phe Val Arg Tyr Glu Arg Gly Phe Val
        435                 440                 445

Thr Pro Phe Ala Asn Gln Leu Thr Asp Lys Ile His Asp Thr Lys Leu
    450                 455                 460
```

Lys Ser Pro Ala Gly Phe Phe Thr Pro Pro Ile Val Asn Val Ser Ser
465 470 475 480

Leu Tyr Val Ala Asn Asn Leu Lys Ser Glu Ile Thr Asp Thr Ile Glu
485 490 495

Val Gly Phe Arg Asp Tyr Ile Phe Asn Ser Leu Ile Ser Ala Ser Phe
500 505 510

Phe Ala Thr Asp Thr Thr Asp Glu Ile Thr Leu Ile Ser Ser Gly Ile
515 520 525

Thr Asn Pro Ala Val Asn Arg Trp Lys Phe Arg Asn Ile Gly Lys Thr
530 535 540

Arg Arg Leu Gly Ile Glu Leu Glu Ala Glu Gln Lys Trp Gly Lys Phe
545 550 555 560

Asp Phe Ser Gln Ser Leu Thr Phe Val Asp Thr Lys Val Leu Lys Thr
565 570 575

Asp Ala Glu Ser Arg Ile Phe Arg Gly Asp Lys Val Pro Met Val Pro
580 585 590

Arg Ile Lys Ala Thr Leu Gly Leu Lys Tyr Asn Val Thr Asp Asn Leu
595 600 605

Ala Leu Ile Gly Thr Tyr Thr Tyr Leu Ser Lys Arg Glu Thr Arg Glu
610 615 620

Leu Asp Glu Lys Asp Lys Val Tyr Lys His Thr Ile Lys Gly Tyr Gly
625 630 635 640

Thr Ala Asp Leu Gly Ile Leu Tyr Lys Val Asp Lys Tyr Ser Asn Phe
645 650 655

Lys Val Gly Ala Lys Asn Ile Phe Gly Lys Lys Tyr Asn Leu Arg Glu
660 665 670

Thr Lys Leu Glu Ala Leu Pro Ala Pro Glu Arg Asn Tyr Tyr Leu Glu
675 680 685

Phe Asn Val Lys Phe Asn
690

<210> SEQ ID NO 81
<211> LENGTH: 680
<212> TYPE: PRT
<213> ORGANISM: F. gonidiaformans

<400> SEQUENCE: 81

Met Arg Lys Met Leu Phe Leu Ile Gly Ala Leu Leu Ser Ile Ser Ala
1 5 10 15

Phe Ala Glu Gln Thr Val Glu Leu Gly Ser Thr Ser Ile Lys Gly Asn
20 25 30

Arg Lys Ala Asp Tyr Thr Leu Thr Pro Lys Glu Tyr Lys Asn Thr Tyr
35 40 45

Thr Ile Thr Gln Glu Lys Ile Gln Glu Arg Asn Tyr Lys Asn Val Glu
50 55 60

Asp Val Leu Arg Asp Ala Pro Gly Val Val Ile Gln Asn Thr Ala Phe
65 70 75 80

Gly Pro Arg Ile Asp Met Arg Gly Ser Gly Glu Lys Ser Leu Ser Arg
85 90 95

Val Lys Val Leu Val Asp Gly Val Ser Ile Asn Pro Thr Glu Glu Thr
100 105 110

Met Ala Ser Leu Pro Ile Asn Ser Ile Pro Ile Glu Thr Val Lys Lys
115 120 125

Ile Glu Ile Ile Pro Gly Gly Gly Ala Thr Leu Tyr Gly Ser Gly Ser
130 135 140

-continued

```
Val Gly Gly Val Val Ser Ile Thr Thr Asn Ser Asn Ala Thr Lys Asn
145                 150                 155                 160

Asn Phe Phe Met Asp Leu Asn Tyr Gly Ser Phe Asp Asn Arg Asn Phe
                165                 170                 175

Gly Phe Ala Gly Gly Tyr Asn Val Thr Asp Lys Leu Tyr Val Asn Tyr
            180                 185                 190

Gly Phe Asn Tyr Leu Asn Ser Glu Asp Tyr Arg Glu His Glu Glu Lys
        195                 200                 205

Glu Asn Lys Ile Tyr Leu Leu Gly Phe Asp Tyr Lys Ile Asn Ala Lys
    210                 215                 220

Asn Arg Phe Arg Val Gln Thr Arg Tyr Ser Lys Met Lys His Asp Gly
225                 230                 235                 240

Ser Asn Trp Leu Ser Gln Asp Glu Leu Lys Thr Ser Arg Lys Lys Ala
                245                 250                 255

Gly Leu Asn Leu Asp Leu Asp Thr Thr Asp Lys Ser Tyr Thr Phe Asp
            260                 265                 270

Tyr Glu Tyr Arg Pro Thr Glu Asn Leu Thr Leu Ala Ala Thr Ala Tyr
        275                 280                 285

Lys Gln Gln Gln Asp Arg Asp Ile Thr Thr Asp Asp Ile Arg Asp Ile
    290                 295                 300

Glu Ile Val Ala Ser Asn Arg Asn Tyr Thr Asp Leu Lys Glu Tyr Met
305                 310                 315                 320

Thr Phe Tyr Asp Val Lys Ser Thr Leu Lys Ala Lys Phe Lys Glu Glu
                325                 330                 335

Lys His Gly Ile Lys Leu Lys Gly Asp Ile Asp Leu Thr Lys Lys Ser
            340                 345                 350

His Gly Phe Tyr Ala Phe Asn Lys Leu Glu Leu Gly Lys Lys Phe Asp
        355                 360                 365

Phe Thr Thr Gly Phe Arg Thr Glu Ile Thr Glu Tyr Asn Gly Tyr Arg
    370                 375                 380

Lys Asn Gly Pro Asn Thr Met Pro Ile Ile Ser Pro Lys Thr Asn Glu
385                 390                 395                 400

Ile Lys Thr Asn Glu Lys Met Thr Asn Tyr Ala Gly Glu Ala Gly Met
                405                 410                 415

Leu Tyr Lys Tyr Ser Asp Thr Gly Arg Ala Phe Val Arg Tyr Glu Arg
            420                 425                 430

Gly Phe Val Thr Pro Phe Ala Asn Gln Leu Thr Asp Lys Ile His Asp
        435                 440                 445

Thr Glu Leu Lys Asn Pro Gly Gly Phe Phe Thr Pro Pro Ile Val Asn
    450                 455                 460

Val Ala Ser Leu Tyr Val Ala Asn Asn Leu Lys Ser Glu Ile Thr Asp
465                 470                 475                 480

Thr Ile Glu Val Gly Phe Arg Asp Tyr Ile Phe Asp Ser Leu Val Ser
                485                 490                 495

Ala Ser Phe Phe Ala Thr Asp Thr Thr Asp Glu Ile Thr Leu Ile Ser
            500                 505                 510

Ser Gly Ile Thr Asn Pro Ala Val Asn Arg Trp Lys Phe Arg Asn Ile
        515                 520                 525

Gly Lys Thr Arg Arg Leu Gly Ile Glu Leu Glu Ala Glu Gln Lys Trp
    530                 535                 540

Gly Asp Phe Glu Phe Ser Gln Ser Leu Thr Phe Val Asp Thr Lys Val
545                 550                 555                 560
```

```
Leu Lys Thr Asp Lys Glu Ser Asn Ile Tyr Arg Gly Asp Lys Val Pro
                565                 570                 575

Met Val Pro Asn Ile Lys Ala Thr Leu Gly Leu Lys Tyr Asn Val Thr
            580                 585                 590

Asp Asn Leu Ser Leu Ile Gly Thr Tyr Thr Tyr Leu Ser Lys Arg Glu
        595                 600                 605

Thr Arg Glu Leu Asp Glu Lys Asp Lys Val Tyr Lys His Thr Ile Lys
    610                 615                 620

Gly Tyr Gly Thr Ala Asp Leu Gly Val Leu Tyr Lys Val Asp Lys Tyr
625                 630                 635                 640

Ser Asn Phe Lys Val Gly Ala Lys Asn Leu Phe Gly Lys Lys Tyr Asn
                645                 650                 655

Leu Arg Glu Thr Lys Leu Glu Ala Leu Pro Ala Pro Glu Arg Asn Tyr
            660                 665                 670

Tyr Leu Glu Phe Asn Val Lys Phe
        675                 680


<210> SEQ ID NO 82
<211> LENGTH: 736
<212> TYPE: PRT
<213> ORGANISM: F. necrophorum

<400> SEQUENCE: 82

Met Arg Lys Thr Leu Leu Leu Phe Ser Ile Leu Ala Thr Leu Ala Tyr
1               5                   10                  15

Ala Glu Gln Thr Val Glu Leu Gly Ser Ser Ser Ile Arg Ser Ser Ala
            20                  25                  30

Lys Lys Thr Asp Tyr Thr Leu Ile Pro Lys Glu Tyr Lys Asn Thr Tyr
        35                  40                  45

Thr Ile Thr Gln Glu Thr Ile Arg Glu Arg Asn Tyr Lys Asn Val Glu
    50                  55                  60

Asp Val Leu Arg Asp Ala Pro Gly Val Ile Ile Gln Asn Thr Ala Phe
65                  70                  75                  80

Gly Pro Arg Val Asp Met Arg Gly Ser Gly Glu Lys Ser Leu Ala Arg
                85                  90                  95

Val Lys Val Leu Val Asp Gly Ile Ser Ile Asn Pro Thr Glu Glu Thr
            100                 105                 110

Met Ala Ser Leu Pro Ile Asn Ser Ile Pro Ile Glu Ser Val Lys Lys
        115                 120                 125

Ile Glu Ile Ile Pro Gly Gly Gly Ala Thr Leu Tyr Gly Ser Gly Ser
    130                 135                 140

Val Gly Gly Val Val Ser Ile Ser Thr Asn Ser Asn Val Thr Lys Asn
145                 150                 155                 160

Asn Phe Phe Met Asp Leu Asn Tyr Gly Ser Phe Asp Asn Arg Asn Phe
                165                 170                 175

Gly Phe Ala Gly Gly Tyr Asn Val Asn Lys Lys Leu Tyr Val Asn Tyr
            180                 185                 190

Gly Phe Asn Tyr Leu Asn Ser Glu Ser Tyr Arg Lys His Glu Glu Lys
        195                 200                 205

Glu Asn Lys Ile Tyr Leu Val Gly Phe Asp Tyr Lys Phe Asn Gly Lys
    210                 215                 220

Asn Arg Val Arg Phe Gln Thr Arg Gln Ser Asp Ile Met Asp His Gly
225                 230                 235                 240

Ser Asn Gln Leu Arg Lys Thr Glu Leu Glu Gly Asp Arg Arg Ala Pro
                245                 250                 255
```

```
Gly Leu Ala Leu Asn Leu Asp Thr Lys Asp Gln Ser Tyr Thr Met Asp
            260                 265                 270

Tyr Glu Tyr Arg Pro Thr Glu Lys Leu Thr Leu Gly Ala Thr Ala Tyr
        275                 280                 285

Gln Gln Gln Gln Asp Arg Asp Ile Tyr Thr Glu Asp Ile Arg Asp Ile
    290                 295                 300

Glu Ile Val Ala Ser Asp Arg Asn Tyr Thr Asp Ile Lys Glu Tyr Met
305                 310                 315                 320

Ile Phe His Asp Val Lys Ser Thr Met Lys Ala Lys Phe Lys Glu Lys
                325                 330                 335

Lys His Gly Ile Lys Leu Lys Gly Lys Tyr Asp Tyr Gly Lys Gly Glu
            340                 345                 350

Ile Ile Phe Gly Tyr Asp Tyr Tyr Asp Ser Asn Asn Arg Arg Asp Ser
        355                 360                 365

His Val Arg Ser Glu Thr Leu Lys Thr Tyr Asn Thr Lys Tyr Thr Asp
    370                 375                 380

Ser Val Leu Ser Pro Glu Glu Arg Leu Pro Ile Ile Asn Asn Val Lys
385                 390                 395                 400

Ile Asp Leu Thr Lys Lys Ser His Gly Phe Tyr Ala Phe Asn Lys Trp
                405                 410                 415

Asn Val Asn Lys Asn Phe Asp Phe Thr Thr Gly Phe Arg Ile Glu Lys
            420                 425                 430

Thr Lys Tyr Asn Gly Tyr Arg Lys Asn Gly Lys Asn Thr Met Pro Ile
        435                 440                 445

Ala Val Ala Lys Thr Asp Val Ile Arg Thr Asp Glu Arg His Thr Asn
    450                 455                 460

Phe Ala Gly Glu Val Gly Gly Leu Trp Lys Tyr Ser Asp Thr Gly Arg
465                 470                 475                 480

Phe Phe Thr Arg Tyr Glu Arg Gly Phe Val Thr Pro Phe Ser Thr Gln
                485                 490                 495

Leu Thr Asp Lys Ile His Asp Thr Glu Leu Lys Asn Pro Asn Gly Phe
            500                 505                 510

Phe Ile Pro Pro Ile Val Asn Ser Ala Ser Lys Tyr Val Ala Asn His
        515                 520                 525

Leu Gln Pro Glu Ile Thr Asp Thr Val Glu Ile Gly Phe Arg Asp Tyr
    530                 535                 540

Phe Tyr Asn Ser Leu Phe Ser Ala Ser Phe Phe Val Thr Asp Thr Lys
545                 550                 555                 560

Asp Glu Ile Thr Leu Ile Ser Ser Gly Ile Thr Asn Pro Ala Val Asn
                565                 570                 575

Arg Trp Arg Tyr Arg Asn Ile Gly Lys Thr Arg Arg Phe Gly Ile Glu
            580                 585                 590

Leu Glu Ala Glu Gln Lys Phe Gly Lys Phe Gly Leu Thr Glu Ser Leu
        595                 600                 605

Thr Phe Val Asp Ser Lys Val Leu Lys Thr Asp Ala Asn Ser Asn Ile
    610                 615                 620

Phe Arg Gly Asp Arg Val Pro Met Val Pro Arg Leu Lys Ala Thr Leu
625                 630                 635                 640

Gly Ile Lys Tyr Arg Met Thr Asp Asp Leu Thr Leu Leu Ala Asn Tyr
                645                 650                 655

Thr Tyr Leu Ser Lys Arg Glu Ala Arg Glu Leu Asp Glu Lys Asp Lys
            660                 665                 670
```

Ile Tyr Arg His Thr Ile Lys Gly His Gly Val Leu Asp Val Gly Ala
675 680 685

Leu Tyr Arg Ile Asp Lys Tyr Ser Asn Val Lys Val Gly Ala Lys Asn
690 695 700

Leu Phe Ser Lys Lys Tyr Asn Leu Arg Glu Thr Lys Val Glu Ala Leu
705 710 715 720

Pro Ala Pro Glu Arg Asn Tyr Tyr Leu Glu Phe Asn Val Lys Phe Asp
725 730 735

<210> SEQ ID NO 83
<211> LENGTH: 744
<212> TYPE: PRT
<213> ORGANISM: F. nucleatum

<400> SEQUENCE: 83

Met Lys Lys Leu Leu Val Leu Leu Thr Ile Leu Ser Ser Ile Ile Ala
1 5 10 15

His Ala Glu Asp Thr Ile Glu Leu Lys Glu Thr Thr Val Lys Ser Ser
20 25 30

Pro Arg Ser Ser Asp Tyr Thr Leu Ile Pro Lys Glu Gln Lys Asn Thr
35 40 45

Tyr Val Ile Thr Gln Glu Lys Ile Arg Glu Arg Asn Tyr Lys Asn Val
50 55 60

Glu Asp Val Leu Arg Asp Ala Pro Gly Val Thr Ile Gln Asn Thr Ala
65 70 75 80

Phe Gly Pro Arg Val Asp Met Arg Gly Ser Gly Glu Lys Ser Leu Ser
85 90 95

Arg Val Lys Val Leu Ile Asp Gly Val Ser Ile Asn Pro Thr Glu Glu
100 105 110

Thr Met Ala Ser Leu Pro Ile Asn Ser Ile Pro Ile Glu Ser Val Lys
115 120 125

Lys Ile Glu Ile Ile Pro Gly Gly Gly Ala Thr Leu Tyr Gly Ser Gly
130 135 140

Ser Val Gly Gly Val Ile Ser Ile Thr Thr Asn Ser Asn Val Thr Lys
145 150 155 160

Asn Asn Phe Phe Ala Asp Leu Asn Tyr Gly Ser Phe Asp Asn Arg Asn
165 170 175

Phe Gly Phe Ala Gly Gly Tyr Asn Val Thr Lys Asn Leu Tyr Val Asn
180 185 190

Tyr Gly Phe Asn Tyr Leu Asn Ser Glu Gly Tyr Arg Arg Glu Glu Glu
195 200 205

Lys Glu Asn Lys Ile Tyr Leu Leu Gly Phe Asp Tyr Lys Ile Asn Ser
210 215 220

Lys Asn Arg Phe Arg Phe Gln Thr Arg Tyr Ser Lys Phe Lys Asp Asp
225 230 235 240

Gly Ser Asn Gln Val Thr Arg Glu Val Leu Glu Tyr Asp Arg Arg Ala
245 250 255

Ile Gly Leu Asn Leu Asp Met Ile Thr Lys Asp Lys Ser Tyr Thr Phe
260 265 270

Asp Tyr Glu Tyr Arg Pro Lys Asn Asn Leu Thr Leu Ala Ala Thr Ile
275 280 285

Tyr Lys Gln Glu Gln Asp Arg Asp Ile Gln Thr Glu Ser Ile Asp Asp
290 295 300

Ile Arg Ile Val Ser Ser Pro Ala Gly Tyr Thr Tyr Gly Ser Tyr Lys
305 310 315 320

-continued

```
Glu Glu Met Asn Phe Tyr Gly Val Thr Ser Lys Met Asn Ala Lys Phe
                325                 330                 335

Glu Glu Asp Lys Lys Gly Leu Lys Leu Lys Ser Lys Tyr Asp Tyr Ser
            340                 345                 350

Asn Gly Gln Ile Ile Phe Gly Tyr Asp Tyr Gln Lys Ala Val Asn Lys
        355                 360                 365

Arg Asp Ser Phe Val Gln Ser Glu Thr Leu Lys Ser Tyr Asn Asn Gly
    370                 375                 380

Tyr Ser Asn Lys Thr Leu Glu Gly Glu Asp Ile Gln Pro Val Ile Asn
385                 390                 395                 400

Arg Val Lys Val Asn Met Glu Lys Glu Ser His Gly Phe Tyr Val Phe
                405                 410                 415

Asn Lys Phe Asp Val Thr Asp Lys Leu Asp Ile Thr Thr Gly Phe Arg
            420                 425                 430

Thr Glu Ile Thr Lys Tyr Asn Gly Lys Arg Val Asn Gly Pro Asn Thr
        435                 440                 445

Met Pro Phe Val Ala Ala Lys Thr Ala Glu Ile Asn Thr Asp Arg Lys
    450                 455                 460

Leu Glu Asn Tyr Ala Gly Glu Phe Gly Ala Leu Tyr Glu Tyr Arg Asp
465                 470                 475                 480

Thr Gly Arg Val Phe Leu Arg Tyr Glu Lys Gly Phe Val Thr Pro Phe
                485                 490                 495

Ala Asn Gln Leu Thr Asp Lys Val Arg Asp Thr Thr Leu Pro Lys Lys
            500                 505                 510

Val Gly Phe Phe Asp Pro Pro Gln Val Asn Val Ala Ser Lys Tyr Val
        515                 520                 525

Asp Asn Asn Leu Lys Ser Glu Lys Thr Asp Thr Val Glu Leu Gly Val
    530                 535                 540

Arg Asp Tyr Phe Phe Gly Ser Leu Phe Ser Ala Ser Val Phe Leu Thr
545                 550                 555                 560

Asp Thr Lys Asp Glu Ile Thr Leu Ile Ser Ser Gly Val Thr Asn Pro
                565                 570                 575

Ala Val Asn Arg Trp Lys Tyr Arg Asn Ile Gly Lys Thr Arg Arg Met
            580                 585                 590

Gly Leu Glu Leu Glu Ala Glu Gln Asn Phe Gly Asn Trp Ser Leu Ser
        595                 600                 605

Gln Ser Leu Thr Leu Leu Asn Thr Lys Val Leu Lys Ala Asn Glu Glu
    610                 615                 620

Ala Arg Leu Glu Lys Gly Asp Lys Val Pro Leu Val Pro Arg Val Lys
625                 630                 635                 640

Ala Thr Leu Gly Val Lys Tyr Asn Phe Thr Asp Lys Ile Ala Leu Ile
                645                 650                 655

Gly Thr Tyr Thr Tyr Phe Ser Lys Arg Glu Thr Arg Glu Ile Arg Glu
            660                 665                 670

Ser Glu Asp Leu Asn Lys Asp Asp Asn Ile Ile Lys His Thr Ile Gly
        675                 680                 685

Gly Tyr Gly Ile Thr Asp Leu Gly Val Leu Tyr Lys Ala Asp Ala Tyr
    690                 695                 700

Ser Asn Ile Lys Val Gly Ala Lys Asn Ile Phe Asn Lys Lys Tyr Asn
705                 710                 715                 720

Leu Arg Glu Thr Ser Leu Glu Ala Leu Pro Ala Pro Glu Lys Thr Tyr
                725                 730                 735
```

Tyr Leu Glu Met Asn Val Arg Phe
740

<210> SEQ ID NO 84
<211> LENGTH: 689
<212> TYPE: PRT
<213> ORGANISM: F. nucleatum

<400> SEQUENCE: 84

Met Lys Lys Leu Leu Val Leu Leu Thr Ile Leu Ser Ser Ile Ile Ala
1 5 10 15

Tyr Ala Glu Asp Thr Ile Glu Leu Asn Gln Thr Thr Val Lys Ser Ser
20 25 30

Pro Arg Ser Ser Asp Tyr Thr Leu Ile Pro Lys Glu Gln Lys Asn Thr
35 40 45

Tyr Val Ile Thr Gln Glu Lys Ile Arg Glu Arg Asn Tyr Lys Asn Val
50 55 60

Glu Asp Val Leu Arg Asp Ala Pro Gly Val Thr Ile Gln Asn Thr Ala
65 70 75 80

Phe Gly Pro Arg Val Asp Met Arg Gly Ser Gly Glu Lys Ser Leu Ser
85 90 95

Arg Val Lys Val Leu Ile Asp Gly Val Ser Ile Asn Pro Thr Glu Glu
100 105 110

Thr Met Ala Ser Leu Pro Ile Asn Ser Ile Pro Ile Glu Ser Val Lys
115 120 125

Lys Ile Glu Ile Ile Pro Gly Gly Gly Ala Thr Leu Tyr Gly Ser Gly
130 135 140

Ser Val Gly Gly Val Ile Ser Ile Thr Thr Asn Ser Asn Val Thr Lys
145 150 155 160

Asn Asn Phe Phe Ala Asp Leu Asn Tyr Gly Ser Phe Asp Asn Arg Asn
165 170 175

Phe Gly Phe Ala Gly Gly Tyr Asn Val Thr Lys Asn Leu Tyr Val Asn
180 185 190

Tyr Gly Phe Asn Tyr Leu Asn Ser Glu Gly Tyr Arg Arg Glu Glu Glu
195 200 205

Lys Glu Asn Lys Ile Tyr Leu Leu Gly Phe Asp Tyr Lys Ile Asn Ala
210 215 220

Lys Asn Arg Phe Arg Phe Gln Thr Arg Tyr Ser Lys Phe Lys Asp Asp
225 230 235 240

Gly Ser Asn Gln Val Ala Arg Glu Val Leu Glu Tyr Asp Arg Arg Ala
245 250 255

Val Gly Leu Asn Leu Asp Met Ile Thr Lys Asp Lys Ser Tyr Thr Phe
260 265 270

Asp Tyr Glu Tyr Arg Pro Lys Asn Asn Leu Thr Leu Ala Ala Thr Ile
275 280 285

Tyr Lys Gln Glu Gln Asp Arg Asp Ile Gln Thr Glu Ser Ile Asp Asp
290 295 300

Ile Arg Ile Val Ser Ser Pro Ala Gly Tyr Thr Tyr Gly Ser Tyr Lys
305 310 315 320

Glu Glu Met Asn Phe Tyr Gly Val Thr Ser Lys Met Asn Ala Lys Phe
325 330 335

Glu Glu Asp Lys Lys Gly Leu Lys Leu Lys Ser Lys Val Asn Met Glu
340 345 350

Lys Glu Ser His Gly Phe Tyr Val Phe Asn Lys Phe Asp Ala Thr Asp
355 360 365

Lys Leu Asp Ile Thr Thr Gly Phe Arg Thr Glu Ile Thr Lys Tyr Asn
    370                 375                 380

Gly Lys Arg Val Asn Gly Pro Asn Thr Met Pro Phe Val Ala Ala Lys
385                 390                 395                 400

Thr Ala Glu Ile Asn Thr Asp Arg Lys Leu Glu Asn Tyr Ala Gly Glu
                405                 410                 415

Phe Gly Ala Leu Tyr Lys Tyr Arg Asp Thr Gly Arg Val Phe Leu Arg
            420                 425                 430

Tyr Glu Lys Gly Phe Val Thr Pro Phe Ala Asn Gln Leu Thr Asp Lys
        435                 440                 445

Val Arg Asp Thr Thr Leu Pro Lys Lys Val Gly Phe Phe Asp Pro Pro
    450                 455                 460

Gln Val Asn Val Ala Ser Lys Tyr Val Asp Asn Asn Leu Lys Ser Glu
465                 470                 475                 480

Lys Thr Asp Thr Val Glu Leu Gly Val Arg Asp Tyr Phe Phe Gly Ser
                485                 490                 495

Leu Phe Ser Ala Ser Val Phe Leu Thr Asp Thr Lys Asp Glu Ile Thr
            500                 505                 510

Leu Ile Ser Ser Gly Val Thr Asn Pro Ala Val Asn Arg Trp Lys Tyr
        515                 520                 525

Arg Asn Ile Gly Lys Thr Arg Arg Met Gly Leu Glu Leu Glu Ala Glu
    530                 535                 540

Gln Asn Phe Gly Asn Trp Ser Leu Ser Gln Ser Leu Thr Leu Leu Asn
545                 550                 555                 560

Thr Lys Val Leu Lys Ala Asn Glu Glu Ala Arg Leu Glu Lys Gly Asp
                565                 570                 575

Gln Val Pro Leu Val Pro Arg Val Lys Ala Thr Leu Gly Val Lys Tyr
            580                 585                 590

Asn Phe Thr Asp Lys Ile Ala Leu Val Gly Thr Tyr Thr Tyr Phe Ser
        595                 600                 605

Lys Arg Asp Thr Arg Glu Ile Arg Glu Ser Glu Asp Leu Asn Lys Asp
    610                 615                 620

Asp Asp Ile Ile Lys His Thr Ile Gly Gly Tyr Gly Val Thr Asp Leu
625                 630                 635                 640

Gly Val Leu Tyr Lys Ala Asp Ala Tyr Ser Asn Ile Lys Val Gly Ala
                645                 650                 655

Lys Asn Ile Phe Asn Lys Lys Tyr Asn Leu Arg Glu Thr Ser Leu Glu
            660                 665                 670

Ala Leu Pro Ala Pro Glu Lys Thr Tyr Tyr Leu Glu Met Asn Val Arg
        675                 680                 685

Phe

<210> SEQ ID NO 85
<211> LENGTH: 747
<212> TYPE: PRT
<213> ORGANISM: F. periodonticum

<400> SEQUENCE: 85

Met Lys Lys Leu Leu Val Leu Leu Thr Ile Leu Thr Ser Ile Ala Ser
1               5                   10                  15

Phe Ser Glu Asp Val Ile Glu Leu Gly Gln Thr Thr Val Lys Gly Ser
            20                  25                  30

Lys Thr Ser Asp Tyr Thr Ala Pro Pro Lys Glu Gln Lys Asn Thr Phe
        35                  40                  45

-continued

```
Val Ile Thr Gln Glu Arg Ile Arg Glu Lys Asn Tyr Lys Asn Val Glu
    50                  55                  60

Asp Ile Leu Arg Asp Ala Pro Gly Val Val Val Gln Asn Thr Ala Phe
65                  70                  75                  80

Gly Pro Arg Ile Asp Met Arg Gly Ser Gly Glu Lys Ser Leu Ser Arg
                85                  90                  95

Val Lys Val Leu Val Asp Gly Val Ser Ile Asn Pro Thr Glu Glu Thr
            100                 105                 110

Met Ala Ser Leu Pro Ile Asn Ala Ile Pro Val Glu Ser Ile Lys Lys
        115                 120                 125

Ile Glu Ile Ile Pro Gly Gly Gly Ala Thr Leu Tyr Gly Ser Gly Ser
    130                 135                 140

Val Gly Gly Val Val Asn Ile Ser Thr Asn Ser Asn Val Thr Lys Asp
145                 150                 155                 160

Asn Phe Phe Met Asp Leu Asn Tyr Gly Ser Phe Asp Asn Arg Asn Phe
                165                 170                 175

Gly Phe Ala Gly Gly Tyr Asn Phe Asn Lys His Leu Tyr Val Asn Tyr
            180                 185                 190

Gly Phe Ser Tyr Leu Asn Ser Glu Asp Tyr Arg Glu His Glu Glu Lys
        195                 200                 205

Glu Asn Lys Ile Tyr Leu Leu Gly Phe Asp Tyr Lys Ile Asn Ala Lys
    210                 215                 220

His Arg Phe Arg Phe Gln Thr Arg Phe Ser Asp Ile Lys Gln Asp Ser
225                 230                 235                 240

Ser Asn Gln Ile Pro Val Glu Glu Leu Lys Asn Asp Arg Arg Lys Ala
                245                 250                 255

Gly Leu Asn Met Asp Ile Asn Thr Lys Asp Arg Ser Tyr Thr Phe Asp
            260                 265                 270

Tyr Glu Tyr Arg Pro Thr Gln Asn Ala Thr Leu Ser Thr Thr Phe Tyr
        275                 280                 285

Lys Gln Lys Gln Glu Arg Asp Ile Asp Thr Glu Ser Ile Asp Asp Ile
    290                 295                 300

Lys Ile Ile Ala Ser Asp Arg Thr His Thr Trp His Lys Glu Glu Met
305                 310                 315                 320

Asn Phe Tyr Asp Ile Lys Ser Lys Met His Ala Asp Phe Lys Glu Asp
                325                 330                 335

Lys Asp Gly Ala Lys Leu Lys Ala Lys Phe Asp Tyr Asn Leu Val Glu
            340                 345                 350

Asn Leu Pro Ser Glu Thr Ile Ile Gly Tyr Asp Tyr Gln Ser Ala Thr
        355                 360                 365

Asn Lys Arg Asn Ser Leu Val Gln Ser Glu Thr Leu Lys Thr Tyr Asn
    370                 375                 380

Asn Gly Tyr Met Asp Ile Asn Leu Ser Gln Ser Glu Arg Leu Pro Val
385                 390                 395                 400

Ile Asn Arg Val Asp Met Glu Met Lys Arg Lys Ser Gln Gly Ile Tyr
                405                 410                 415

Val Phe Asn Lys Trp Gly Leu Ala Asn Trp Leu Asp Val Thr Leu Gly
            420                 425                 430

Gly Arg Met Glu Lys Thr Lys Tyr Asn Gly Tyr Arg Glu Asn Gly Pro
        435                 440                 445

Asn Val Met Pro Tyr Val Glu Pro Glu Val Lys Arg Ile Glu Thr Asn
    450                 455                 460
```

-continued

```
Arg Lys Leu Asp Asn Tyr Ala Glu Glu Leu Gly Phe Leu Phe Lys Tyr
465                 470                 475                 480

Asn Asp Thr Gly Arg Phe Tyr Thr Arg Tyr Glu Arg Gly Phe Val Thr
                485                 490                 495

Pro Phe Gly Asn Gln Leu Thr Asp Lys Ile His Asp Thr Thr Leu Lys
            500                 505                 510

Asn Pro Asn Ser Gly Phe Ile Ile Pro Pro Thr Val Asn Val Ala Ser
        515                 520                 525

Lys Tyr Val Asp Asn Asn Leu Asn Ala Glu Lys Thr Asp Thr Phe Glu
    530                 535                 540

Ile Gly Phe Arg Asp Tyr Ile Leu Gly Ser Thr Leu Ser Thr Ser Phe
545                 550                 555                 560

Phe Leu Thr Asn Thr Lys Asp Glu Ile Thr Leu Ile Ser Ser Gly Val
                565                 570                 575

Thr Asn Pro Ala Val Asn Arg Trp Lys Tyr Arg Asn Ile Gly Lys Thr
            580                 585                 590

Arg Arg Phe Gly Leu Glu Phe Glu Ala Glu Gln Asn Phe Gly Lys Phe
        595                 600                 605

Arg Phe Asn Gln Ser Leu Thr Leu Val Arg Thr Lys Val Leu Val Ala
    610                 615                 620

Asn Glu Glu Ala Lys Leu Glu Arg Gly Asp Gln Val Pro Met Val Pro
625                 630                 635                 640

Arg Leu Lys Ala Thr Leu Gly Leu Arg Tyr Asn Phe Thr Asp Arg Leu
                645                 650                 655

Ala Gly Phe Val Asn Tyr Thr Tyr Leu Ala Lys Gln Glu Ser Arg Glu
            660                 665                 670

Leu Arg Glu Asn Glu Asp Leu Asn Lys Asp Asp Ile Val Val Lys His
        675                 680                 685

Thr Ile Gly Gly His Gly Val Val Asp Ala Gly Phe Ser Tyr Lys Pro
    690                 695                 700

Asp Ala Tyr Ser Asp Ile Lys Ile Gly Ala Lys Asn Leu Phe Ser Lys
705                 710                 715                 720

Lys Tyr Asn Leu Arg Glu Thr Ser Leu Glu Ala Leu Pro Ala Pro Glu
                725                 730                 735

Arg Asn Tyr Tyr Leu Glu Leu Asn Val Arg Phe
            740                 745
```